(12) United States Patent
McFarland

(10) Patent No.: US 9,345,769 B2
(45) Date of Patent: May 24, 2016

(54) METAL-BASED THIOPHENE PHOTODYNAMIC COMPOUNDS AND THEIR USE

(71) Applicant: Sherri Ann McFarland, Mount Uniacke (CA)

(72) Inventor: Sherri Ann McFarland, Mount Uniacke (CA)

(*) Notice: Subject to any disclaimer, the term of this patent is extended or adjusted under 35 U.S.C. 154(b) by 433 days.

(21) Appl. No.: 13/863,089

(22) Filed: Apr. 15, 2013

(65) Prior Publication Data

US 2013/0331367 A1    Dec. 12, 2013

Related U.S. Application Data

(60) Provisional application No. 61/624,391, filed on Apr. 15, 2012.

(51) Int. Cl.
| | | |
|---|---|---|
| *C07F 15/00* | (2006.01) | |
| *A61K 31/28* | (2006.01) | |
| *A61K 41/00* | (2006.01) | |

(52) U.S. Cl.
CPC ............ *A61K 41/0057* (2013.01); *A61K 31/28* (2013.01); *C07F 15/0026* (2013.01); *C07F 15/0053* (2013.01)

(58) Field of Classification Search
None
See application file for complete search history.

(56) References Cited

FOREIGN PATENT DOCUMENTS

PL    197232 B1    3/2008

OTHER PUBLICATIONS

Database Registry Chemical Abstracts Service, Columbus, Ohio, Accession No. RN 1268159-46-1, Entered STN: Mar. 11, 2011.*
Database Registry Chemical Abstracts Service, Columbus, Ohio, Accession No. RN 1233733-23-7, Entered STN: Jul. 23, 2010.*
Batista, Rosa M.F. Synthesis and characterization of novel (oligo)thienyl-imidazo-phenanthrolines as versatile π-conjugated systems for several optical applications. Tetrahedron. 64 (2008) 9230-9238.*
Cai et al., "Degenerate four-wave mixing determination of third-order optical nonlinearities of three mixed ligan nickel (II) complexes", Journal of Molecular Structure, vol. 1006, pp. 282-287 (2011).
Gringauz, "Introduction to Medicinal Chemistry", pp. 32-35 (1997).
Li et al., "pH effects on optical and DNA binding properties of a thiophene-containing ruthenium(II) complex", Inorganica Chimica Acta, vol. 370m oo, 132-140 (2011).
Pedra et al, "Synthesis, characterization, photophysical studies and interaction with DNA of a new family of Ru(II) furyl- and thienyl-imidazo-phenanthroline polypyridyl complexes", Inorganica Chimica Acta, vol. 381, pp. 95-103 (2012).
Srinivasan et al., "Metal-metal communication in diruthenium complexes of the bridging ligan bis(imidazo[4,5-f][1,10]phenanthroline)", Inorganica Chimica Acta, vol. 366, pp. 116-121 (2011).
International Search Report for PCT/US2013/036595 dated Jul. 18, 2013.
Written Opinion of the International Preliminary Examining Authority for PCT/US2013/036595 dated Jul. 25, 2014.

* cited by examiner

*Primary Examiner* — Samantha Shterengarts
(74) *Attorney, Agent, or Firm* — Caesar Rivise, PC

(57) ABSTRACT

Compositions of the invention include tunable metal-based thiophene photodynamic compounds useful as therapeutic agents and as in vivo diagnostic agents for treating or preventing diseases that involve hyperproliferating cell etiology including cancer and diseases associated with hyperproliferating cells. The compositions are also useful for treating infectious diseases and for pathogen disinfection.

20 Claims, 32 Drawing Sheets
(9 of 32 Drawing Sheet(s) Filed in Color)

bpy = [2,2']Bipyridine, phen = [1,10]Phenanthroline (a)

(b)

$$\frac{\epsilon_a - \epsilon_f}{\epsilon_b - \epsilon_f} = \frac{b - (b^2 - 2K_b^2 C_t [DNA]_t/s)^{1/2}}{2K_b C_t}$$

METAL-BASED THIOPHENE PHOTODYNAMIC COMPOUNDS AND THEIR USE

BACKGROUND OF THE INVENTION

1. Field of Invention

This invention relates to photodynamic compounds useful as therapeutic agents and as in vivo diagnostic agents. In particular, the invention provides tunable metal-based thiophene photodynamic compounds that can be activated to cleave DNA upon irradiation with visible light by either a Type 1 or Type 2 photoprocess.

2. Description of Related Art

Photodynamic therapy (PDT) is currently an active area of research for the treatment of diseases associated with hyperproliferating cells such as cancer and non-malignant lesions. PDT has also found use in other contexts, including but not limited to the treatment of acne, psoriasis, proliferative non-malignant conditions, ulcers and wounds. The development of new photodynamic compounds (PDCs) (or photosensitizers (PSs)) for photodynamic therapy (PDT) has been increasingly focused on metallosupramolecular complexes derived from metals such as ruthenium and rhodium. The ongoing investigation of new PSs for PDT stems from the limitations associated with traditional organic-based porphyrins such as PHOTOFRIN, which must be activated with relatively short wavelengths of light and do not function in hypoxic environments. Significant advances have been made toward overcoming these limitations with the introduction of mixed-metal complexes that possess low-lying $^3$MMCT (metal-to-metal charge transfer) excited states. To date, however, there has been limited reporting of photodynamic compounds, particularly those with a mononuclear or dinuclear design, that are capable of providing photodynamic therapy for the treatment of diseases associated with hyperproliferating cells such as cancer and non-malignant lesions, and/or capable of treating other conditions including but not limited to infectious diseases and pathogen infections.

There is a long felt need for new photodynamic compounds (PDCs) that are useful as photosensitizers for PDT that are both disease-modifying and effective in treating patients with diseases caused by hyperproliferating cells, for example, cancer. There is also a long felt need for new PDCs that are useful as in vivo diagnostic agents. Moreover, it is desired to provide novel PDCs having: (1) increased photo stability, (2) increased absorption at activation wavelength, (3) red-light, and preferably NIR, absorption, (4) maximal activity regardless of oxygen levels (possibly utilizing a mechanism for switching between type 1 and type 2 photosensitzation), and (5) intracellular nuclear DNA targeting.

The present invention addresses the need to develop novel PDCs that are useful as photo sensitizers for PDT that are both disease-modifying and effective in treating one or more of the conditions discussed above, such as treating patients with diseases caused by hyperproliferating cells, for example, cancer. The present invention also addresses the long felt need for new PDCs that are useful as in vivo diagnostic agents.

All references cited herein are incorporated herein by reference in their entireties.

BRIEF SUMMARY OF THE INVENTION

The present invention is directed toward novel compounds of formula (I),

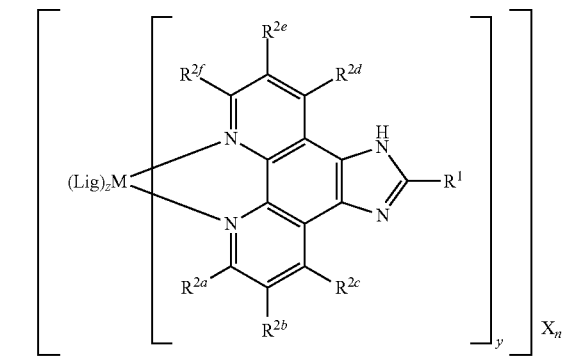

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

y=1, 2, or 3;

z=0, 1, or 2;

Lig at each occurrence is independently selected from the group consisting of

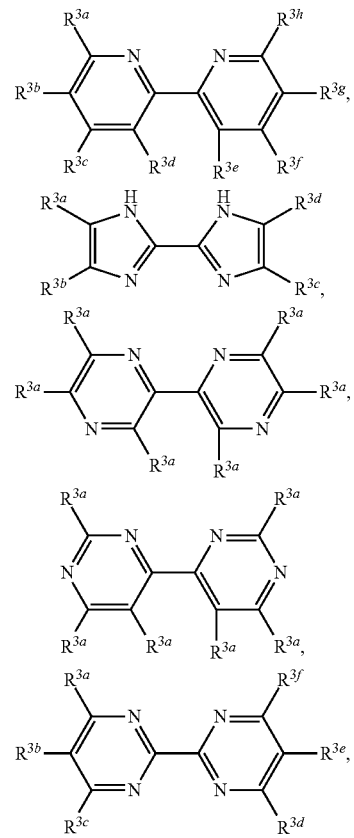

-continued
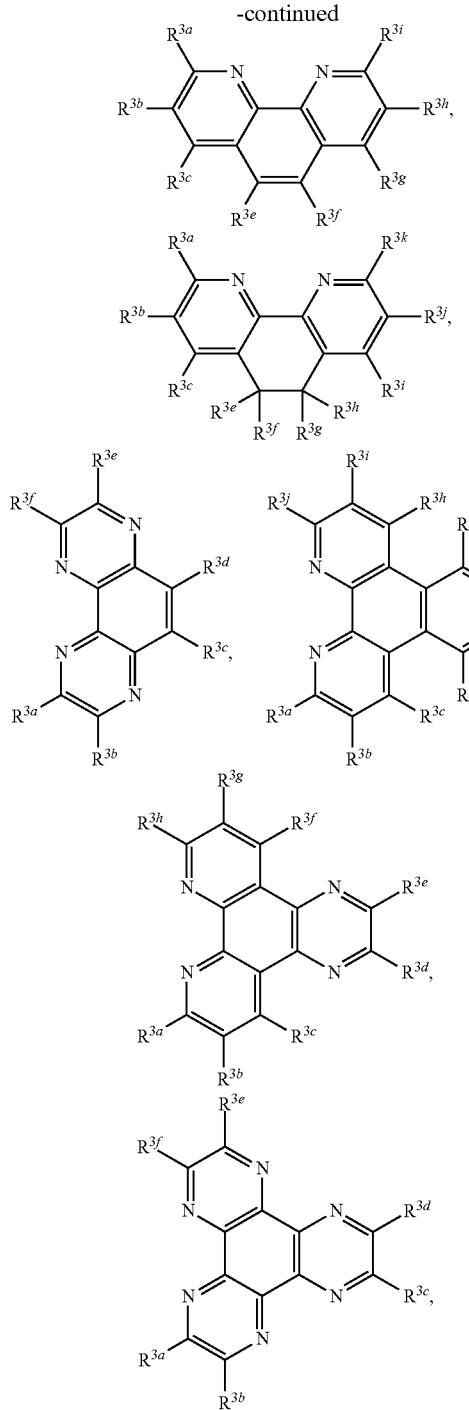
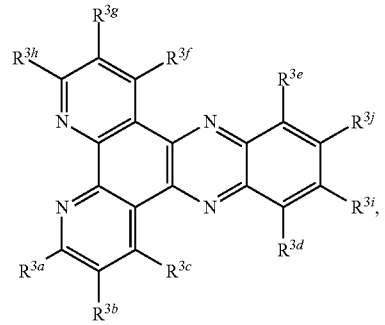
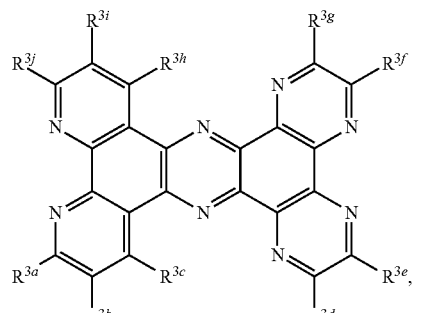
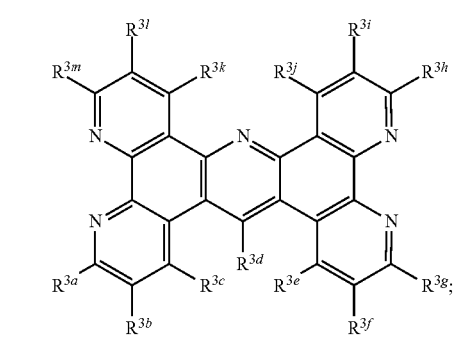
R¹ is selected from the group consisting of
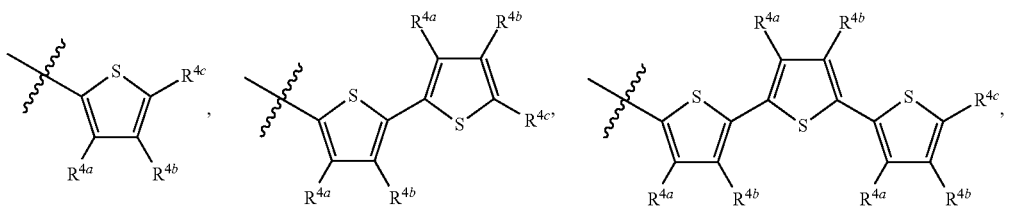

-continued

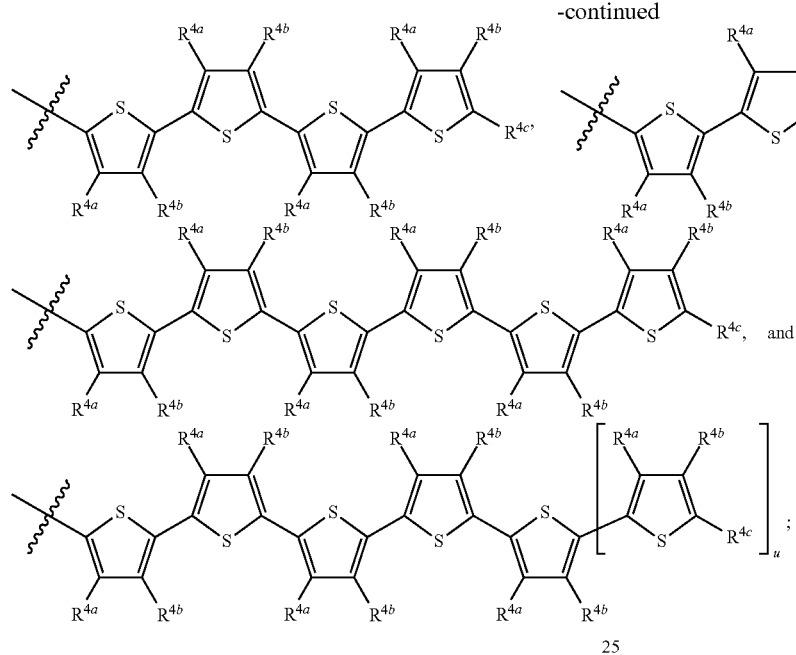
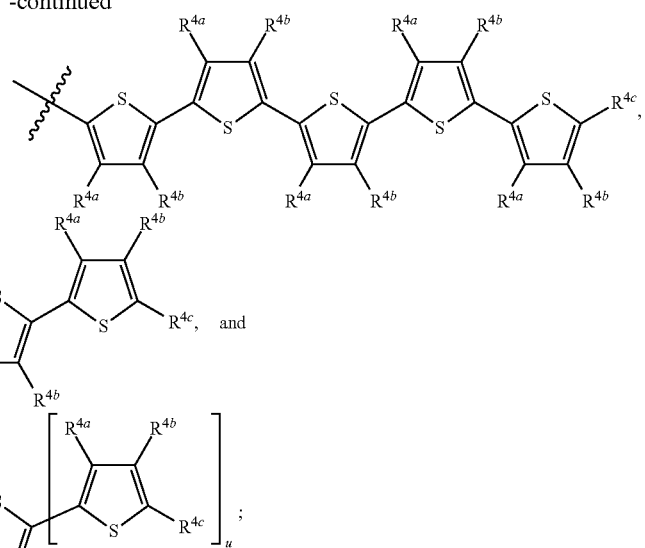

u is an integer;

$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted halo alkyl, C1-6 optionally substituted alkoxy, and $CO_2R^8$;

$R^{4a}$ and $R^{4b}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted halo alkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl;

$R^8$ at each occurrence is independently selected from the group consisting of hydrogen and optionally substituted alkyl;

Compounds having the following structures are excluded from certain embodiments of the compounds of formula (I):

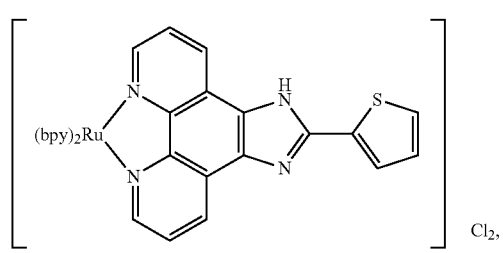

1a

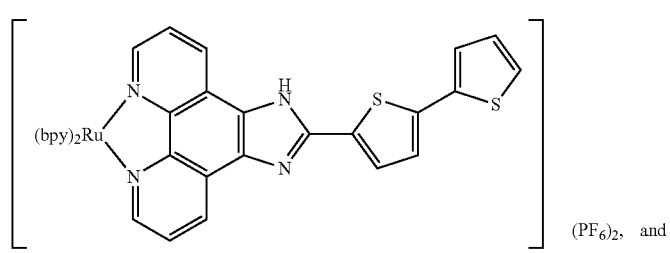

10a

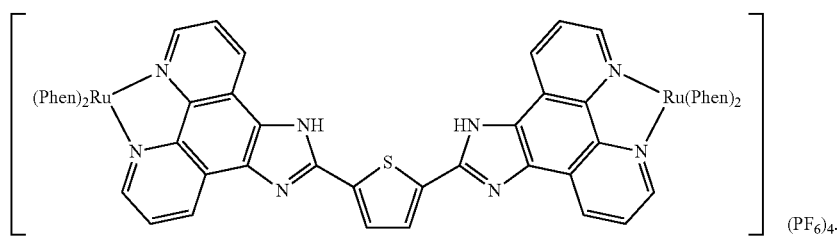

The compounds of the present invention include compounds having formula (II),

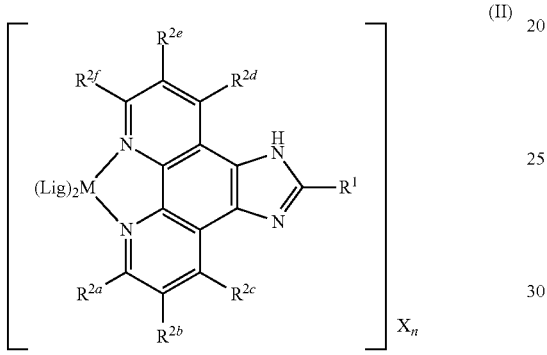

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, or 3;

Lig at each occurrence is independently selected from the group consisting of

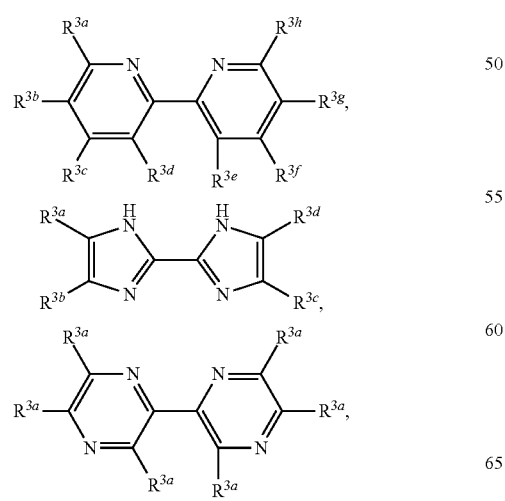

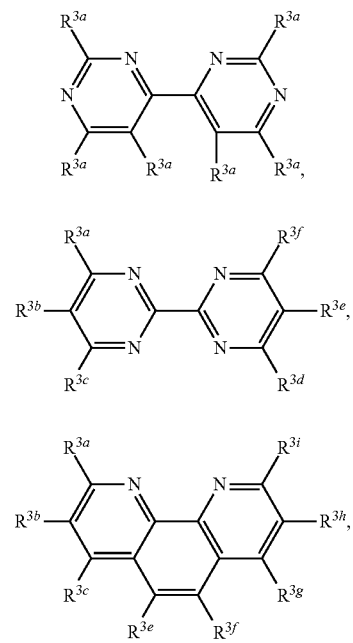

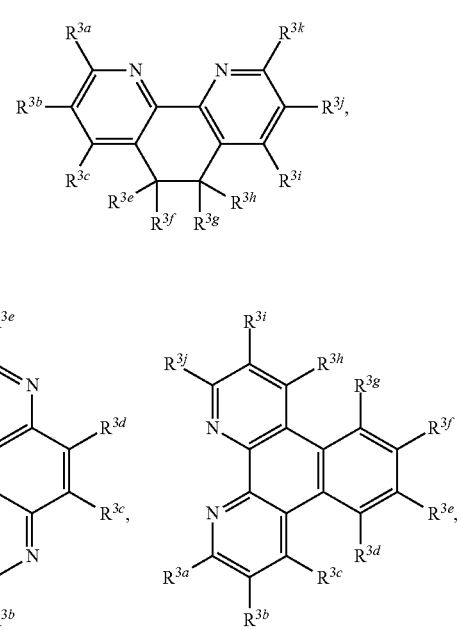

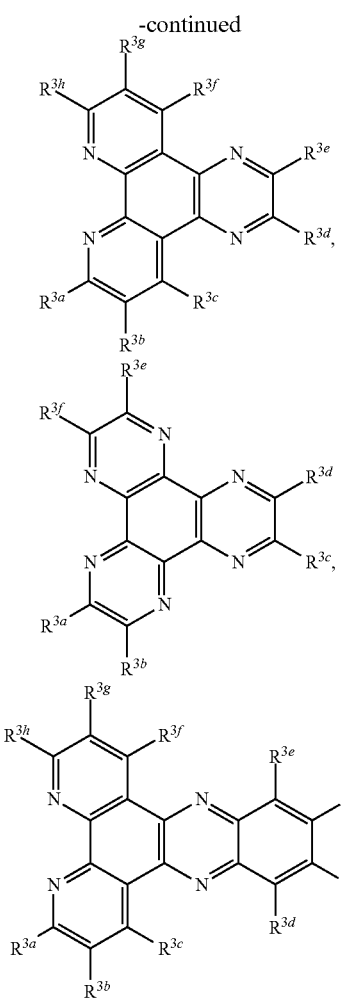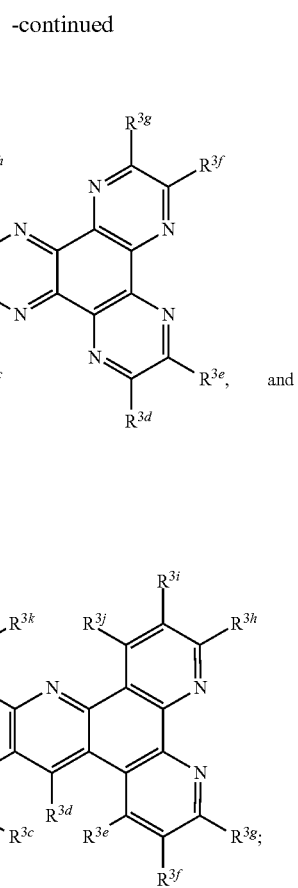
$R^1$ is selected from the group consisting of
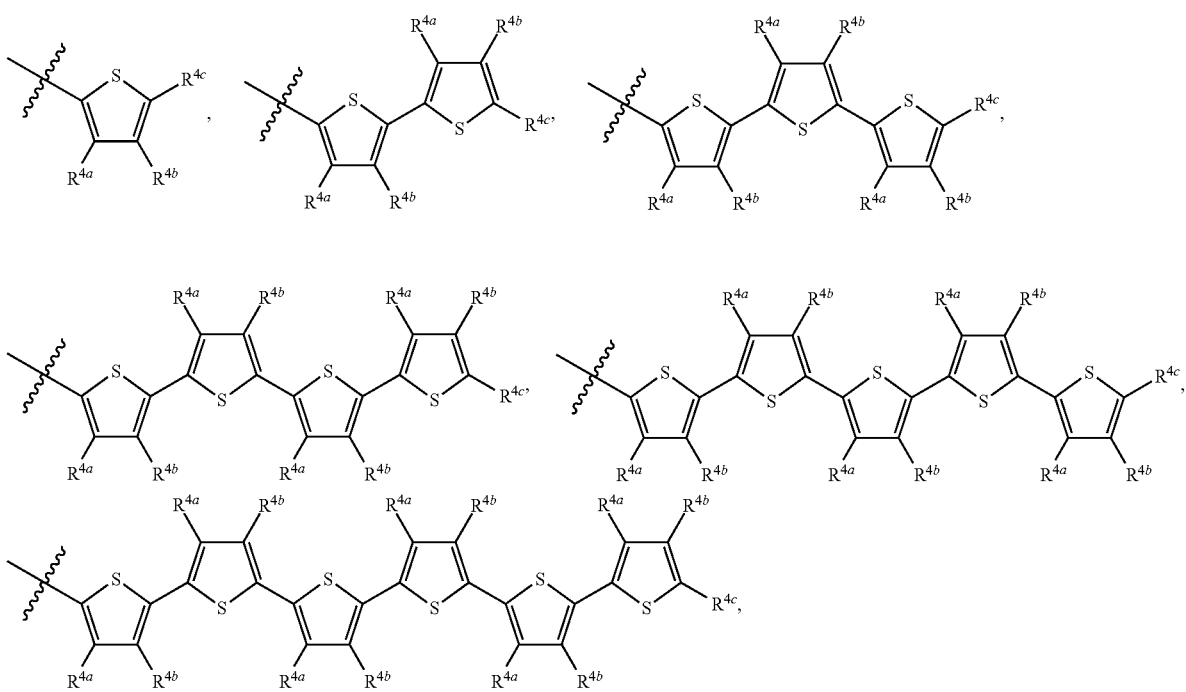

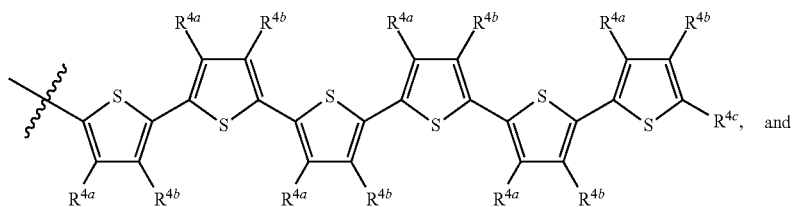

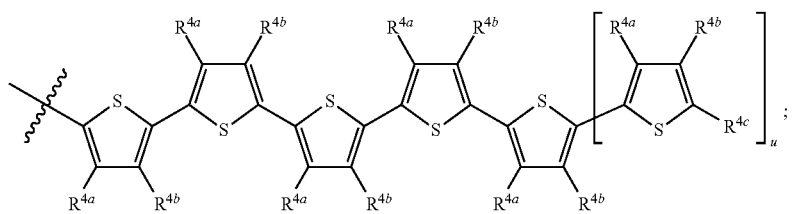

u is an integer;

$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3g}$, $R^{3h}$, $R^{3i}$, $R^{3j}$, $R^{3k}$, $R^{3l}$ and $R^{3m}$ at each occurrence are each independently selected from the group consisting of hydrogen, C1-6 optionally substituted alkyl, C1-6 optionally substituted branched alkyl, C1-6 optionally substituted halo alkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted halo alkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl;

$R^8$ at each occurrence is independently selected from the group consisting of hydrogen and optionally substituted alkyl;

Compounds having the following structures are excluded from certain embodiments of the compounds of formula (II):

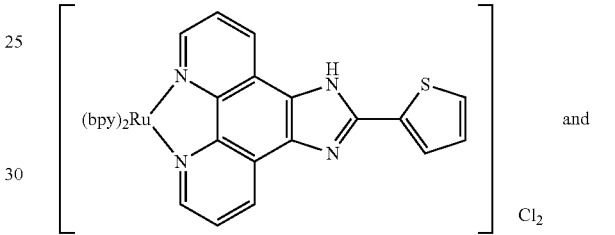

1a and

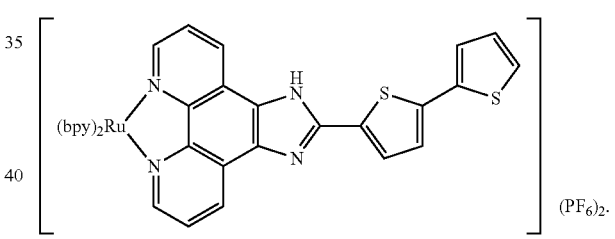

10a

The compounds of the present invention includes compounds having formula (III):

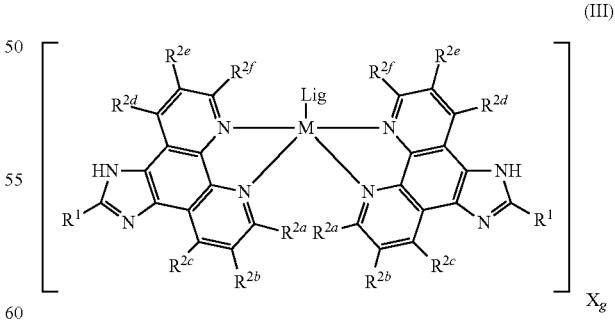

(III)

including hydrates, solvates, pharmaceutically acceptable salts, prodrugs and complexes thereof wherein M, Lig, X and the R groups are as defined above, and g is 0, 1, 2, 3, 4, or 5.

The compounds of the present invention includes compounds having formula (IV):

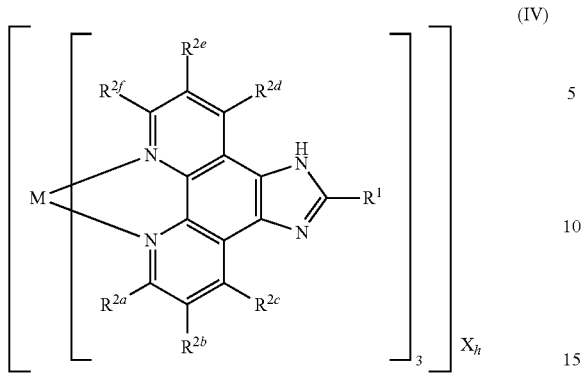

including hydrates, solvates, pharmaceutically acceptable salts, prodrugs and complexes thereof wherein M, X and the R groups are as defined above, and h is 0, 1, 2, 3, 4, or 5.

The present invention is also directed toward novel compounds of formula (V):

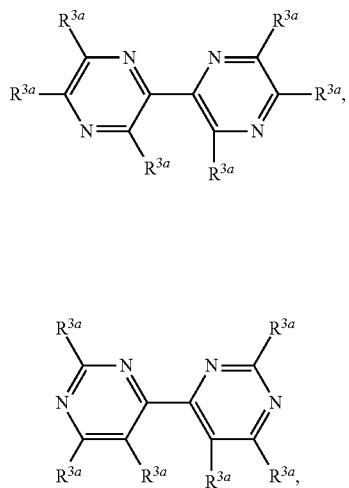

including hydrates, solvates, pharmaceutically acceptable salts, prodrugs and complexes thereof, wherein:

Lig at each occurrence is independently selected from the group consisting of

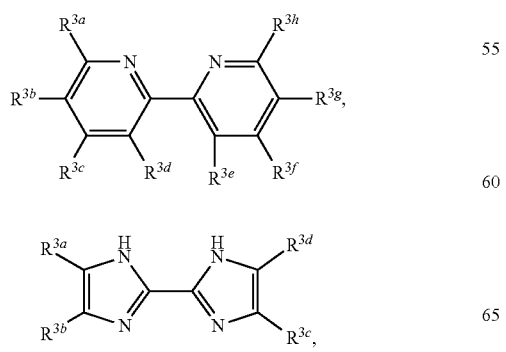

-continued

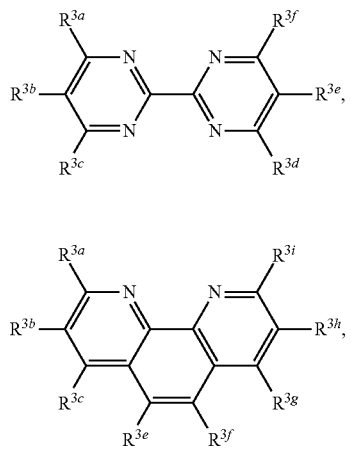

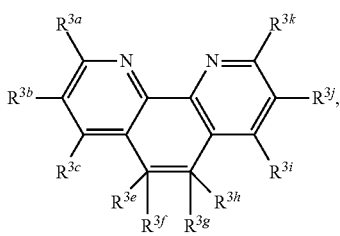

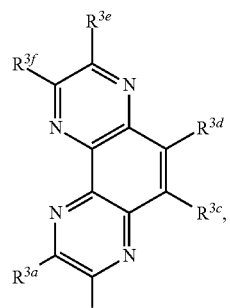

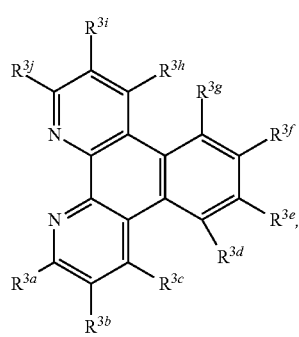

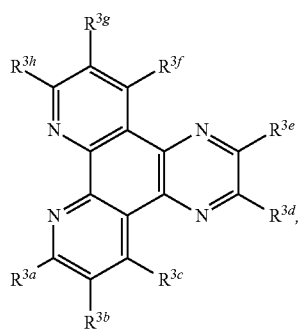

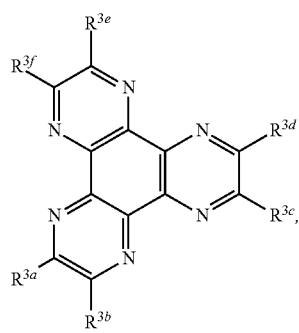

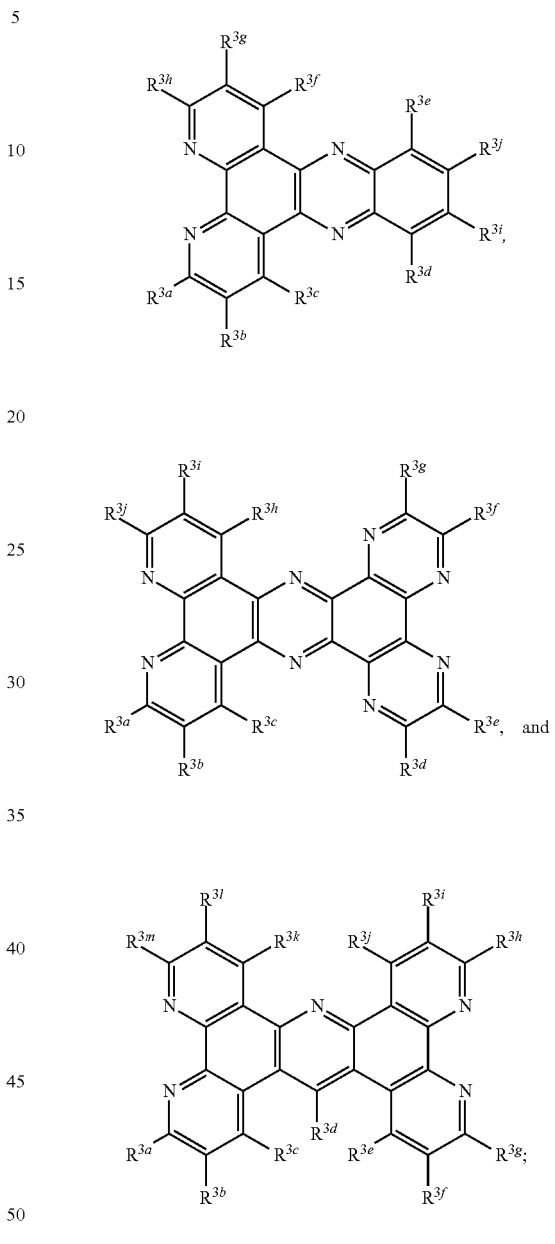

M at each occurrence is independently selected from the group consisting of manganese, molybdenum, rhenium, iron, ruthenium, osmium, cobalt, rhodium, iridium, nickel, platinum, and copper;

X and the R groups are as defined above;

t is an integer, and is preferably 1, 2, 3, 4, 5 or 6;

q=0, 1, 2, 3, 4 or 5;

The compound having the following structure is excluded from certain embodiments of the compounds of formula (V):

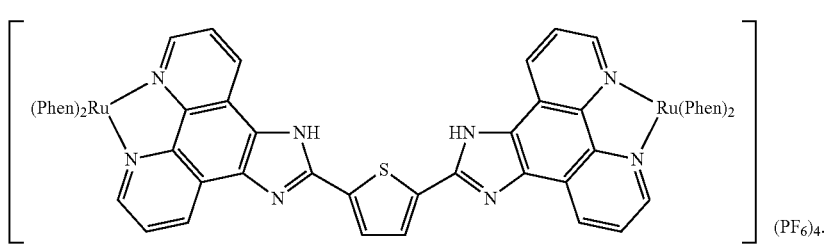

The present invention is also directed toward novel methods of use of compounds of the structures

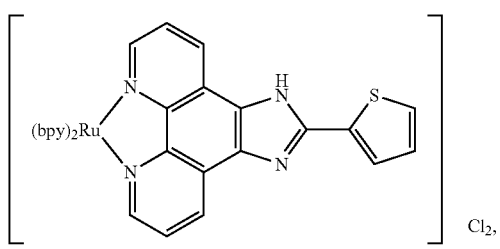

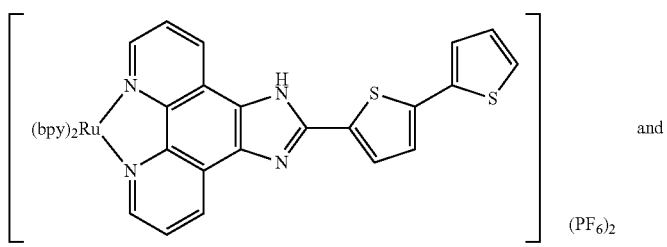

and

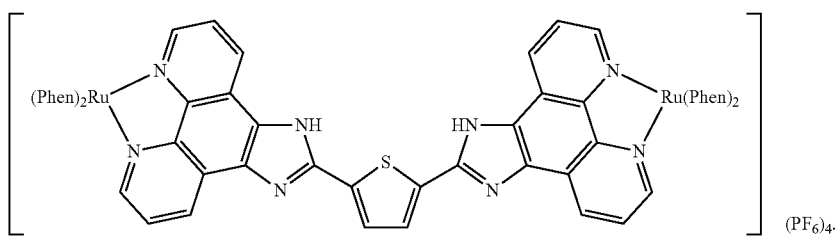

The present invention further relates to compositions comprising an effective amount of one or more compounds according to the present invention and an excipient.

The present invention also relates to a method of using the photodynamic compounds of the invention as a DNA binding agent.

The present invention also relates to a method of using the photodynamic compounds according to the present invention and an excipient as a DNA binding agent.

The present invention also relates to a method of using the photodynamic compounds of the invention as a DNA photocleavage agent.

The present invention also relates to a method of using the photodynamic compounds according to the present invention and an excipient as a DNA photocleavage agent.

The present invention also relates to a method of using the photodynamic compounds of the invention as a DNA condensation agent.

The present invention also relates to a method of using the photodynamic compounds according to the present invention and an excipient as DNA condensation agent.

The present invention also relates to a method of using the photodynamic compounds of the invention as an agent that produces the DNA light-switch effect.

The present invention also relates to a method of using the photodynamic compounds according to the present invention and an excipient as an agent that produces the DNA light-switch effect.

The present invention also relates to a method of using the photodynamic compounds of the invention as a photosensitizer with 100% efficiency for singlet oxygen production.

The present invention also relates to a method of using the photodynamic compounds according to the present invention and an excipient as a photosensitizer with 100% efficiency for singlet oxygen production.

The present invention also relates to a method of using the photodynamic compounds of the invention as a photosensitizer that can function in both Type I and Type II photoprocesses.

The present invention also relates to a method of using the photodynamic compounds according to the present invention and an excipient as a photosensitizer that can function in both Type I and Type II photoprocesses.

The present invention also relates to a method of using the photodynamic compounds of the invention to destroy cells, including hyperproliferating cells.

The present invention also related to a method of using the photodynamic compounds of the invention to destroy cells, including hyperproliferating cells, using light as an activator.

The present invention also relates to a method of using the photodynamic compounds according to the present invention and an excipient to destroy cells, including hyperproliferating cells.

The present invention also relates to a method of using the photodynamic compounds of the invention to induce apoptosis in cells, including hyperproliferating cells.

The present invention also relates to a method of using the photodynamic compounds according to the present invention and an excipient to induce apoptosis in cells, including hyperproliferating cells.

The present invention also relates to a method of using the photodynamic compounds of the invention to impart DNA crosslinking in cells, including hyperproliferating cells.

The present invention also relates to a method of using the photodynamic compounds according to the present invention and an excipient to impart DNA crosslinking in cells, including hyperproliferating cells.

The present invention also relates to a method for treating or preventing diseases that involve hyperproliferating cells etiology, including, for example, cancer, said method comprising administering to a subject an effective amount of a compound or composition according to the present invention.

The present invention yet further relates to a method for treating or preventing diseases that hyperproliferating cells etiology, including, for example, cancer, wherein said method comprises administering to a subject a composition comprising an effective amount of one or more compounds according to the present invention and an excipient.

The present invention also relates to a method for treating or preventing diseases that involve hyperproliferating cells in their etiology, including, for example, cancer, said method comprising administering to a subject an effective amount of a compound or composition according to the present invention and an intracellular reducing agent such as glutathione.

The present invention also relates to a method for treating or preventing diseases that involve hyperproliferating cells in their etiology, including, for example, cancer, said method comprising administering to a subject an effective amount of a compound or composition according to the present invention and an excipient and an intracellular reducing agent such as glutathione.

The present invention also relates to a method for treating or preventing diseases that involve hyperproliferating cells in their etiology, including, for example, cancer, said method comprising administering to a subject an effective amount of a compound or composition according to the present invention and an intracellular oxidizing agent such as oxygen.

The present invention also relates to a method for treating or preventing diseases that involve hyperproliferating cells in their etiology, including, for example, cancer, said method comprising administering to a subject an effective amount of a compound or composition according to the present invention and an excipient and an intracellular oxidizing agent such as oxygen.

The present invention also relates to a method of using the photodynamic compounds of the invention as an anti-pathogen medicinal agent and disinfectant, e.g., to kill microbes in normoxic and hypoxic environments.

The present invention also relates to a method of using the photodynamic compounds of the invention as an in vivo diagnostic agent via intracellular luminescence.

The present invention further relates to a method of preparing the photodynamic compounds of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

BRIEF DESCRIPTION OF SEVERAL VIEWS OF THE DRAWINGS

The patent or application file contains at least one drawing executed in color. Copies of this patent or patent application publication with color drawing(s) will be provided by the Office upon request and payment of the necessary fee.

The invention will be described in conjunction with the following drawings in which like reference numerals designate like elements and wherein:

FIG. 8: DNA light-switch effect produced by PDCs: (a) 1a, (b) 10a, and 14a.

1a (100 μM), 5 min. dark (c) 1a (100 μM), 40 hr. dark, and (d) 1a (100 μM), 40 hr. post-irradiation. EL images were collected using a TRITC filter cube ($\lambda_{ex}$=540 nm, $\lambda_{em}$=605 nm) with no staining. Luminescence observed is from 1a.

Figure 10:
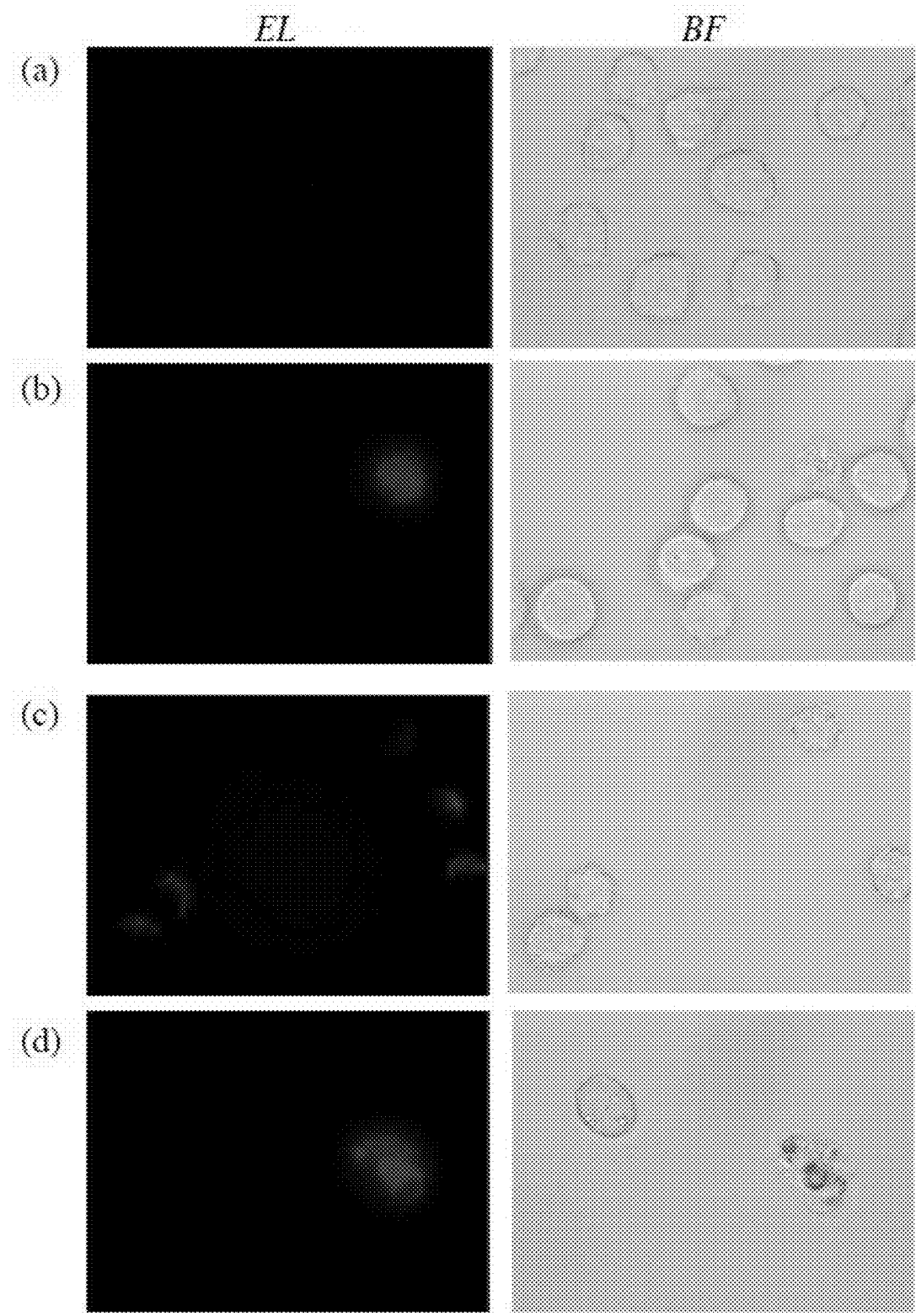

FIG. 10: Epi-luminescence (EL) and bright field (BF) images of PDC-treated HL-60 cells: (a) untreated control, (b) 10a (100 μM), 5 min. dark (c) 10a (100 μM), 40 hr. dark, and (d) 10a (100 μM), 40 hr. post-irradiation. EL images were collected using a TRITC filter cube ($\lambda_{ex}$=540 nm, $\lambda_{em}$=605 nm) with no staining. Luminescence observed is from 10a.

Figure 11:
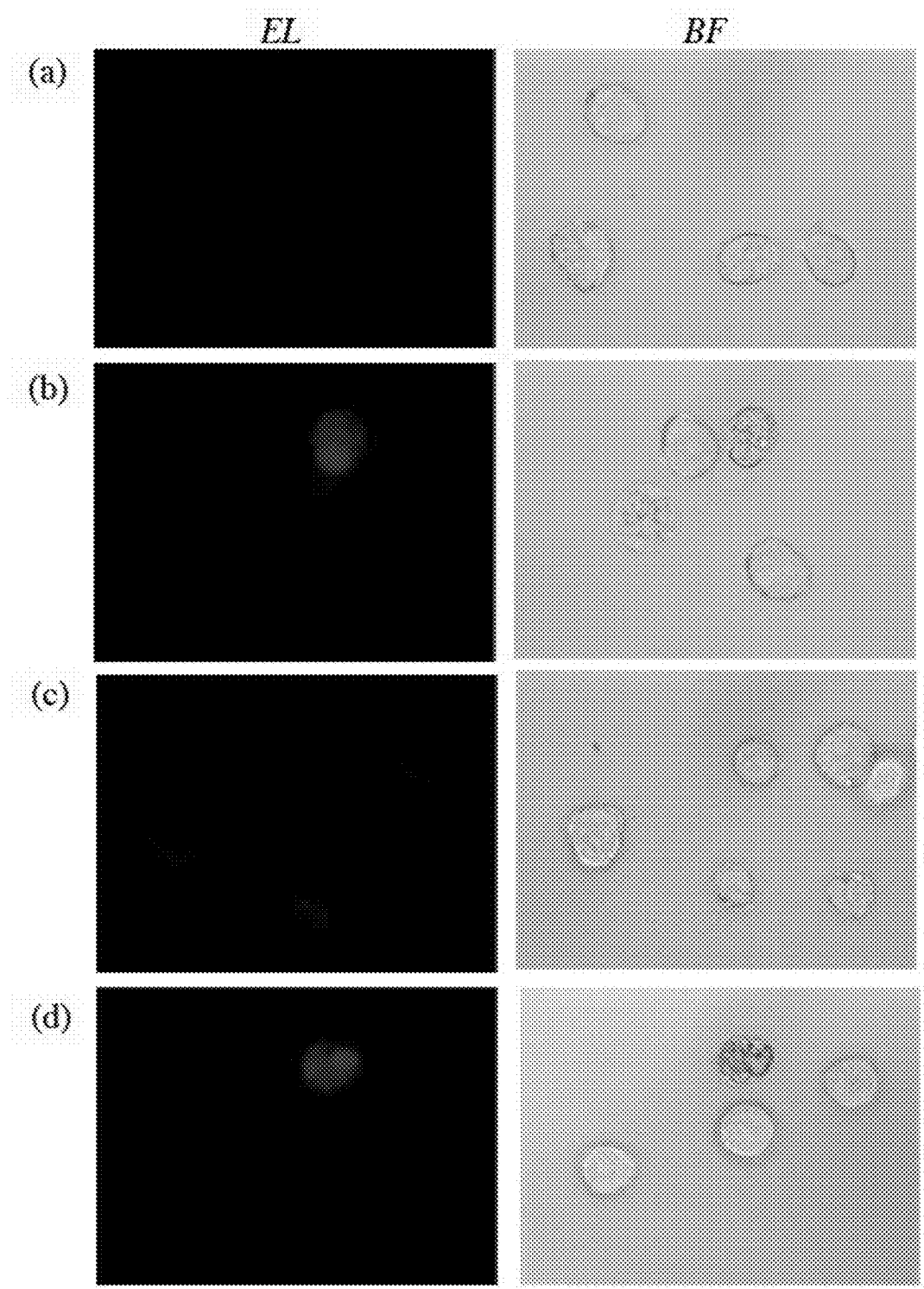

FIG. 11: Epi-luminescence (EL) and bright field (BF) images of PDC-treated HL-60 cells: (a) untreated control, (b) 10b (100 μM), 5 min. dark (c) 10b (100 μM), 40 hr. dark, and (d) 10b (100 μM), 40 hr. post-irradiation. EL images were collected using a TRITC filter cube ($\lambda_{ex}$=540 nm, $\lambda_{em}$=605 nm) with no staining. Luminescence observed is from 10b.

Figure 12:
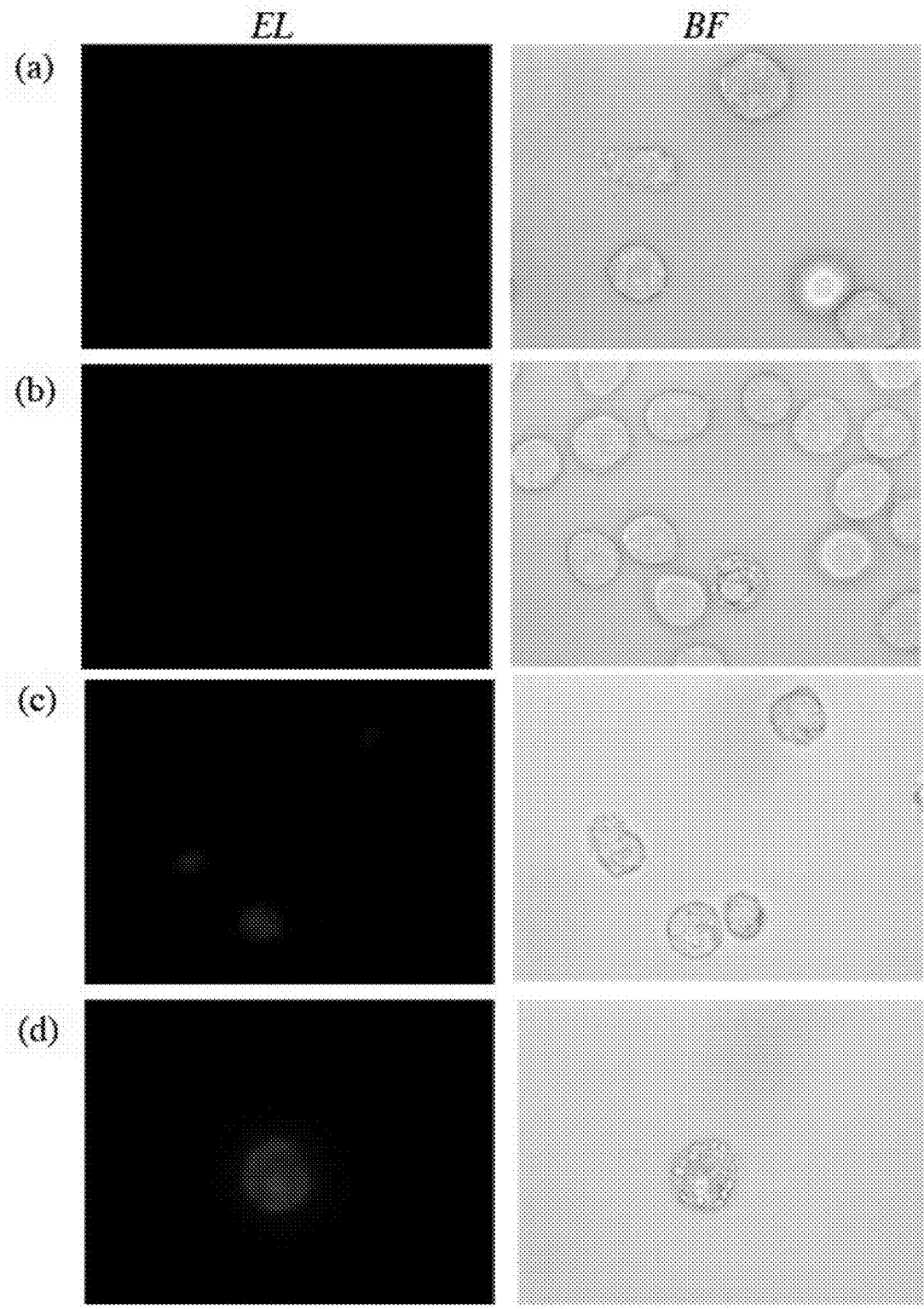

FIG. 12: Epi-luminescence (EL) and bright field (BF) images of PDC-treated HL-60 cells: (a) untreated control, (b) 14a (100 μM), 5 min. dark (c) 14a (100 μM), 40 hr. dark, and (d) 14a (100 μM), 40 hr. post-irradiation. EL images were collected using a TRITC filter cube ($\lambda_{ex}$=540 nm, $\lambda_{em}$=605 nm) with no staining. Luminescence observed is from 14a.

Figure 13:
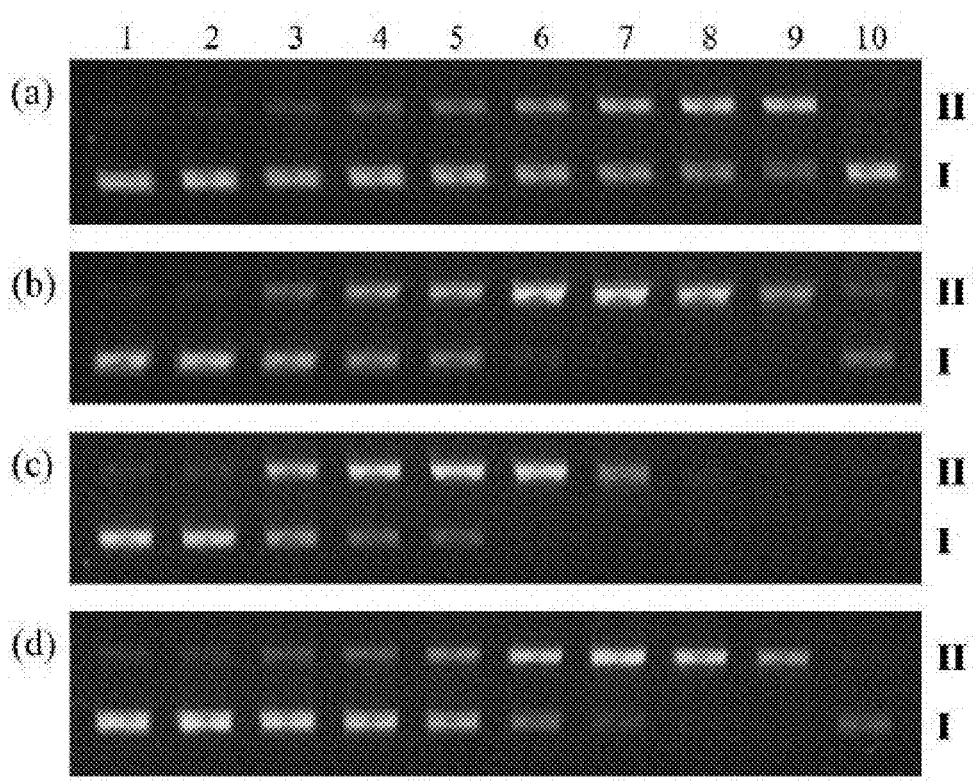

FIG. 13: Gel electrophoretic analysis (1% agarose gel containing 0.75 μg mL$^{-1}$ ethidium bromide, 1×TAE, 8 V cm$^{-1}$, 30 min.) of DNA photocleavage by PDCs of the disclosure in air-saturated solution with 420-nm irradiation: (a) 1a, (b) 10a, (b) 10b, and (d) 14a. Lanes 1, 2 and 10 are control lanes, and lanes 3-9 are reaction lanes: lane 1, 0 μM (−hv); lane 2, 0 μM; lane 3, 0.5 μM; lane 4, 0.75 μM; lane 5, 1.0 μM; lane 6, 2.5 μM; lane 7, 5.0 μM; lane 8, 7.5 μM; lane 9, 10 μM; lane 10, 10 μM (−hv).

Figure 14:
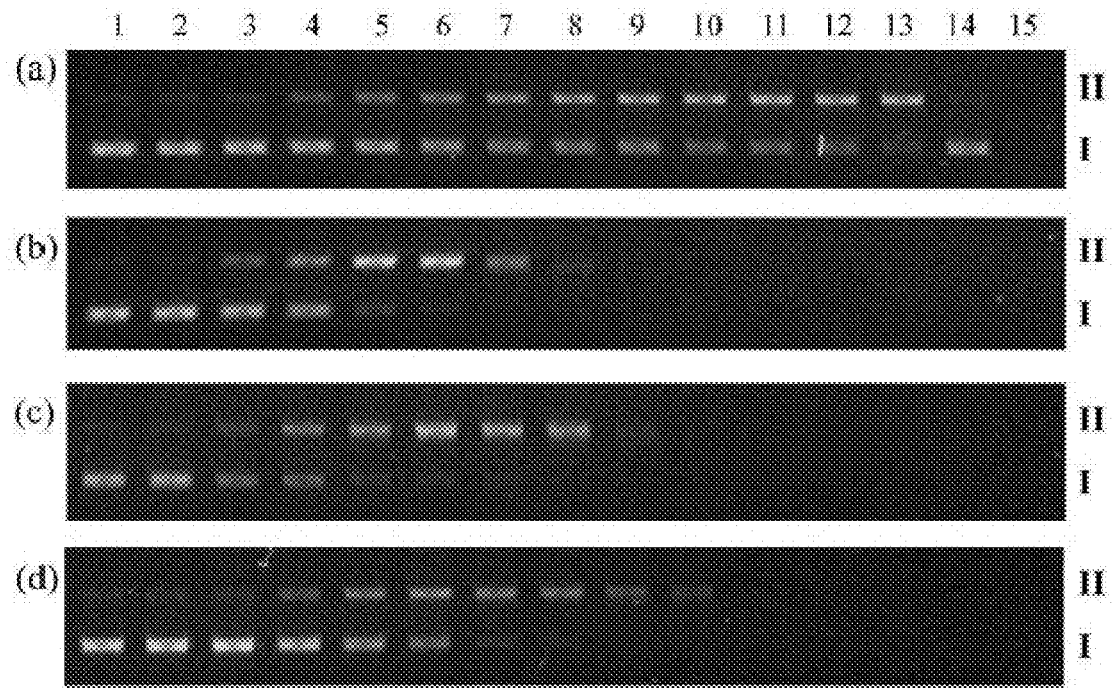

FIG. 14: Gel electrophoretic analysis (1% agarose gel containing 0.75 μg mL-1 ethidium bromide, 1×TAE, 8 V cm-1, 30 min.) of DNA photocleavage by PDCs in air-saturated solution with visible irradiation: (a) 1a, (b) 10a, (b) 10b, and (d) 14a. Lanes 1, 2, 14 and 15 are control lanes, and lanes 2-13 are reaction lanes: lane 1, 0 μM (−hv); lane 2, 0 μM; lane 3, 0.75 μM; lane 4, 1.5 μM; lane 5, 3 μM; lane 6, 5 μM; lane 7, 8 μM; lane 8, 10 μM; lane 9, 12 μM; lane 10, 16 μM; lane 11, 18 μM; lane 12, 20 μM; lane 13, 25 μM; lane 14, 25 μM (−hv); lane 15, 25 μM (−pUC19).

Figure 15:
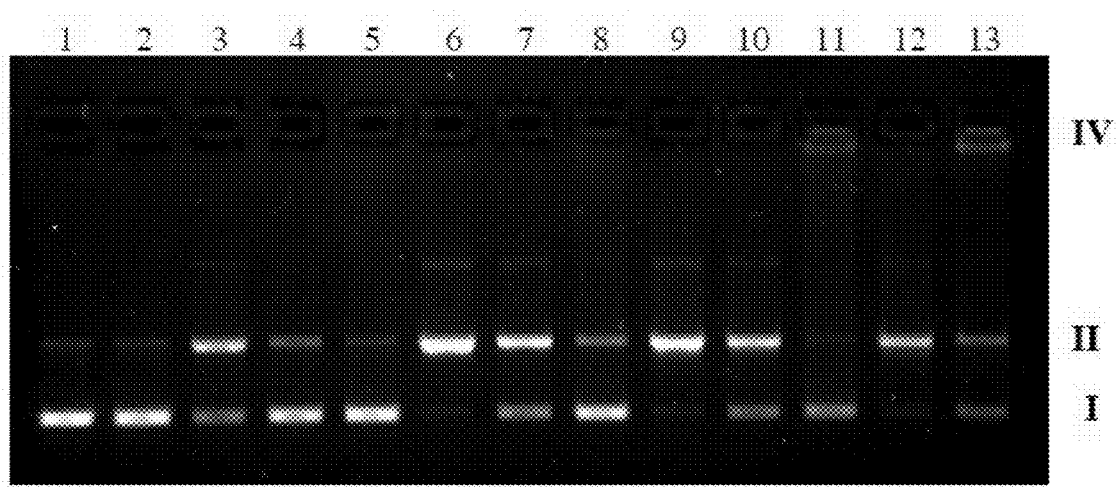

FIG. 15: Gel electrophoretic analysis (1% agarose gel pre-cast with 0.75 μg mL$^{-1}$ ethidium bromide, 1×TAE, 8 V cm$^{-1}$, 30 min.) of PDC-mediated pUC19 photocleavage in air-saturated and deoxygenated solution: 420-nm irradiation of pUC19 (20 μM NP in 10 mM Tris·100 mM NaCl, pH 7.4) for 1 hr. Lanes 1 (−PDC, −hv), 2 (300 μM [Ru(bpy)$_3$]$_{2+}$, −hv), 5 (2 μM 10a, −hv), 8 (4 μM 10b, −hv), and 11 (8 μM 14a, −hv) are dark controls. Lanes 3 (300 μM [Ru(bpy)$_3$]$_{2+}$, +hv), 6 (2 μM 10a, +hv), 9 (4 μM 10b, +hv), and 12 (8 μM 14a, +hv) are samples that were irradiated in air; lanes 4, 7, 10, and 13 are the corresponding samples irradiated in argon.

Figure 16:
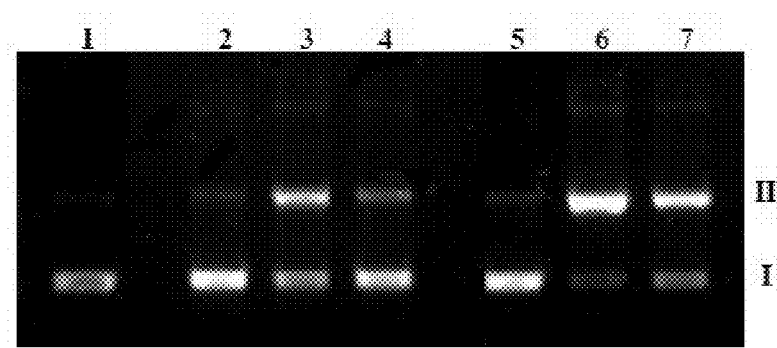

FIG. 16: Gel electrophoretic analysis (1% agarose gel pre-cast with 0.75 μg mL$^{-1}$ ethidium bromide, 1×TAE, 8 V cm$^{-1}$, 30 min.) of PDC-mediated pUC19 photocleavage in air-saturated and deoxygenated solution: visible irradiation of pUC19 (20 μM NP in 10 mM Tris·100 mM NaCl, pH 7.4) for 1 hr. with cool white fluorescent tubes, 21 W/m$^2$. Lanes 1 (−PDC, −hv), 2 (500 μM [Ru(bpy)$_3$]$^{2+}$, −hv), and 5 (2 μM 10a, −hv) are controls. Lanes 3 (500 μM [Ru(bpy)$_3$]$^{2+}$, +hv) and 6 (2 μM 10a, +hv) contain samples that were irradiated in air; lanes 4 and 7 are the corresponding samples irradiated in argon.

Figure 17:
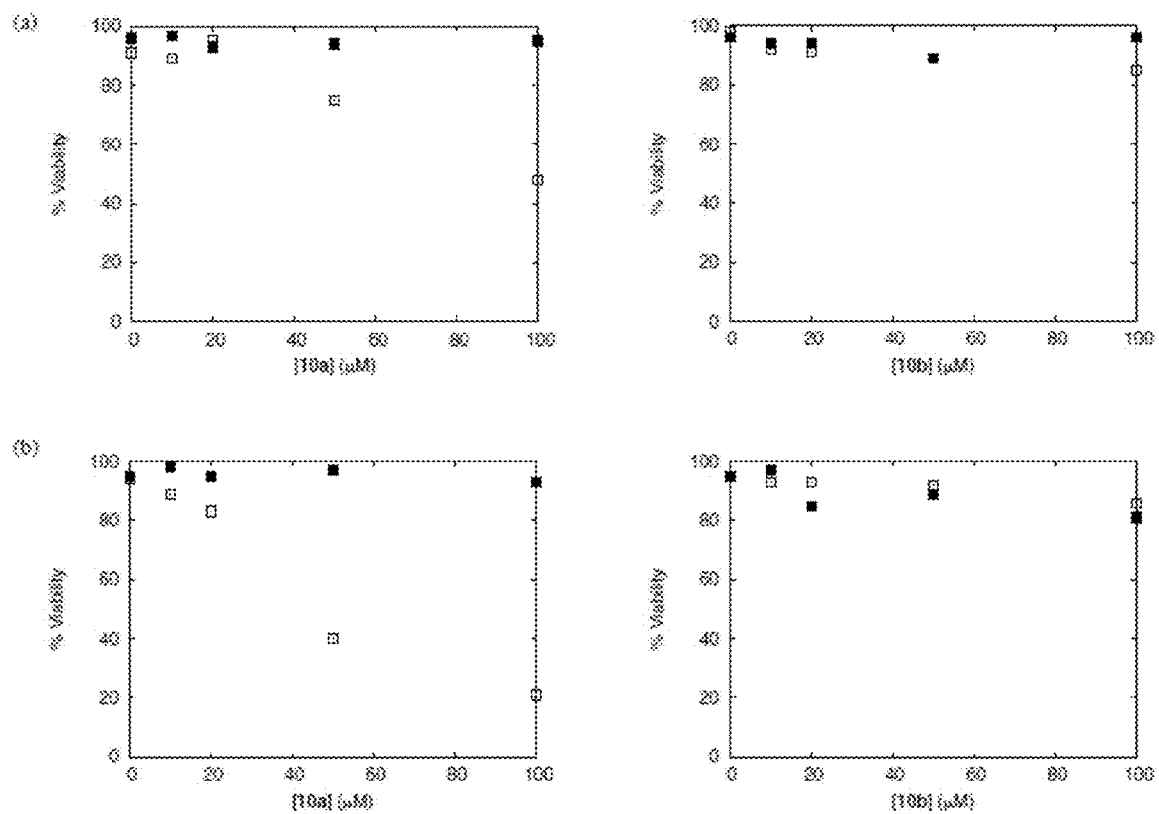

FIG. 17: Cytotoxicity (■) and photocytotoxicity (□) of HL-60 cells (4 hr. pre-incubation, 15 min. vis irradiation, 4 J/cm$^2$) with increasing concentrations of 10a and 10b observed by viability staining with Trypan Blue. (a) 18 hr. and (b) 40 hr. At 100 μM [PDC], the photodynamic action for 10a is 47% at 18 hr. and 72% at 40 hr while for 10b it is 11% at 18 hr. and 0% (actually 5% increase in viability) at 40 hr. (referenced relative to 100 μM dark well).

Figure 18:
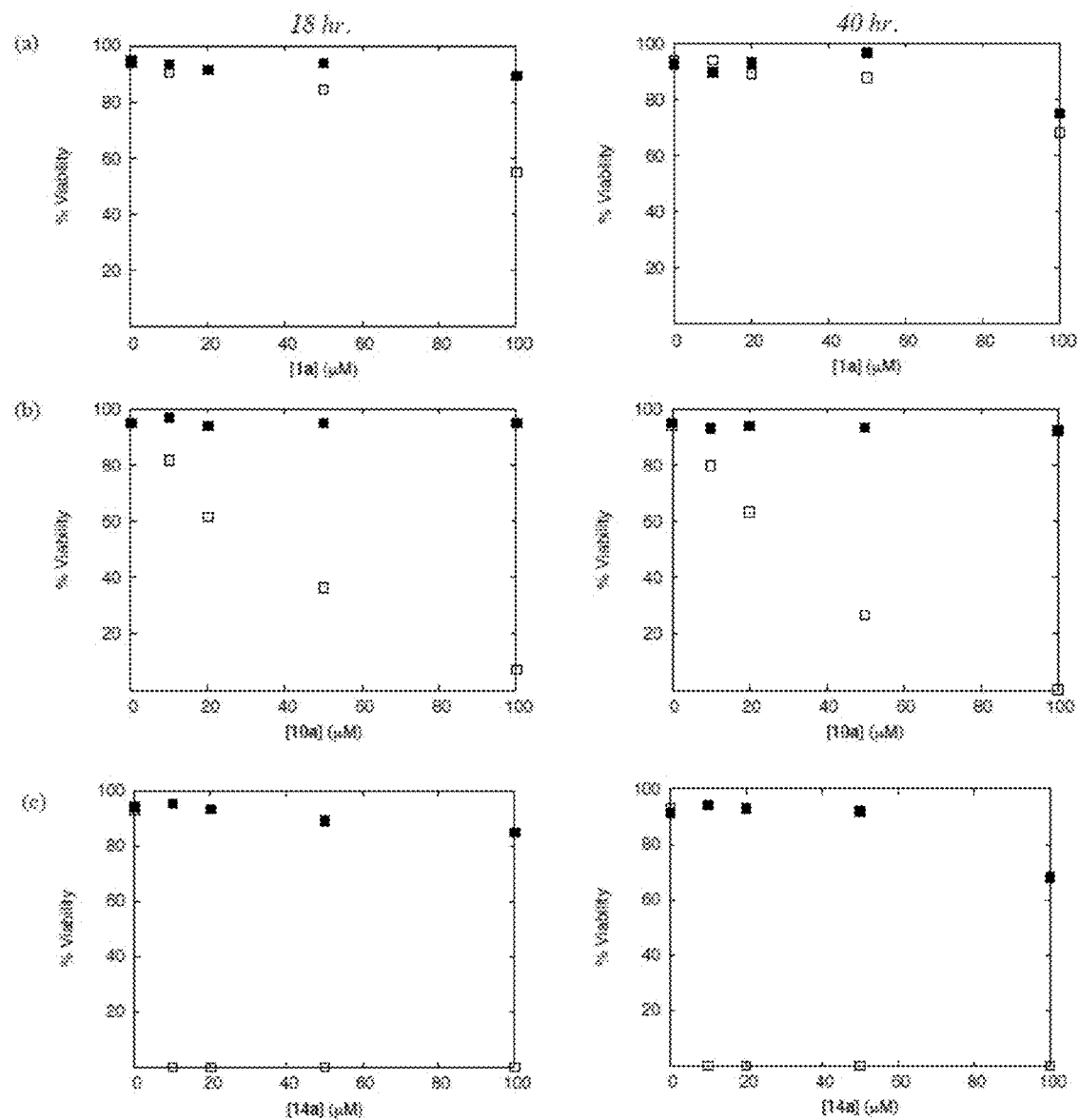

FIG. 18: Cytotoxicity (■) and photocytotoxicity (□) of HL-60 cells (4 hr. pre-incubation, 15 min. vis irradiation 4 J/cm$^2$) with increasing concentrations of (a) 1a, (b) 10a, and (c) 14a observed by viability staining with Trypan Blue.

Figure 19:
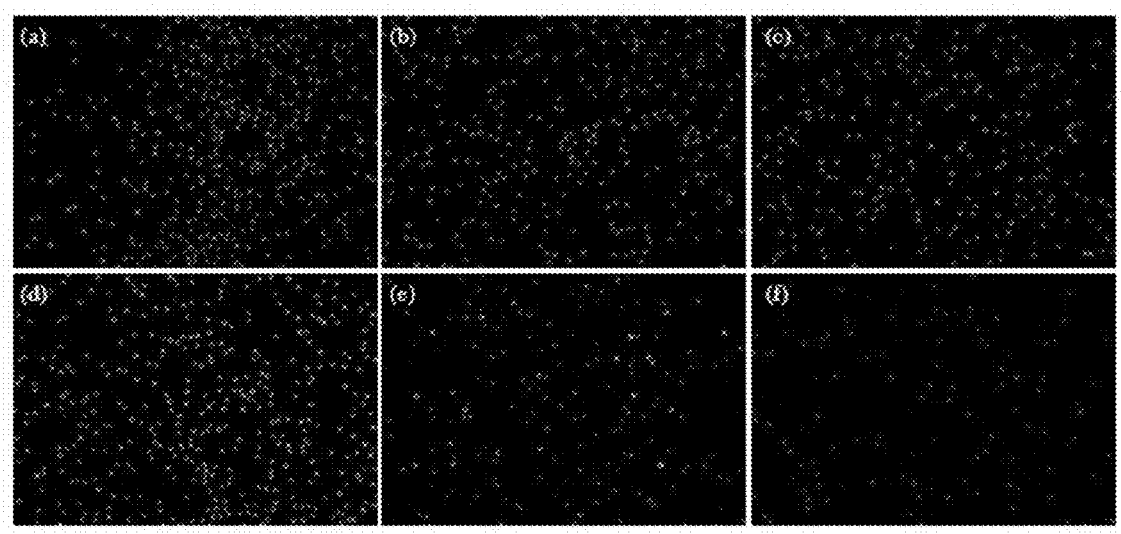

FIG. 19: Cytotoxicity and photocytotoxicity of HL-60 cells with varying concentrations of 14a observed by nuclear morphology staining with AO-EB. (a) 1 M 14a, −hv; (b) 5 μM 14a, −hv; (c) 10 μM 14a, −hv; (d) 1 μM 14a, +hv; (e) 5 μM 14a, +hv; (f) 10 μM 14a, +hv. AO (green fluorescence) stains viable cells; EB (red fluorescence) stains nonviable cells.

Figure 20:
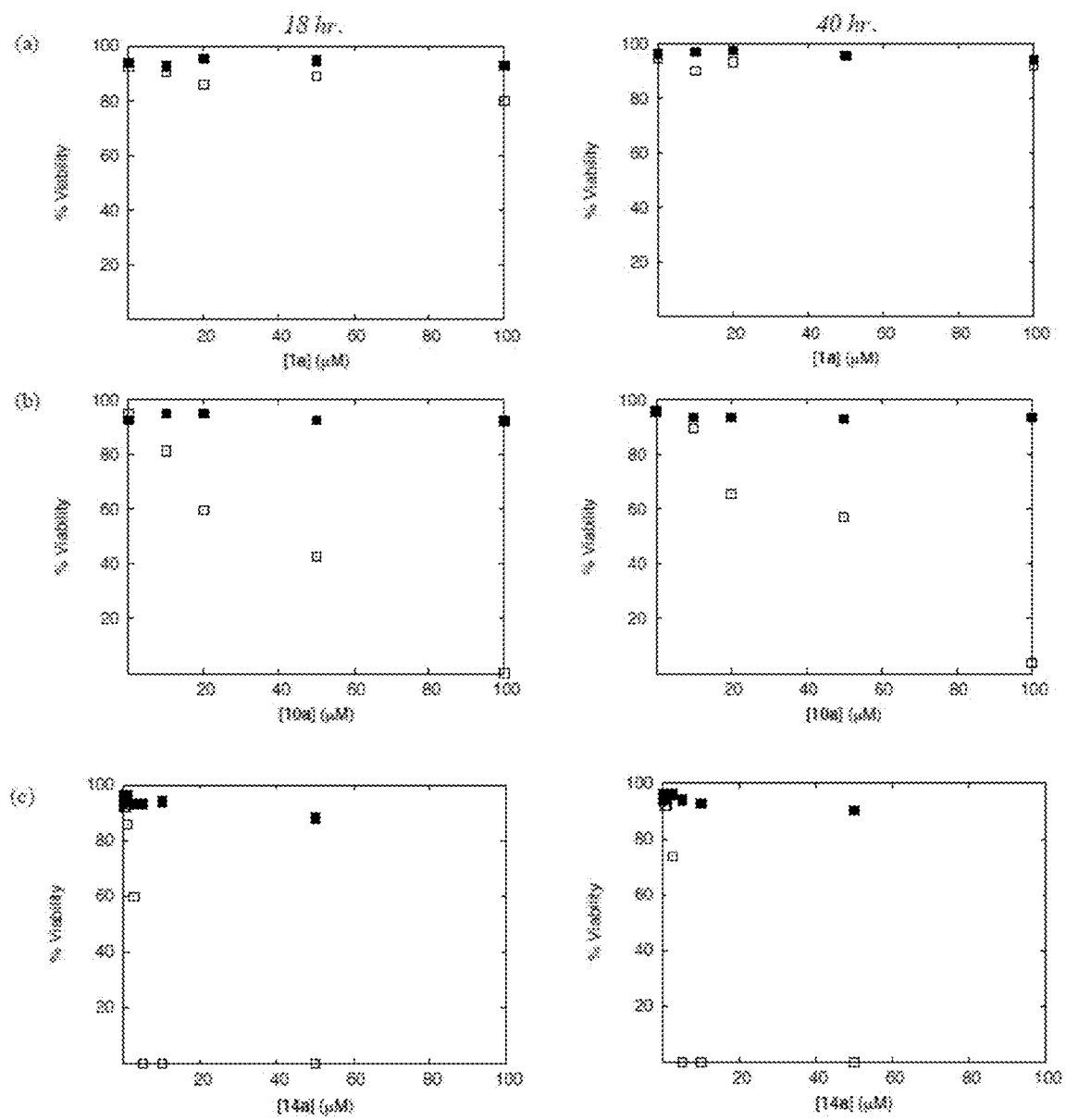

FIG. 20: Cytotoxicity (■) and photocytotoxicity (□) of HL-60 cells (4 hr. pre-incubation, 15 min. visible irradiation, 4 J/cm$^2$) with increasing concentrations of (a) 1a, (b) 10a, and (c) 14a observed by viability staining with Trypan Blue.

Figure 21:
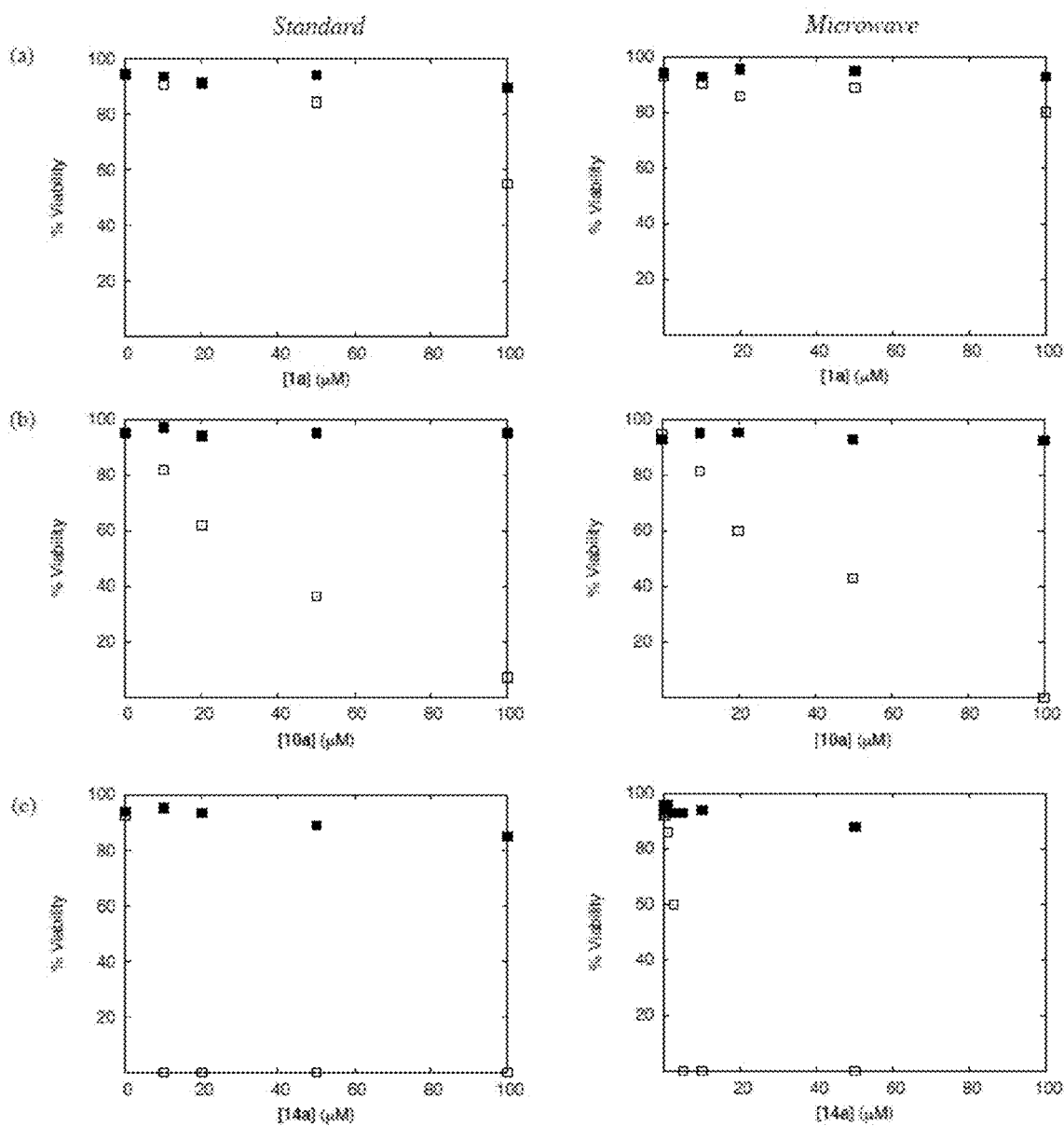

FIG. 21: Cytotoxicity (■) and photocytotoxicity (□) of PDC-treated HL-60 cells (4 hr. pre-incubation, 15 min. vis irradiation, 4 J/cm$^2$) with increasing concentrations of (a) 1a, (b) 10a, and (c) 14a observed by viability staining at 18 hr. post-irradiation with Trypan Blue.

Figure 22:
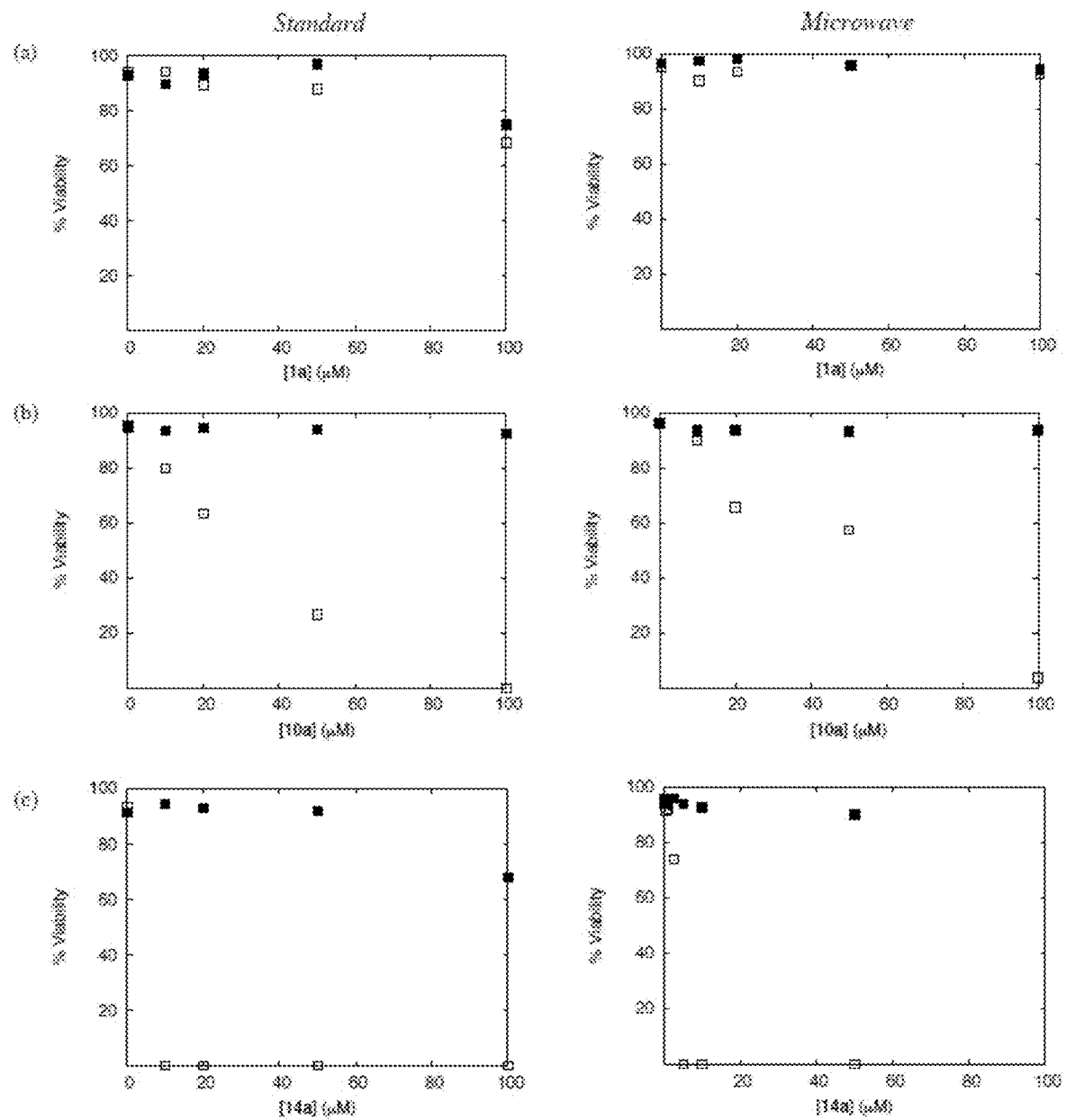

FIG. 22: Cytotoxicity (■) and photocytotoxicity (□) of PDC-treated HL-60 cells (4 hr. pre-incubation, 15 min. vis irradiation, 4 J/cm$^2$) with increasing concentrations of (a) 1a, (b) 10a, and (c) 14a observed by viability staining at 40 hr. post-irradiation with Trypan Blue.

Figure 23:
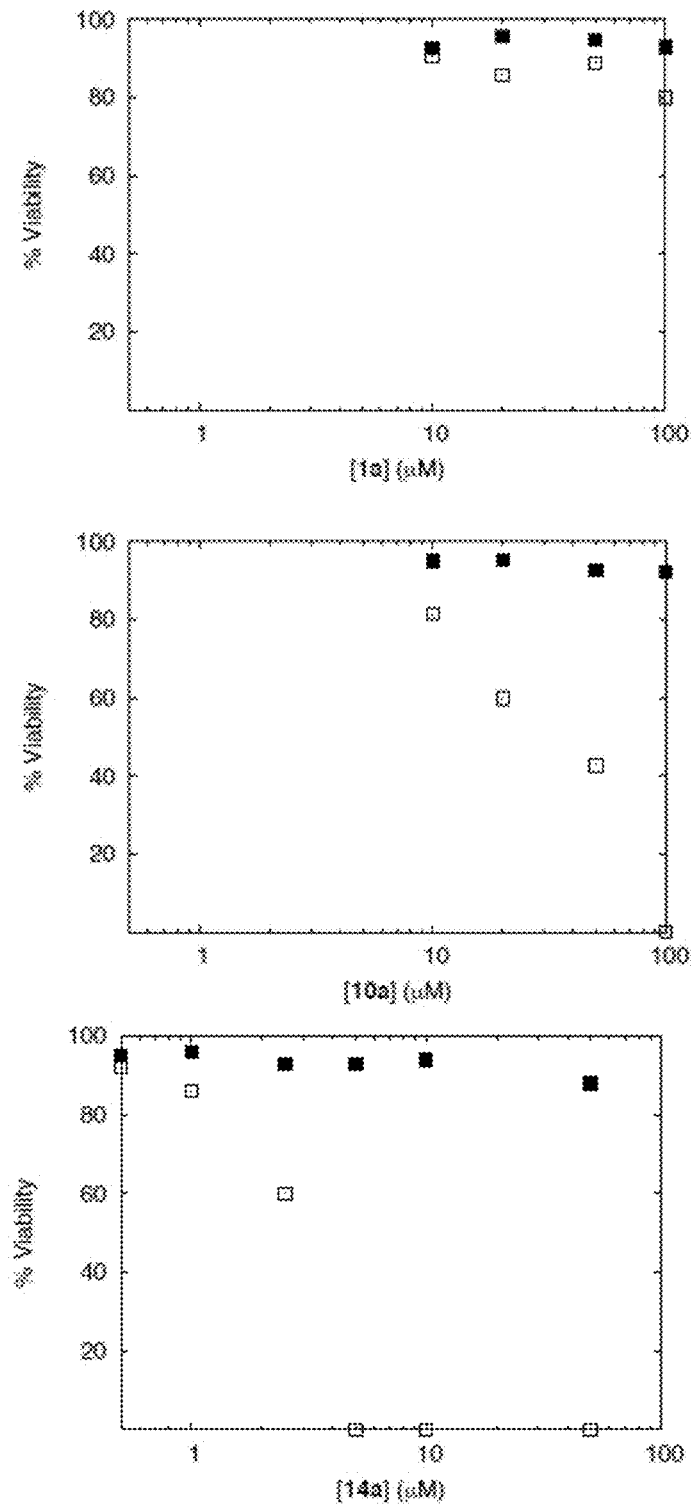

FIG. 23: Cytotoxicity (■) and photocytotoxicity (□) of PDC-treated HL-60 cells (4 hr. pre-incubation, 15 min. visible irradiation, 4 J/cm$^2$) with increasing concentrations of (a) 1a, (b) 10a, and (c) 14a observed by viability staining at 18 hr. post-irradiation with Trypan Blue. PDCs prepared by microwave synthesis.

Figure 24:
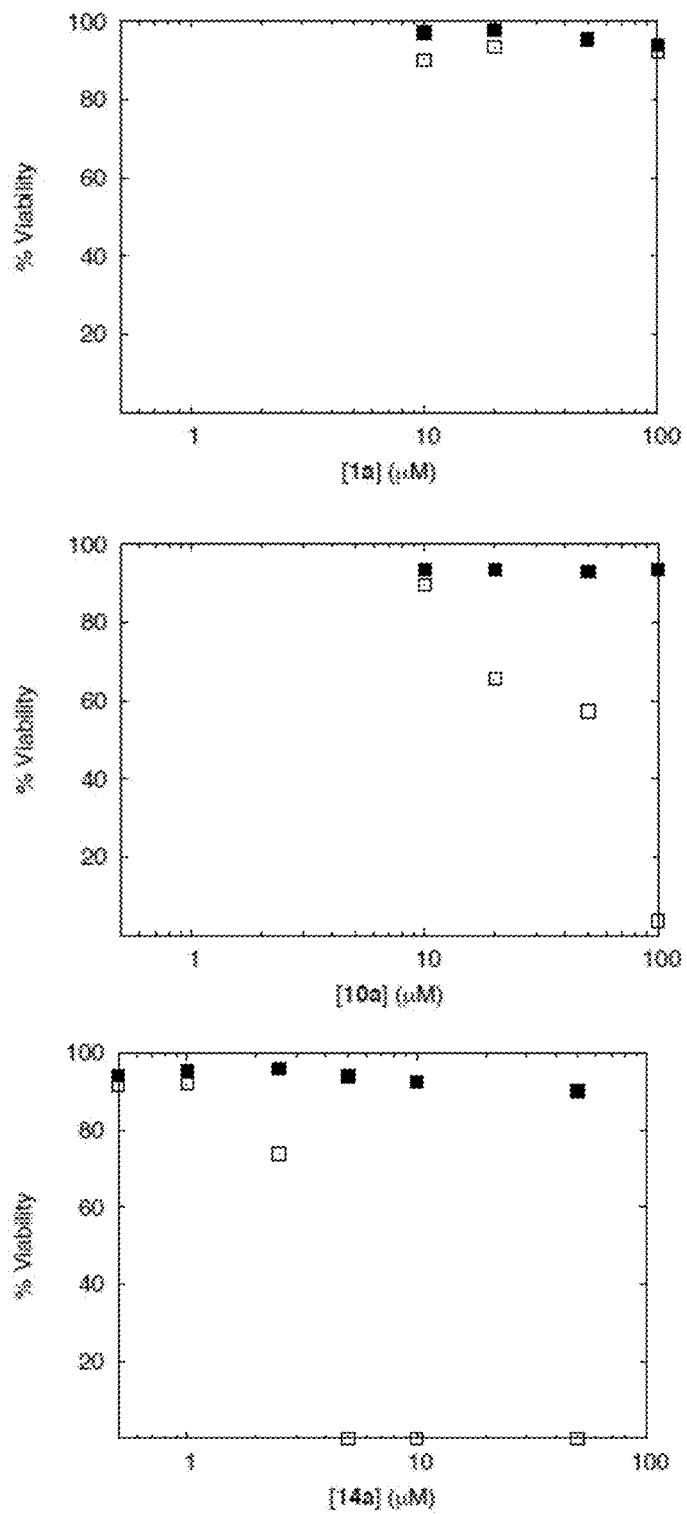

FIG. 24: Cytotoxicity (■) and photocytotoxicity (□) of PDC-treated HL-60 cells (4 hr. pre-incubation, 15 min. visible irradiation, 4 J/cm$^2$) with increasing concentrations of (a) 1a, (b) 10a, and (c) 14a observed by viability staining at 40 hr. post-irradiation with Trypan Blue. PDCs prepared by microwave synthesis.

Figure 25:
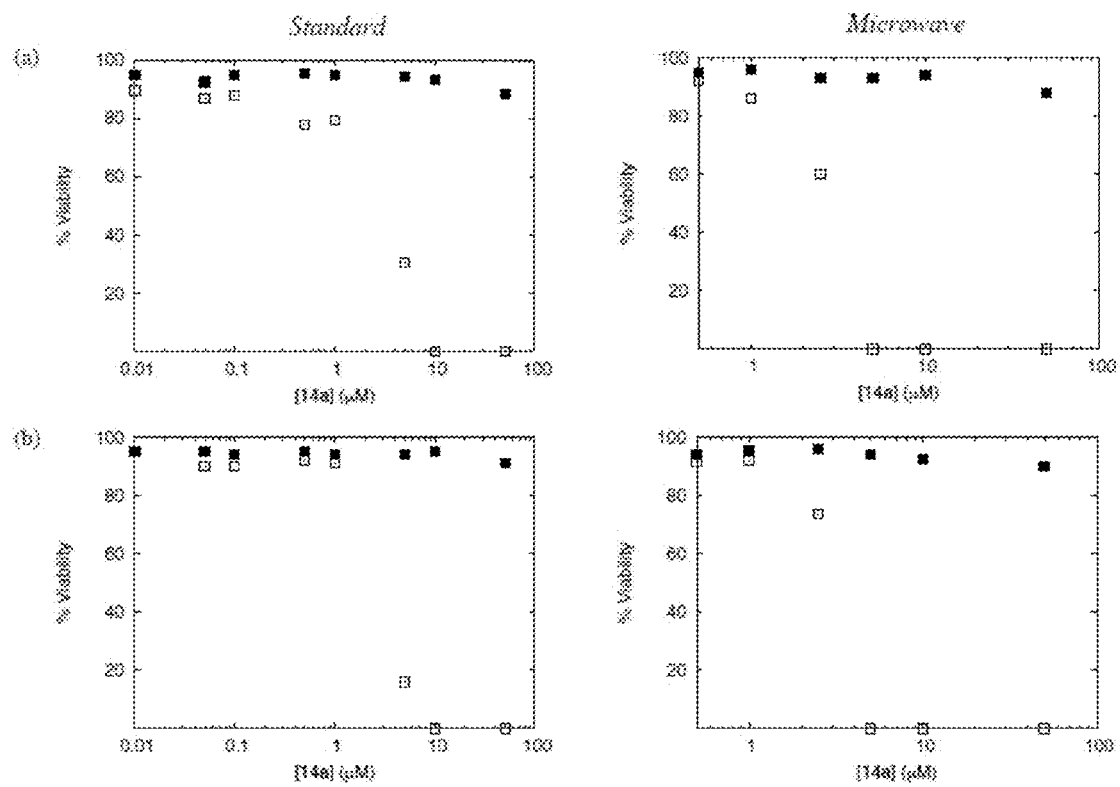

FIG. 25: Cytotoxicity (■) and photocytotoxicity (□) of PDC-treated HL-60 cells (4 hr. pre-incubation, 15 min. visible irradiation, 4 J/cm$^2$) with increasing concentration of 14a at (a) 18 hr. and (b) 40 hr. post-irradiation observed by viability staining with Trypan Blue.

Figure 26:
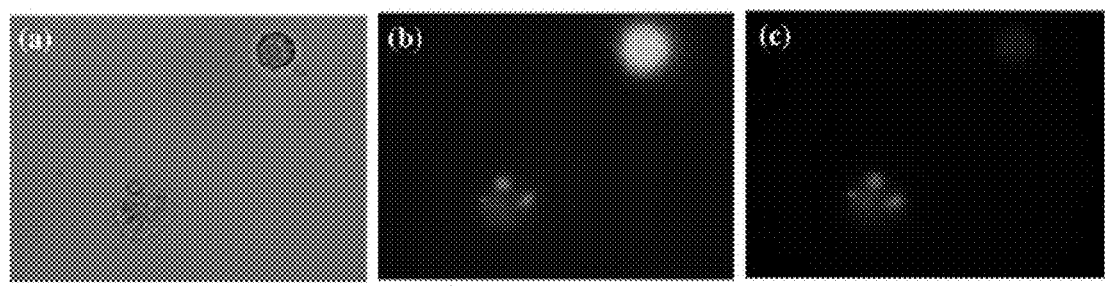

FIG. 26: Formation of apoptotic bodies in HL-60 cells with 100 μM 10a [bottom, left cell in (a)-(c)] observed by nuclear morphology staining with AO-EB. (a) Bright-field 130 ms exposure, 100 μM 10a, +hv, 1000×; (b) epi-fluorescence (FITC) 40 ms exposure, 100 μM 10a, +hv, 1000×; (c) epi-fluorescence (TRITC) 40 ms exposure, 100 μM 10a, +hv, 1000×.

Figure 27:
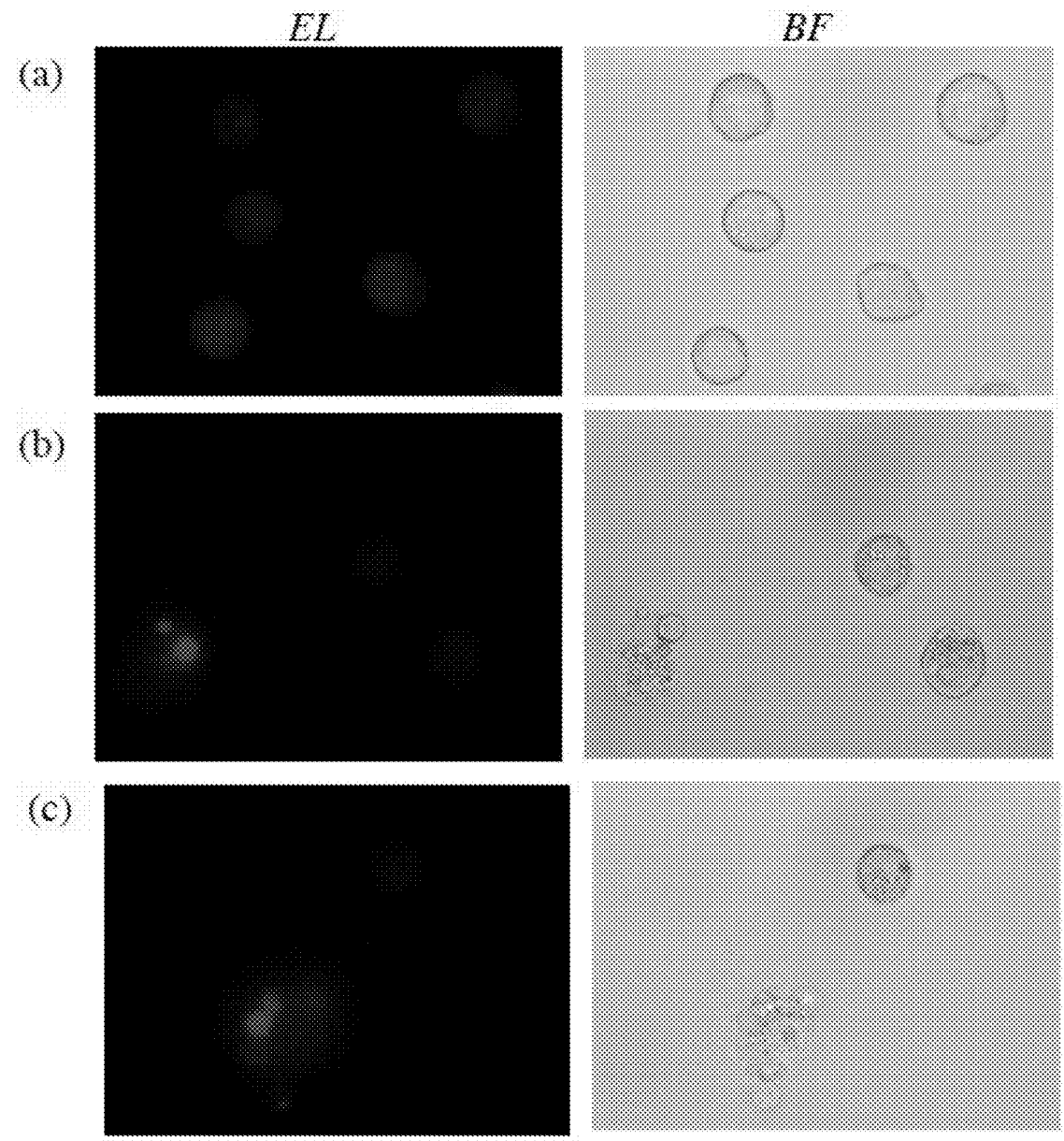

FIG. 27: Epi-luminescence (EL) and bright field (BF) apoptotic images of PDC-treated HL-60 cells at 18 hr. post-irradiation: (a) dark control, 14a (5 μM) (b) 14a (5 μM), and (c) 14a (5 μM). EL images were collected using a TRITC filter cube ($\lambda_{ex}$=540 nm, $\lambda_{em}$=605 nm) with EB staining.

Figure 28:
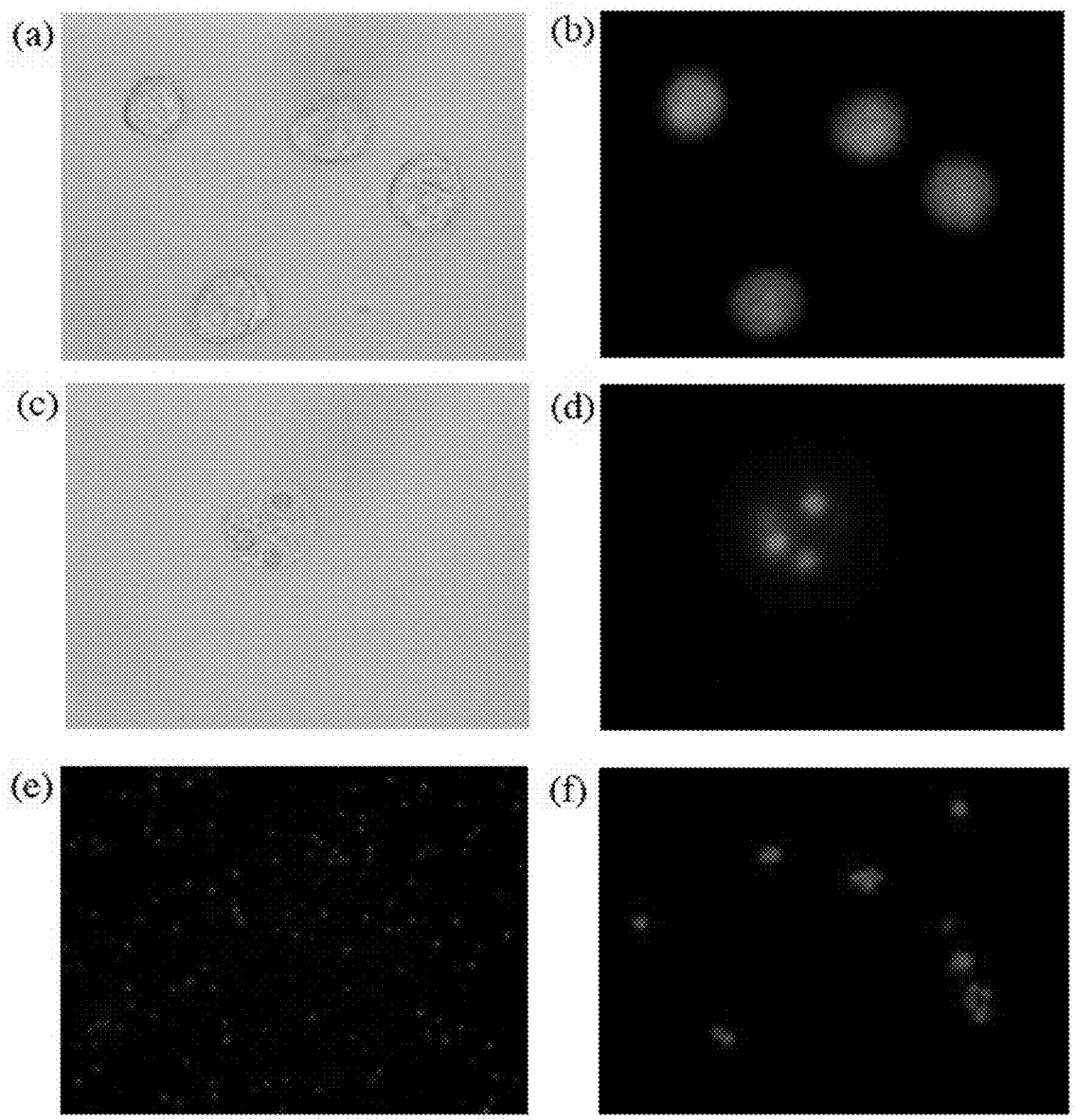

FIG. 28: Bright field (BF) and epi-luminescence (EL) images of PDC-treated HL-60 cells in the dark [(a)-(b)] and with visible irradiation [(c)-(f)] observed by nuclear morphology staining with AO-EB at 40 hr. post-irradiation. (a) 5 μM 14a, −hv, BF 1000×; (b) 5 μM 14a, −hv, EL 1000×; (c) 5 μM 14a, +hv, BF 1000×; (d) 5 μM 14a, +hv, EL 1000×; (e) 5 μM 14a, +hv, EL 100×; (f) 5 μM 14a, +hv, EL 100× (zoomed). AO (green fluorescence) stains viable cells; EB (red fluorescence) stains nonviable cells. Apoptotic bodies are evident in (d) and (f).

Figure 29:
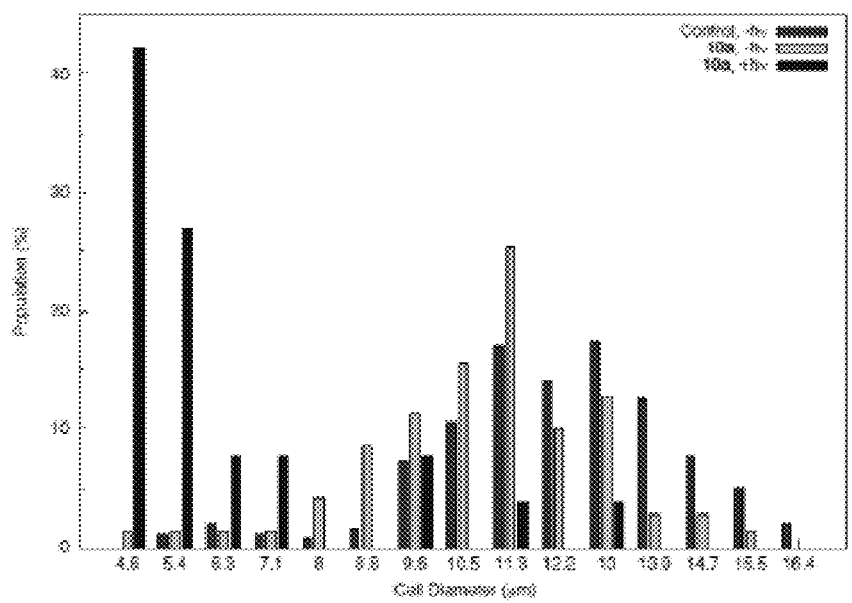
Figure 29:
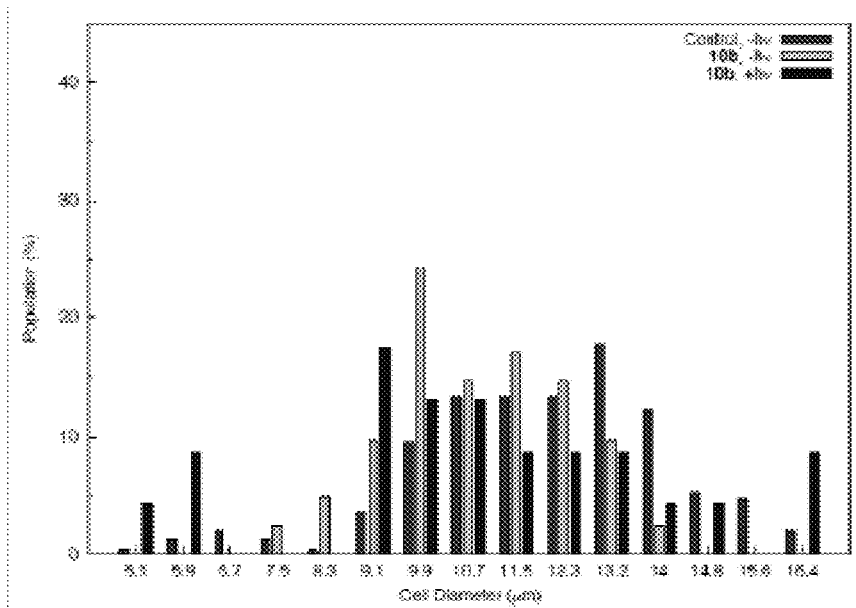

FIG. 29: Size distribution of PDC-treated HL-60 cells at 40 hr. post-irradiation for control, 10a, and 10b.

Figure 30:
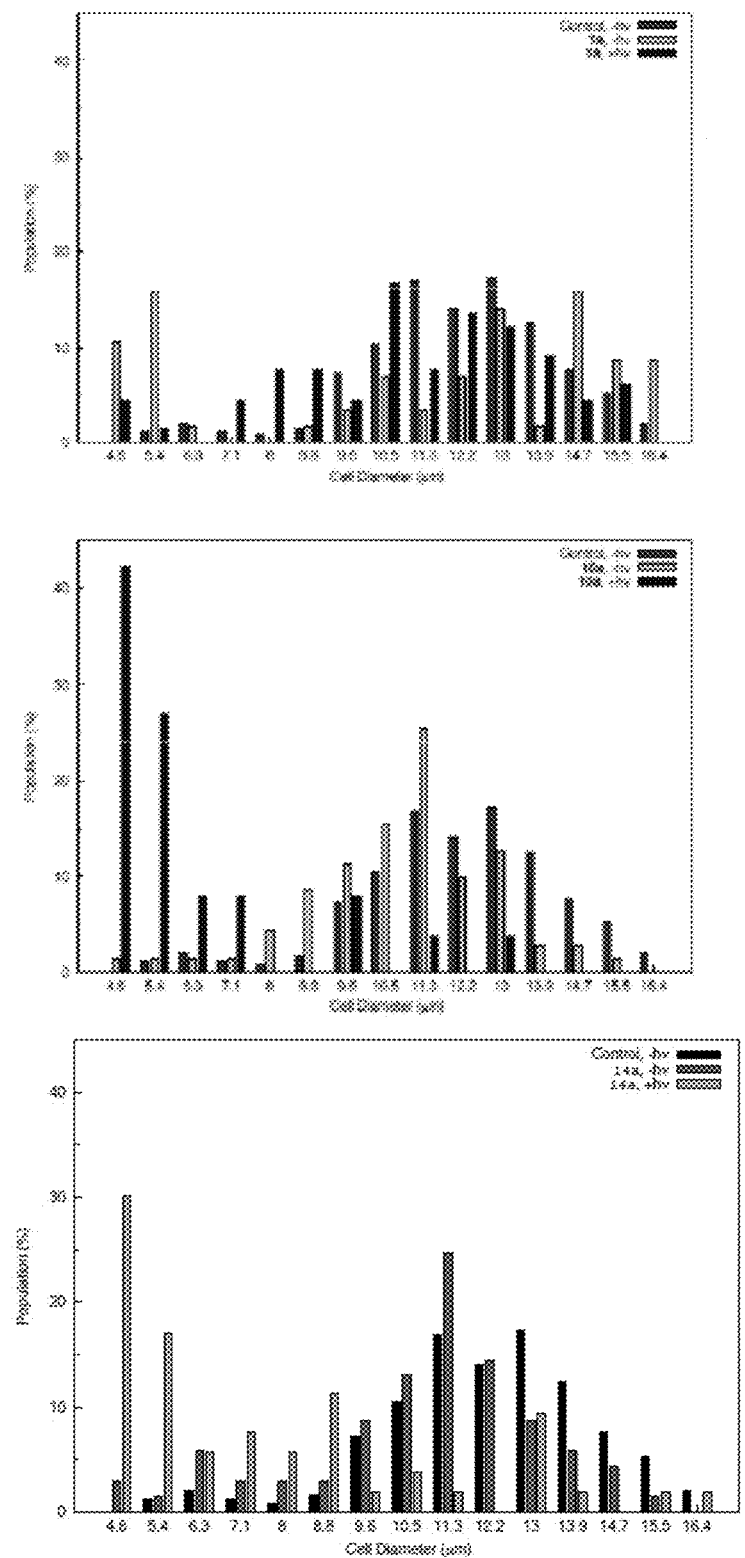

FIG. 30: Size distribution of PDC-treated HL-60 cells at 40 hours post-irradiation.

Figure 31:
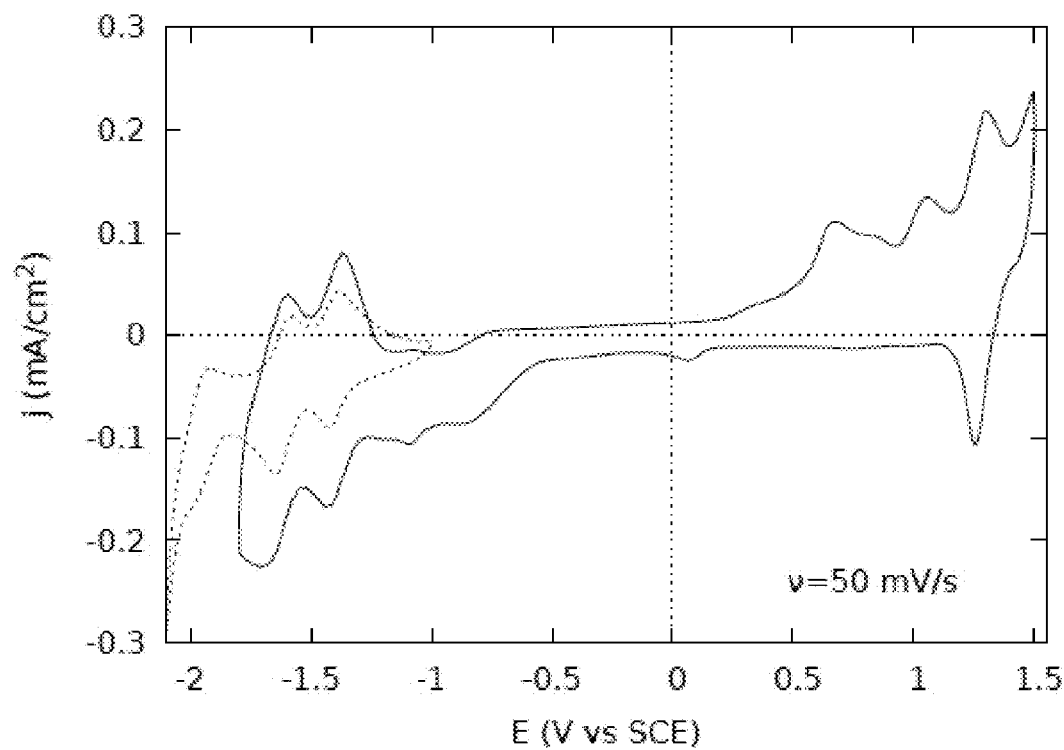

FIG. 31: Cyclic voltammogram of 14a.

Figure 32:
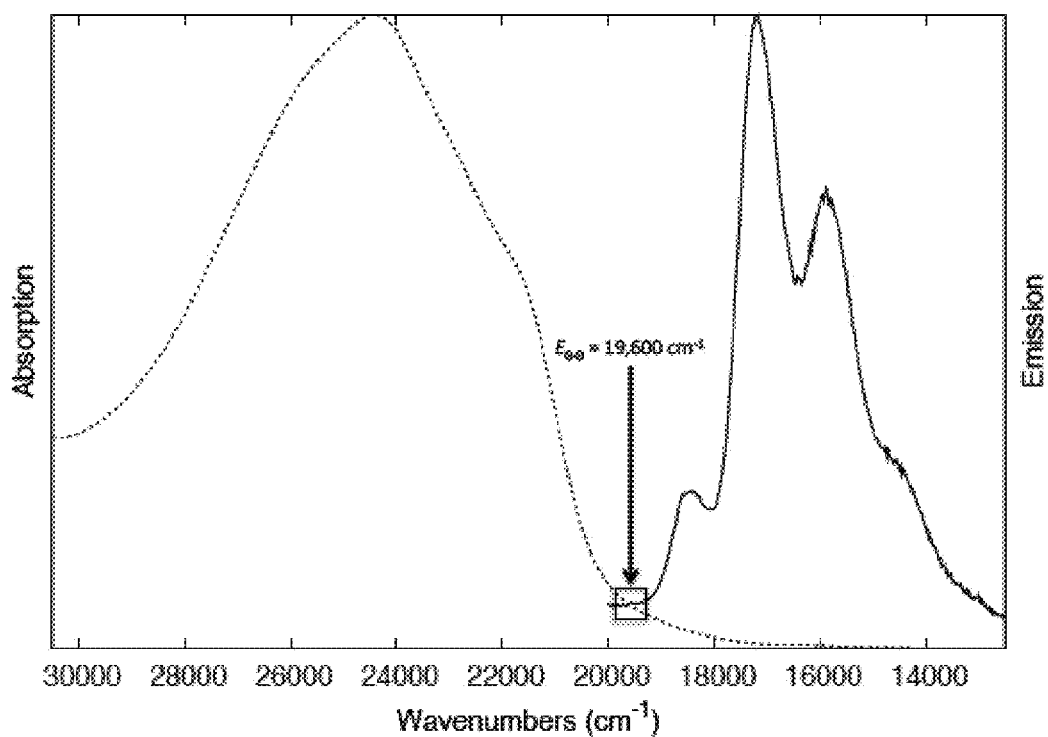

FIG. 32: Absorption and emission of 14a at 77K.

Figure 33:
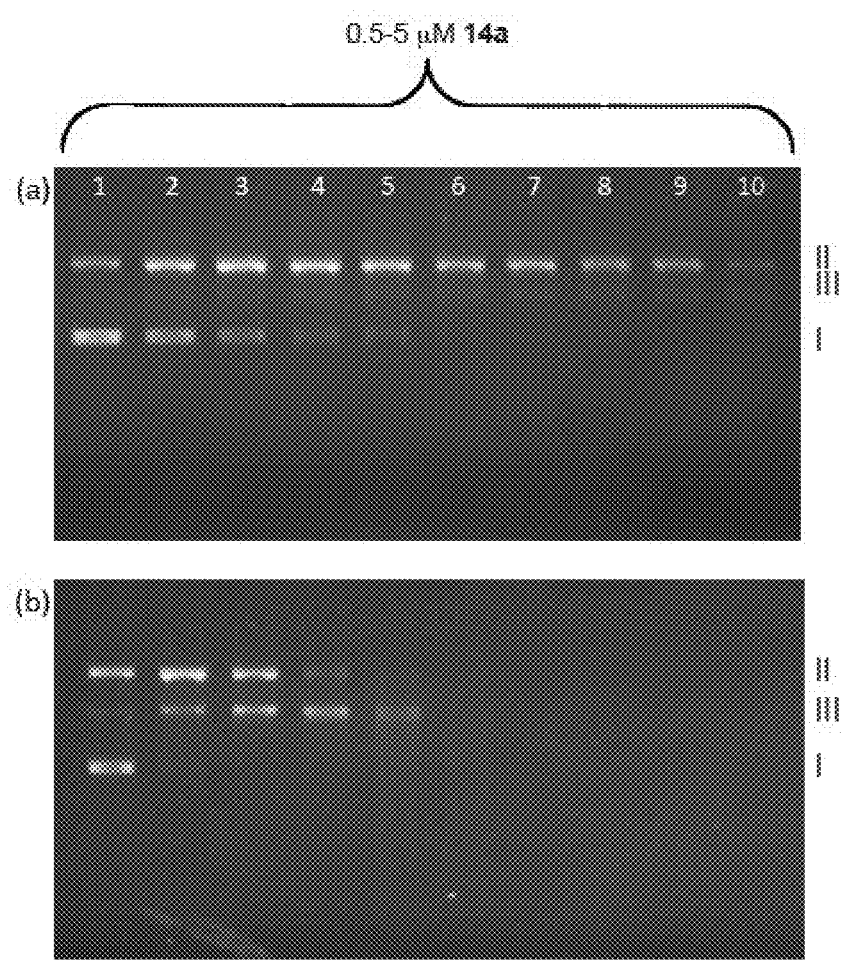

FIG. 33: DNA photocleavage by increasing concentration of 14a: (a) no GSH, and (b) 4 mM GSH. Lanes 1-10 contain pBR322 plasmid DNA (20 µM-NP) exposed to 14a (0.5-5 µM) and irradiated at 420 nm for 30 min. in 5 mM Tris, 50 mM NaCl, pH 7.5.

Figure 34:
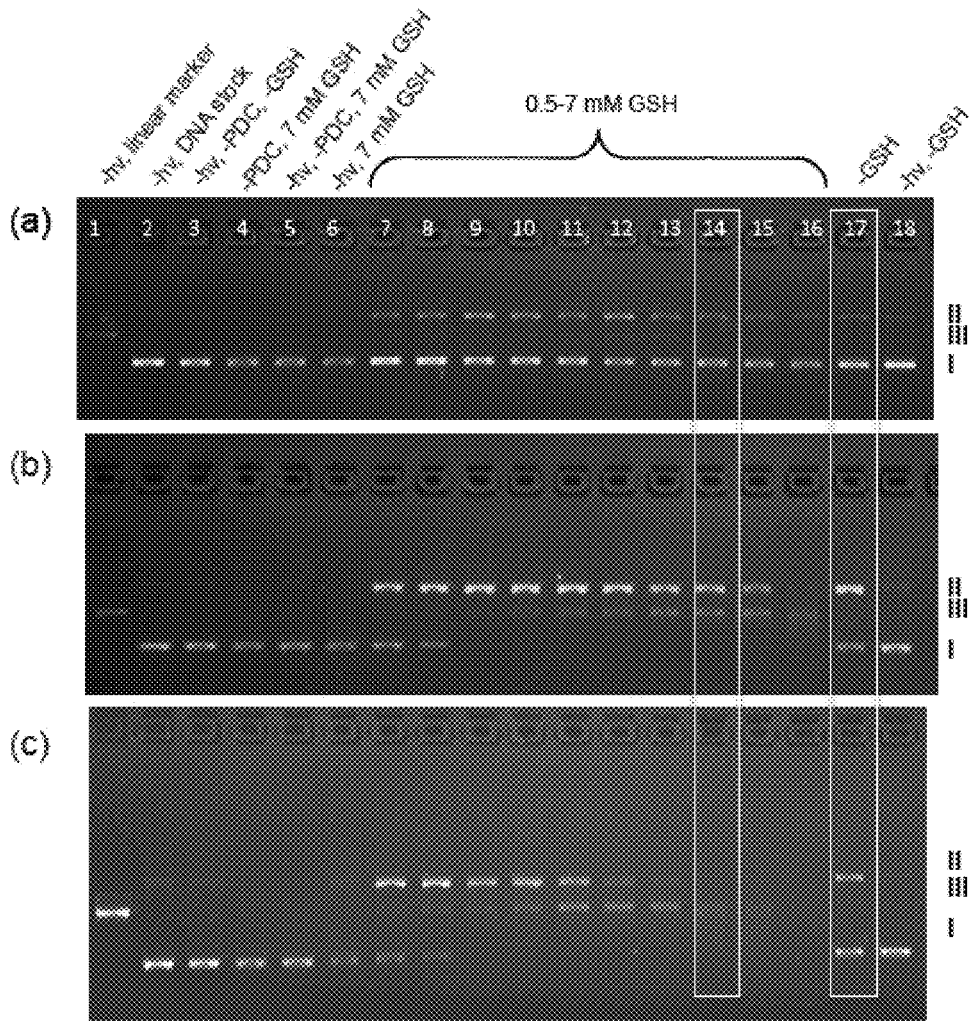

FIG. 34: The effect of GSH on DNA photodamage increases with increasing n: (a) 1a, n=1, (b) 10a, n=2, and (c) 14a, n=3. Lanes 1-6 and 17-18 are control lanes. Lanes 7-16 contain pBR322 plasmid DNA (20 µM-NP) exposed to PDC (2 µM) and increasing concentration of GSH and irradiated at 420 nm for 30 min. in 5 mM Tris, 50 mM NaCl, pH 7.5.

Figure 35:
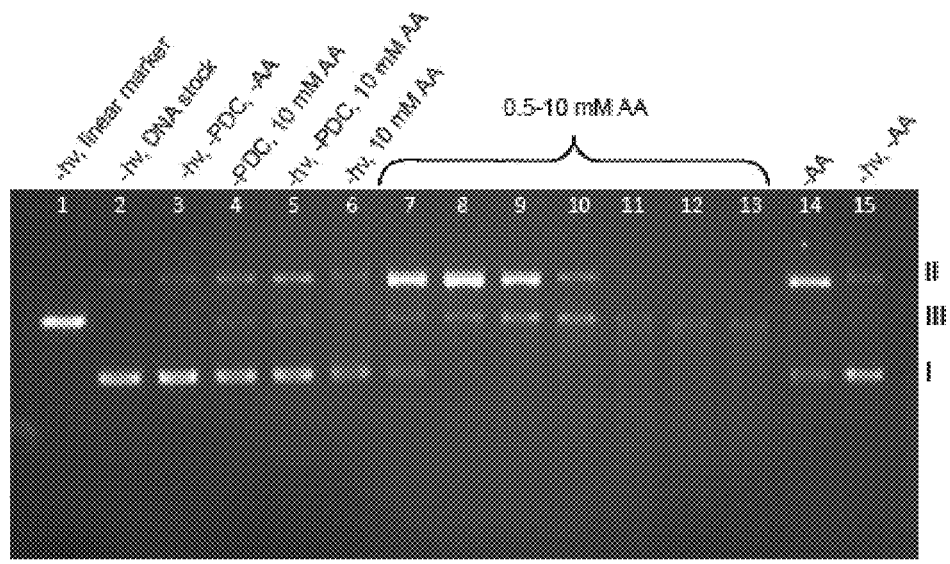

FIG. 35: The effect of AA on DNA photodamage by 14a. Lanes 1-6 and 14-15 are control lanes. Lanes 7-13 contain pBR322 plasmid DNA (20 µM-NP) exposed to PDC (2 µM) and increasing concentration of AA and irradiated at 420 nm for 30 min. in 5 mM Tris, 50 mM NaCl, pH 7.5.

Figures 36, 37:
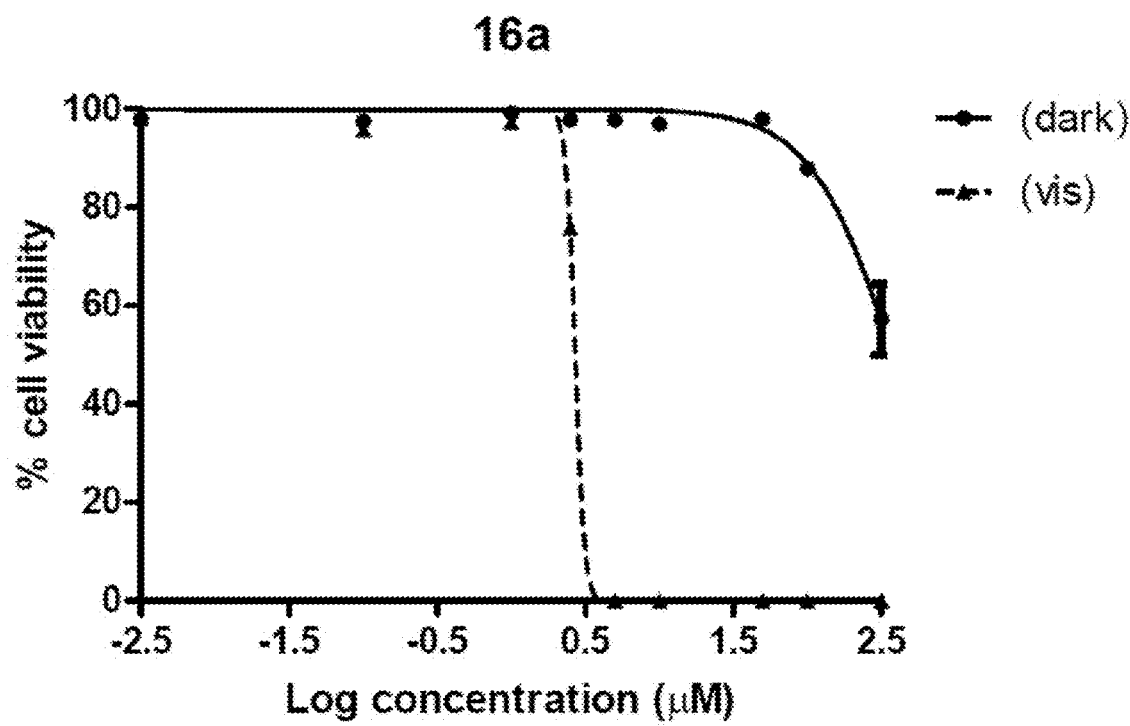

FIG. 36: Formula for determining DNA binding constant for compounds of the disclosure.

FIG. 37: Cytotoxicity (●) and photocytotoxicity (▲) of HL-60 cells (4 hr. pre-incubation, 15 min. vis irradiation, 4 J/cm$^2$) with increasing concentrations of 16a.

Figure 38:
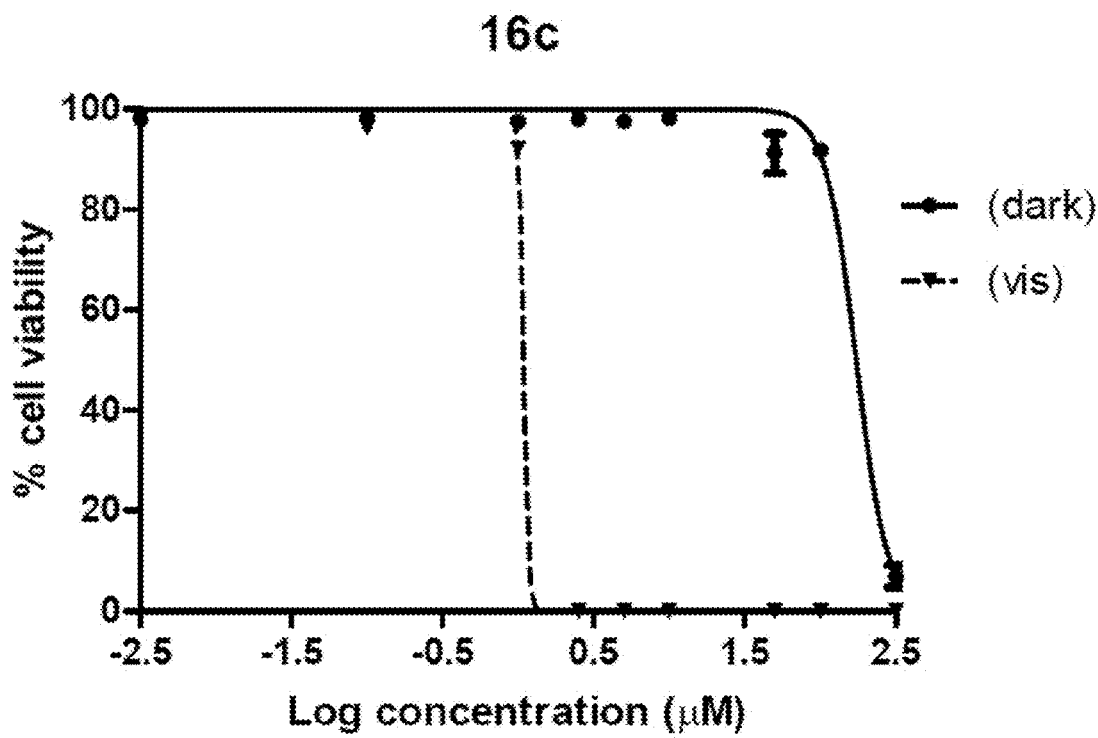

FIG. 38: Cytotoxicity (●) and photocytotoxicity (▲) of HL-60 cells (4 hr. pre-incubation, 15 min. vis irradiation, 4 J/cm$^2$) with increasing concentrations of 16c.

Figure 39:
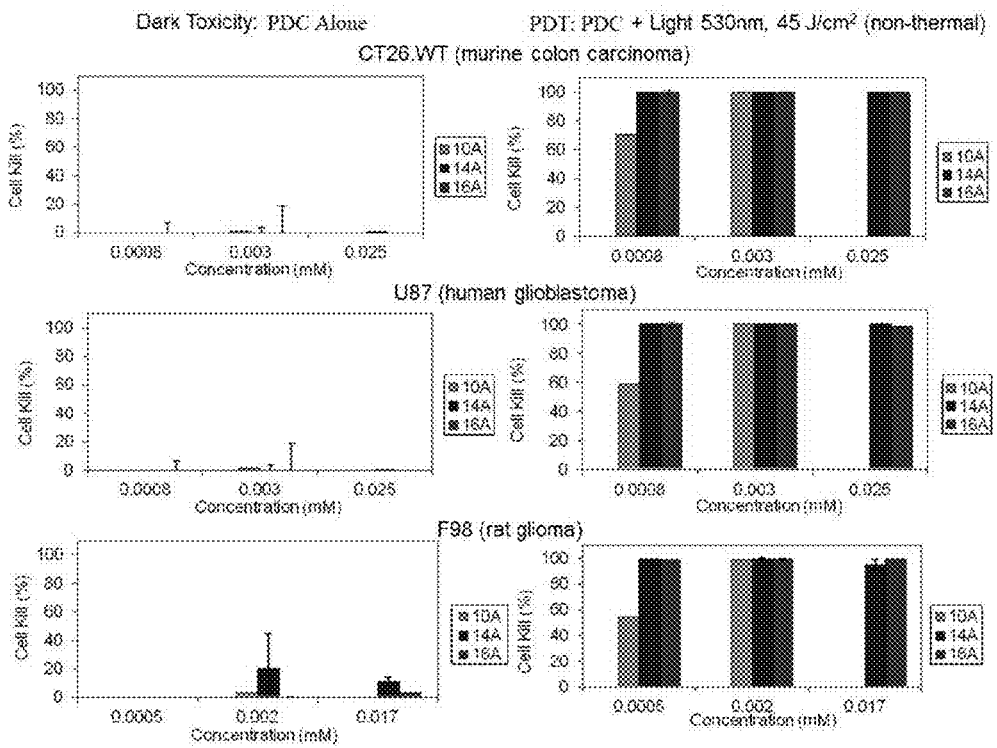

FIG. 39: The efficacy of PDCs 10A, 14A and 16A on cell kill in CT26.WT (top), U87 (middle), and F98 (bottom) cells expressed as the number of cells killed as a percentage of control (no PDC, no light). The effects of PDCs without light (dark toxicity, left panels) and with light (PDT, right panels) are shown. Data are shown as means +/− standard error bars.

Figure 40:
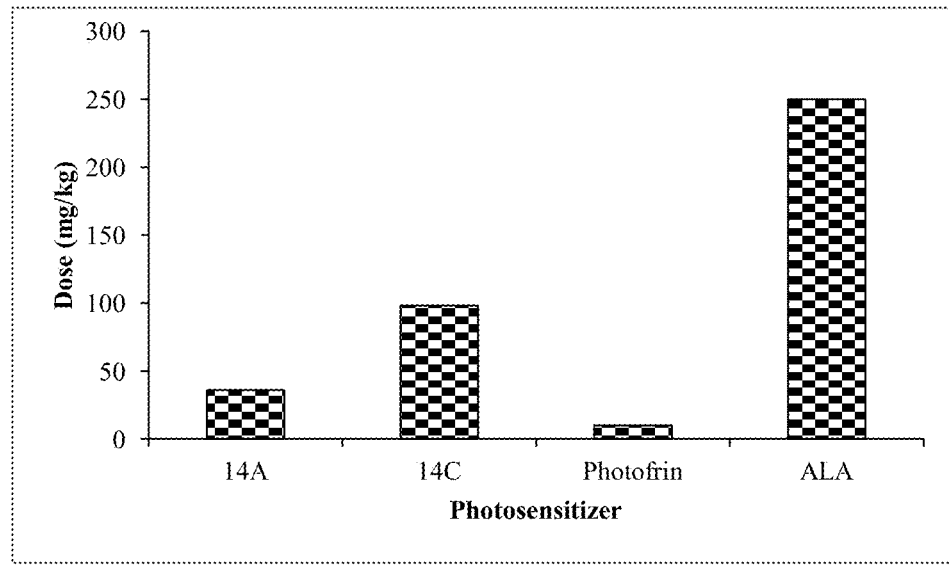

FIG. 40: A comparison of the effective doses for PDCs 14A, 14C, PHOTOFRIN, and Aminolevulinic Acid (ALA) used in PDT studies for tumour destruction in mouse models.

Figure 41:
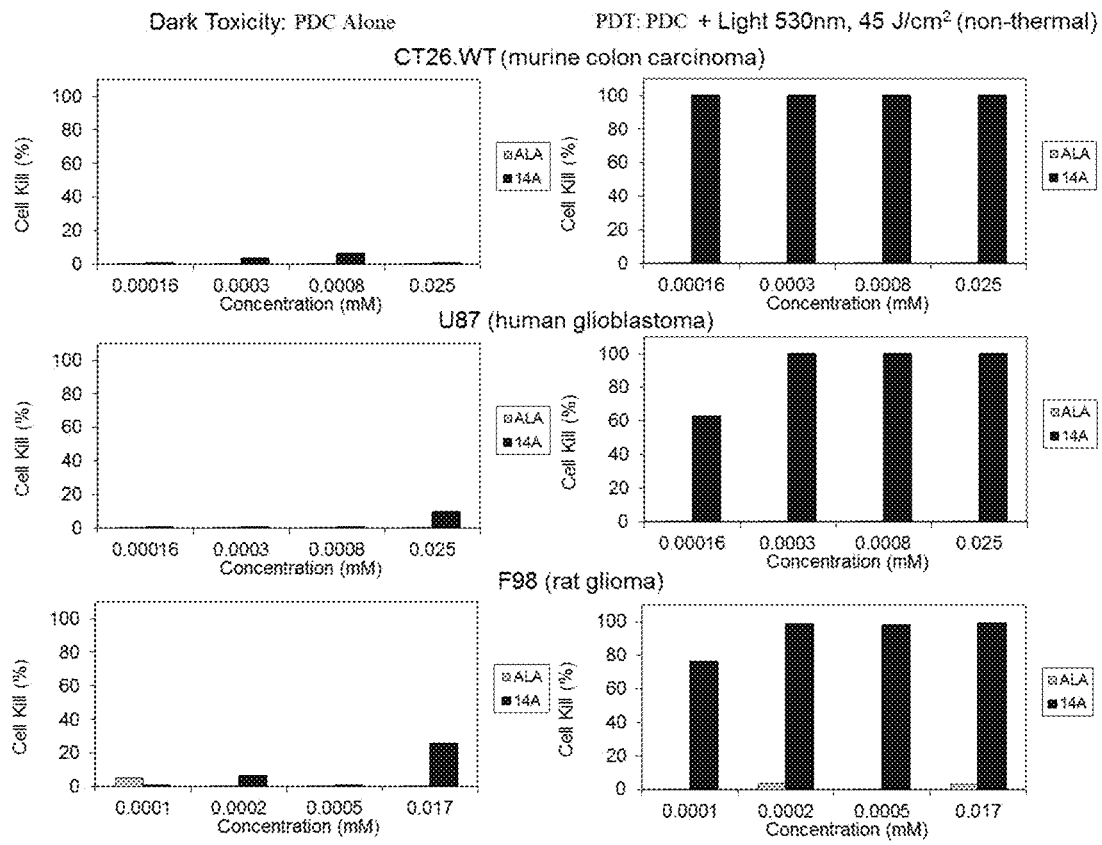

FIG. 41: Cell kill efficacy of PDC 14A versus ALA on CT26.WT (top), U87 (middle), and F98 (bottom) cells expressed as the number of cells killed as a percentage of control (no PDC, no light). The effects of PDC without light (dark toxicity, left panels) and with light (PDT, right panels) are shown.

Figure 42:
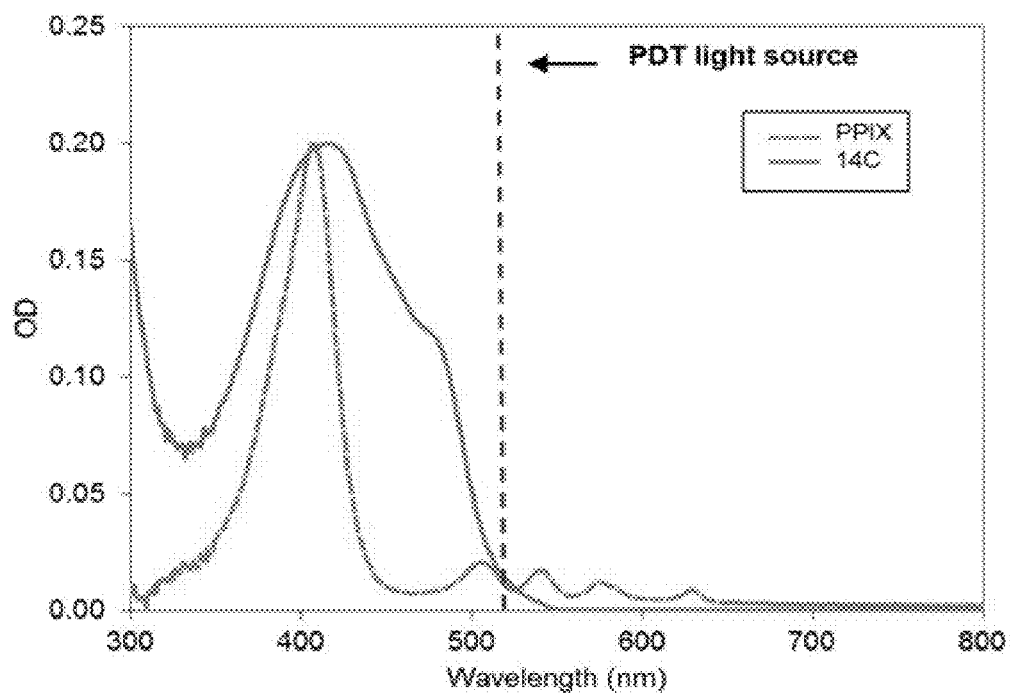

FIG. 42: The absorption spectra for the photosensitizers 14C (solid) and PPIX (dashed). The wavelength used for PDT experiments is shown by a vertical dashed line.

Figure 43:
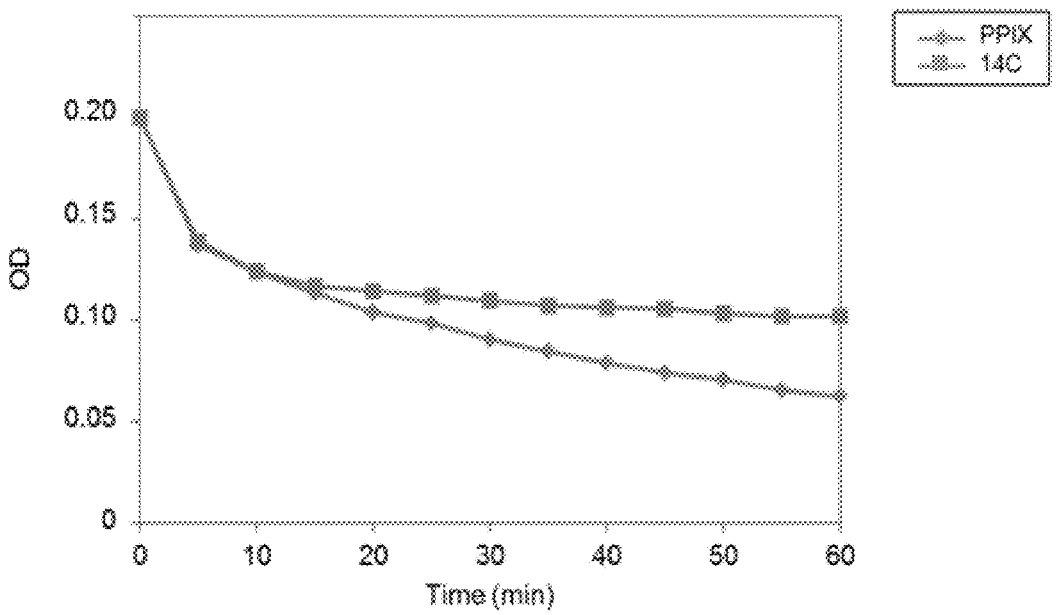

FIG. 43: The absorbance spectra for PDC 14C (square) compared to PPIX (diamond) after 60 minutes of irradiation (525 nm, 78 mW/cm$^2$). ODs were recorded at the maximal absorbance in the visible region for each PDC, 423 nm for 14C, 411 nm for PPIX.

DETAILED DESCRIPTION OF PREFERRED EMBODIMENTS OF THE INVENTION

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloro ethyl, 2-hydroxyethyl, 1,2-difluoroethyl, 3-carboxypropyl, and the like. In substituent groups with multiple alkyl groups such as ($C_{1-6}$alkyl)$_2$-amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclo hex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbo cyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., $-CF_3$, $-CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic mono cyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indo le, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxyquinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

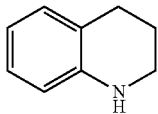

is, for the purposes of the present invention, considered a heterocyclic unit. 6,7-Dihydro-5H-cyclopentapyrimidine having the formula:

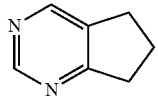

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

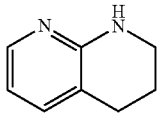

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^9$, —SR$^9$, —N(R$^9$)$_2$, —NR$^9$C(O)R$^9$, —SO$_2$R$^9$, —SO$_2$OR$^9$, —SO$_2$N(R$^9$)$_2$, —C(O)R$^9$, —C(O)OR$^9$, —C(O)N(R$^9$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^x$; wherein R$^x$, at each occurrence, independently is hydrogen, —OR$^{10}$, —SR$^{10}$, —C(O)R$^{10}$, —C(O)OR$^{10}$, —C(O)N(R$^{10}$)$_2$, —SO$_2$R$^{10}$, —S(O)$_2$OR$^{10}$, —N(R$^{10}$)$_2$, —NR$^{10}$C(O)R$^{10}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^x$ units taken together with the atom(s) to which they are bound form an optionally substituted carbocycle or heterocycle wherein said carbocycle or heterocycle has 3 to 7 ring atoms; wherein R$^{10}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{10}$ units taken together with the atom(s) to which they are bound form an optionally substituted carbocycle or heterocycle wherein said carbocycle or heterocycle preferably has 3 to 7 ring atoms.

In certain embodiments, the substituents are selected from
i) —OR$^{11}$; for example, —OH, —OCH$_3$, —OCH$_2$CH$_3$, —OCH$_2$CH$_2$CH$_3$;
ii) —C(O)R$^{11}$; for example, —COCH$_3$, —COCH$_2$CH$_3$, —COCH$_2$CH$_2$CH$_3$;
iii) —C(O)OR$^{11}$; for example, —CO$_2$CH$_3$, —CO$_2$CH$_2$CH$_3$, —CO$_2$CH$_2$CH$_2$CH$_3$;
iv) —C(O)N(R$^{11}$)$_2$; for example, —CONH$_2$, —CONHCH$_3$, —CON(CH$_3$)$_2$;
v) —N(R$^{11}$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_e$X$_g$; wherein X is halogen, m is from 0 to 2, e+g=3; for example, —CH$_2$F, —CHF$_2$, —CF$_3$, —CCl$_3$, or —CBr$_3$;
viii) —SO$_2$R$^{11}$; for example, —SO$_2$H; —SO$_2$CH$_3$; —SO$_2$C$_6$H$_5$;
ix) $C_1$-$C_6$ linear, branched, or cyclic alkyl;
x) Cyano
xi) Nitro;
xii) N(R$^{11}$)C(O)R$^{11}$;
xiii) Oxo (=O);
xiv) Heterocycle; and
xv) Heteroaryl.
wherein each R$^{11}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two R$^{11}$ units can be taken together to form a ring comprising 3-7 ring atoms. In certain aspects, each R$^{11}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the photodynamic compounds described herein, including all enantiomeric forms, diastereomeric forms, salts, and the like, and the terms "compound," "analog," and "composition of matter" are used interchangeably throughout the present specification.

For the purposes of the present invention the term "bpy" will stand equally well for 2,2'-bipyridine and [2,2']bipyridine.

For the purposes of the present invention the term "phen" will stand equally well for [1,10]phenanthroline and 1,10-phenanthroline.

For the purposes of the present invention the term "dmb" will stand equally well for 4,4'-dimethyl-2,2'-bipyridine.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, $LiOH$, $NaOH$, $KOH$, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^6)_2$, each $R^6$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

As used herein, the term "photodynamic therapy" shall mean a treatment for destroying cells and tissue through use of a drug that can be activated by light of a certain wavelength and dose.

As used herein, the term "photodynamic compound" shall mean a compound that provides photodynamic therapy.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Photodynamic Compounds

The photodynamic compounds of the present invention are tunable metal-based thiophenes, and include all enantiomeric and diastereomeric forms and pharmaceutically accepted salts thereof having the formula (I),

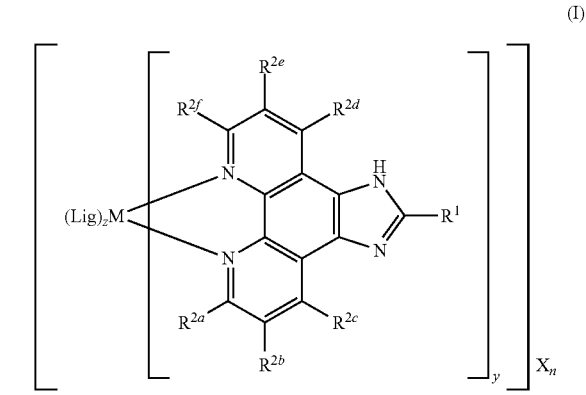

(I)

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;
X is selected from the group consisting of $Cl^-$, $PF_6^-$, $Br^-$, $BF_4^-$, $ClO_4^-$, $CF_3SO_3^-$, and $SO_4^{-2}$;
n=0, 1, 2, 3, 4, or 5;
y=1, 2, or 3;
z=0, 1, or 2;
Lig at each occurrence is independently selected from the group consisting of
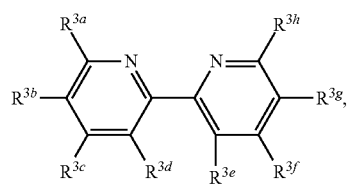
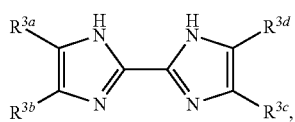
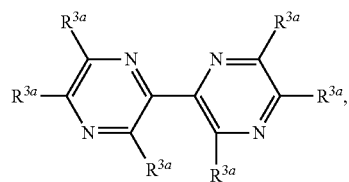
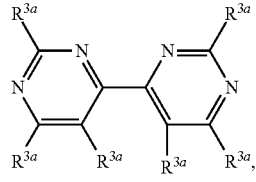
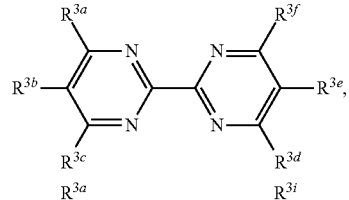
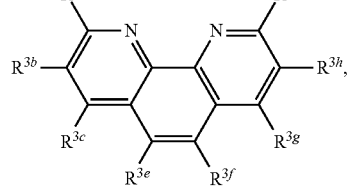
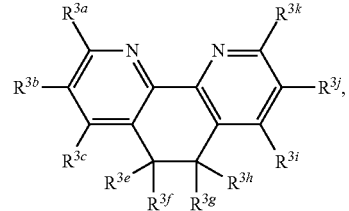
-continued
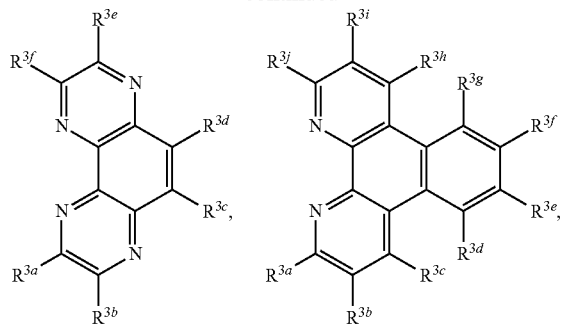
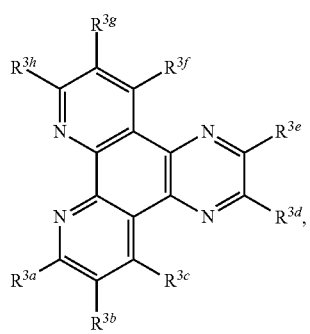
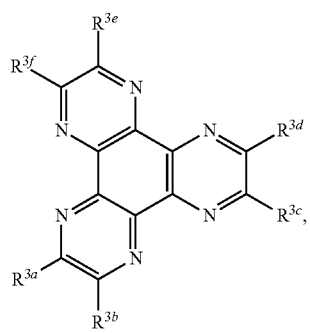
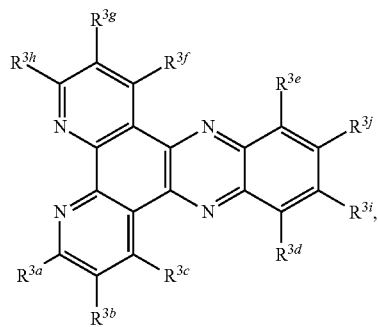
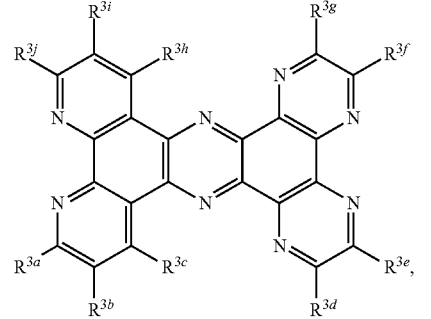
and -continued

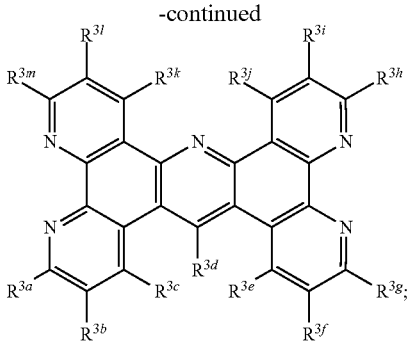

$R^1$ is selected from the group consisting of stituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3l}$ and $R^{3m}$ at each occurrence are each independently selected from the group consisting of hydrogen, C1-6 optionally substituted alkyl, C1-6 optionally substituted branched alkyl, C1-6 optionally substituted halo alkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cyclo alkyl, C1-6 optionally substituted halo alkyl, C1-6 optionally substituted alkoxy, $CO_2R^5$, $CONR^6_2$, $NR^7_2$, sulfate, sul-

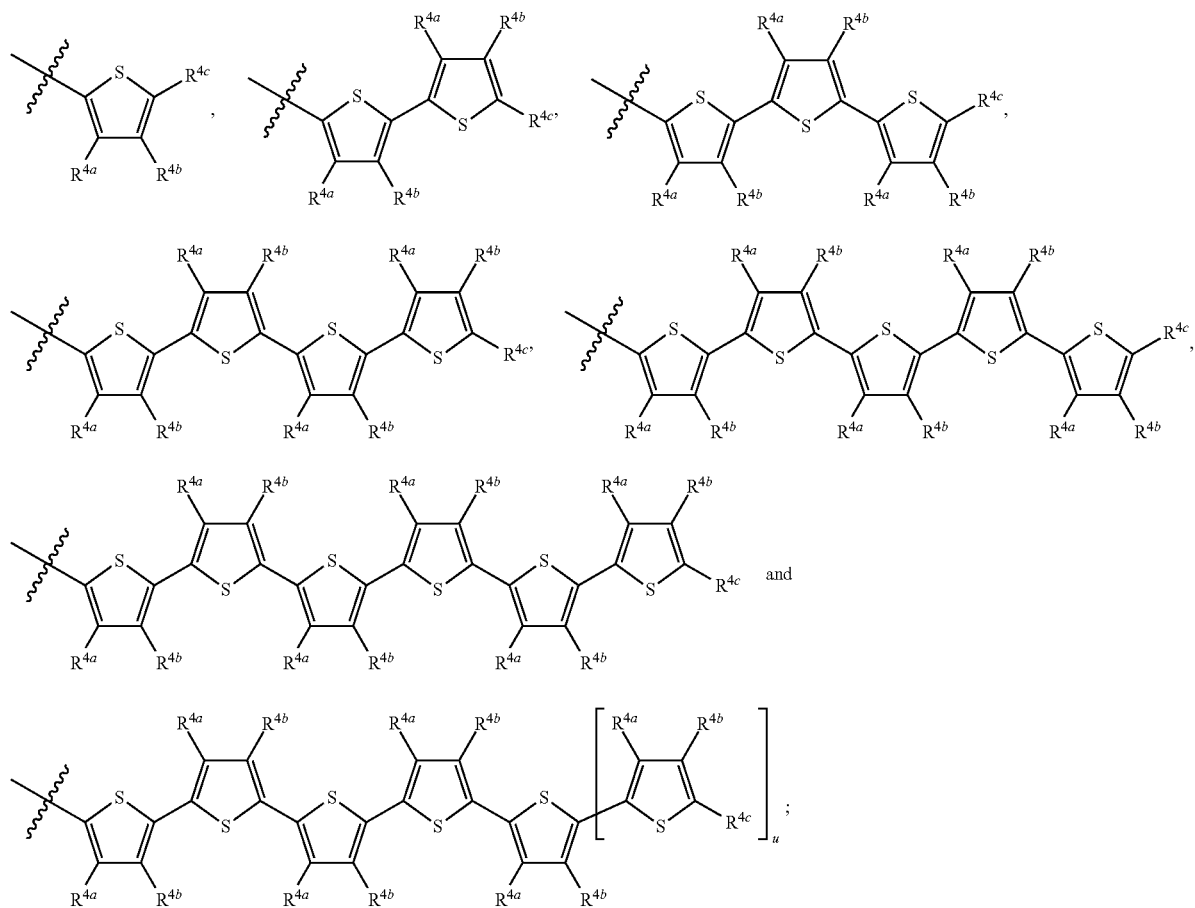

u is an integer, and in certain embodiments, is 1-1000 or 1-500 or 1-100 or 1-10, or is at least 2 or at least 3 or at least 4 or at least 5 or at least 10, or is any integer from 1-5 or 1-10 or 1-20, or any value up to the point where processability becomes problematic due to aggregation and/or insolubility;

$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally subfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

R[7] at each occurrence is independently selected from the group consisting of hydrogen and optionally substituted alkyl;

R[8] at each occurrence is independently selected from the group consisting of hydrogen and optionally substituted alkyl.

Compounds of the structures

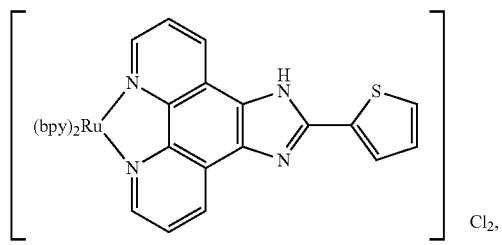

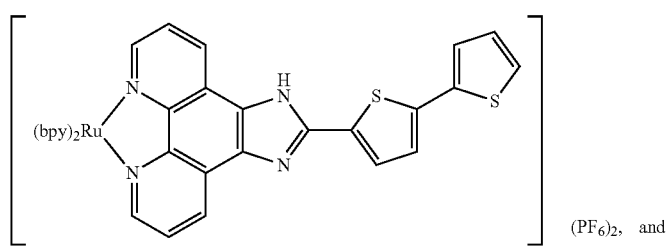

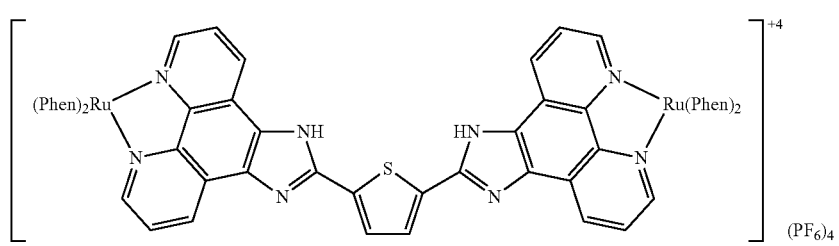

are excluded from the novel compounds of formula (I).

The compounds of the present invention includes compounds having formula (II),

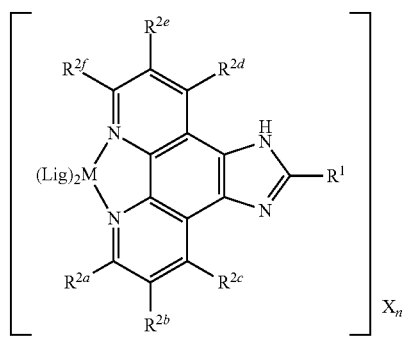

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2 or 3;

Lig at each occurrence is independently selected from the group consisting of

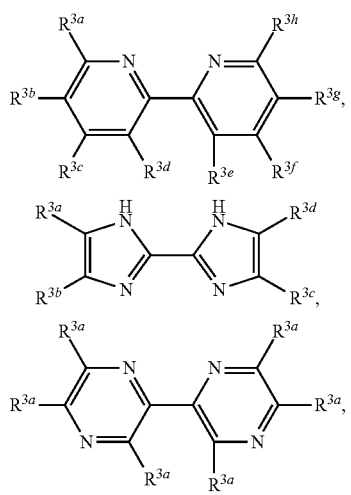

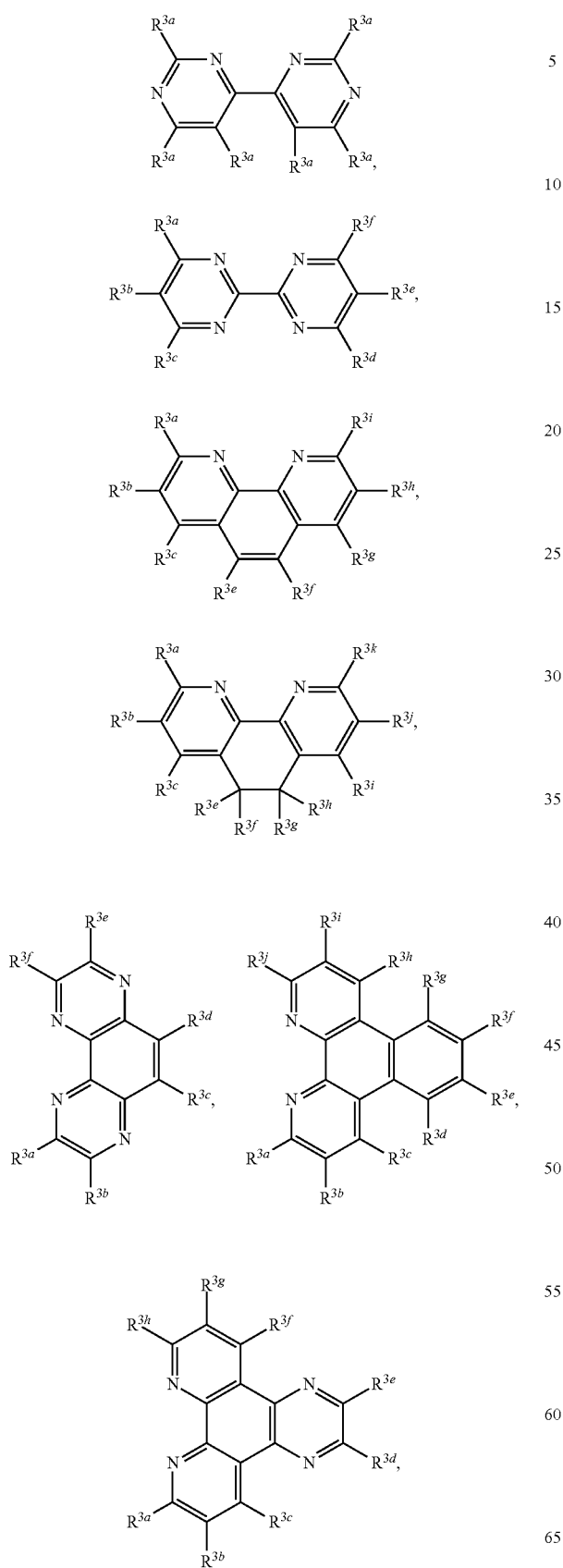
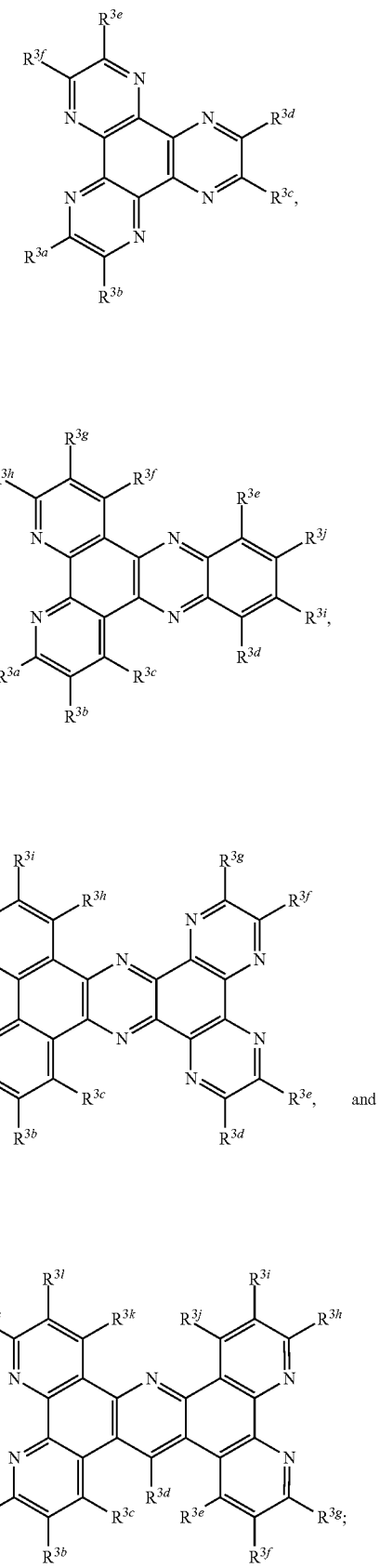

R[1] is selected from the group consisting of

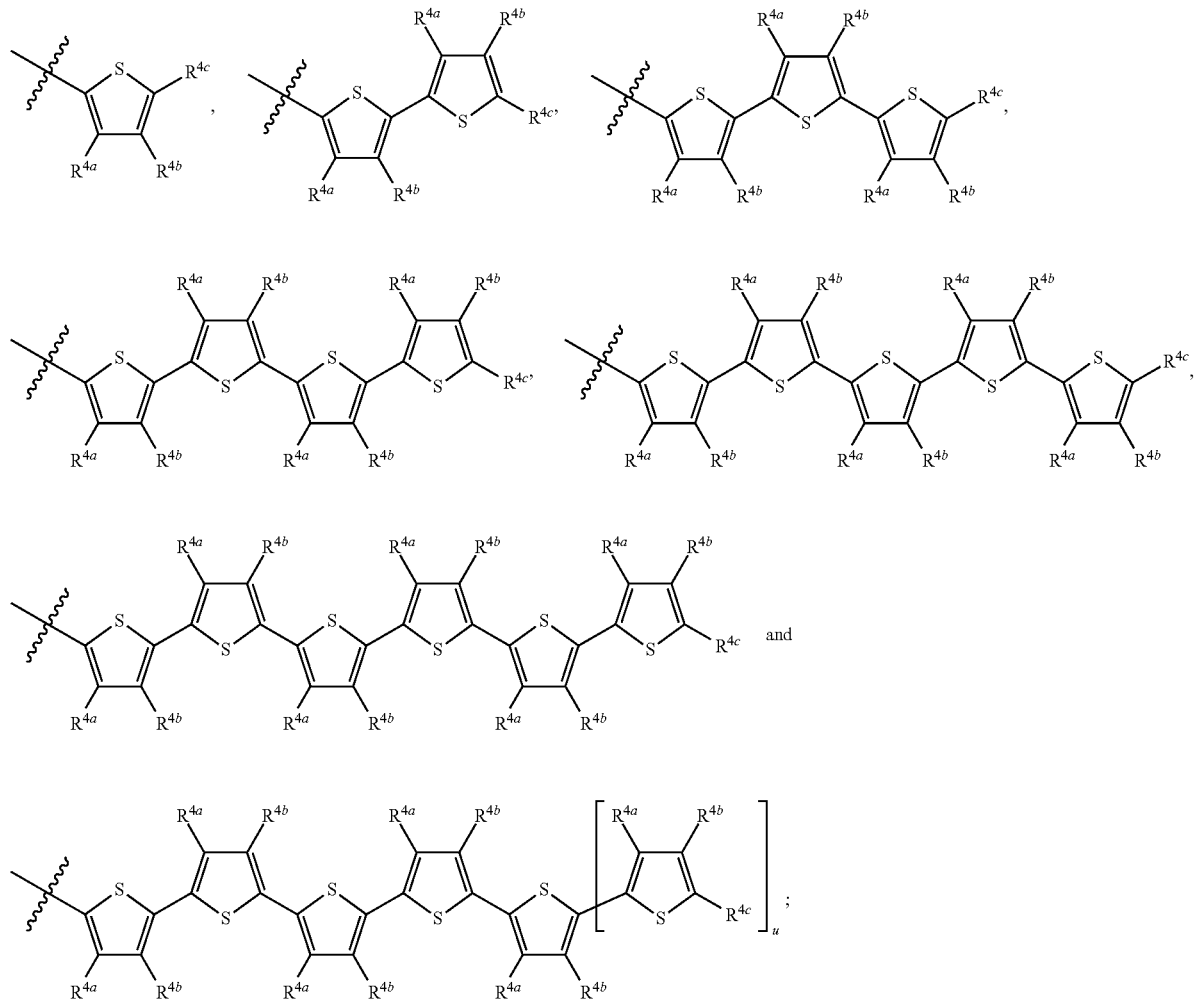

u is an integer, and in certain embodiments, is 1-1000 or 1-500 or 1-100 or 1-10, or is at least 2 or at least 3 or at least 4 or at least 5 or at least 10, or is any integer from 1-5 or 1-10 or 1-20, or any value up to the point where processability becomes problematic due to aggregation and/or insolubility;

$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3l}$ and $R^{3m}$ at each occurrence are each independently selected from the group consisting of hydrogen, C1-6 optionally substituted alkyl, C1-6 optionally substituted branched alkyl, C1-6 optionally substituted halo alkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted halo alkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl;

$R^8$ at each occurrence is independently selected from the group consisting of hydrogen and optionally substituted alkyl;

Compounds of the structures

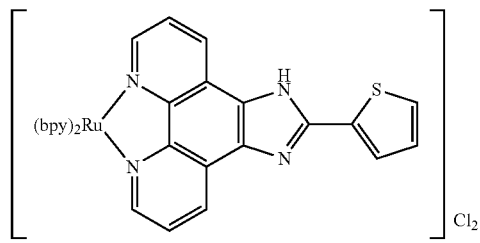

1a and

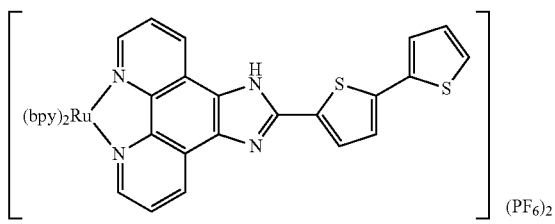

10a are excluded from the novel compounds of formula (II).

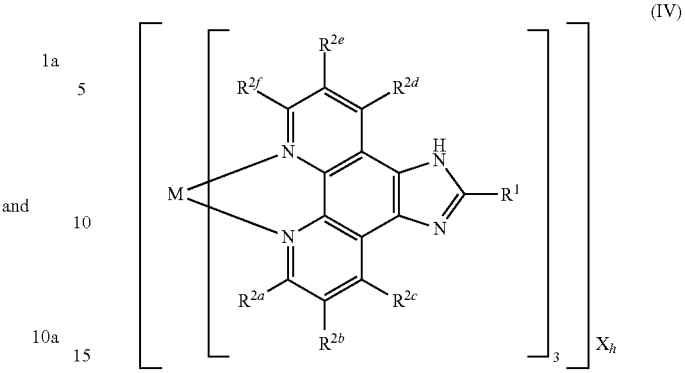

(IV)

including hydrates, solvates, pharmaceutically acceptable salts, prodrugs and complexes thereof wherein M, X and the R groups are as defined above, and h is 0, 1, 2, 3, 4, or 5.

The present invention is also directed toward novel compounds of formula (V):

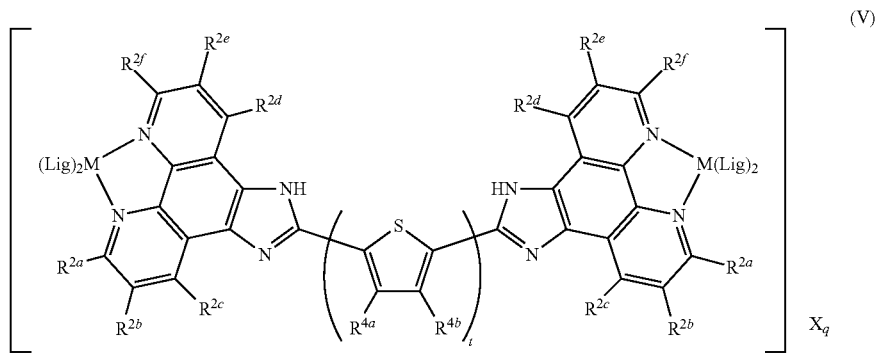

The compounds of the present invention includes compounds having formula (III),

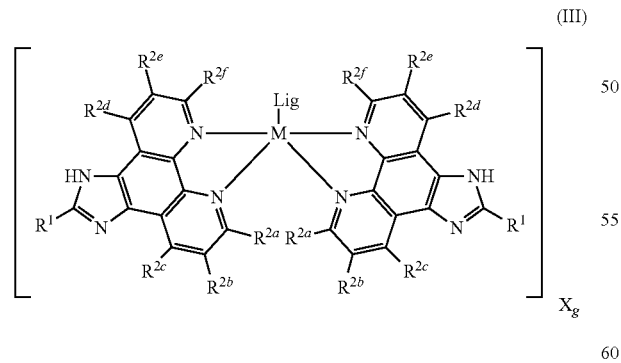

(III)

including hydrates, solvates, pharmaceutically acceptable salts, prodrugs and complexes thereof wherein M, Lig, X and the R groups are as defined above, and g is 0, 1, 2, 3, 4, or 5.

The present is also directed toward novel compounds of formula (IV):

including hydrates, solvates, pharmaceutically acceptable salts, prodrugs and complexes thereof, wherein:

Lig at each occurrence is independently selected from the group consisting of

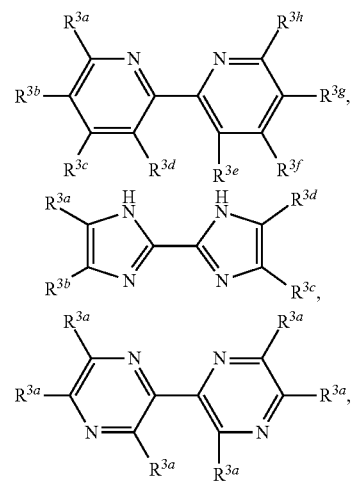

-continued
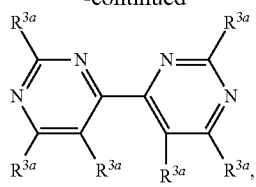
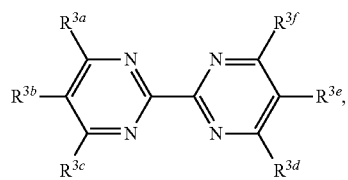
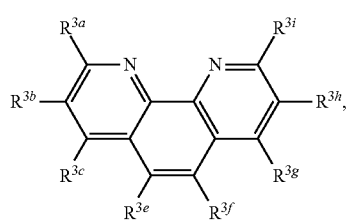
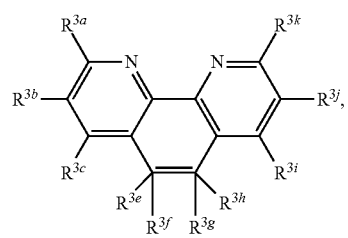
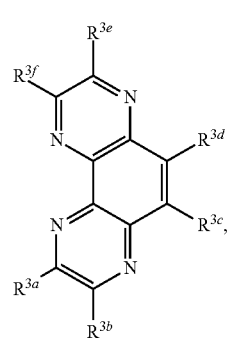
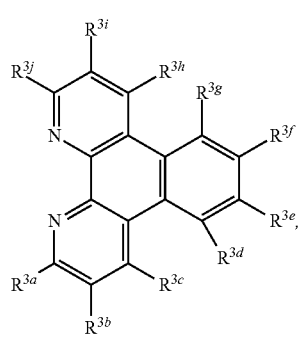
-continued
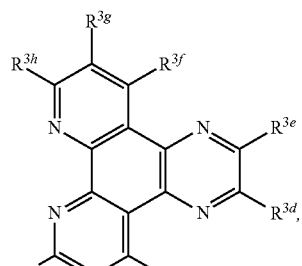
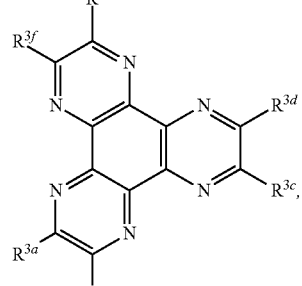
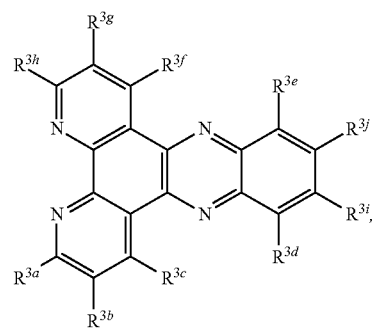
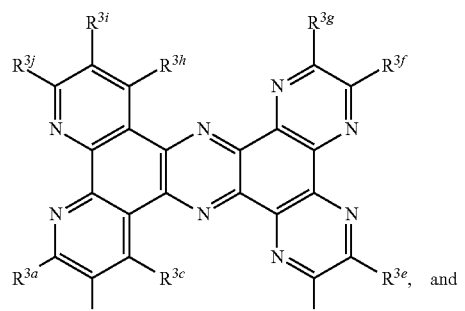
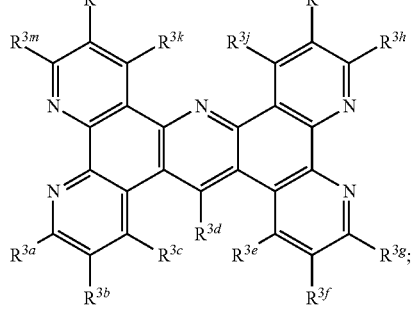
M at each occurrence is independently selected from the group consisting of manganese, molybdenum, rhenium, iron, ruthenium, osmium, cobalt, rhodium, iridium, nickel, platinum, and copper;
X and the R groups are as defined above;
t is an integer, and is preferably 1, 2, 3, 4, 5 or 6;
q=0, 1, 2, 3, 4 or 5.

The compound having the following structure is excluded from certain embodiments of the compounds of formula (V):

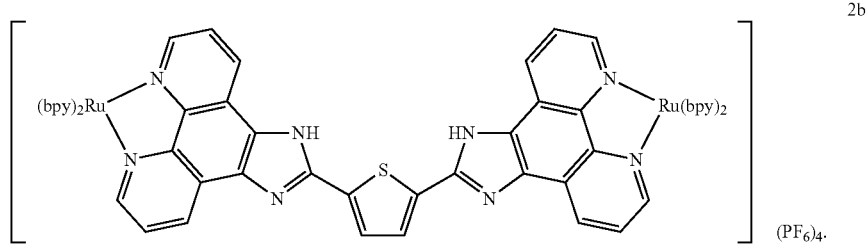

The present invention is also directed toward novel methods of use of compounds of the structure

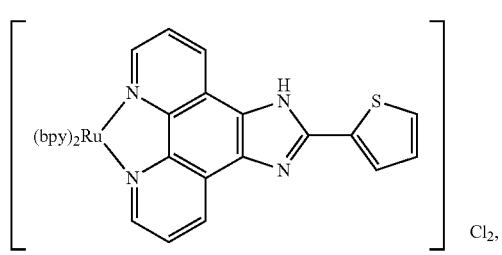

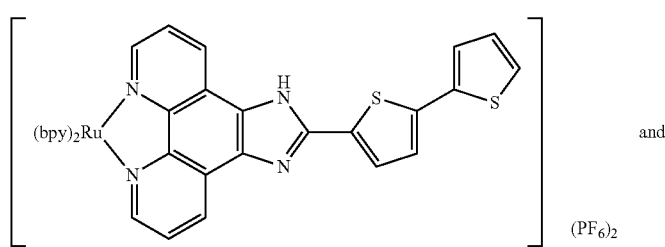

and

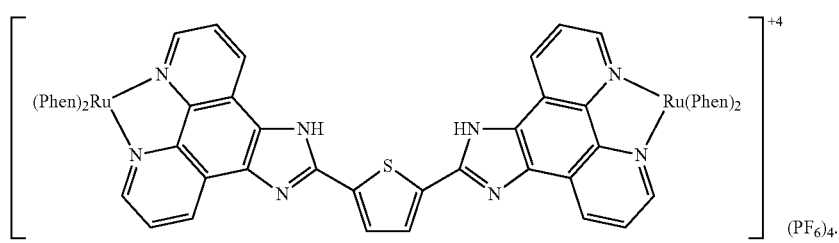

In certain embodiments, M is manganese molybdenum, rhenium, iron, ruthenium, osmium, cobalt, rhodium, iridium, nickel, platinum, or copper.

In certain embodiments, X is $Cl^-$, $PF_6^-$, $Br^-$, $BF_4^-$, $ClO_4^-$, $CF_3SO_3^-$, or $SO_4^{-2}$.

In certain embodiments, n is 0 or 1 or 2 or 3 or 4 or 5.
In certain embodiments, y is 1 or 2 or 3.

In certain embodiments, z is 0 or 1 or 2.
In certain embodiments, g is 0 or 1 or 2 or 3 or 4 or 5.
In certain embodiments, h is 0 or 1 or 2 or 3 or 4 or 5.
In certain embodiments, t is an integer.
In certain embodiments, t is 1 or 2 or 3 or 4 or 5 or 6.
In certain embodiments, q is 0 or 1 or 2 or 3 or 4 or 5.

In certain embodiments, Lig is

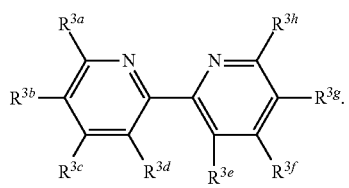

In certain embodiments, Lig is
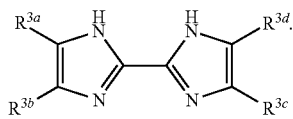
In certain embodiments, Lig is
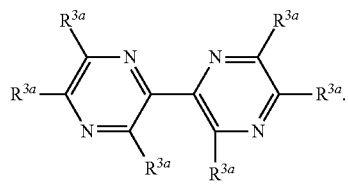
In certain embodiments, Lig is
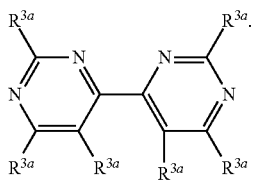
In certain embodiments, Lig is
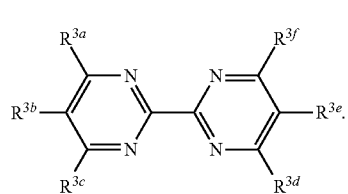
In certain embodiments, Lig is
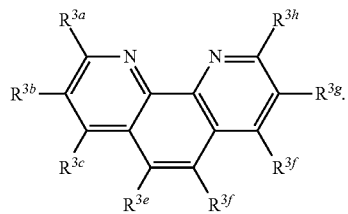
In certain embodiments, Lig is
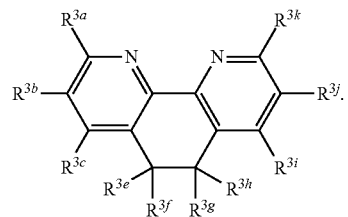
In certain embodiments, Lig is
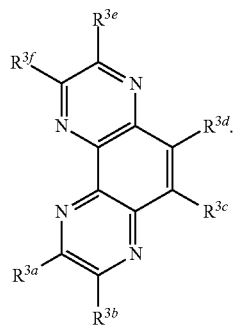
In certain embodiments, Lig is
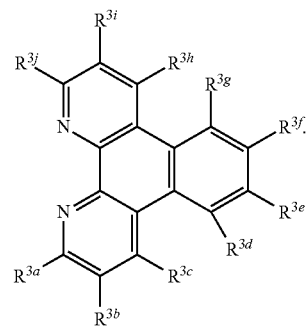
In certain embodiments, Lig is
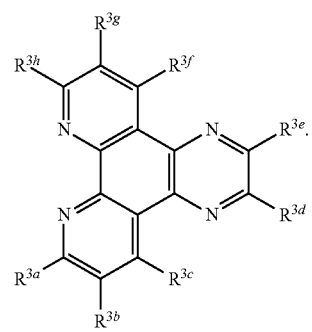
In certain embodiments, Lig is
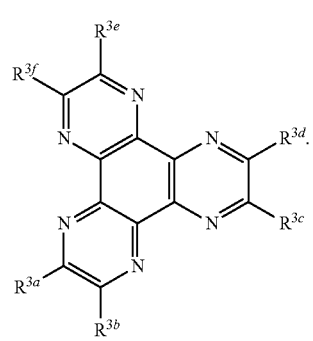

In certain embodiments, Lig is
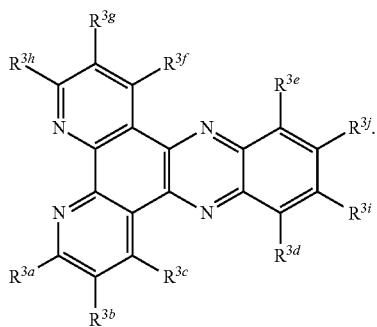
In certain embodiments, Lig is
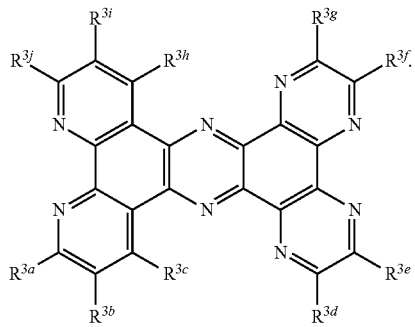
In certain embodiments, Lig is
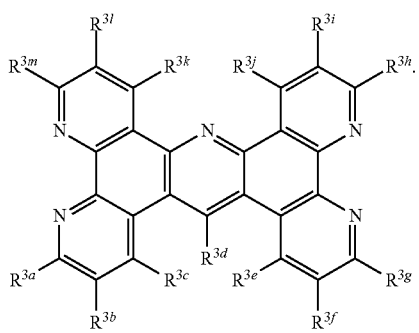
In certain embodiments, $R^1$ is
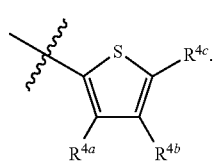
In certain embodiments, $R^1$ is
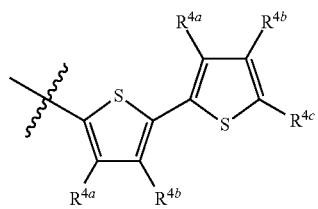
In certain embodiments, $R^1$ is
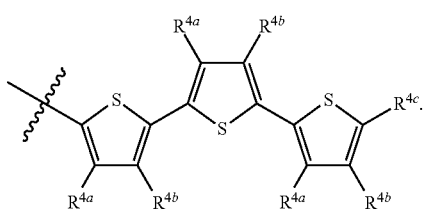
In certain embodiments, $R^1$ is
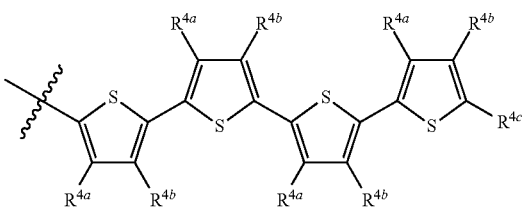
In certain embodiments, $R^1$ is
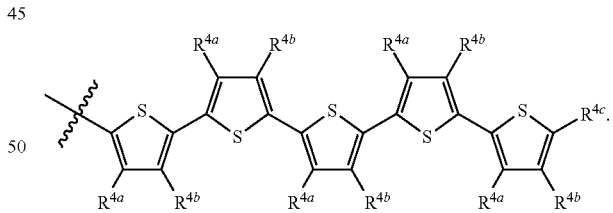
In certain embodiments, $R^1$ is
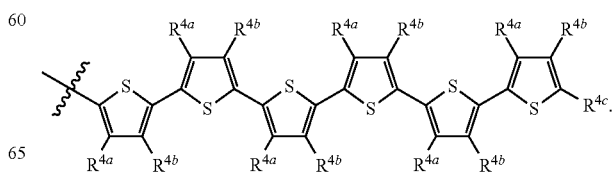

In certain embodiments, $R^1$ is

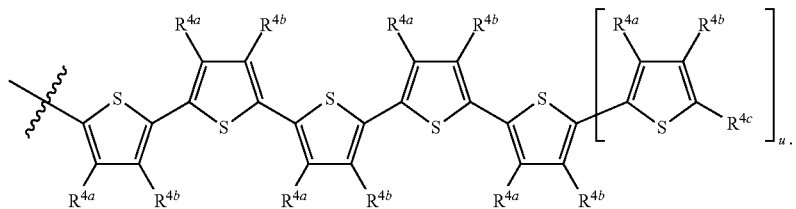

In certain embodiments, u is an integer, and in certain of these embodiments, is 1-1000 or 1-500 or 1-100 or 1-10, or is at least 2 or at least 3 or at least 4 or at least 5 or at least 10, or is any integer from 1-5 or 1-10 or 1-20, or any value up to the point where processability becomes problematic due to aggregation and/or insolubility.

In certain embodiments, $R^1$ is

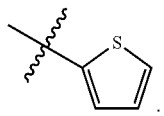

In certain embodiments, $R^1$ is

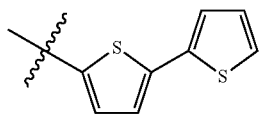

In certain embodiments, $R^1$ is

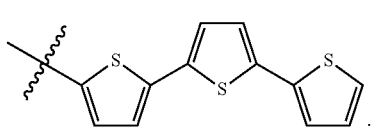 [SMILES: *c1ccc(-c2ccc(-c3cccs3)s2)s1]

In certain embodiments, $R^1$ is

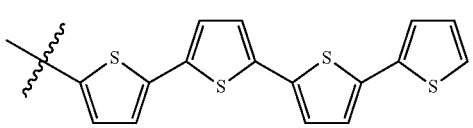

In certain embodiments, $R^1$ is

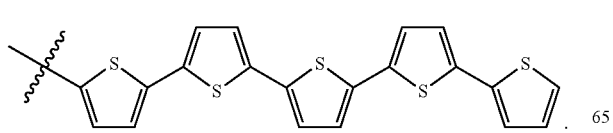

In certain embodiments, $R^1$ is

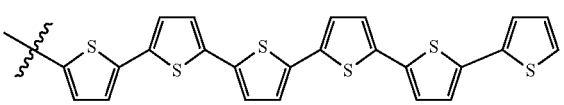

In certain embodiments, $R^1$ is

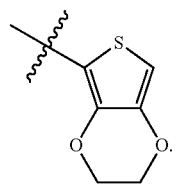 [SMILES: *c1scc2c1OCCO2]

In certain embodiments, $R^1$ is

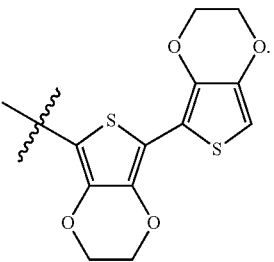 [SMILES: *c1sc(-c2scc3c2OCCO3)c2c1OCCO2]

In certain embodiments, $R^1$ is

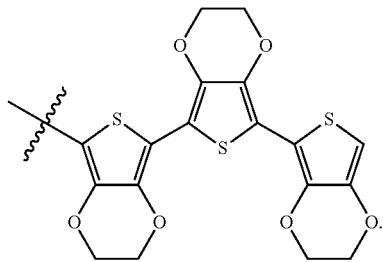 [SMILES: *c1sc(-c2sc(-c3scc4c3OCCO4)c3c2OCCO3)c2c1OCCO2]

In certain embodiments, $R^1$ is

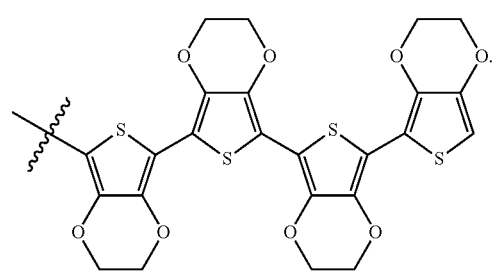 [SMILES: *c1sc(-c2sc(-c3sc(-c4scc5c4OCCO5)c4c3OCCO4)c3c2OCCO3)c2c1OCCO2]

In certain embodiments, $R^1$ is

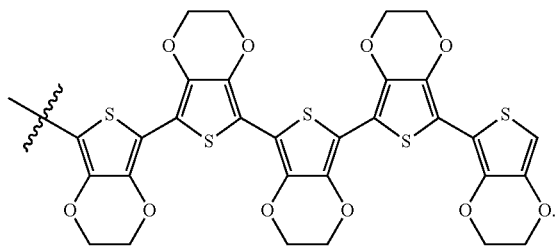 [SMILES: *c1sc(-c2sc(-c3sc(-c4sc(-c5scc6c5OCCO6)c5c4OCCO5)c4c3OCCO4)c3c2OCCO3)c2c1OCCO2]

In certain embodiments, $R^1$ is

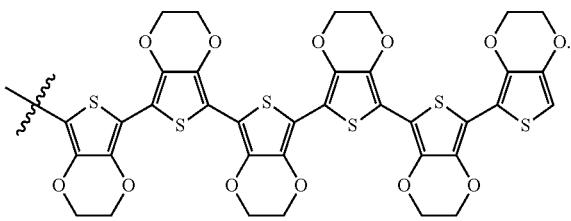 [SMILES: *c1sc(-c2sc(-c3sc(-c4sc(-c5sc(-c6scc7c6OCCO7)c6c5OCCO6)c5c4OCCO5)c4c3OCCO4)c3c2OCCO3)c2c1OCCO2]

In certain embodiments, $R^{2a}$ is hydrogen.
In certain embodiments, $R^{2a}$ is C1-6 optionally substituted alkyl.
In certain embodiments, $R^{2a}$ is C1-6 optionally substituted branched alkyl.
In certain embodiments, $R^{2a}$ is C3-7 optionally substituted cycloalkyl.
In certain embodiments, $R^{2a}$ is C1-6 optionally substituted haloalkyl.
In certain embodiments, $R^{2a}$ is C1-6 optionally substituted alkoxy.
In certain embodiments, $R^{2a}$ is $CO_2R^5$.
In certain embodiments, $R^{2b}$ is $CONR^6_2$.
In certain embodiments, $R^{2a}$ is $NR^7_2$.
In certain embodiments, $R^{2a}$ is sulfate.
In certain embodiments, $R^{2a}$ is sulfonate.
In certain embodiments, $R^{2a}$ is optionally substituted aryl.
In certain embodiments, $R^{2a}$ is optionally substituted aryloxy.
In certain embodiments, $R^{2a}$ is optionally substituted heteroaryl.
In certain embodiments, $R^{2a}$ is optionally substituted heterocycle.
In certain embodiments, $R^{2b}$ is hydrogen.
In certain embodiments, $R^{2b}$ is C1-6 optionally substituted alkyl.
In certain embodiments, $R^{2b}$ is C1-6 optionally substituted branched alkyl.
In certain embodiments, $R^{2b}$ is C3-7 optionally substituted cycloalkyl.
In certain embodiments, $R^{2b}$ is C1-6 optionally substituted haloalkyl.
In certain embodiments, $R^{2b}$ is C1-6 optionally substituted alkoxy.
In certain embodiments, $R^{2b}$ is $CO_2R^5$.
In certain embodiments, $R^{2b}$ is $CONR^6_2$.
In certain embodiments, $R^{2b}$ is $NR^7_2$.
In certain embodiments, $R^{2b}$ is sulfate.
In certain embodiments, $R^{2b}$ is sulfonate.
In certain embodiments, $R^{2b}$ is optionally substituted aryl.
In certain embodiments, $R^{2b}$ is optionally substituted aryloxy.
In certain embodiments, $R^{2b}$ is optionally substituted heteroaryl.
In certain embodiments, $R^{2a}$ is optionally substituted heterocycle.
In certain embodiments, $R^{2c}$ is hydrogen.
In certain embodiments, $R^{2c}$ is C1-6 optionally substituted alkyl.
In certain embodiments, $R^{2c}$ is C1-6 optionally substituted branched alkyl.
In certain embodiments, $R^{2c}$ is C3-7 optionally substituted cycloalkyl.
In certain embodiments, $R^{2c}$ is C1-6 optionally substituted haloalkyl.
In certain embodiments, $R^{2c}$ is C1-6 optionally substituted alkoxy.
In certain embodiments, $R^{2c}$ is $CO_2R^5$.
In certain embodiments, $R^{2c}$ is $CONR^6_2$.
In certain embodiments, $R^{2c}$ is $NR^7_2$.
In certain embodiments, $R^{2c}$ is sulfate.
In certain embodiments, $R^{2c}$ is sulfonate.
In certain embodiments, $R^{2c}$ is optionally substituted aryl.
In certain embodiments, $R^{2c}$ is optionally substituted aryloxy.
In certain embodiments, $R^{2c}$ is optionally substituted heteroaryl.
In certain embodiments, $R^{2c}$ is optionally substituted heterocycle.
In certain embodiments, $R^{2d}$ is hydrogen.
In certain embodiments, $R^{2d}$ is C1-6 optionally substituted alkyl.
In certain embodiments, $R^{2d}$ is C1-6 optionally substituted branched alkyl.
In certain embodiments, $R^{2d}$ is C3-7 optionally substituted cycloalkyl.
In certain embodiments, $R^{2d}$ is C1-6 optionally substituted haloalkyl.
In certain embodiments, $R^{2d}$ is C1-6 optionally substituted alkoxy.
In certain embodiments, $R^{2d}$ is $CO_2R^5$.
In certain embodiments, $R^{2d}$ is $CONR^6_2$.
In certain embodiments, $R^{2d}$ is $NR^7_2$.
In certain embodiments, $R^{2d}$ is sulfate.
In certain embodiments, $R^{2d}$ is sulfonate.
In certain embodiments, $R^{2d}$ is optionally substituted aryl.
In certain embodiments, $R^{2d}$ is optionally substituted aryloxy.
In certain embodiments, $R^{2d}$ is optionally substituted heteroaryl.
In certain embodiments, $R^{2d}$ is optionally substituted heterocycle.
In certain embodiments, $R^{2e}$ is hydrogen.
In certain embodiments, $R^{2e}$ is C1-6 optionally substituted alkyl.
In certain embodiments, $R^{2e}$ is C1-6 optionally substituted branched alkyl.
In certain embodiments, $R^{2e}$ is C3-7 optionally substituted cycloalkyl.
In certain embodiments, $R^{2e}$ is C1-6 optionally substituted haloalkyl.
In certain embodiments, $R^{2e}$ is C1-6 optionally substituted alkoxy.
In certain embodiments, $R^{2e}$ is $CO_2R^5$.
In certain embodiments, $R^{2e}$ is $CONR^6_2$.
In certain embodiments, $R^{2e}$ is $NR^7_2$.
In certain embodiments, $R^{2e}$ is sulfate.

In certain embodiments, $R^{2e}$ is sulfonate.
In certain embodiments, $R^{2e}$ is optionally substituted aryl.
In certain embodiments, $R^{2e}$ is optionally substituted aryloxy.
In certain embodiments, $R^{2e}$ is optionally substituted heteroaryl.
In certain embodiments, $R^{2e}$ is optionally substituted heterocycle.
In certain embodiments, $R^{2f}$ is hydrogen.
In certain embodiments, $R^{2f}$ is C1-6 optionally substituted alkyl.
In certain embodiments, $R^{2f}$ is C1-6 optionally substituted branched alkyl.
In certain embodiments, $R^{2f}$ is C3-7 optionally substituted cycloalkyl.
In certain embodiments, $R^{2f}$ is C1-6 optionally substituted haloalkyl.
In certain embodiments, $R^{2f}$ is C1-6 optionally substituted alkoxy.
In certain embodiments, $R^{2f}$ is $CO_2R^5$.
In certain embodiments, $R^{2f}$ is $CONR^6_2$.
In certain embodiments, $R^{2f}$ is $NR^7_2$.
In certain embodiments, $R^{2f}$ is sulfate.
In certain embodiments, $R^{2f}$ is sulfonate.
In certain embodiments, $R^{2f}$ is optionally substituted aryl.
In certain embodiments, $R^{2f}$ is optionally substituted aryloxy.
In certain embodiments, $R^{2f}$ is optionally substituted heteroaryl.
In certain embodiments, $R^{2f}$ is optionally substituted heterocycle.
In certain embodiments, $R^{3a}$ is hydrogen.
In certain embodiments, $R^{3a}$ is C1-6 optionally substituted alkyl.
In certain embodiments, $R^{3a}$ is C1-6 optionally substituted branched alkyl.
In certain embodiments, $R^{3a}$ is C1-6 optionally substituted haloalkyl.
In certain embodiments, $R^{3a}$ is C1-6 optionally substituted alkoxy.
In certain embodiments, $R^{3a}$ is $CO_2R^8$.
In certain embodiments, $R^{3b}$ is hydrogen.
In certain embodiments, $R^{3b}$ is C1-6 optionally substituted alkyl.
In certain embodiments, $R^{3b}$ is C1-6 optionally substituted branched alkyl.
In certain embodiments, $R^{3b}$ is C1-6 optionally substituted haloalkyl.
In certain embodiments, $R^{3b}$ is C1-6 optionally substituted alkoxy.
In certain embodiments, $R^{3b}$ is $CO_2R^8$.
In certain embodiments, $R^{3c}$ is hydrogen.
In certain embodiments, $R^{3c}$ is C1-6 optionally substituted alkyl.
In certain embodiments, $R^{3c}$ is C1-6 optionally substituted branched alkyl.
In certain embodiments, $R^{3c}$ is C1-6 optionally substituted haloalkyl.
In certain embodiments, $R^{3c}$ is C1-6 optionally substituted alkoxy.
In certain embodiments, $R^{3c}$ is $CO_2R^8$.
In certain embodiments, $R^{3d}$ is hydrogen.
In certain embodiments, $R^{3d}$ is C1-6 optionally substituted alkyl.
In certain embodiments, $R^{3d}$ is C1-6 optionally substituted branched alkyl.
In certain embodiments, $R^{3d}$ is C1-6 optionally substituted haloalkyl.
In certain embodiments, $R^{3d}$ is C1-6 optionally substituted alkoxy.
In certain embodiments, $R^{3d}$ is $CO_2R^8$.
In certain embodiments, $R^{3e}$ is hydrogen.
In certain embodiments, $R^{3e}$ is C1-6 optionally substituted alkyl.
In certain embodiments, $R^{3e}$ is C1-6 optionally substituted branched alkyl.
In certain embodiments, $R^{3e}$ is C1-6 optionally substituted haloalkyl.
In certain embodiments, $R^{3e}$ is C1-6 optionally substituted alkoxy.
In certain embodiments, $R^{3e}$ is $CO_2R^8$.
In certain embodiments, $R^{3f}$ is hydrogen.
In certain embodiments, $R^{3f}$ is C1-6 optionally substituted alkyl.
In certain embodiments, $R^{3f}$ is C1-6 optionally substituted branched alkyl.
In certain embodiments, $R^{3f}$ is C1-6 optionally substituted haloalkyl.
In certain embodiments, $R^{3f}$ C1-6 optionally substituted alkoxy.
In certain embodiments, $R^{3f}$ is $CO_2R^8$.
In certain embodiments, $R^{3g}$ is hydrogen.
In certain embodiments, $R^{3g}$ is C1-6 optionally substituted alkyl.
In certain embodiments, $R^{3g}$ is C1-6 optionally substituted branched alkyl.
In certain embodiments, $R^{3g}$ is C1-6 optionally substituted haloalkyl.
In certain embodiments, $R^{3g}$ is C1-6 optionally substituted alkoxy.
In certain embodiments, $R^{3g}$ is $CO_2R^8$.
In certain embodiments, $R^{3h}$ is hydrogen.
In certain embodiments, $R^{3h}$ is C1-6 optionally substituted alkyl.
In certain embodiments, $R^{3h}$ is C1-6 optionally substituted branched alkyl.
In certain embodiments, $R^{3h}$ is C1-6 optionally substituted haloalkyl
In certain embodiments, $R^{3h}$ is C1-6 optionally substituted alkoxy.
In certain embodiments, $R^{3h}$ is $CO_2R^8$.
In certain embodiments, $R^{3i}$ is hydrogen.
In certain embodiments, $R^{3i}$ is C1-6 optionally substituted alkyl.
In certain embodiments, $R^{3i}$ is C1-6 optionally substituted branched alkyl.
In certain embodiments, $R^{3i}$ is C1-6 optionally substituted haloalkyl.
In certain embodiments, $R^{3i}$ is C1-6 optionally substituted alkoxy.
In certain embodiments, $R^{3i}$ is $CO_2R^8$.
In certain embodiments, $R^{3i}$ is hydrogen.
In certain embodiments, $R^{3j}$ is C1-6 optionally substituted alkyl.
In certain embodiments, $R^{3j}$ is C1-6 optionally substituted branched alkyl.
In certain embodiments, $R^{3j}$ is C1-6 optionally substituted haloalkyl.
In certain embodiments, $R^{3j}$ is C1-6 optionally substituted alkoxy.
In certain embodiments, $R^{3j}$ is $CO_2R^8$.
In certain embodiments, $R^{3k}$ is hydrogen.

In certain embodiments, $R^{3k}$ is C1-6 optionally substituted alkyl.
In certain embodiments, $R^{3k}$ is C1-6 optionally substituted branched alkyl.
In certain embodiments, $R^{3k}$ is C1-6 optionally substituted haloalkyl.
In certain embodiments, $R^{3k}$ is C1-6 optionally substituted alkoxy.
In certain embodiments, $R^{3k}$ is $CO_2R^8$.
In certain embodiments, $R^{3l}$ is hydrogen.
In certain embodiments, $R^{3l}$ is C1-6 optionally substituted alkyl.
In certain embodiments, $R^{3l}$ is C1-6 optionally substituted branched alkyl.
In certain embodiments, $R^{3l}$ is C1-6 optionally substituted haloalkyl.
In certain embodiments, $R^{3l}$ is C1-6 optionally substituted alkoxy.
In certain embodiments, $R^{3l}$ is $CO_2R^8$.
In certain embodiments, $R^{3m}$ is hydrogen.
In certain embodiments, $R^{3m}$ is C1-6 optionally substituted alkyl.
In certain embodiments, $R^{3m}$ is C1-6 optionally substituted branched alkyl.
In certain embodiments, $R^{3m}$ is C1-6 optionally substituted haloalkyl.
In certain embodiments, $R^{3m}$ is C1-6 optionally substituted alkoxy.
In certain embodiments, $R^{3m}$ is $CO_2R^8$.
In certain embodiments, $R^{4a}$ is hydrogen.
In certain embodiments, $R^{4a}$ is C1-6 optionally substituted alkyl.
In certain embodiments, $R^{4a}$ is C1-6 optionally substituted branched alkyl.
In certain embodiments, $R^{4a}$ is C1-6 optionally substituted cycloalkyl.
In certain embodiments, $R^{4a}$ is C1-6 optionally substituted haloalkyl.
In certain embodiments, $R^{4a}$ is C1-6 optionally substituted alkoxy.
In certain embodiments, $R^{4a}$ is $CO_2R^5$.
In certain embodiments, $R^{4a}$ is $CONR^6_2$.
In certain embodiments, $R^{4a}$ is $NR^7_2$.
In certain embodiments, $R^{4a}$ is sulfate.
In certain embodiments, $R^{4a}$ is sulfonate.
In certain embodiments, $R^{4a}$ is optionally substituted aryl.
In certain embodiments, $R^{4a}$ is optionally substituted aryloxy.
In certain embodiments, $R^{4a}$ is optionally substituted heteroaryl.
In certain embodiments, $R^{4a}$ is optionally substituted heterocycle.
In certain embodiments, $R^{4b}$ is hydrogen.
In certain embodiments, $R^{4b}$ is C1-6 optionally substituted alkyl.
In certain embodiments, $R^{4b}$ is C1-6 optionally substituted branched alkyl.
In certain embodiments, $R^{4b}$ is C1-6 optionally substituted cycloalkyl.
In certain embodiments, $R^{4b}$ is C1-6 optionally substituted haloalkyl.
In certain embodiments, $R^{4b}$ is C1-6 optionally substituted alkoxy.
In certain embodiments, $R^{4b}$ is $CO_2R^5$.
In certain embodiments, $R^{4b}$ is $CONR^6_2$
In certain embodiments, $R^{4b}$ is $NR^7_2$.
In certain embodiments, $R^{4b}$ is sulfate.
In certain embodiments, $R^{4b}$ is sulfonate.
In certain embodiments, $R^{4b}$ is optionally substituted aryl.
In certain embodiments, $R^{4b}$ is optionally substituted aryloxy.
In certain embodiments, $R^{4b}$ is optionally substituted heteroaryl.
In certain embodiments, $R^{4b}$ is optionally substituted heterocycle.
In certain embodiments, $R^{4c}$ is hydrogen.
In certain embodiments, $R^{4c}$ is C1-6 optionally substituted alkyl.
In certain embodiments, $R^{4c}$ is C1-6 optionally substituted branched alkyl.
In certain embodiments, $R^{4c}$ is C1-6 optionally substituted cycloalkyl.
In certain embodiments, $R^{4c}$ is C1-6 optionally substituted haloalkyl.
In certain embodiments, $R^{4c}$ is C1-6 optionally substituted alkoxy.
In certain embodiments, $R^{4c}$ is $CO_2R^5$.
In certain embodiments, $R^{4c}$ is $CONR^6_2$
In certain embodiments, $R^{4c}$ is $NR^7_2$.
In certain embodiments, $R^{4c}$ is sulfate.
In certain embodiments, $R^{4c}$ is sulfonate.
In certain embodiments, $R^{4c}$ is optionally substituted aryl.
In certain embodiments, $R^{4c}$ is optionally substituted aryloxy.
In certain embodiments, $R^{4c}$ is optionally substituted heteroaryl.
In certain embodiments, $R^{4c}$ is optionally substituted heterocycle.
In certain embodiments, $R^{4a}$ and $R^{4b}$ are taken together with the atom to which they are bound to form an optionally substituted ring having from 6 ring atoms containing 2 oxygen atoms.
In certain embodiments, $R^5$ is hydrogen.
In certain embodiments, $R^5$ is optionally substituted alkyl.
In certain embodiments, $R^6$ is hydrogen.
In certain embodiments, $R^6$ is optionally substituted alkyl.
In certain embodiments, $R^7$ is hydrogen.
In certain embodiments, $R^7$ is optionally substituted alkyl.
In certain embodiments, $R^8$ is hydrogen.
In certain embodiments, $R^8$ is optionally substituted alkyl.
In certain embodiments, q is 0 or 1 or 2 or 3 or 4 or 5.
In certain embodiments, t is 1 or 2 or 3 or 4 or 5 or 6.
Exemplary embodiments include compounds having the formula (VI) or a pharmaceutically acceptable salt form thereof:

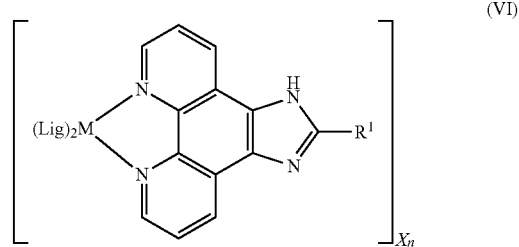

wherein non-limiting examples of M, Lig, and $R^1$ are defined herein below in Table 1.

TABLE 1

| Entry | M | Lig | R¹ | X | n |
|---|---|---|---|---|---|
| 1 | Ru | 2,2'-bipyridine | 2-thienyl | Cl | 2 |
| 2 | Ru | 2,2'-bipyridine | 2,2'-bithiophen-5-yl | Cl | 2 |
| 3 | Ru | 2,2'-bipyridine | 2,2':5',2''-terthiophen-5-yl | Cl | 2 |
| 4 | Ru | 2,2'-bipyridine | quaterthiophen-5-yl | Cl | 2 |
| 5 | Ru | 2,2'-bipyridine | quinquethiophen-5-yl | Cl | 2 |
| 6 | Ru | 2,2'-bipyridine | sexithiophen-5-yl | Cl | 2 |
| 7 | Ru | 2,2'-bipyridine | EDOT-yl | Cl | 2 |
| 8 | Ru | 2,2'-bipyridine | thiophene-bis(EDOT) | Cl | 2 |
| 9 | Ru | 2,2'-bipyridine | bis(EDOT)-thiophene extended | Cl | 2 |

TABLE 1-continued

| Entry | M | Lig | R¹ | X | n |
|---|---|---|---|---|---|
| 10 | Ru | 2,2'-bipyridine | tetrakis(EDOT) group | Cl | 2 |
| 11 | Ru | 2,2'-bipyridine | pentakis(EDOT) group | Cl | 2 |
| 12 | Ru | 2,2'-bipyridine | hexakis(EDOT) group | Cl | 2 |
| 13 | Ru | 6,6'-dimethyl-2,2'-bipyridine | thienyl | Cl | 2 |
| 14 | Ru | 6,6'-dimethyl-2,2'-bipyridine | bithienyl | Cl | 2 |
| 15 | Ru | 6,6'-dimethyl-2,2'-bipyridine | terthienyl | Cl | 2 |
| 16 | Ru | 6,6'-dimethyl-2,2'-bipyridine | quaterthienyl | Cl | 2 |
| 17 | Ru | 6,6'-dimethyl-2,2'-bipyridine | quinquethienyl | Cl | 2 |
| 18 | Ru | 6,6'-dimethyl-2,2'-bipyridine | sexithienyl | Cl | 2 |

TABLE 1-continued

| Entry | M | Lig | R¹ | X | n |
|---|---|---|---|---|---|
| 19 | Ru | 6,6'-dimethyl-2,2'-bipyridine | EDOT | Cl | 2 |
| 20 | Ru | 6,6'-dimethyl-2,2'-bipyridine | bi-EDOT | Cl | 2 |
| 21 | Ru | 6,6'-dimethyl-2,2'-bipyridine | ter-EDOT | Cl | 2 |
| 22 | Ru | 6,6'-dimethyl-2,2'-bipyridine | tetra-EDOT | Cl | 2 |
| 23 | Ru | 6,6'-dimethyl-2,2'-bipyridine | penta-EDOT | Cl | 2 |
| 24 | Ru | 6,6'-dimethyl-2,2'-bipyridine | hexa-EDOT | Cl | 2 |

TABLE 1-continued

| Entry | M | Lig | R¹ | X | n |
|---|---|---|---|---|---|
| 25 | Ru | 5,5'-dimethyl-2,2'-bipyridine | thiophen-2-yl | Cl | 2 |
| 26 | Ru | 5,5'-dimethyl-2,2'-bipyridine | 2,2'-bithiophen-5-yl | Cl | 2 |
| 27 | Ru | 5,5'-dimethyl-2,2'-bipyridine | 2,2':5',2''-terthiophen-5-yl | Cl | 2 |
| 28 | Ru | 5,5'-dimethyl-2,2'-bipyridine | quaterthiophen-5-yl | Cl | 2 |
| 29 | Ru | 5,5'-dimethyl-2,2'-bipyridine | quinquethiophen-5-yl | Cl | 2 |
| 30 | Ru | 5,5'-dimethyl-2,2'-bipyridine | sexithiophen-5-yl | Cl | 2 |
| 31 | Ru | 5,5'-dimethyl-2,2'-bipyridine | EDOT (3,4-ethylenedioxythiophen-2-yl) | Cl | 2 |
| 32 | Ru | 5,5'-dimethyl-2,2'-bipyridine | bi-EDOT | Cl | 2 |
| 33 | Ru | 5,5'-dimethyl-2,2'-bipyridine | ter-EDOT | Cl | 2 |

TABLE 1-continued
| Entry | M | Lig | R[1] | X | n |
|---|---|---|---|---|---|
| 34 | Ru |  | 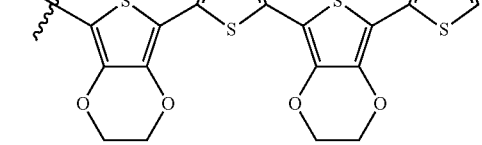 | Cl | 2 |
| 35 | Ru |  | 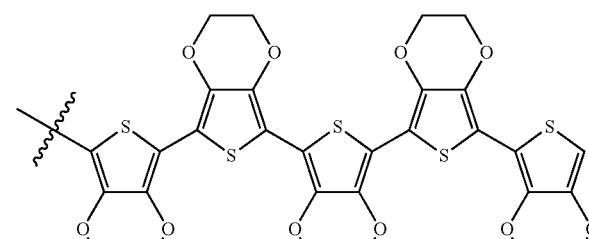 | Cl | 2 |
| 36 | Ru |  | 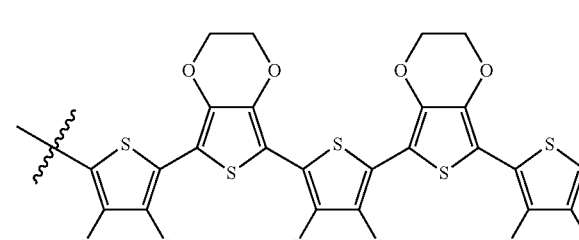 | Cl | 2 |
| 37 | Ru |  | 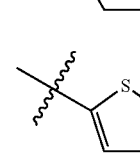 | Cl | 2 |
| 38 | Ru |  | 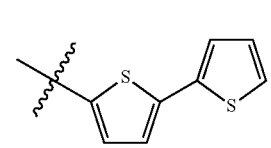 [SMILES: *c1ccc(-c2cccs2)s1] | Cl | 2 |
| 39 | Ru |  | 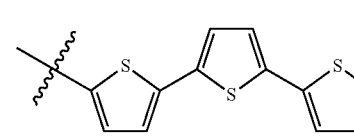 | Cl | 2 |
| 40 | Ru |  | 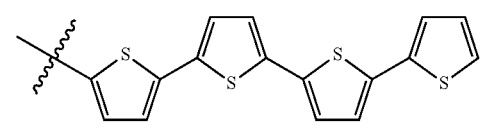 [SMILES: *c1ccc(-c2ccc(-c3ccc(-c4cccs4)s3)s2)s1] | Cl | 2 |
| 41 | Ru |  | 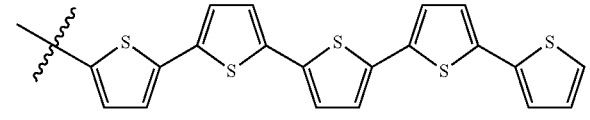 [SMILES: *c1ccc(-c2ccc(-c3ccc(-c4ccc(-c5cccs5)s4)s3)s2)s1] | Cl | 2 |

TABLE 1-continued

| Entry | M | Lig | R¹ | X | n |
|---|---|---|---|---|---|
| 42 | Ru | 4,4'-dimethyl-2,2'-bipyridine | sexithiophene | Cl | 2 |
| 43 | Ru | 4,4'-dimethyl-2,2'-bipyridine | EDOT | Cl | 2 |
| 44 | Ru | 4,4'-dimethyl-2,2'-bipyridine | bi(EDOT-thiophene) | Cl | 2 |
| 45 | Ru | 4,4'-dimethyl-2,2'-bipyridine | tri(EDOT-thiophene) | Cl | 2 |
| 46 | Ru | 4,4'-dimethyl-2,2'-bipyridine | tetra(EDOT-thiophene) | Cl | 2 |
| 47 | Ru | 4,4'-dimethyl-2,2'-bipyridine | penta(EDOT-thiophene) | Cl | 2 |

TABLE 1-continued

| Entry | M | Lig | R¹ | X | n |
|---|---|---|---|---|---|
| 48 | Ru | 4,4'-dimethyl-2,2'-bipyridine | EDOT-thiophene-EDOT-thiophene-EDOT pentamer | Cl | 2 |
| 49 | Ru | 3,3'-dimethyl-2,2'-bipyridine | thiophene | Cl | 2 |
| 50 | Ru | 3,3'-dimethyl-2,2'-bipyridine | bithiophene | Cl | 2 |
| 51 | Ru | 3,3'-dimethyl-2,2'-bipyridine | terthiophene | Cl | 2 |
| 52 | Ru | 3,3'-dimethyl-2,2'-bipyridine | quaterthiophene | Cl | 2 |
| 53 | Ru | 3,3'-dimethyl-2,2'-bipyridine | quinquethiophene | Cl | 2 |
| 54 | Ru | 3,3'-dimethyl-2,2'-bipyridine | sexithiophene | Cl | 2 |
| 55 | Ru | 3,3'-dimethyl-2,2'-bipyridine | EDOT | Cl | 2 |
| 56 | Ru | 3,3'-dimethyl-2,2'-bipyridine | EDOT-thiophene | Cl | 2 |

TABLE 1-continued

| Entry | M | Lig | R¹ | X | n |
|---|---|---|---|---|---|
| 57 | Ru | 3,3'-dimethyl-2,2'-bipyridine | EDOT-thiophene-EDOT trimer | Cl | 2 |
| 58 | Ru | 3,3'-dimethyl-2,2'-bipyridine | bis-EDOT-bithiophene tetramer | Cl | 2 |
| 59 | Ru | 3,3'-dimethyl-2,2'-bipyridine | EDOT-containing pentamer | Cl | 2 |
| 60 | Ru | 3,3'-dimethyl-2,2'-bipyridine | EDOT-containing hexamer | Cl | 2 |
| 61 | Ru | 4,4'-di-tert-butyl-2,2'-bipyridine | thiophene | Cl | 2 |
| 62 | Ru | 4,4'-di-tert-butyl-2,2'-bipyridine | bithiophene | Cl | 2 |
| 63 | Ru | 4,4'-di-tert-butyl-2,2'-bipyridine | terthiophene | Cl | 2 |

TABLE 1-continued

| Entry | M | Lig | R¹ | X | n |
|---|---|---|---|---|---|
| 64 | Ru | 4,4'-di-tert-butyl-2,2'-bipyridine | quaterthiophene | Cl | 2 |
| 65 | Ru | 4,4'-di-tert-butyl-2,2'-bipyridine | quinquethiophene | Cl | 2 |
| 66 | Ru | 4,4'-di-tert-butyl-2,2'-bipyridine | sexithiophene | Cl | 2 |
| 67 | Ru | 4,4'-di-tert-butyl-2,2'-bipyridine | EDOT | Cl | 2 |
| 68 | Ru | 4,4'-di-tert-butyl-2,2'-bipyridine | bi-EDOT | Cl | 2 |
| 69 | Ru | 4,4'-di-tert-butyl-2,2'-bipyridine | ter-EDOT | Cl | 2 |
| 70 | Ru | 4,4'-di-tert-butyl-2,2'-bipyridine | quater-EDOT | Cl | 2 |

TABLE 1-continued

| Entry | M | Lig | R¹ | X | n |
|---|---|---|---|---|---|
| 71 | Ru | 4,4'-di-tert-butyl-2,2'-bipyridine | terthiophene with three EDOT units | Cl | 2 |
| 72 | Ru | 4,4'-di-tert-butyl-2,2'-bipyridine | hexathiophene with EDOT units | Cl | 2 |
| 73 | Ru | 4,4'-dimethoxy-2,2'-bipyridine | thiophene | Cl | 2 |
| 74 | Ru | 4,4'-dimethoxy-2,2'-bipyridine | bithiophene | Cl | 2 |
| 75 | Ru | 4,4'-dimethoxy-2,2'-bipyridine | terthiophene | Cl | 2 |
| 76 | Ru | 4,4'-dimethoxy-2,2'-bipyridine | quaterthiophene | Cl | 2 |
| 77 | Ru | 4,4'-dimethoxy-2,2'-bipyridine | quinquethiophene | Cl | 2 |
| 78 | Ru | 4,4'-dimethoxy-2,2'-bipyridine | sexithiophene | Cl | 2 |

TABLE 1-continued

| Entry | M | Lig | R¹ | X | n |
|---|---|---|---|---|---|
| 79 | Ru | 4,4'-dimethoxy-2,2'-bipyridine | EDOT | Cl | 2 |
| 80 | Ru | 4,4'-dimethoxy-2,2'-bipyridine | bis-EDOT | Cl | 2 |
| 81 | Ru | 4,4'-dimethoxy-2,2'-bipyridine | ter-EDOT | Cl | 2 |
| 82 | Ru | 4,4'-dimethoxy-2,2'-bipyridine | tetra-EDOT | Cl | 2 |
| 83 | Ru | 4,4'-dimethoxy-2,2'-bipyridine | penta-EDOT | Cl | 2 |
| 84 | Ru | 4,4'-dimethoxy-2,2'-bipyridine | hexa-EDOT | Cl | 2 |

TABLE 1-continued

| Entry | M | Lig | R¹ | X | n |
|---|---|---|---|---|---|
| 85 | Ru | 4,4'-bis(methoxycarbonyl)-2,2'-bipyridine | thiophen-2-yl | Cl | 2 |
| 86 | Ru | 4,4'-bis(methoxycarbonyl)-2,2'-bipyridine | 2,2'-bithiophen-5-yl | Cl | 2 |
| 87 | Ru | 4,4'-bis(methoxycarbonyl)-2,2'-bipyridine | 2,2':5',2''-terthiophen-5-yl | Cl | 2 |
| 88 | Ru | 4,4'-bis(methoxycarbonyl)-2,2'-bipyridine | quaterthiophen-5-yl | Cl | 2 |
| 89 | Ru | 4,4'-bis(methoxycarbonyl)-2,2'-bipyridine | quinquethiophen-5-yl | Cl | 2 |
| 90 | Ru | 4,4'-bis(methoxycarbonyl)-2,2'-bipyridine | sexithiophen-5-yl | Cl | 2 |
| 91 | Ru | 4,4'-bis(methoxycarbonyl)-2,2'-bipyridine | 2,3-dihydrothieno[3,4-b][1,4]dioxin-5-yl (EDOT) | Cl | 2 |
| 92 | Ru | 4,4'-bis(methoxycarbonyl)-2,2'-bipyridine | bi-EDOT | Cl | 2 |

TABLE 1-continued
| Entry | M | Lig | R¹ | X | n |
|---|---|---|---|---|---|
| 93 | Ru |  |  | Cl | 2 |
| 94 | Ru |  |  | Cl | 2 |
| 95 | Ru |  | 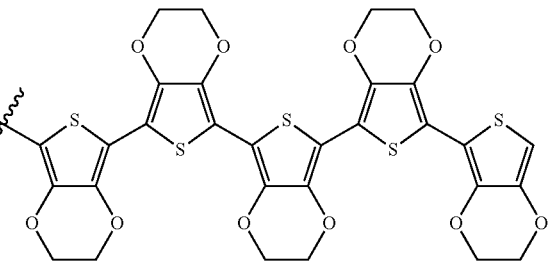 | Cl | 2 |
| 96 | Ru |  |  | Cl | 2 |
| 97 | Ru |  |  | Cl | 2 |
| 98 | Ru |  | 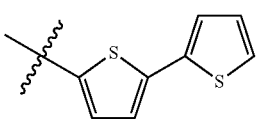 [SMILES: *c1ccc(-c2cccs2)s1] | Cl | 2 |
| 99 | Ru | 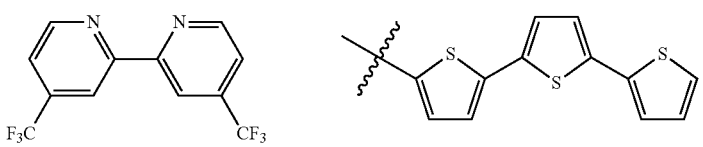 | 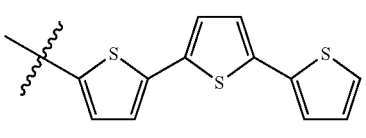 [SMILES: *c1ccc(-c2ccc(-c3cccs3)s2)s1] | Cl | 2 |

TABLE 1-continued
| Entry | M | Lig | R¹ | X | n |
|---|---|---|---|---|---|
| 100 | Ru | 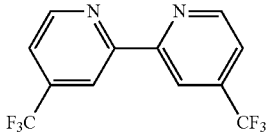 | 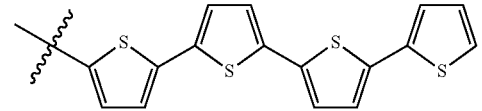 [SMILES: *c1ccc(-c2ccc(-c3ccc(-c4cccs4)s3)s2)s1] | Cl | 2 |
| 101 | Ru | 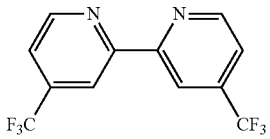 | 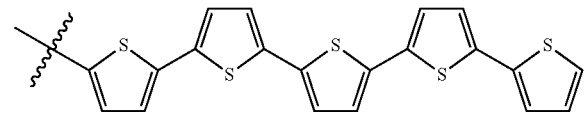 [SMILES: *c1ccc(-c2ccc(-c3ccc(-c4ccc(-c5cccs5)s4)s3)s2)s1] | Cl | 2 |
| 102 | Ru | 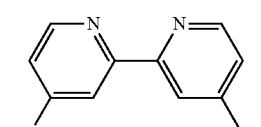 | 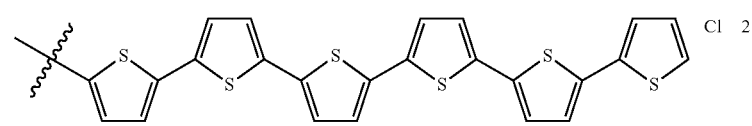 | Cl | 2 |
| 103 | Ru | 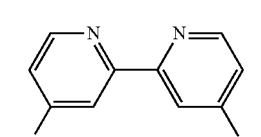 | 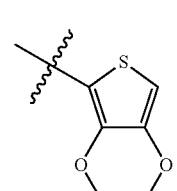 | Cl | 2 |
| 104 | Ru | 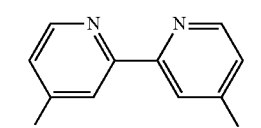 | 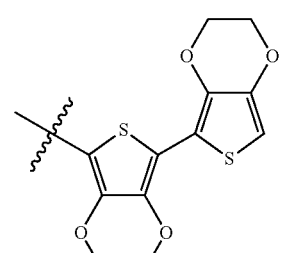 | Cl | 2 |
| 105 | Ru | 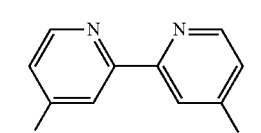 | 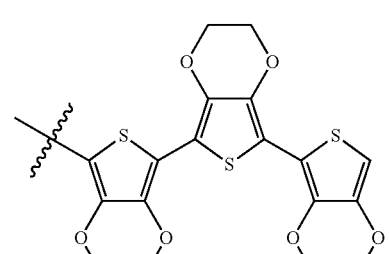 | Cl | 2 |
| 106 | Ru | 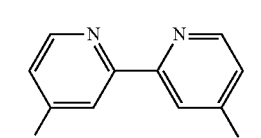 | 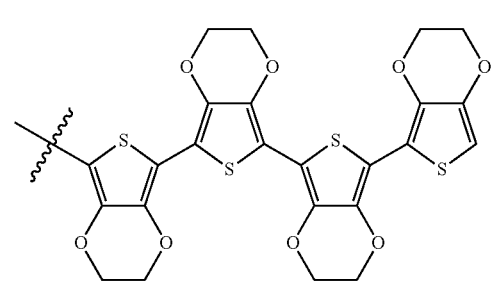 [SMILES: *c1sc(-c2sc(-c3sc(-c4scc5c4OCCO5)c4c3OCCO4)c3c2OCCO3)c2c1OCCO2] | Cl | 2 |

TABLE 1-continued
| Entry | M | Lig | R¹ | X | n |
|---|---|---|---|---|---|
| 107 | Ru | 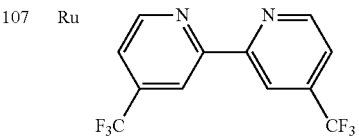 | 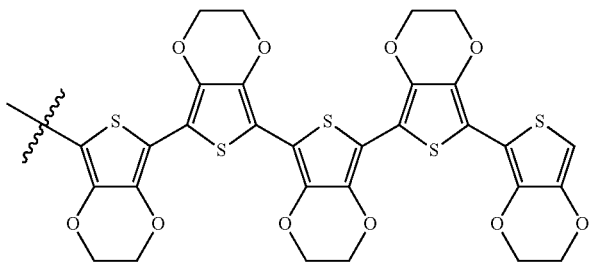 [SMILES: *c1sc(-c2sc(-c3sc(-c4sc(-c5scc6c5OCCO6)c5c4OCCO5)c4c3OCCO4)c3c2OCCO3)c2c1OCCO2] | Cl | 2 |
| 108 | Ru | 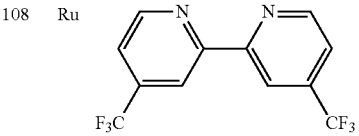 | 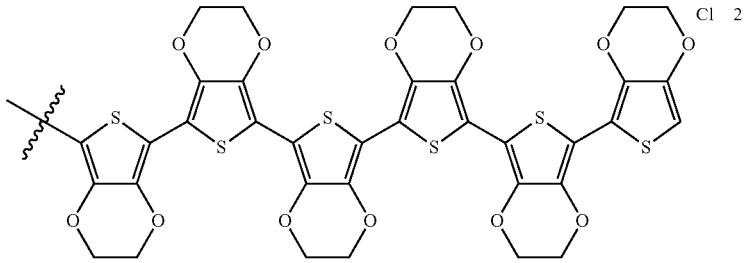 | Cl | 2 |
| 109 | Ru | 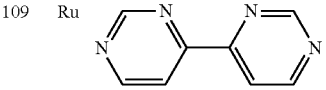 | 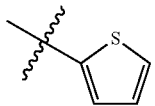 [SMILES: *c1cccs1] | Cl | 2 |
| 110 | Ru | 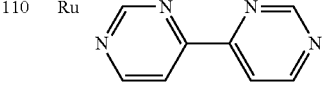 | 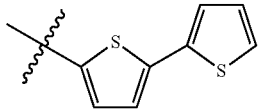 [SMILES: *c1ccc(-c2cccs2)s1] | Cl | 2 |
| 111 | Ru | 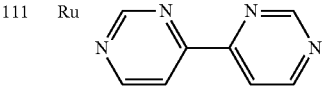 | 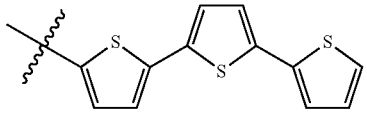 [SMILES: *c1ccc(-c2ccc(-c3cccs3)s2)s1] | Cl | 2 |
| 112 | Ru | 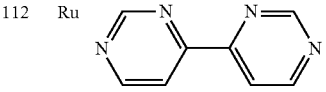 | 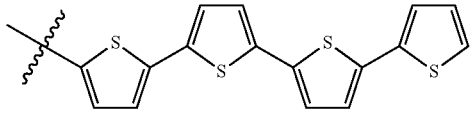 [SMILES: *c1ccc(-c2ccc(-c3ccc(-c4cccs4)s3)s2)s1] | Cl | 2 |
| 113 | Ru | 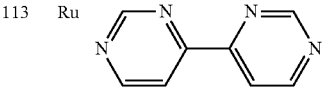 | 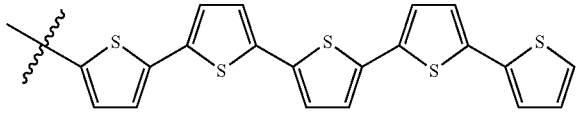 [SMILES: *c1ccc(-c2ccc(-c3ccc(-c4ccc(-c5cccs5)s4)s3)s2)s1] | Cl | 2 |
| 114 | Ru | 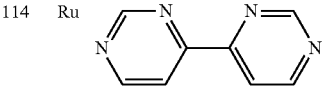 | 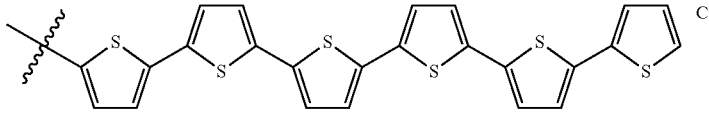 | Cl | 2 |
| 115 | Ru | 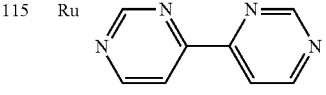 | 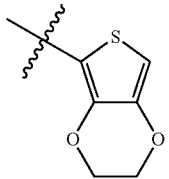 [SMILES: *c1scc2c1OCCO2] | Cl | 2 |

TABLE 1-continued

| Entry | M | Lig | R¹ | X | n |
|---|---|---|---|---|---|
| 116 | Ru | 4,4'-bipyrimidine | EDOT-thiophene-EDOT fragment | Cl | 2 |
| 117 | Ru | 4,4'-bipyrimidine | bis(EDOT)-thiophene fragment | Cl | 2 |
| 118 | Ru | 4,4'-bipyrimidine | tris-EDOT/thiophene oligomer | Cl | 2 |
| 119 | Ru | 4,4'-bipyrimidine | tetra-EDOT/thiophene oligomer | Cl | 2 |
| 120 | Ru | 4,4'-bipyrimidine | penta-EDOT/thiophene oligomer | Cl | 2 |
| 121 | Ru | 2,2'-bipyrazine | thiophene | Cl | 2 |
| 122 | Ru | 2,2'-bipyrazine | bithiophene | Cl | 2 |

TABLE 1-continued

| Entry | M | Lig | R¹ | X | n |
|---|---|---|---|---|---|
| 123 | Ru | 2,2'-bipyrazine | terthiophene | Cl | 2 |
| 124 | Ru | 2,2'-bipyrazine | quaterthiophene | Cl | 2 |
| 125 | Ru | 2,2'-bipyrazine | quinquethiophene | Cl | 2 |
| 126 | Ru | 2,2'-bipyrazine | sexithiophene | Cl | 2 |
| 127 | Ru | 2,2'-bipyrazine | EDOT | Cl | 2 |
| 128 | Ru | 2,2'-bipyrazine | bi-EDOT | Cl | 2 |
| 129 | Ru | 2,2'-bipyrazine | EDOT-thiophene-EDOT | Cl | 2 |
| 130 | Ru | 2,2'-bipyrazine | tetra(EDOT) | Cl | 2 |

TABLE 1-continued

| Entry | M | Lig | R¹ | X | n |
|---|---|---|---|---|---|
| 131 | Ru | 2,2'-bipyrazine | tetrakis(EDOT-thiophene) substituent | Cl | 2 |
| 132 | Ru | 2,2'-bipyrazine | pentakis(EDOT-thiophene) substituent | Cl | 2 |
| 133 | Ru | 1,10-phenanthroline | thiophene | Cl | 2 |
| 134 | Ru | 1,10-phenanthroline | bithiophene | Cl | 2 |
| 135 | Ru | 1,10-phenanthroline | terthiophene | Cl | 2 |
| 136 | Ru | 1,10-phenanthroline | quaterthiophene | Cl | 2 |
| 137 | Ru | 1,10-phenanthroline | quinquethiophene | Cl | 2 |
| 138 | Ru | 1,10-phenanthroline | sexithiophene | Cl | 2 |
| 139 | Ru | 1,10-phenanthroline | EDOT | Cl | 2 |

TABLE 1-continued
| Entry | M | Lig | R¹ | X | n |
|---|---|---|---|---|---|
| 140 | Ru | 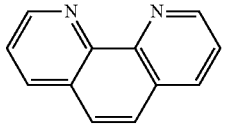 | 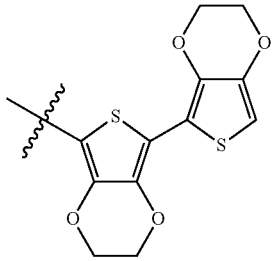 [SMILES: *c1sc(-c2scc3c2OCCO3)c2c1OCCO2] | Cl | 2 |
| 141 | Ru | 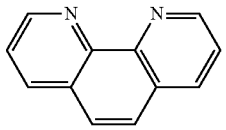 | 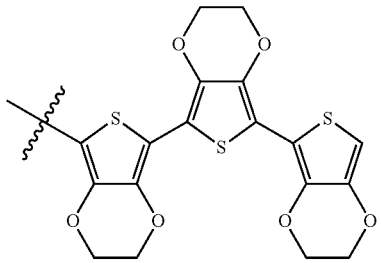 [SMILES: *c1sc(-c2sc(-c3scc4c3OCCO4)c3c2OCCO3)c2c1OCCO2] | Cl | 2 |
| 142 | Ru | 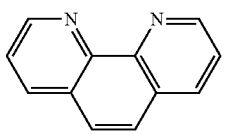 | 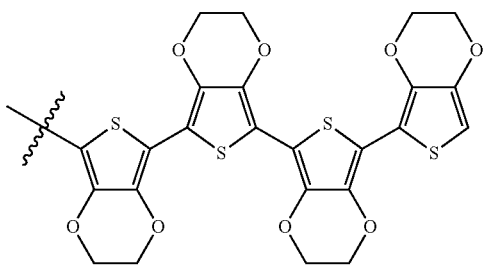 [SMILES: *c1sc(-c2sc(-c3sc(-c4scc5c4OCCO5)c4c3OCCO4)c3c2OCCO3)c2c1OCCO2] | Cl | 2 |
| 143 | Ru | 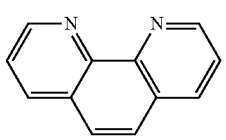 [SMILES: c1cnc2c(c1)ccc1cccnc12] | 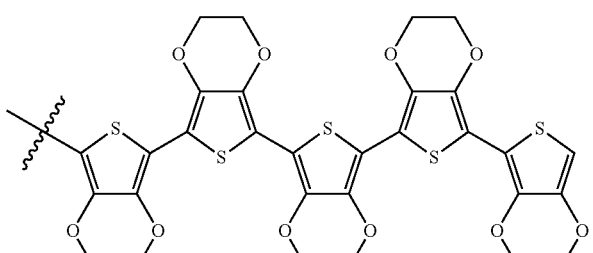 | Cl | 2 |
| 144 | Ru | 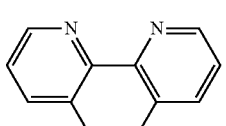 | 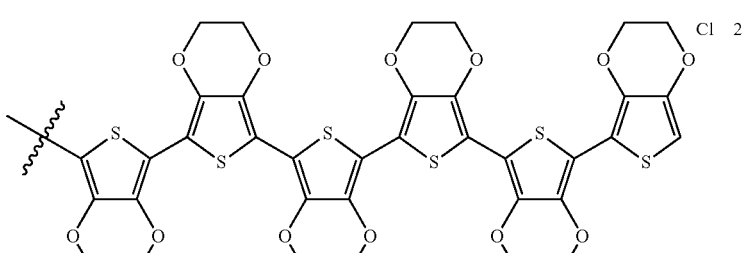 | Cl | 2 |
| 145 | Ru | 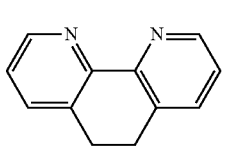 [SMILES: c1cnc2c(c1)CCc1cccnc1-2] | 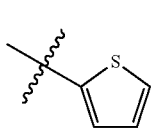 [SMILES: *c1cccs1] | Cl | 2 |

TABLE 1-continued

| Entry | M | Lig | R¹ | X | n |
|---|---|---|---|---|---|
| 146 | Ru | phenanthroline | bithiophene | Cl | 2 |
| 147 | Ru | phenanthroline | terthiophene | Cl | 2 |
| 148 | Ru | phenanthroline | quaterthiophene | Cl | 2 |
| 149 | Ru | phenanthroline | quinquethiophene | Cl | 2 |
| 150 | Ru | phenanthroline | sexithiophene | Cl | 2 |
| 151 | Ru | phenanthroline | EDOT | Cl | 2 |
| 152 | Ru | phenanthroline | bis-EDOT-thiophene | Cl | 2 |
| 153 | Ru | phenanthroline | tris-EDOT-thiophene | Cl | 2 |

TABLE 1-continued
| Entry | M | Lig | R¹ | X | n |
|---|---|---|---|---|---|
| 154 | Ru | 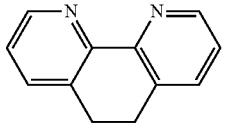 [SMILES: c1cnc2c(c1)CCc1cccnc1-2] | 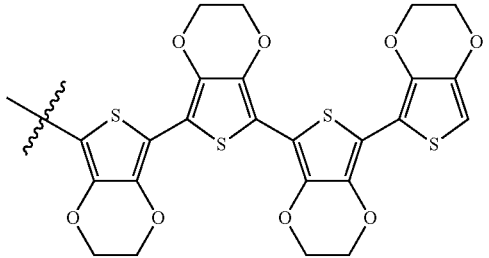 [SMILES: *c1sc(-c2sc(-c3sc(-c4scc5c4OCCO5)c4c3OCCO4)c3c2OCCO3)c2c1OCCO2] | Cl | 2 |
| 155 | Ru | 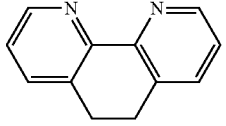 [SMILES: c1cnc2c(c1)CCc1cccnc1-2] | 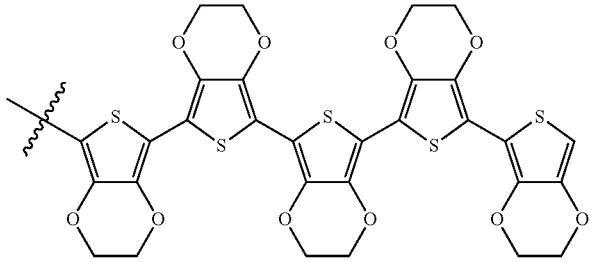 [SMILES: *c1sc(-c2sc(-c3sc(-c4sc(-c5scc6c5OCCO6)c5c4OCCO5)c4c3OCCO4)c3c2OCCO3)c2c1OCCO2] | Cl | 2 |
| 156 | Ru | 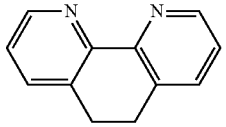 [SMILES: c1cnc2c(c1)CCc1cccnc1-2] | 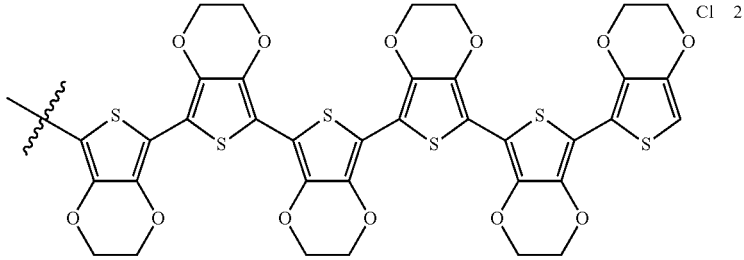 | Cl | 2 |
| 157 | Ru | 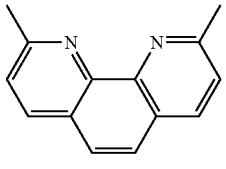 [SMILES: Cc1ccc2ccc3ccc(C)nc3c2n1] | 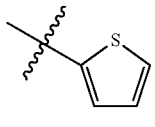 [SMILES: *c1cccs1] | Cl | 2 |
| 158 | Ru | 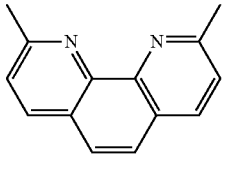 | 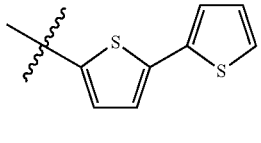 [SMILES: *c1ccc(-c2cccs2)s1] | Cl | 2 |
| 159 | Ru | 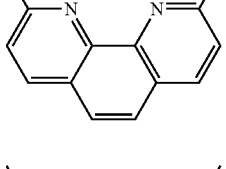 | 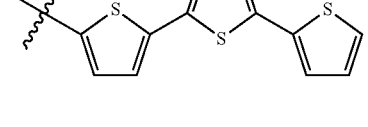 | Cl | 2 |
| 160 | Ru | 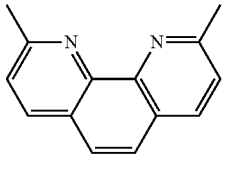 [SMILES: Cc1ccc2ccc3ccc(C)nc3c2n1] | 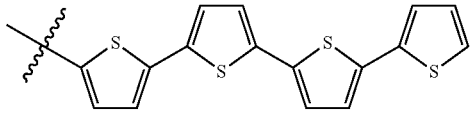 [SMILES: *c1ccc(-c2ccc(-c3ccc(-c4cccs4)s3)s2)s1] | Cl | 2 |

TABLE 1-continued

| Entry | M | Lig | R¹ | X | n |
|---|---|---|---|---|---|
| 161 | Ru | 2,9-dimethyl-phenanthroline | pentathiophene | Cl | 2 |
| 162 | Ru | 2,9-dimethyl-phenanthroline | hexathiophene | Cl | 2 |
| 163 | Ru | 2,9-dimethyl-phenanthroline | EDOT | Cl | 2 |
| 164 | Ru | 2,9-dimethyl-phenanthroline | bis-EDOT | Cl | 2 |
| 165 | Ru | 2,9-dimethyl-phenanthroline | tris-EDOT | Cl | 2 |
| 166 | Ru | 2,9-dimethyl-phenanthroline | tetra-EDOT | Cl | 2 |
| 167 | Ru | 2,9-dimethyl-phenanthroline | penta-EDOT | Cl | 2 |

TABLE 1-continued

| Entry | M | Lig | R¹ | X | n |
|---|---|---|---|---|---|
| 168 | Ru | 2,9-dimethyl-1,10-phenanthroline | penta(EDOT) | Cl | 2 |
| 169 | Ru | 3,8-dimethyl-1,10-phenanthroline | thienyl | Cl | 2 |
| 170 | Ru | 3,8-dimethyl-1,10-phenanthroline | bithienyl | Cl | 2 |
| 171 | Ru | 3,8-dimethyl-1,10-phenanthroline | terthienyl | Cl | 2 |
| 172 | Ru | 3,8-dimethyl-1,10-phenanthroline | quaterthienyl | Cl | 2 |
| 173 | Ru | 3,8-dimethyl-1,10-phenanthroline | quinquethienyl | Cl | 2 |
| 174 | Ru | 3,8-dimethyl-1,10-phenanthroline | sexithienyl | Cl | 2 |
| 175 | Ru | 3,8-dimethyl-1,10-phenanthroline | EDOT | Cl | 2 |
| 176 | Ru | 3,8-dimethyl-1,10-phenanthroline | bi(EDOT) | Cl | 2 |

TABLE 1-continued
| Entry | M | Lig | R¹ | X | n |
|---|---|---|---|---|---|
| 177 | Ru | 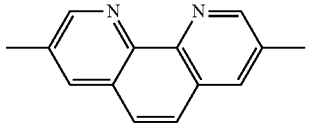 | 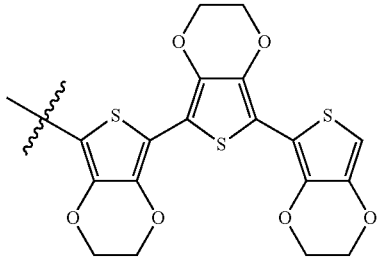 [SMILES: *c1sc(-c2sc(-c3scc4c3OCCO4)c3c2OCCO3)c2c1OCCO2] | Cl | 2 |
| 178 | Ru | 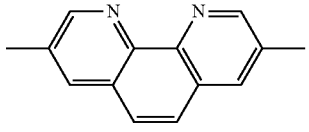 | 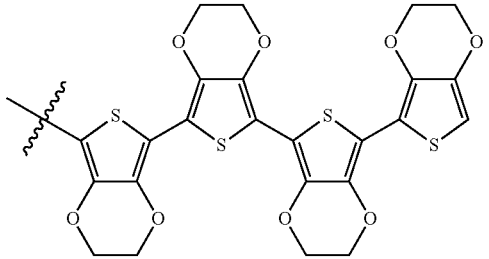 [SMILES: *c1sc(-c2sc(-c3sc(-c4scc5c4OCCO5)c4c3OCCO4)c3c2OCCO3)c2c1OCCO2] | Cl | 2 |
| 179 | Ru | 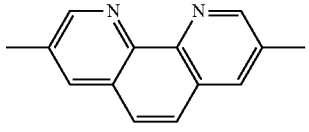 | 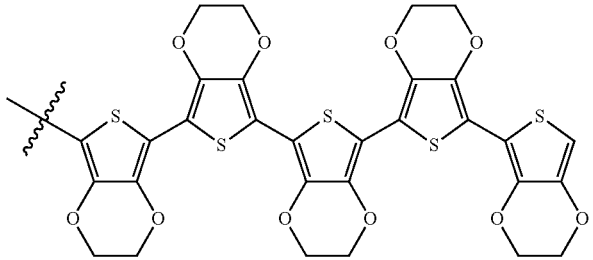 [SMILES: *c1sc(-c2sc(-c3sc(-c4sc(-c5scc6c5OCCO6)c5c4OCCO5)c4c3OCCO4)c3c2OCCO3)c2c1OCCO2] | Cl | 2 |
| 180 | Ru | 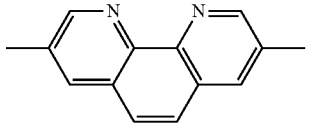 | 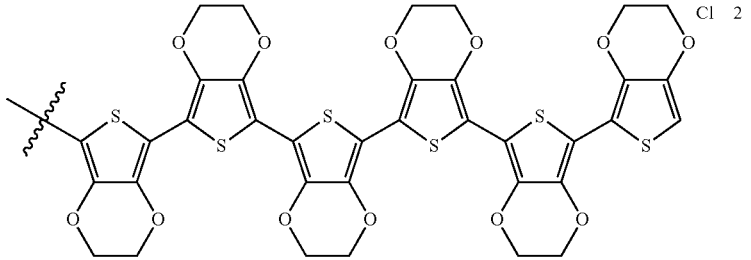 | Cl | 2 |
| 181 | Ru | 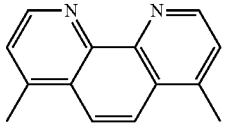 [SMILES: Cc1ccnc2c1ccc1c(C)ccnc12] | 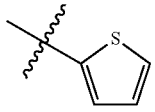 | Cl | 2 |
| 182 | Ru | 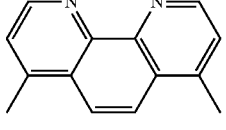 | 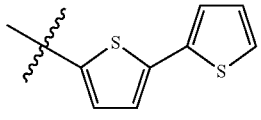 [SMILES: *c1ccc(-c2cccs2)s1] | Cl | 2 |
| 183 | Ru | 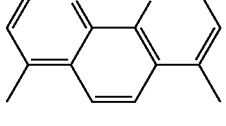 | 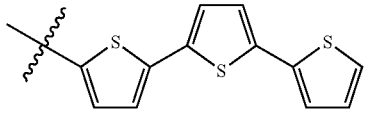 [SMILES: *c1ccc(-c2ccc(-c3cccs3)s2)s1] | Cl | 2 |

TABLE 1-continued

| Entry | M | Lig | R¹ | X | n |
|---|---|---|---|---|---|
| 184 | Ru | 4,7-dimethyl-1,10-phenanthroline | quaterthiophene | Cl | 2 |
| 185 | Ru | 4,7-dimethyl-1,10-phenanthroline | quinquethiophene | Cl | 2 |
| 186 | Ru | 4,7-dimethyl-1,10-phenanthroline | sexithiophene | Cl | 2 |
| 187 | Ru | 4,7-dimethyl-1,10-phenanthroline | EDOT | Cl | 2 |
| 188 | Ru | 4,7-dimethyl-1,10-phenanthroline | bi-EDOT | Cl | 2 |
| 189 | Ru | 4,7-dimethyl-1,10-phenanthroline | EDOT-thiophene-EDOT | Cl | 2 |
| 190 | Ru | 4,7-dimethyl-1,10-phenanthroline | bi-EDOT-bi-EDOT | Cl | 2 |

TABLE 1-continued

| Entry | M | Lig | R¹ | X | n |
|---|---|---|---|---|---|
| 191 | Ru | 4,7-dimethyl-1,10-phenanthroline | EDOT-thiophene-EDOT-thiophene-EDOT pentamer | Cl | 2 |
| 192 | Ru | 4,7-dimethyl-1,10-phenanthroline | EDOT-thiophene-EDOT-thiophene-EDOT-thiophene hexamer | Cl | 2 |
| 193 | Ru | 2,2'-bipyrimidine | thiophene | Cl | 2 |
| 194 | Ru | 2,2'-bipyrimidine | bithiophene | Cl | 2 |
| 195 | Ru | 2,2'-bipyrimidine | terthiophene | Cl | 2 |
| 196 | Ru | 2,2'-bipyrimidine | quaterthiophene | Cl | 2 |
| 197 | Ru | 2,2'-bipyrimidine | quinquethiophene | Cl | 2 |
| 198 | Ru | 2,2'-bipyrimidine | sexithiophene | Cl | 2 |
| 199 | Ru | 2,2'-bipyrimidine | EDOT | Cl | 2 |

TABLE 1-continued

| Entry | M | Lig | R¹ | X | n |
|---|---|---|---|---|---|
| 200 | Ru | 2,2'-bipyrimidine | EDOT-EDOT (bi-EDOT) | Cl | 2 |
| 201 | Ru | 2,2'-bipyrimidine | ter-EDOT | Cl | 2 |
| 202 | Ru | 2,2'-bipyrimidine | tetra-EDOT | Cl | 2 |
| 203 | Ru | 2,2'-bipyrimidine | penta-EDOT | Cl | 2 |
| 204 | Ru | 2,2'-bipyrimidine | hexa-EDOT | Cl | 2 |
| 205 | Ru | 2,2'-bipyridine | thiophene | PF₆ | 2 |
| 206 | Ru | 2,2'-bipyridine | bithiophene | PF₆ | 2 |

TABLE 1-continued

| Entry | M | Lig | R¹ | X | n |
|---|---|---|---|---|---|
| 207 | Ru | 2,2'-bipyridine | terthiophene | PF₆ | 2 |
| 208 | Ru | 2,2'-bipyridine | quaterthiophene | PF₆ | 2 |
| 209 | Ru | 2,2'-bipyridine | quinquethiophene | PF₆ | 2 |
| 210 | Ru | 2,2'-bipyridine | sexithiophene | PF₆ | 2 |
| 211 | Ru | 2,2'-bipyridine | EDOT | PF₆ | 2 |
| 212 | Ru | 2,2'-bipyridine | bi-EDOT | PF₆ | 2 |
| 213 | Ru | 2,2'-bipyridine | EDOT-thiophene-EDOT | PF₆ | 2 |
| 214 | Ru | 2,2'-bipyridine | EDOT-EDOT-EDOT-EDOT | PF₆ | 2 |

TABLE 1-continued

| Entry | M | Lig | R¹ | X | n |
|---|---|---|---|---|---|
| 215 | Ru | 2,2'-bipyridine | EDOT-thiophene-EDOT-thiophene-thiophene (structure) | PF₆ | 2 |
| 216 | Ru | 2,2'-bipyridine | EDOT-thiophene-EDOT-thiophene-EDOT-thiophene (structure) | PF₆ | 2 |
| 217 | Ru | 6,6'-dimethyl-2,2'-bipyridine | thiophene | PF₆ | 2 |
| 218 | Ru | 6,6'-dimethyl-2,2'-bipyridine | bithiophene | PF₆ | 2 |
| 219 | Ru | 6,6'-dimethyl-2,2'-bipyridine | terthiophene | PF₆ | 2 |
| 220 | Ru | 6,6'-dimethyl-2,2'-bipyridine | quaterthiophene | PF₆ | 2 |
| 221 | Ru | 6,6'-dimethyl-2,2'-bipyridine | quinquethiophene | PF₆ | 2 |
| 222 | Ru | 6,6'-dimethyl-2,2'-bipyridine | sexithiophene | PF₆ | 2 |
| 223 | Ru | 6,6'-dimethyl-2,2'-bipyridine | EDOT | PF₆ | 2 |

TABLE 1-continued
| Entry | M | Lig | R¹ | X | n |
|---|---|---|---|---|---|
| 224 | Ru | 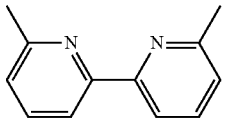 | 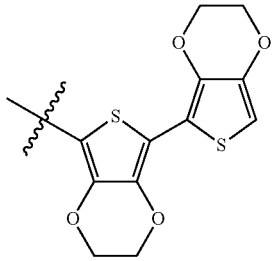 [SMILES: *c1sc(-c2scc3c2OCCO3)c2c1OCCO2] | PF$_6$ | 2 |
| 225 | Ru | 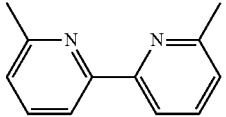 | 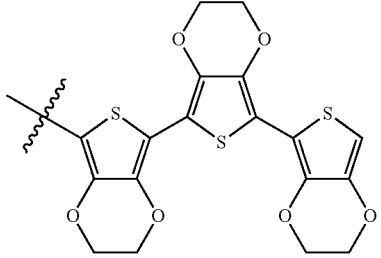 [SMILES: *c1sc(-c2sc(-c3scc4c3OCCO4)c3c2OCCO3)c2c1OCCO2] | PF$_6$ | 2 |
| 226 | Ru | 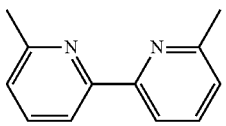 | 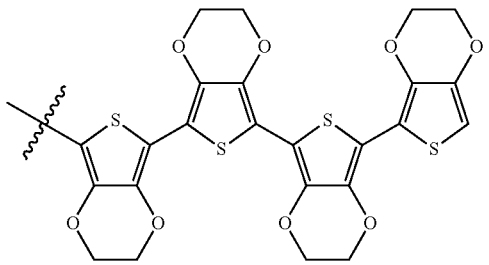 [SMILES: *c1sc(-c2sc(-c3sc(-c4scc5c4OCCO5)c4c3OCCO4)c3c2OCCO3)c2c1OCCO2] | PF$_6$ | 2 |
| 227 | Ru | 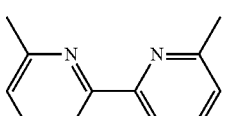 | 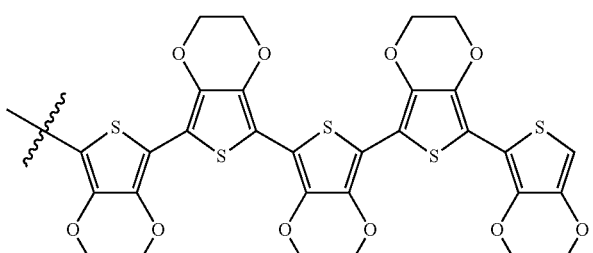 | PF$_6$ | 2 |
| 228 | Ru | 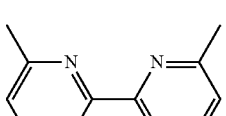 | 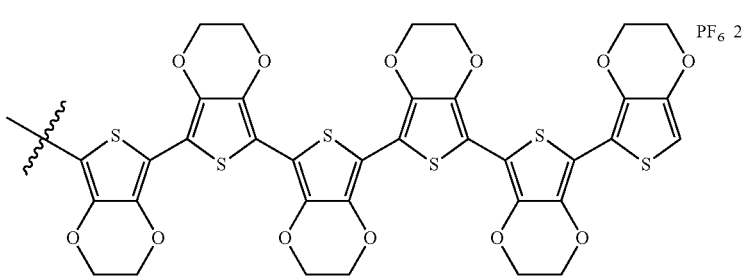 | PF$_6$ | 2 |
| 229 | Ru | 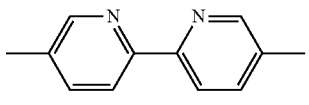 | 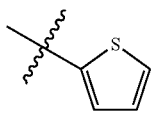 [SMILES: *c1cccs1] | PF$_6$ | 2 |
| 230 | Ru | 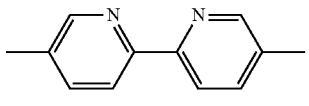 | 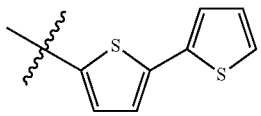 [SMILES: *c1ccc(-c2cccs2)s1] | PF$_6$ | 2 |

TABLE 1-continued

| Entry | M | Lig | R¹ | X | n |
|---|---|---|---|---|---|
| 231 | Ru | 5,5'-dimethyl-2,2'-bipyridine | terthiophene | PF₆ | 2 |
| 232 | Ru | 5,5'-dimethyl-2,2'-bipyridine | quaterthiophene | PF₆ | 2 |
| 233 | Ru | 5,5'-dimethyl-2,2'-bipyridine | quinquethiophene | PF₆ | 2 |
| 234 | Ru | 5,5'-dimethyl-2,2'-bipyridine | sexithiophene | PF₆ | 2 |
| 235 | Ru | 5,5'-dimethyl-2,2'-bipyridine | EDOT | PF₆ | 2 |
| 236 | Ru | 5,5'-dimethyl-2,2'-bipyridine | bis-EDOT | PF₆ | 2 |
| 237 | Ru | 5,5'-dimethyl-2,2'-bipyridine | EDOT-thiophene-EDOT | PF₆ | 2 |
| 238 | Ru | 5,5'-dimethyl-2,2'-bipyridine | tetra-EDOT | PF₆ | 2 |

TABLE 1-continued

| Entry | M | Lig | R¹ | X | n |
|---|---|---|---|---|---|
| 239 | Ru | 5,5'-dimethyl-2,2'-bipyridine | tris(EDOT)-bithiophene linker (5 thiophene units with EDOT groups) | PF₆ | 2 |
| 240 | Ru | 5,5'-dimethyl-2,2'-bipyridine | tris(EDOT)-terthiophene linker (6 thiophene units with EDOT groups) | PF₆ | 2 |
| 241 | Ru | 4,4'-dimethyl-2,2'-bipyridine | thiophene | PF₆ | 2 |
| 242 | Ru | 4,4'-dimethyl-2,2'-bipyridine | bithiophene | PF₆ | 2 |
| 243 | Ru | 4,4'-dimethyl-2,2'-bipyridine | terthiophene | PF₆ | 2 |
| 244 | Ru | 4,4'-dimethyl-2,2'-bipyridine | quaterthiophene | PF₆ | 2 |
| 245 | Ru | 4,4'-dimethyl-2,2'-bipyridine | quinquethiophene | PF₆ | 2 |
| 246 | Ru | 4,4'-dimethyl-2,2'-bipyridine | sexithiophene | PF₆ | 2 |
| 247 | Ru | 4,4'-dimethyl-2,2'-bipyridine | EDOT | PF₆ | 2 |

TABLE 1-continued

| Entry | M | Lig | R¹ | X | n |
|---|---|---|---|---|---|
| 248 | Ru | 4,4'-dimethyl-2,2'-bipyridine | bis(EDOT)-thiophene substituent | PF$_6$ | 2 |
| 249 | Ru | 4,4'-dimethyl-2,2'-bipyridine | EDOT-thiophene-EDOT-thiophene substituent | PF$_6$ | 2 |
| 250 | Ru | 4,4'-dimethyl-2,2'-bipyridine | tetrathiophene with EDOT substituents | PF$_6$ | 2 |
| 251 | Ru | 4,4'-dimethyl-2,2'-bipyridine | pentathiophene with EDOT substituents | PF$_6$ | 2 |
| 252 | Ru | 4,4'-dimethyl-2,2'-bipyridine | hexathiophene with EDOT substituents | PF$_6$ | 2 |
| 253 | Ru | 3,3'-dimethyl-2,2'-bipyridine | thiophene | PF$_6$ | 2 |

TABLE 1-continued

| Entry | M | Lig | R¹ | X | n |
|---|---|---|---|---|---|
| 254 | Ru | 3,3'-dimethyl-2,2'-bipyridine | bithiophene | PF$_6$ | 2 |
| 255 | Ru | 3,3'-dimethyl-2,2'-bipyridine | terthiophene | PF$_6$ | 2 |
| 256 | Ru | 3,3'-dimethyl-2,2'-bipyridine | quaterthiophene | PF$_6$ | 2 |
| 257 | Ru | 3,3'-dimethyl-2,2'-bipyridine | quinquethiophene | PF$_6$ | 2 |
| 258 | Ru | 3,3'-dimethyl-2,2'-bipyridine | sexithiophene | PF$_6$ | 2 |
| 259 | Ru | 3,3'-dimethyl-2,2'-bipyridine | EDOT | PF$_6$ | 2 |
| 260 | Ru | 3,3'-dimethyl-2,2'-bipyridine | bis-EDOT-thiophene | PF$_6$ | 2 |
| 261 | Ru | 3,3'-dimethyl-2,2'-bipyridine | EDOT-thiophene-EDOT | PF$_6$ | 2 |

TABLE 1-continued

| Entry | M | Lig | R¹ | X | n |
|---|---|---|---|---|---|
| 262 | Ru | 3,3'-dimethyl-2,2'-bipyridine | bis(EDOT)-bithiophene substituent | PF₆ | 2 |
| 263 | Ru | 3,3'-dimethyl-2,2'-bipyridine | tris(EDOT)-thiophene-EDOT substituent | PF₆ | 2 |
| 264 | Ru | 3,3'-dimethyl-2,2'-bipyridine | extended EDOT-thiophene oligomer | PF₆ | 2 |
| 265 | Ru | 4,4'-di-tert-butyl-2,2'-bipyridine | thien-2-yl | PF₆ | 2 |
| 266 | Ru | 4,4'-di-tert-butyl-2,2'-bipyridine | 2,2'-bithiophene | PF₆ | 2 |
| 267 | Ru | 4,4'-di-tert-butyl-2,2'-bipyridine | terthiophene | PF₆ | 2 |
| 268 | Ru | 4,4'-di-tert-butyl-2,2'-bipyridine | quaterthiophene | PF₆ | 2 |
| 269 | Ru | 4,4'-di-tert-butyl-2,2'-bipyridine | quinquethiophene | PF₆ | 2 |

TABLE 1-continued

| Entry | M | Lig | R¹ | X | n |
|---|---|---|---|---|---|
| 270 | Ru | 4,4'-di-tert-butyl-2,2'-bipyridine | septithiophene | PF$_6$ | 2 |
| 271 | Ru | 4,4'-di-tert-butyl-2,2'-bipyridine | 3,4-ethylenedioxythiophene (EDOT) | PF$_6$ | 2 |
| 272 | Ru | 4,4'-di-tert-butyl-2,2'-bipyridine | bi-EDOT | PF$_6$ | 2 |
| 273 | Ru | 4,4'-di-tert-butyl-2,2'-bipyridine | ter-EDOT | PF$_6$ | 2 |
| 274 | Ru | 4,4'-di-tert-butyl-2,2'-bipyridine | tetra-EDOT | PF$_6$ | 2 |
| 275 | Ru | 4,4'-di-tert-butyl-2,2'-bipyridine | penta-EDOT | PF$_6$ | 2 |

TABLE 1-continued
| Entry | M | Lig | R¹ | X | n |
|---|---|---|---|---|---|
| 276 | Ru | 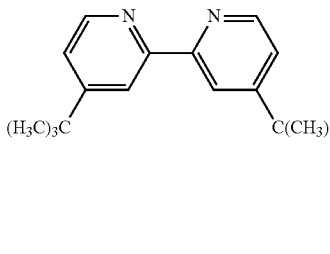 | 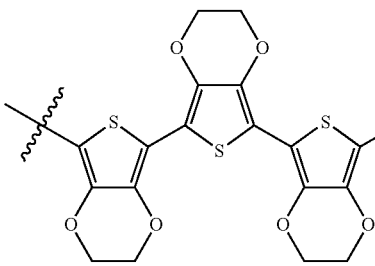 [SMILES: *c1sc(-c2sc(-c3scc4c3OCCO4)c3c2OCCO3)c2c1OCCO2] | PF$_6$ | 2 |
| 277 | Ru | 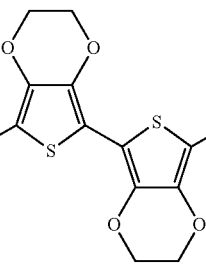 | 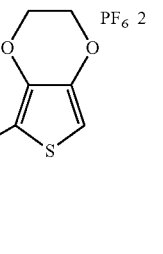 | PF$_6$ | 2 |
| 278 | Ru | 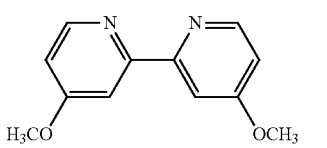 | 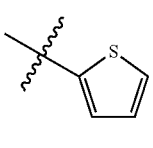 [SMILES: *c1cccs1] | PF$_6$ | 2 |
| 279 | Ru | 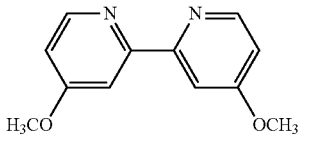 | 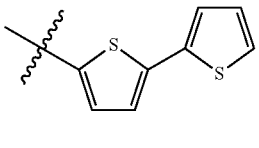 [SMILES: *c1ccc(-c2cccs2)s1] | PF$_6$ | 2 |
| 280 | Ru | 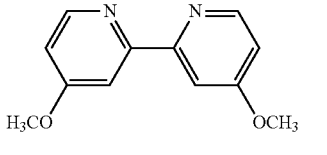 | 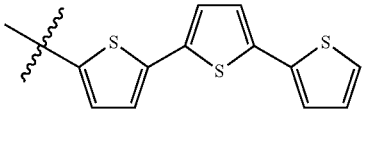 [SMILES: *c1ccc(-c2ccc(-c3cccs3)s2)s1] | PF$_6$ | 2 |
| 281 | Ru | 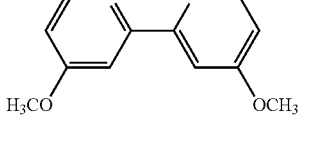 | 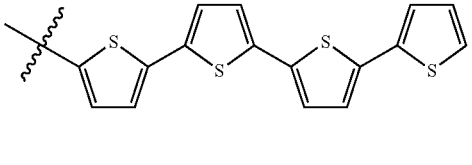 [SMILES: *c1ccc(-c2ccc(-c3ccc(-c4cccs4)s3)s2)s1] | PF$_6$ | 2 |
| 282 | Ru | 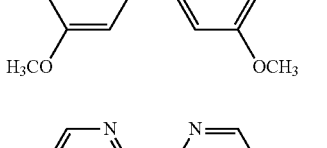 | 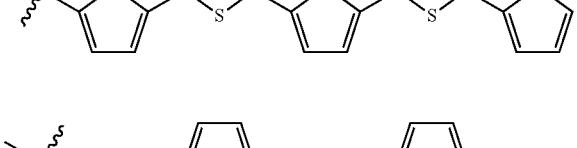 | PF$_6$ | 2 |
| 283 | Ru | 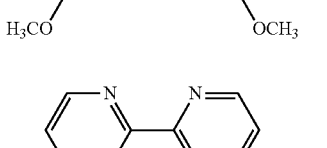 | 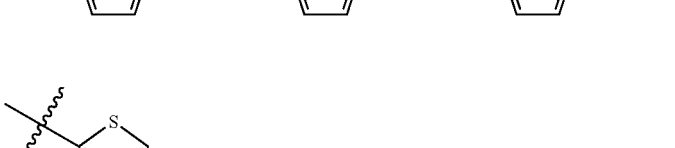 | PF$_6$ | 2 |

TABLE 1-continued

| Entry | M | Lig | R¹ | X | n |
|---|---|---|---|---|---|
| 284 | Ru | 4,4'-dimethoxy-2,2'-bipyridine | EDOT-thiophene-EDOT (bi-EDOT dimer) | PF$_6$ | 2 |
| 285 | Ru | 4,4'-dimethoxy-2,2'-bipyridine | ter(EDOT/thiophene) trimer | PF$_6$ | 2 |
| 286 | Ru | 4,4'-dimethoxy-2,2'-bipyridine | tetra(EDOT/thiophene) | PF$_6$ | 2 |
| 287 | Ru | 4,4'-dimethoxy-2,2'-bipyridine | penta(EDOT/thiophene) | PF$_6$ | 2 |
| 288 | Ru | 4,4'-dimethoxy-2,2'-bipyridine | hexa(EDOT/thiophene) | PF$_6$ | 2 |
| 289 | Ru | 4,4'-bis(methoxycarbonyl)-2,2'-bipyridine | thiophene | PF$_6$ | 2 |

TABLE 1-continued

| Entry | M | Lig | R¹ | X | n |
|---|---|---|---|---|---|
| 290 | Ru | 4,4'-bis(methoxycarbonyl)-2,2'-bipyridine | bithiophene | PF$_6$ | 2 |
| 291 | Ru | 4,4'-bis(methoxycarbonyl)-2,2'-bipyridine | terthiophene | PF$_6$ | 2 |
| 292 | Ru | 4,4'-bis(methoxycarbonyl)-2,2'-bipyridine | quaterthiophene | PF$_6$ | 2 |
| 293 | Ru | 4,4'-bis(methoxycarbonyl)-2,2'-bipyridine | quinquethiophene | PF$_6$ | 2 |
| 294 | Ru | 4,4'-bis(methoxycarbonyl)-2,2'-bipyridine | sexithiophene | PF$_6$ | 2 |
| 295 | Ru | 4,4'-bis(methoxycarbonyl)-2,2'-bipyridine | EDOT | PF$_6$ | 2 |
| 296 | Ru | 4,4'-bis(methoxycarbonyl)-2,2'-bipyridine | bis-EDOT | PF$_6$ | 2 |
| 297 | Ru | 4,4'-bis(methoxycarbonyl)-2,2'-bipyridine | tris-EDOT | PF$_6$ | 2 |

TABLE 1-continued
| Entry | M | Lig | R¹ | X | n |
|---|---|---|---|---|---|
| 298 | Ru | 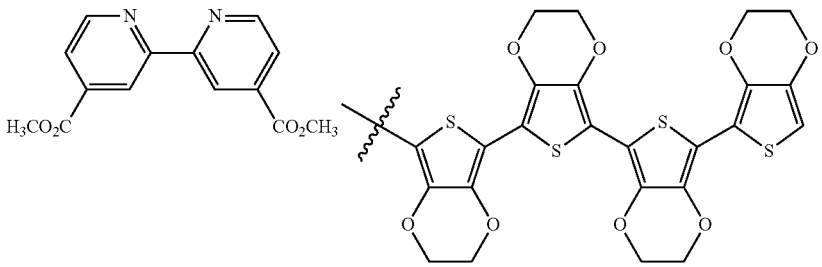 | 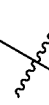 | PF$_6$ | 2 |
| 299 | Ru | 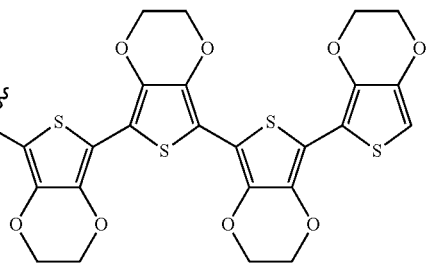 | 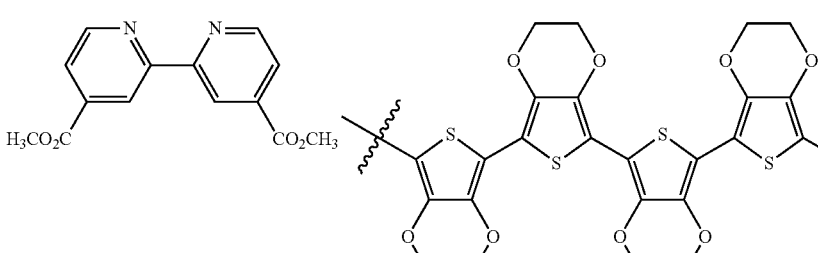 | PF$_6$ | 2 |
| 300 | Ru | 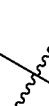 | 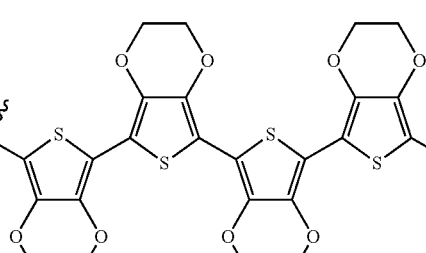 | PF$_6$ | 2 |
| 301 | Ru | 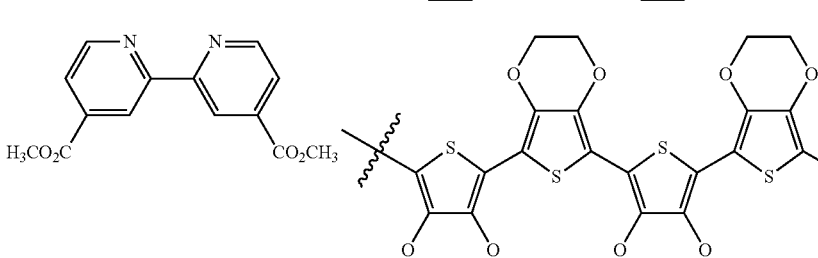 |  | PF$_6$ | 2 |
| 302 | Ru | 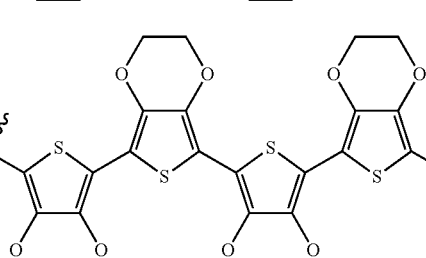 | 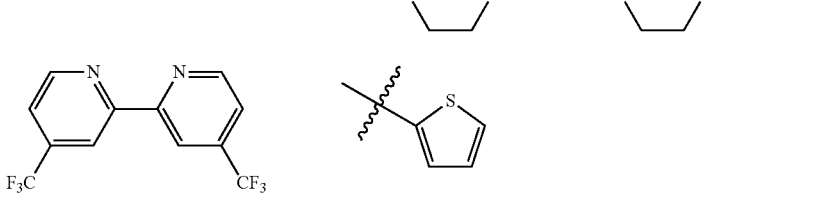 | PF$_6$ | 2 |
| 303 | Ru |  |  | PF$_6$ | 2 |
| 304 | Ru | 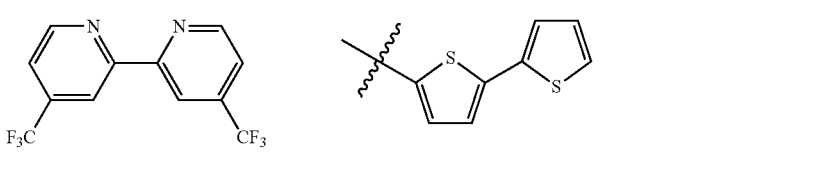 |  | PF$_6$ | 2 |
| 305 | Ru | 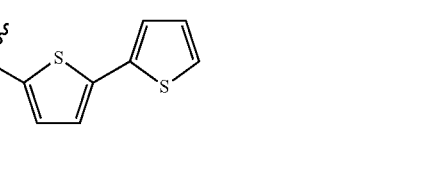 | 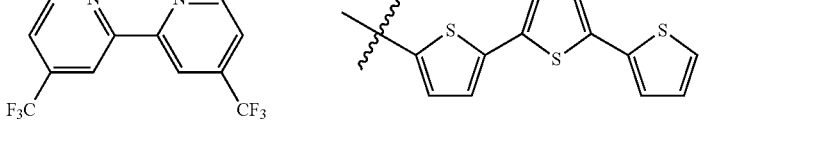 | PF$_6$ | 2 |

TABLE 1-continued
| Entry | M | Lig | R¹ | X | n |
|---|---|---|---|---|---|
| 306 | Ru | 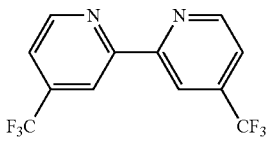 | 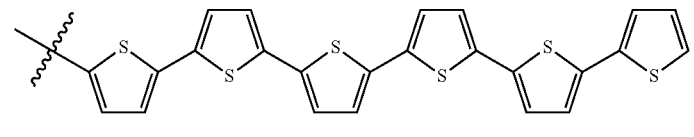 [SMILES: *c1ccc(-c2ccc(-c3ccc(-c4ccc(-c5ccc(-c6cccs6)s5)s4)s3)s2)s1] | PF$_6$ | 2 |
| 307 | Ru | 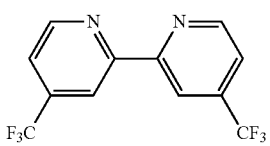 | 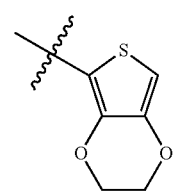 [SMILES: *c1scc2c1OCCO2] | PF$_6$ | 2 |
| 308 | Ru | 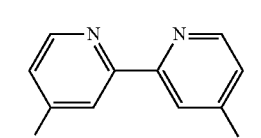 | 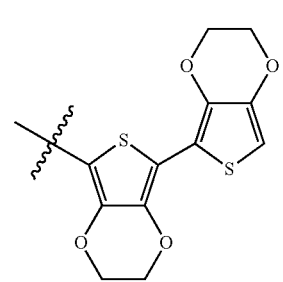 [SMILES: *c1sc(-c2scc3c2OCCO3)c2c1OCCO2] | PF$_6$ | 2 |
| 309 | Ru | 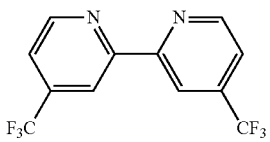 | 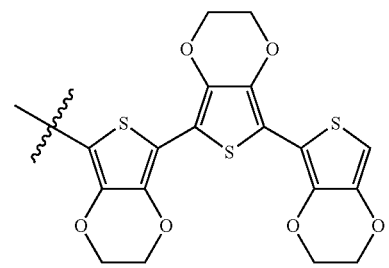 [SMILES: *c1sc(-c2sc(-c3scc4c3OCCO4)c3c2OCCO3)c2c1OCCO2] | PF$_6$ | 2 |
| 310 | Ru | 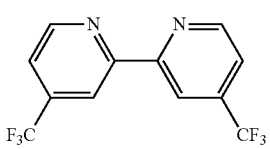 | 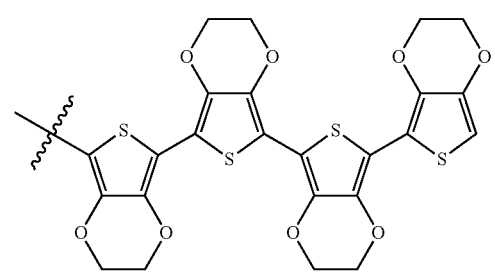 [SMILES: *c1sc(-c2sc(-c3sc(-c4scc5c4OCCO5)c4c3OCCO4)c3c2OCCO3)c2c1OCCO2] | PF$_6$ | 2 |
| 311 | Ru | 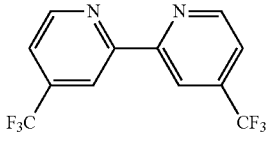 | 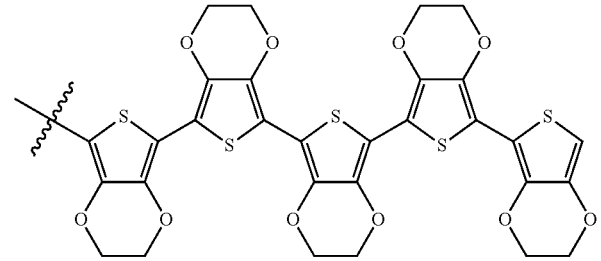 [SMILES: *c1sc(-c2sc(-c3sc(-c4sc(-c5scc6c5OCCO6)c5c4OCCO5)c4c3OCCO4)c3c2OCCO3)c2c1OCCO2] | PF$_6$ | 2 |

TABLE 1-continued
| Entry | M | Lig | R¹ | X | n |
|---|---|---|---|---|---|
| 312 | Ru | 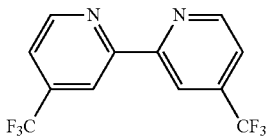 | 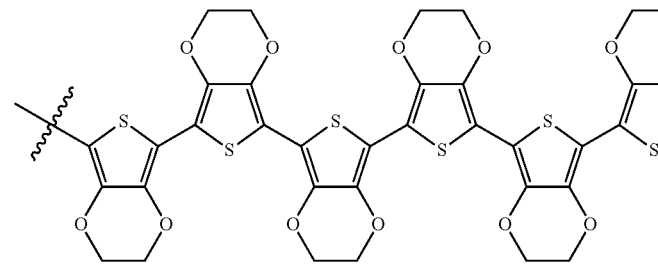 | PF$_6$ | 2 |
| 313 | Ru |  | 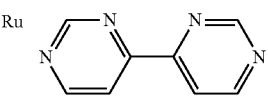 | PF$_6$ | 2 |
| 314 | Ru | 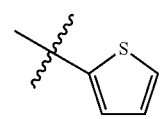 [SMILES: *c1cccs1] | 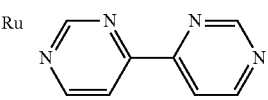 | PF$_6$ | 2 |
| 315 | Ru | 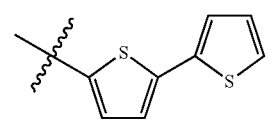 [SMILES: *c1ccc(-c2cccs2)s1] | 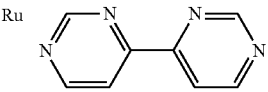 | PF$_6$ | 2 |
| 316 | Ru | 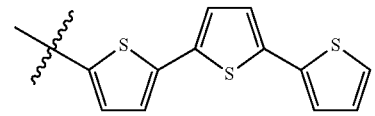 [SMILES: *c1ccc(-c2ccc(-c3cccs3)s2)s1] | 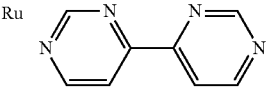 | PF$_6$ | 2 |
| 317 | Ru | 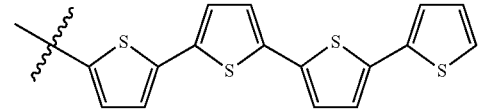 [SMILES: *c1ccc(-c2ccc(-c3ccc(-c4cccs4)s3)s2)s1] | 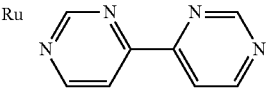 | PF$_6$ | 2 |
| 318 | Ru | 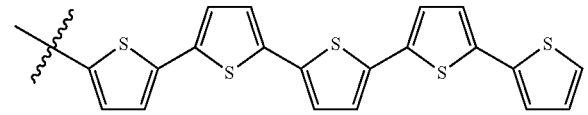 [SMILES: *c1ccc(-c2ccc(-c3ccc(-c4ccc(-c5cccs5)s4)s3)s2)s1] | 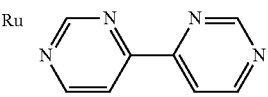 | PF$_6$ | 2 |
| 319 | Ru | 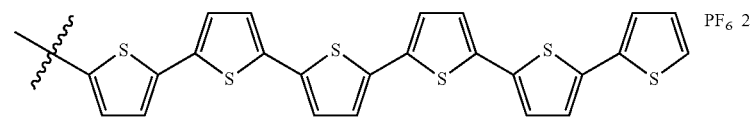 | 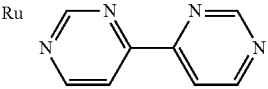 | PF$_6$ | 2 |
| 320 | Ru | 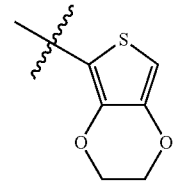 [SMILES: *c1scc2c1OCCO2] | 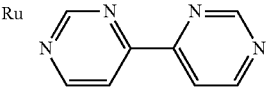 | PF$_6$ | 2 |

TABLE 1-continued

| Entry | M | Lig | R¹ | X | n |
|---|---|---|---|---|---|
| 321 | Ru | 4,4'-bipyrimidine | EDOT-thiophene-EDOT | PF₆ | 2 |
| 322 | Ru | 4,4'-bipyrimidine | (EDOT-thiophene)₂ | PF₆ | 2 |
| 323 | Ru | 4,4'-bipyrimidine | EDOT-thiophene-EDOT-thiophene-EDOT-thiophene | PF₆ | 2 |
| 324 | Ru | 4,4'-bipyrimidine | (EDOT-thiophene)₃-EDOT | PF₆ | 2 |
| 325 | Ru | 2,2'-bipyrazine | thiophene | PF₆ | 2 |
| 326 | Ru | 2,2'-bipyrazine | bithiophene | PF₆ | 2 |
| 327 | Ru | 2,2'-bipyrazine | terthiophene | PF₆ | 2 |
| 328 | Ru | 2,2'-bipyrazine | quaterthiophene | PF₆ | 2 |

TABLE 1-continued

| Entry | M | Lig | R¹ | X | n |
|-------|---|-----|-----|-----|---|
| 329 | Ru | 2,2'-bipyrazine | quinquethiophene | PF₆ | 2 |
| 330 | Ru | 2,2'-bipyrazine | sexithiophene | PF₆ | 2 |
| 331 | Ru | 2,2'-bipyrazine | EDOT | PF₆ | 2 |
| 332 | Ru | 2,2'-bipyrazine | bi-EDOT | PF₆ | 2 |
| 333 | Ru | 2,2'-bipyrazine | EDOT-thiophene-EDOT | PF₆ | 2 |
| 334 | Ru | 2,2'-bipyrazine | tetra(EDOT/thiophene) | PF₆ | 2 |
| 335 | Ru | 2,2'-bipyrazine | penta(EDOT/thiophene) | PF₆ | 2 |

TABLE 1-continued

| Entry | M | Lig | R¹ | X | n |
|---|---|---|---|---|---|
| 336 | Ru | 2,2'-bipyrazine | tetra(EDOT-thiophene) chain | PF₆ | 2 |
| 337 | Ru | 1,10-phenanthroline | thiophene | PF₆ | 2 |
| 338 | Ru | 1,10-phenanthroline | bithiophene | PF₆ | 2 |
| 339 | Ru | 1,10-phenanthroline | terthiophene | PF₆ | 2 |
| 340 | Ru | 1,10-phenanthroline | quaterthiophene | PF₆ | 2 |
| 341 | Ru | 1,10-phenanthroline | quinquethiophene | PF₆ | 2 |
| 342 | Ru | 1,10-phenanthroline | sexithiophene | PF₆ | 2 |
| 343 | Ru | 1,10-phenanthroline | EDOT | PF₆ | 2 |
| 344 | Ru | 1,10-phenanthroline | thiophene-EDOT | PF₆ | 2 |

TABLE 1-continued

| Entry | M | Lig | R¹ | X | n |
|---|---|---|---|---|---|
| 345 | Ru | phenanthroline | EDOT-thiophene-EDOT trimer | PF₆ | 2 |
| 346 | Ru | phenanthroline | EDOT-thiophene-thiophene-EDOT tetramer | PF₆ | 2 |
| 347 | Ru | phenanthroline | EDOT-EDOT-thiophene-EDOT-EDOT pentamer | PF₆ | 2 |
| 348 | Ru | phenanthroline | EDOT-EDOT-thiophene-EDOT-EDOT-EDOT hexamer | PF₆ | 2 |
| 349 | Ru | 5,6-dihydro-phenanthroline | thiophene | PF₆ | 2 |
| 350 | Ru | 5,6-dihydro-phenanthroline | bithiophene | PF₆ | 2 |
| 351 | Ru | 5,6-dihydro-phenanthroline | terthiophene | PF₆ | 2 |

TABLE 1-continued
| Entry | M | Lig | R¹ | X | n |
|---|---|---|---|---|---|
| 352 | Ru | 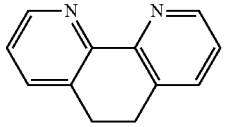 [SMILES: c1cnc2c(c1)CCc1cccnc1-2] | 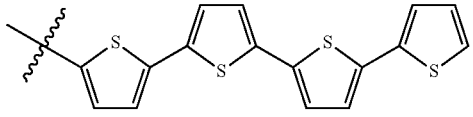 [SMILES: *c1ccc(-c2ccc(-c3ccc(-c4cccs4)s3)s2)s1] | PF$_6$ | 2 |
| 353 | Ru |  | 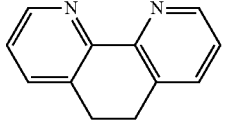 | PF$_6$ | 2 |
| 354 | Ru | 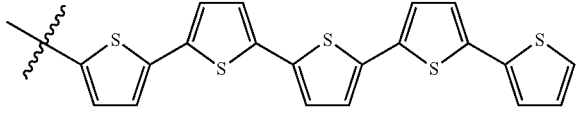 [SMILES: *c1ccc(-c2ccc(-c3ccc(-c4ccc(-c5cccs5)s4)s3)s2)s1] |  | PF$_6$ | 2 |
| 355 | Ru | 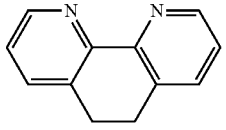 | 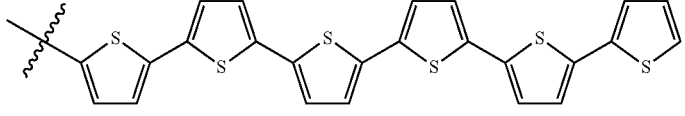 [SMILES: *c1ccc(-c2ccc(-c3ccc(-c4ccc(-c5ccc(-c6cccs6)s5)s4)s3)s2)s1] | PF$_6$ | 2 |
| 356 | Ru |  | 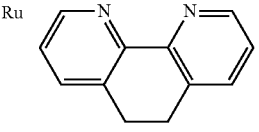 | PF$_6$ | 2 |
| 357 | Ru | 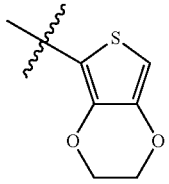 [SMILES: *c1scc2c1OCCO2] |  | PF$_6$ | 2 |
| 358 | Ru | 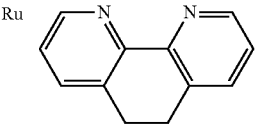 | 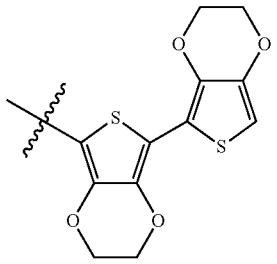 [SMILES: *c1sc(-c2scc3c2OCCO3)c2c1OCCO2] | PF$_6$ | 2 |

TABLE 1-continued

| Entry | M | Lig | R¹ | X | n |
|---|---|---|---|---|---|
| 359 | Ru | phenanthroline | EDOT-thiophene oligomer | PF$_6$ | 2 |
| 360 | Ru | phenanthroline | EDOT-thiophene oligomer (extended) | PF$_6$ | 2 |
| 361 | Ru | 2,9-dimethylphenanthroline | thiophene | PF$_6$ | 2 |
| 362 | Ru | 2,9-dimethylphenanthroline | bithiophene | PF$_6$ | 2 |
| 363 | Ru | 2,9-dimethylphenanthroline | terthiophene | PF$_6$ | 2 |
| 364 | Ru | 2,9-dimethylphenanthroline | quaterthiophene | PF$_6$ | 2 |
| 365 | Ru | 2,9-dimethylphenanthroline | quinquethiophene | PF$_6$ | 2 |
| 366 | Ru | 2,9-dimethylphenanthroline | sexithiophene | PF$_6$ | 2 |

TABLE 1-continued

| Entry | M | Lig | R¹ | X | n |
|---|---|---|---|---|---|
| 367 | Ru | (2,9-dimethyl-1,10-phenanthroline) | (EDOT-thiophene group) | PF₆ | 2 |
| 368 | Ru | (2,9-dimethyl-1,10-phenanthroline) | (bis-EDOT group) | PF₆ | 2 |
| 369 | Ru | (2,9-dimethyl-1,10-phenanthroline) | (tri-EDOT group) | PF₆ | 2 |
| 370 | Ru | (2,9-dimethyl-1,10-phenanthroline) | (tetra-EDOT group) | PF₆ | 2 |
| 371 | Ru | (2,9-dimethyl-1,10-phenanthroline) | (penta-EDOT group) | PF₆ | 2 |
| 372 | Ru | (2,9-dimethyl-1,10-phenanthroline) | (hexa-EDOT group) | PF₆ | 2 |

TABLE 1-continued
| Entry | M | Lig | R¹ | X | n |
|---|---|---|---|---|---|
| 373 | Ru | 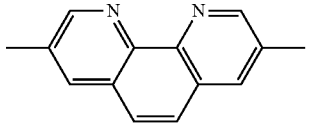 | 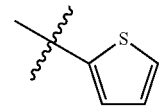 [SMILES: *c1cccs1] | PF₆ | 2 |
| 374 | Ru | 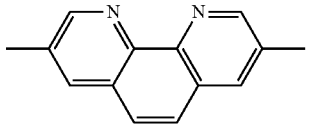 | 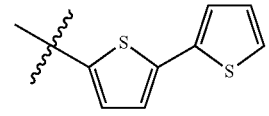 [SMILES: *c1ccc(-c2cccs2)s1] | PF₆ | 2 |
| 375 | Ru | 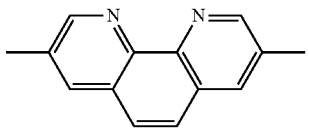 | 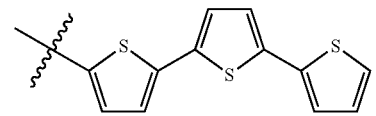 [SMILES: *c1ccc(-c2ccc(-c3cccs3)s2)s1] | PF₆ | 2 |
| 376 | Ru | 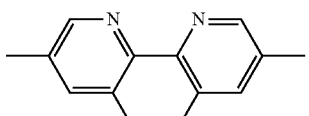 | 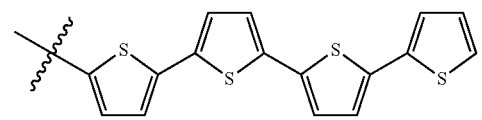 [SMILES: *c1ccc(-c2ccc(-c3ccc(-c4cccs4)s3)s2)s1] | PF₆ | 2 |
| 377 | Ru | 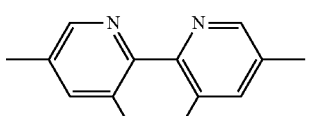 | 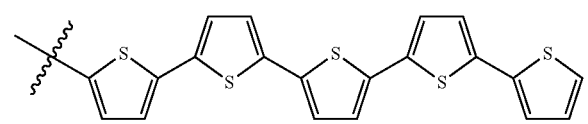 [SMILES: *c1ccc(-c2ccc(-c3ccc(-c4ccc(-c5cccs5)s4)s3)s2)s1] | PF₆ | 2 |
| 378 | Ru | 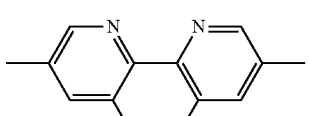 | 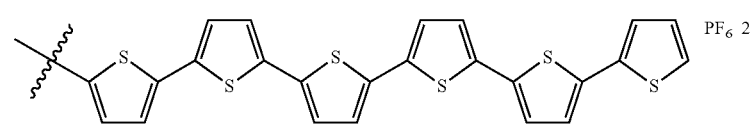 | PF₆ | 2 |
| 379 | Ru | 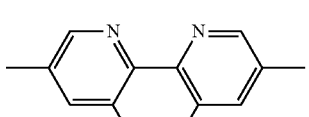 | 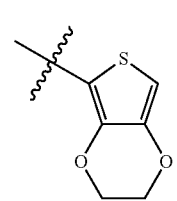 [SMILES: *c1scc2c1OCCO2] | PF₆ | 2 |
| 380 | Ru | 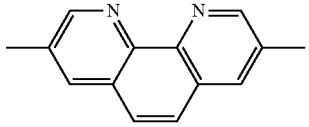 | 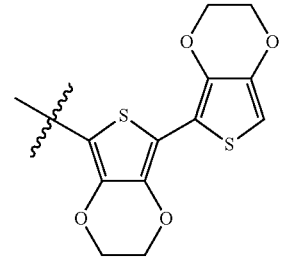 [SMILES: *c1sc(-c2scc3c2OCCO3)c2c1OCCO2] | PF₆ | 2 |
| 381 | Ru | 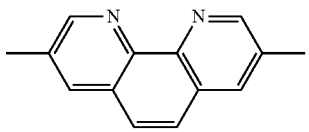 | 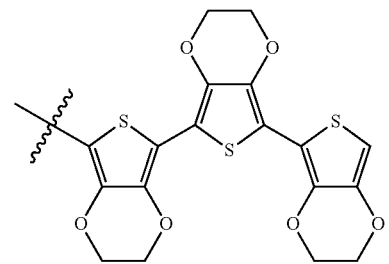 [SMILES: *c1sc(-c2sc(-c3scc4c3OCCO4)c3c2OCCO3)c2c1OCCO2] | PF₆ | 2 |

TABLE 1-continued

| Entry | M | Lig | R¹ | X | n |
|---|---|---|---|---|---|
| 382 | Ru | | | PF₆ | 2 |
| 383 | Ru | | | PF₆ | 2 |
| 384 | Ru | | | PF₆ | 2 |
| 385 | Ru | | | PF₆ | 2 |
| 386 | Ru | | | PF₆ | 2 |
| 387 | Ru | | | PF₆ | 2 |
| 388 | Ru | | | PF₆ | 2 |
| 389 | Ru | | | PF₆ | 2 |

TABLE 1-continued
| Entry | M | Lig | R¹ | X | n |
|---|---|---|---|---|---|
| 390 | Ru | 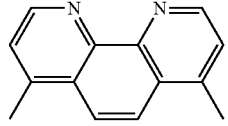 | 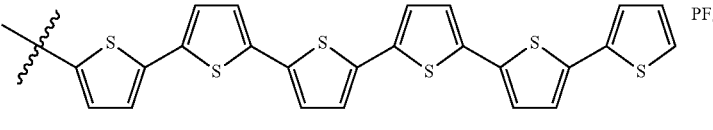 | PF$_6$ | 2 |
| 391 | Ru | 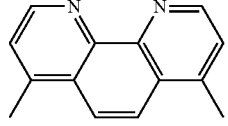 [SMILES: Cc1ccnc2c1ccc1c(C)ccnc12] | 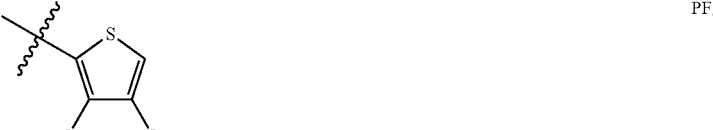 | PF$_6$ | 2 |
| 392 | Ru | 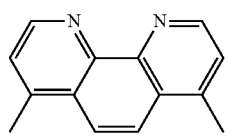 |  | PF$_6$ | 2 |
| 393 | Ru |  |  | PF$_6$ | 2 |
| 394 | Ru | 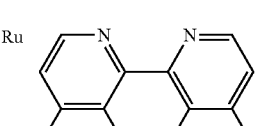 | 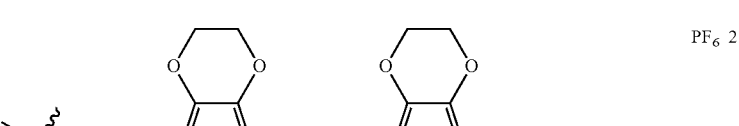 | PF$_6$ | 2 |
| 395 | Ru | 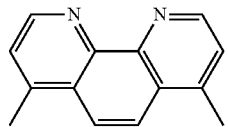 [SMILES: Cc1ccnc2c1ccc1c(C)ccnc12] | 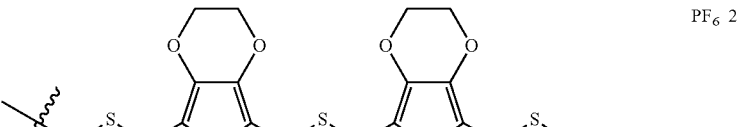 | PF$_6$ | 2 |

TABLE 1-continued

| Entry | M | Lig | R¹ | X | n |
|---|---|---|---|---|---|
| 396 | Ru | 4,7-dimethyl-1,10-phenanthroline | tris(EDOT)-bithiophene hexamer | PF$_6$ | 2 |
| 397 | Ru | 2,2'-bipyrimidine | thiophene | PF$_6$ | 2 |
| 398 | Ru | 2,2'-bipyrimidine | bithiophene | PF$_6$ | 2 |
| 399 | Ru | 2,2'-bipyrimidine | terthiophene | PF$_6$ | 2 |
| 400 | Ru | 2,2'-bipyrimidine | quaterthiophene | PF$_6$ | 2 |
| 401 | Ru | 2,2'-bipyrimidine | quinquethiophene | PF$_6$ | 2 |
| 402 | Ru | 2,2'-bipyrimidine | sexithiophene | PF$_6$ | 2 |
| 403 | Ru | 2,2'-bipyrimidine | EDOT | PF$_6$ | 2 |
| 404 | Ru | 2,2'-bipyrimidine | EDOT-thiophene | PF$_6$ | 2 |

TABLE 1-continued
| Entry | M | Lig | R¹ | X | n |
|---|---|---|---|---|---|
| 405 | Ru | | | $PF_6$ | 2 |
| 406 | Ru | | | $PF_6$ | 2 |
| 407 | Ru | | | $PF_6$ | 2 |
| 408 | Ru | | | $PF_6$ | 2 |
Exemplary embodiments include compounds having the formula (VII) or a pharmaceutically acceptable salt form thereof:
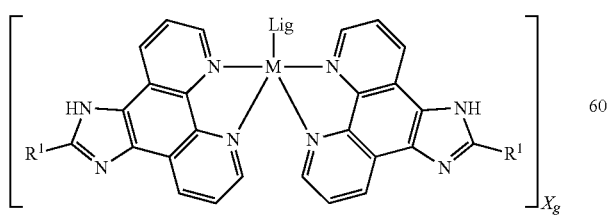
(VII)
wherein non-limiting examples of M, Lig, and R1 are defined herein below in Table 2.

TABLE 2

| Entry | M | Lig | R¹ | X | G |
|---|---|---|---|---|---|
| 1 | Ru | bipy | thiophene | Cl | 2 |
| 2 | Ru | bipy | bithiophene | Cl | 2 |
| 3 | Ru | bipy | terthiophene | Cl | 2 |
| 4 | Ru | bipy | quaterthiophene | Cl | 2 |
| 5 | Ru | bipy | quinquethiophene | Cl | 2 |
| 6 | Ru | bipy | sexithiophene | Cl | 2 |
| 7 | Ru | bipy | EDOT-thiophene | Cl | 2 |

TABLE 2-continued
| | | | | |
|---|---|---|---|---|
| 8 | Ru | 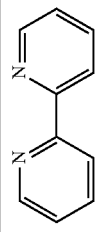 | 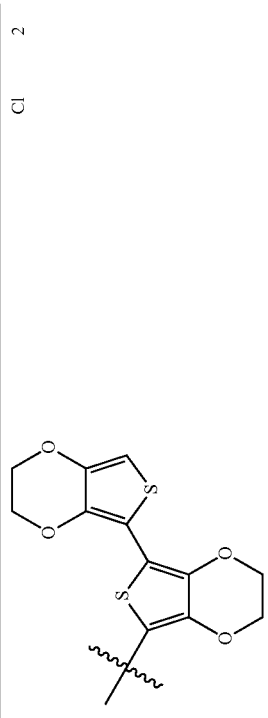 | Cl 2 |
| 9 | Ru | 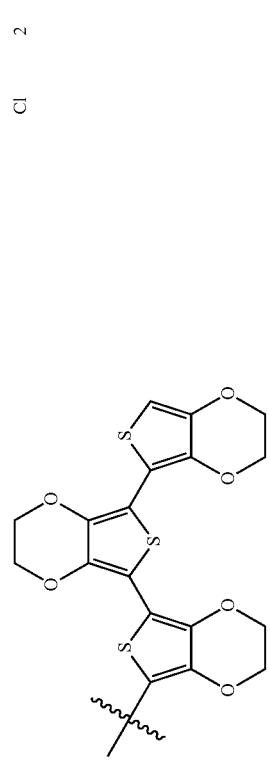 | 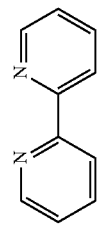 | Cl 2 |
| 10 | Ru | 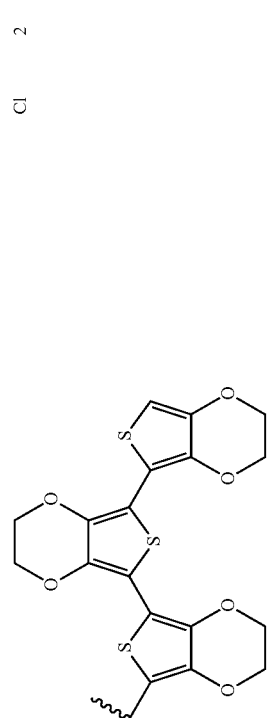 | 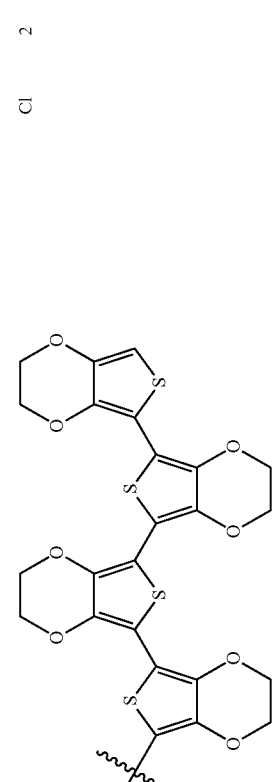 | Cl 2 |
| 11 | Ru | 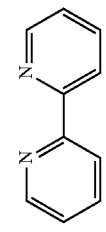 | 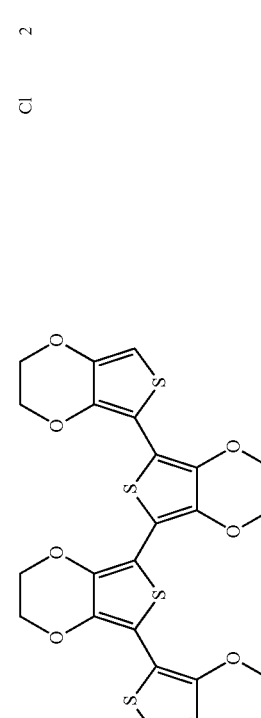 | Cl 2 |

TABLE 2-continued
| | | | | | |
|---|---|---|---|---|---|
| 12 | Ru | 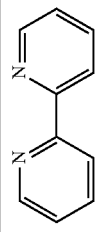 | 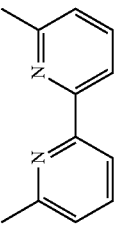 | Cl | 2 |
| 13 | Ru | 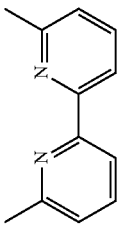 | 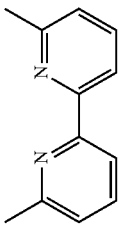 | Cl | 2 |
| 14 | Ru | 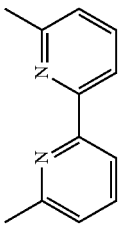 | 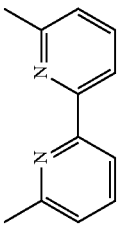 | Cl | 2 |
| 15 | Ru | 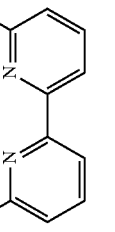 | 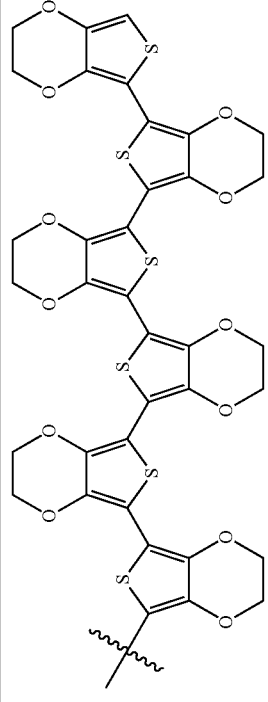 | Cl | 2 |
| 16 | Ru |  | 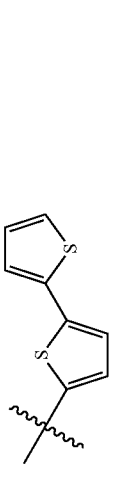 | Cl | 2 |
| 17 | Ru | 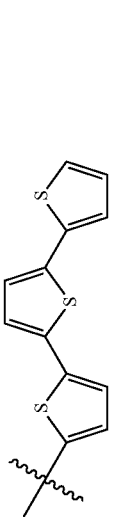 | 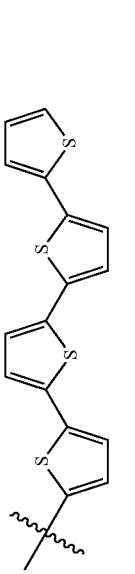 | Cl | 2 |
| 18 | Ru | 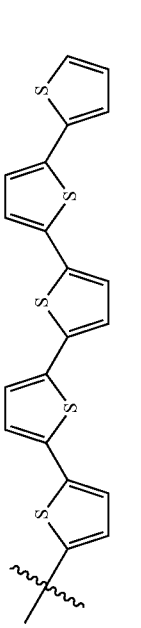 | 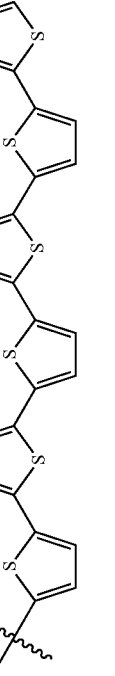 | Cl | 2 |

TABLE 2-continued
| | | | | |
|---|---|---|---|---|
| 19 | Ru | 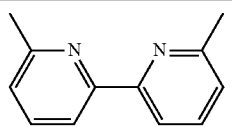 |  | Cl 2 |
| 20 | Ru | | | Cl 2 |
| 21 | Ru | | | Cl 2 |
| 22 | Ru | | | Cl 2 |

TABLE 2-continued

| | | | | |
|---|---|---|---|---|
| 23 | Ru | (6,6'-dimethyl-2,2'-bipyridine) | (EDOT tetramer) | Cl 2 |
| 24 | Ru | (6,6'-dimethyl-2,2'-bipyridine) | (EDOT pentamer) | Cl 2 |
| 25 | Ru | (5,5'-dimethyl-2,2'-bipyridine) | (thiophene) | Cl 2 |
| 26 | Ru | (5,5'-dimethyl-2,2'-bipyridine) | (bithiophene) | Cl 2 |
| 27 | Ru | (5,5'-dimethyl-2,2'-bipyridine) | (terthiophene) | Cl 2 |
| 28 | Ru | (5,5'-dimethyl-2,2'-bipyridine) | (quaterthiophene) | Cl 2 |

TABLE 2-continued

| | | | | |
|---|---|---|---|---|
| 29 | Ru | (5,5'-dimethyl-2,2'-bipyridine) | (quinquethiophene) | Cl 2 |
| 30 | Ru | (5,5'-dimethyl-2,2'-bipyridine) | (sexithiophene) | Cl 2 |
| 31 | Ru | (5,5'-dimethyl-2,2'-bipyridine) | (EDOT) | Cl 2 |
| 32 | Ru | (5,5'-dimethyl-2,2'-bipyridine) | (bi-EDOT) | Cl 2 |
| 33 | Ru | (5,5'-dimethyl-2,2'-bipyridine) | (ter-EDOT) | Cl 2 |

TABLE 2-continued
| | | | | |
|---|---|---|---|---|
| 34 | Ru | 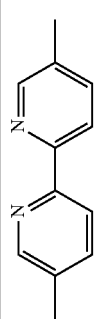 | 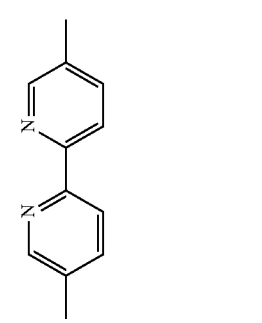 | Cl 2 |
| 35 | Ru | 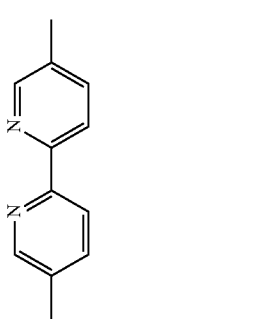 | 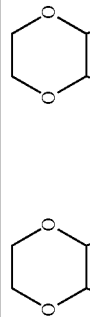 | Cl 2 |
| 36 | Ru | 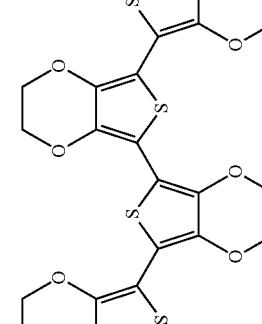 |  | Cl 2 |
| 37 | Ru |  | 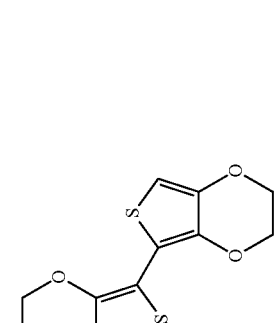 | Cl 2 |
| 38 | Ru | 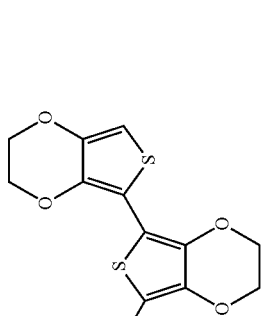 |  | Cl 2 |

TABLE 2-continued

| | | | | |
|---|---|---|---|---|
| 39 | Ru | (4,4'-dimethyl-2,2'-bipyridine) | (terthiophene) | Cl | 2 |
| 40 | Ru | (4,4'-dimethyl-2,2'-bipyridine) | (quaterthiophene) | Cl | 2 |
| 41 | Ru | (4,4'-dimethyl-2,2'-bipyridine) | (quaterthiophene) | Cl | 2 |
| 42 | Ru | (4,4'-dimethyl-2,2'-bipyridine) | (quinquethiophene) | Cl | 2 |
| 43 | Ru | (4,4'-dimethyl-2,2'-bipyridine) | (EDOT) | Cl | 2 |
| 44 | Ru | (4,4'-dimethyl-2,2'-bipyridine) | (bis-EDOT) | Cl | 2 |

TABLE 2-continued
| | | | | |
|---|---|---|---|---|
| 45 | Ru | 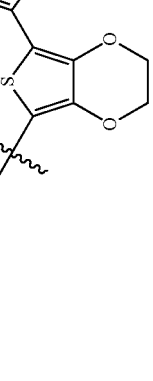 | 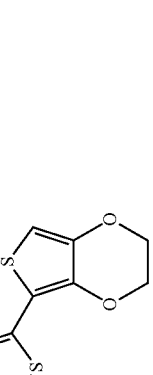 | Cl 2 |
| 46 | Ru | 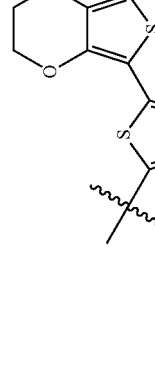 | 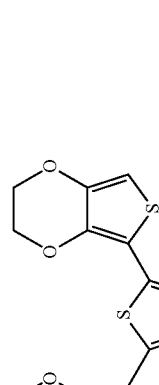 | Cl 2 |
| 47 | Ru | 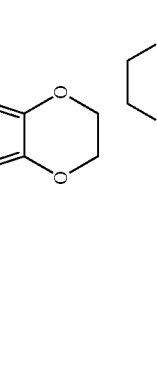 | 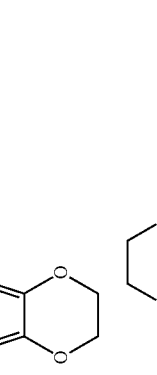 | Cl 2 |
| 48 | Ru | 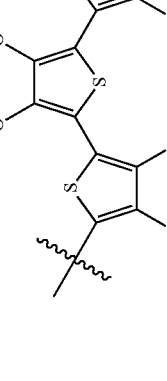 | 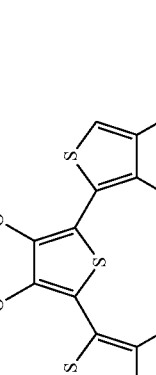 | Cl 2 |

TABLE 2-continued

| | | | | |
|---|---|---|---|---|
| 49 | Ru | (3,3'-dimethyl-2,2'-bipyridine) | (2-thienyl) | Cl | 2 |
| 50 | Ru | (3,3'-dimethyl-2,2'-bipyridine) | (2,2'-bithiophene-5-yl) | Cl | 2 |
| 51 | Ru | (3,3'-dimethyl-2,2'-bipyridine) | (terthiophene-yl) | Cl | 2 |
| 52 | Ru | (3,3'-dimethyl-2,2'-bipyridine) | (quaterthiophene-yl) | Cl | 2 |
| 53 | Ru | (3,3'-dimethyl-2,2'-bipyridine) | (quinquethiophene-yl) | Cl | 2 |
| 54 | Ru | (3,3'-dimethyl-2,2'-bipyridine) | (sexithiophene-yl) | Cl | 2 |
| 55 | Ru | (3,3'-dimethyl-2,2'-bipyridine) | (3,4-ethylenedioxythiophene-yl) | Cl | 2 |

TABLE 2-continued

TABLE 2-continued
| | | | | |
|---|---|---|---|---|
| 60 | Ru | 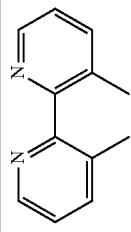 | 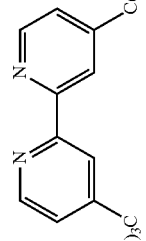 | Cl 2 |
| 61 | Ru | 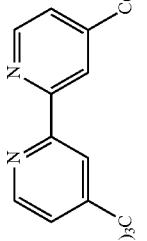 | 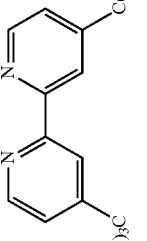 | Cl 2 |
| 62 | Ru | 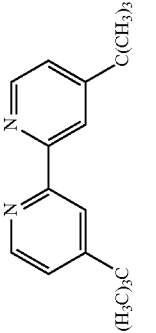 | 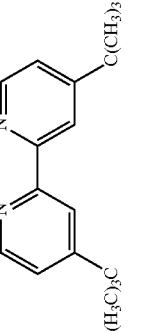 | Cl 2 |
| 63 | Ru | 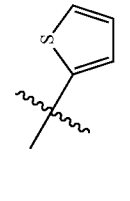 | 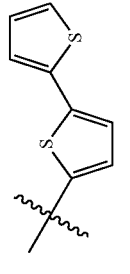 | Cl 2 |
| 64 | Ru | 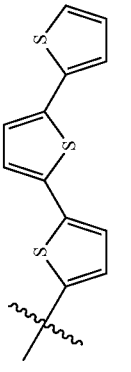 | 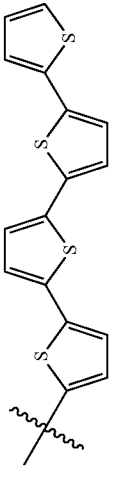 | Cl 2 |
| 65 | Ru | 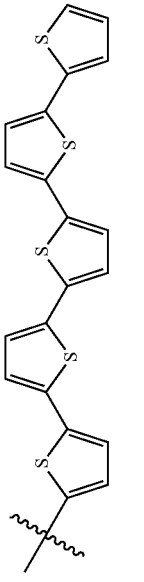 | | Cl 2 |

TABLE 2-continued
| | | | | |
|---|---|---|---|---|
| 66 | Ru | 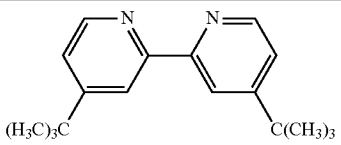 |  | Cl 2 |
| 67 | Ru | (same bipyridine) | (EDOT group) | Cl 2 |
| 68 | Ru | (same bipyridine) | (bis-EDOT group) | Cl 2 |
| 69 | Ru | (same bipyridine) | (tris-EDOT group) | Cl 2 |

TABLE 2-continued

| | | | | |
|---|---|---|---|---|
| 70 | Ru | [4,4'-di-tert-butyl-2,2'-bipyridine] | [tri-EDOT substituent] | Cl 2 |
| 71 | Ru | [4,4'-di-tert-butyl-2,2'-bipyridine] | [tri-EDOT substituent] | Cl 2 |
| 72 | Ru | [4,4'-di-tert-butyl-2,2'-bipyridine] | [tri-EDOT substituent] | Cl 2 |
| 73 | Ru | [4,4'-dimethoxy-2,2'-bipyridine] | [thiophene] | Cl 2 |
| 74 | Ru | [4,4'-dimethoxy-2,2'-bipyridine] | [bithiophene] | Cl 2 |

TABLE 2-continued

| | | | | |
|---|---|---|---|---|
| 75 | Ru | (bipyridine-OMe structure) | (terthiophene) | Cl 2 |
| 76 | Ru | (bipyridine-OMe structure) | (terthiophene variant) | Cl 2 |
| 77 | Ru | (bipyridine-OMe structure) | (quaterthiophene) | Cl 2 |
| 78 | Ru | (bipyridine-OMe structure) | (quinquethiophene) | Cl 2 |
| 79 | Ru | (bipyridine-OMe structure) | (EDOT) | Cl 2 |
| 80 | Ru | (bipyridine-OMe structure) | (bis-EDOT) | Cl 2 |

TABLE 2-continued
| | | | | |
|---|---|---|---|---|
| 81 | Ru |  |  | Cl 2 |
| 82 | Ru |  |  | Cl 2 |
| 83 | Ru |  |  | Cl 2 |
| 84 | Ru |  |  | Cl 2 |

TABLE 2-continued

| | | | | |
|---|---|---|---|---|
| 85 | Ru | ![bpy-diester] | ![thiophene] | Cl 2 |
| 86 | Ru | ![bpy-diester] | ![bithiophene] | Cl 2 |
| 87 | Ru | ![bpy-diester] | ![terthiophene] | Cl 2 |
| 88 | Ru | ![bpy-diester] | ![quaterthiophene] | Cl 2 |
| 89 | Ru | ![bpy-diester] | ![quinquethiophene] | Cl 2 |
| 90 | Ru | ![bpy-diester] | ![sexithiophene] | Cl 2 |
| 91 | Ru | ![bpy-diester] | ![EDOT] | Cl 2 |

TABLE 2-continued

| | | | | |
|---|---|---|---|---|
| 92 | Ru | [bipyridine-4,3'-dicarboxylate methyl ester ligand] | [EDOT-EDOT substituent] | Cl | 2 |
| 93 | Ru | [bipyridine-4,3'-dicarboxylate methyl ester ligand] | [tri-EDOT substituent] | Cl | 2 |
| 94 | Ru | [bipyridine-4,3'-dicarboxylate methyl ester ligand] | [tri-EDOT branched substituent] | Cl | 2 |
| 95 | Ru | [bipyridine-4,3'-dicarboxylate methyl ester ligand] | [tetra-EDOT branched substituent] | Cl | 2 |

TABLE 2-continued
| | | | | |
|---|---|---|---|---|
| 96 | Ru | 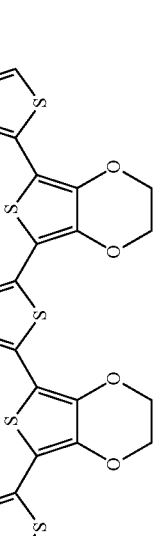 |  | Cl 2 |
| 97 | Ru | | | Cl 2 |
| 98 | Ru | | | Cl 2 |
| 99 | Ru | | | Cl 2 |
| 100 | Ru | | | Cl 2 |
| 101 | Ru | | | Cl 2 |

TABLE 2-continued

| | | | | |
|---|---|---|---|---|
| 102 | Ru | (4,4'-bis(CF₃)-2,2'-bipyridine) | (quinquethiophene) | Cl 2 |
| 103 | Ru | (4,4'-bis(CF₃)-2,2'-bipyridine) | (EDOT) | Cl 2 |
| 104 | Ru | (4,4'-bis(CF₃)-2,2'-bipyridine) | (bis-EDOT) | Cl 2 |
| 105 | Ru | (4,4'-bis(CF₃)-2,2'-bipyridine) | (tris-EDOT) | Cl 2 |

TABLE 2-continued

| | | | | |
|---|---|---|---|---|
| 106 | Ru | (4,4'-bis(CF3)-2,2'-bipyridine) | (EDOT)3 | Cl | 2 |
| 107 | Ru | (4,4'-bis(CF3)-2,2'-bipyridine) | (EDOT)3 | Cl | 2 |
| 108 | Ru | (4,4'-bis(CF3)-2,2'-bipyridine) | (EDOT)3 | Cl | 2 |
| 109 | Ru | 2,2'-bipyrimidine | thiophene | Cl | 2 |
| 110 | Ru | 2,2'-bipyrimidine | bithiophene | Cl | 2 |

TABLE 2-continued

| | | | | |
|---|---|---|---|---|
| 111 | Ru | [bipyrimidine] | [terthiophene] | Cl 2 |
| 112 | Ru | [bipyrimidine] | [terthiophene] | Cl 2 |
| 113 | Ru | [bipyrimidine] | [terthiophene] | Cl 2 |
| 114 | Ru | [bipyrimidine] | [quaterthiophene] | Cl 2 |
| 115 | Ru | [bipyrimidine] | [EDOT] | Cl 2 |
| 116 | Ru | [bipyrimidine] | [bis-EDOT] | |

TABLE 2-continued
| | | | | |
|---|---|---|---|---|
| 117 | Ru | 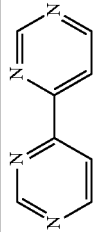 | 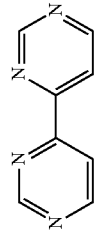 | Cl 2 |
| 118 | Ru | 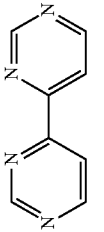 | 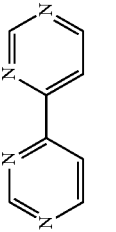 | Cl 2 |
| 119 | Ru | 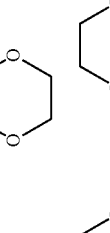 | 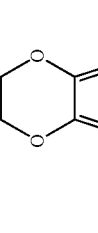 | Cl 2 |
| 120 | Ru | | | Cl 2 |

TABLE 2-continued

| | | | | | |
|---|---|---|---|---|---|
| 121 | Ru | (bipyrimidine) | (thiophene) | Cl | 2 |
| 122 | Ru | (bipyrimidine) | (bithiophene) | Cl | 2 |
| 123 | Ru | (bipyrimidine) | (terthiophene) | Cl | 2 |
| 124 | Ru | (bipyrimidine) | (quaterthiophene) | Cl | 2 |
| 125 | Ru | (bipyrimidine) | (quinquethiophene) | Cl | 2 |
| 126 | Ru | (bipyrimidine) | (sexithiophene) | Cl | 2 |
| 127 | Ru | (bipyrimidine) | (EDOT) | | |

TABLE 2-continued
| | | | | |
|---|---|---|---|---|
| 128 | Ru | 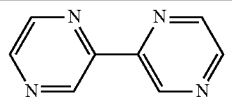 |  | Cl 2 |
| 129 | Ru | | | Cl 2 |
| 130 | Ru | 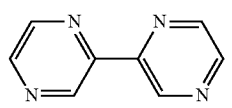 | | Cl 2 |
| 131 | Ru | 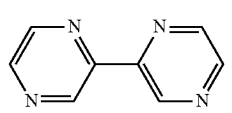 [SMILES: c1cnc(-c2cnccn2)cn1] | | Cl 2 |

TABLE 2-continued
| | | | | | |
|---|---|---|---|---|---|
| 132 | Ru | 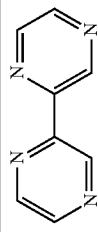 | 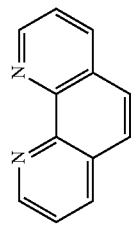 | Cl | 2 |
| 133 | Ru | 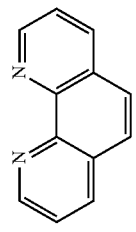 | 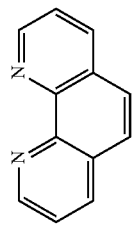 | Cl | 2 |
| 134 | Ru | 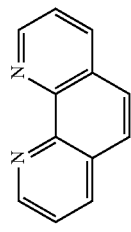 | 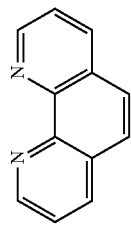 | Cl | 2 |
| 135 | Ru | 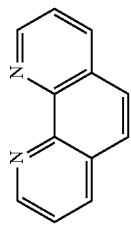 | | Cl | 2 |
| 136 | Ru | 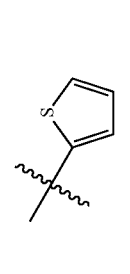 | | Cl | 2 |
| 137 | Ru | 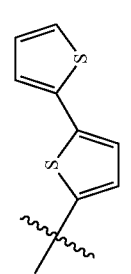 | | Cl | 2 |
| 138 | Ru | | | Cl | 2 |

TABLE 2-continued
| | | | | |
|---|---|---|---|---|
| 139 | Ru | 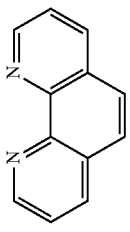 | 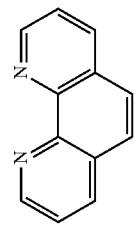 | Cl 2 |
| 140 | Ru | 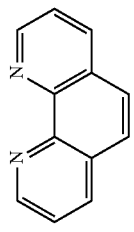 | 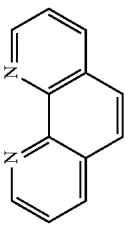 | Cl 2 |
| 141 | Ru | 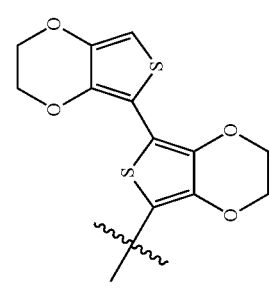 | 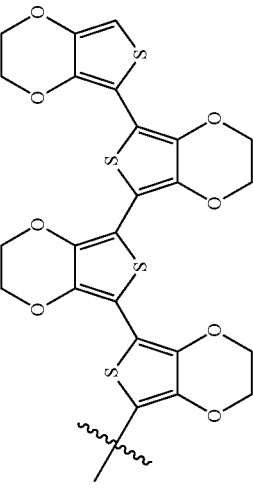 | Cl 2 |
| 142 | Ru | | | Cl 2 |

TABLE 2-continued
| | | | | |
|---|---|---|---|---|
| 143 | Ru | 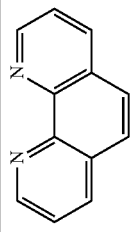 | 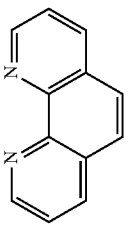 | Cl 2 |
| 144 | Ru | | | Cl 2 |
| 145 | Ru | | | Cl 2 |
| 146 | Ru | | | Cl 2 |
| 147 | Ru | | | Cl 2 |
| 148 | Ru | | | Cl 2 |

TABLE 2-continued

| | | | | |
|---|---|---|---|---|
| 149 | Ru | (structure) | (structure) | Cl 2 |
| 150 | Ru | (structure) | (structure) | Cl 2 |
| 151 | Ru | (structure) | (structure) | Cl 2 |
| 152 | Ru | (structure) | (structure) | Cl 2 |
| 153 | Ru | (structure) | (structure) | Cl 2 |

TABLE 2-continued
| | | | | |
|---|---|---|---|---|
| 154 | Ru | 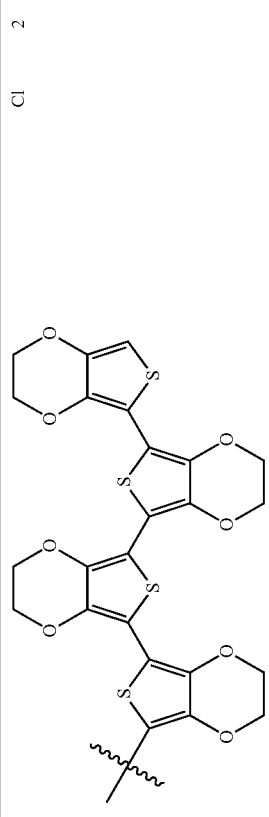 | 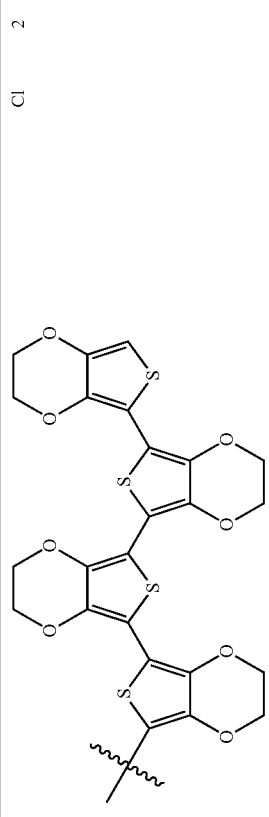 | Cl 2 |
| 155 | Ru | 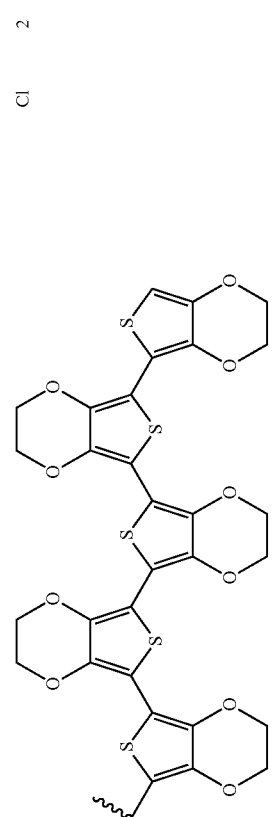 | 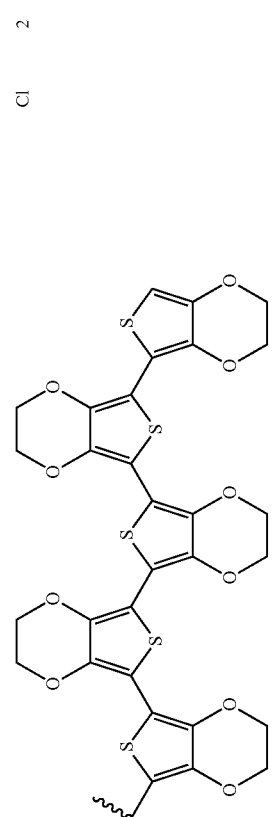 | Cl 2 |
| 156 | Ru | 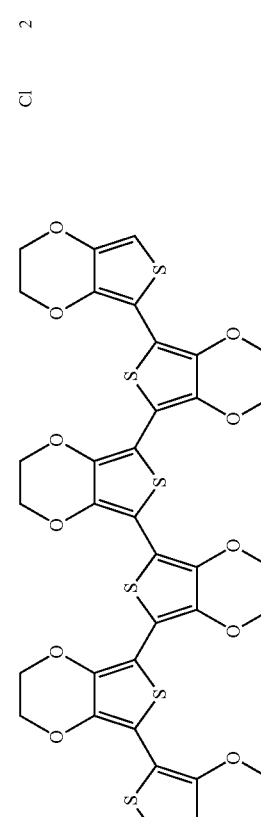 | 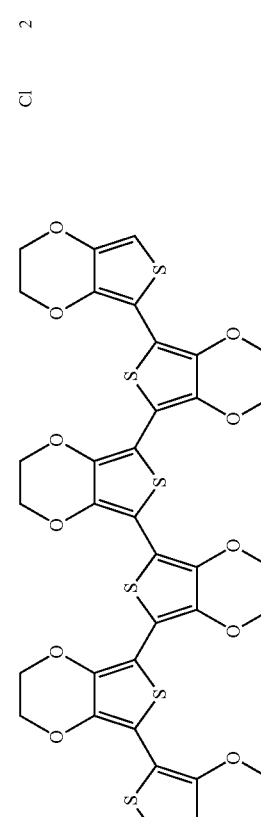 | Cl 2 |
| 157 | Ru | 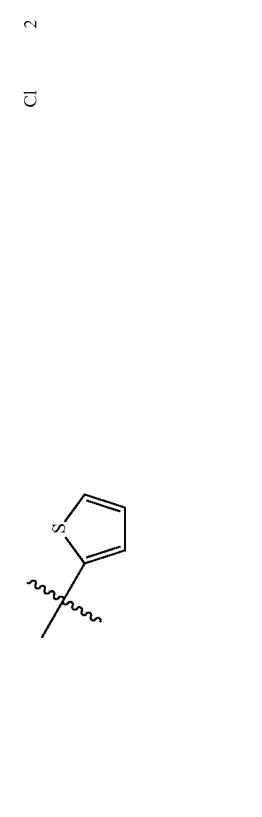 | 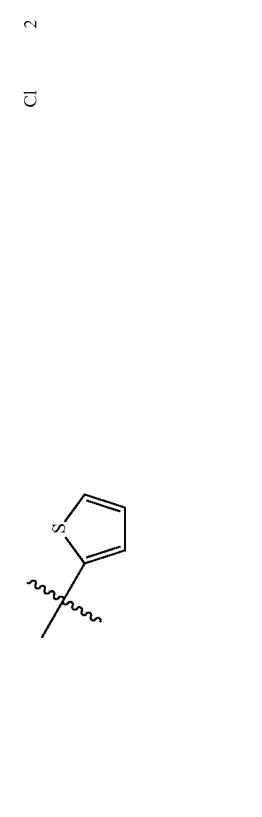 | Cl 2 |

TABLE 2-continued

| | | | | |
|---|---|---|---|---|
| 158 | Ru | (2,9-dimethyl-1,10-phenanthroline) | 2,2'-bithiophene | Cl | 2 |
| 159 | Ru | (2,9-dimethyl-1,10-phenanthroline) | terthiophene | Cl | 2 |
| 160 | Ru | (2,9-dimethyl-1,10-phenanthroline) | quaterthiophene | Cl | 2 |
| 161 | Ru | (2,9-dimethyl-1,10-phenanthroline) | quinquethiophene | Cl | 2 |
| 162 | Ru | (2,9-dimethyl-1,10-phenanthroline) | sexithiophene | Cl | 2 |
| 163 | Ru | (2,9-dimethyl-1,10-phenanthroline) | 3,4-ethylenedioxythiophene | Cl | 2 |

TABLE 2-continued
| | | | |
|---|---|---|---|
| 164 Ru | 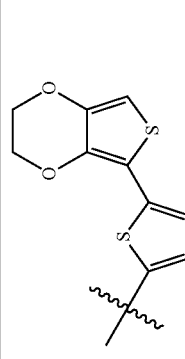 | 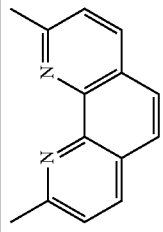 | Cl 2 |
| 165 Ru | 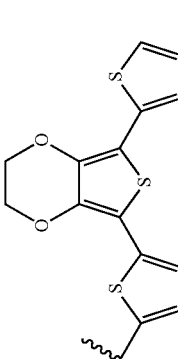 | 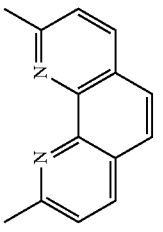 | Cl 2 |
| 166 Ru | 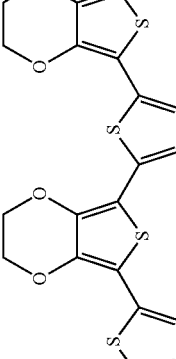 | 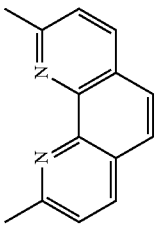 | Cl 2 |
| 167 Ru | 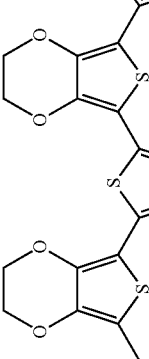 | 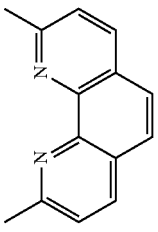 | Cl 2 |

TABLE 2-continued

| | | | | |
|---|---|---|---|---|
| 168 | Ru | (phenanthroline-dimethyl) | (5-EDOT chain) | Cl $_2$ |
| 169 | Ru | (phenanthroline-dimethyl) | (thiophene) | Cl $_2$ |
| 170 | Ru | (phenanthroline-dimethyl) | (bithiophene) | Cl $_2$ |
| 171 | Ru | (phenanthroline-dimethyl) | (terthiophene) | Cl $_2$ |
| 172 | Ru | (phenanthroline-dimethyl) | (quaterthiophene) | Cl $_2$ |
| 173 | Ru | (phenanthroline-dimethyl) | (quinquethiophene) | Cl $_2$ |
| 174 | Ru | (phenanthroline-dimethyl) | (sexithiophene) | Cl $_2$ |

TABLE 2-continued
| | | | | |
|---|---|---|---|---|
| 175 | Ru |  |  | Cl 2 |
| 176 | Ru | 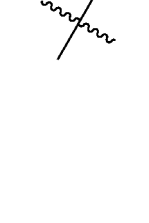 |  | Cl 2 |
| 177 | Ru |  |  | Cl 2 |
| 178 | Ru | 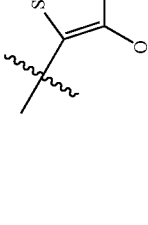 |  | Cl 2 |

TABLE 2-continued
| | | | |
|---|---|---|---|
| 179 | Ru | 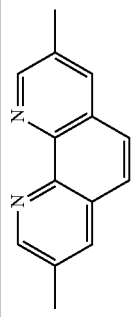 | 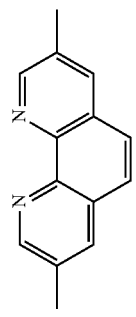 | Cl | 2 |
| 180 | Ru | | | Cl | 2 |
| 181 | Ru | | | Cl | 2 |
| 182 | Ru | | | Cl | 2 |
| 183 | Ru | | | Cl | 2 |
| 184 | Ru | | | Cl | 2 |

TABLE 2-continued

| | | | | |
|---|---|---|---|---|
| 185 | Ru | [4,7-dimethyl-phenanthroline] | [quaterthiophene] | Cl 2 |
| 186 | Ru | [4,7-dimethyl-phenanthroline] | [quinquethiophene] | Cl 2 |
| 187 | Ru | [4,7-dimethyl-phenanthroline] | [EDOT] | Cl 2 |
| 188 | Ru | [4,7-dimethyl-phenanthroline] | [bi-EDOT] | Cl 2 |
| 189 | Ru | [4,7-dimethyl-phenanthroline] | [tri-EDOT] | Cl 2 |

TABLE 2-continued

| | | | | |
|---|---|---|---|---|
| 190 | Ru | (4,7-dimethyl-phenanthroline) | (EDOT)₃ | Cl 2 |
| 191 | Ru | (4,7-dimethyl-phenanthroline) | (EDOT)₃ | Cl 2 |
| 192 | Ru | (4,7-dimethyl-phenanthroline) | (EDOT)₃ | Cl 2 |
| 193 | Ru | (2,2'-bipyrimidine) | thiophene | Cl 2 |
| 194 | Ru | (2,2'-bipyrimidine) | bithiophene | Cl 2 |

TABLE 2-continued
| | | | | |
|---|---|---|---|---|
| 195 | Ru | 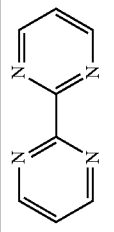 | 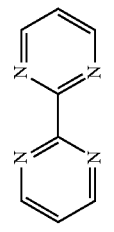 | Cl 2 |
| 196 | Ru | | | Cl 2 |
| 197 | Ru | | | Cl 2 |
| 198 | Ru | | | Cl 2 |
| 199 | Ru | | | Cl 2 |
| 200 | Ru | | | Cl 2 |

TABLE 2-continued

| | | | | |
|---|---|---|---|---|
| 201 | Ru | [2,2'-bipyridine] | [bis-EDOT substituent] | Cl 2 |
| 202 | Ru | [2,2'-bipyridine] | [tris-EDOT substituent] | Cl 2 |
| 203 | Ru | [2,2'-bipyridine] | [tetra-EDOT substituent] | Cl 2 |
| 204 | Ru | [2,2'-bipyridine] | [penta-EDOT substituent] | Cl 2 |

TABLE 2-continued

| | | | | |
|---|---|---|---|---|
| 205 | Ru | bipy | thiophene | PF6 2 |
| 206 | Ru | bipy | bithiophene | PF6 2 |
| 207 | Ru | bipy | terthiophene | PF6 2 |
| 208 | Ru | bipy | quaterthiophene | PF6 2 |
| 209 | Ru | bipy | quinquethiophene | PF6 2 |
| 210 | Ru | bipy | sexithiophene | PF6 2 |
| 211 | Ru | bipy | EDOT | PF6 2 |

TABLE 2-continued

| | | | | |
|---|---|---|---|---|
| 212 | Ru | (bpy) | (EDOT-EDOT) | PF₆ 2 |
| 213 | Ru | (bpy) | (EDOT-EDOT-EDOT) | PF₆ 2 |
| 214 | Ru | (bpy) | (EDOT-EDOT-EDOT) | PF₆ 2 |
| 215 | Ru | (bpy) | (EDOT-EDOT-EDOT-EDOT) | PF₆ 2 |

TABLE 2-continued
| | | | | |
|---|---|---|---|---|
| 216 | Ru | 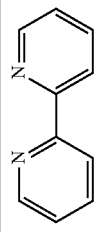 | 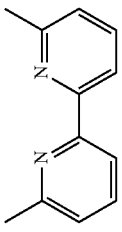 | PF$_6$ 2 |
| 217 | Ru | 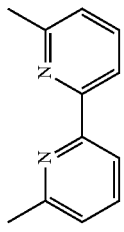 | 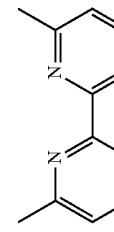 | PF$_6$ 2 |
| 218 | Ru | 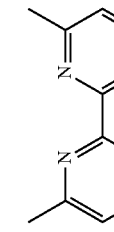 | 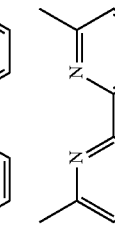 | PF$_6$ 2 |
| 219 | Ru | 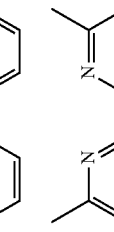 | 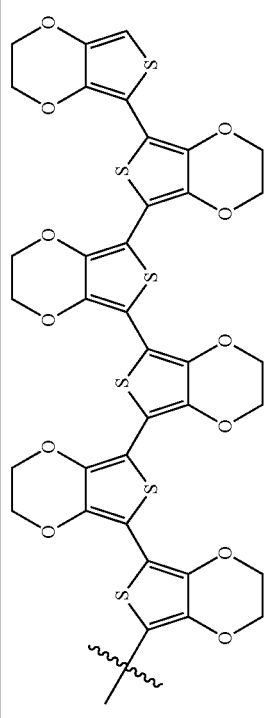 | PF$_6$ 2 |
| 220 | Ru | 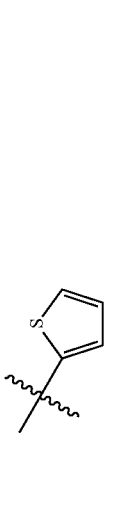 | 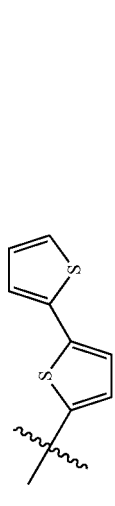 | PF$_6$ 2 |
| 221 | Ru | 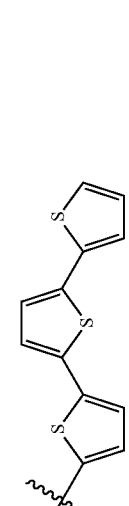 | 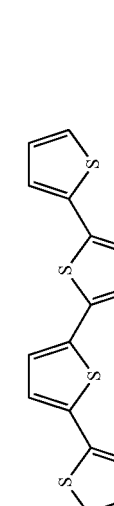 | PF$_6$ 2 |
| 222 | Ru | 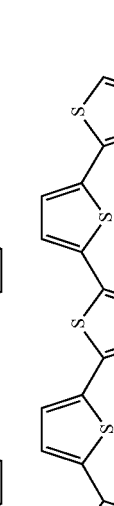 | 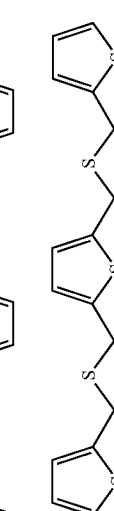 | PF$_6$ 2 |

TABLE 2-continued
| | | | | |
|---|---|---|---|---|
| 223 | Ru | 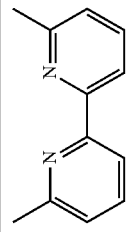 | 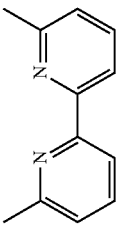 | PF$_6$ 2 |
| 224 | Ru | | | PF$_6$ 2 |
| 225 | Ru | | | PF$_6$ 2 |
| 226 | Ru | | | PF$_6$ 2 |

TABLE 2-continued
| | | | | |
|---|---|---|---|---|
| 227 | Ru | 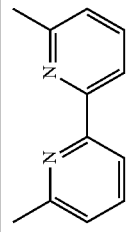 | 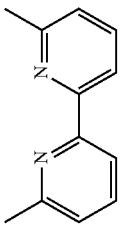 | PF$_6$ 2 |
| 228 | Ru | 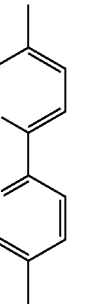 | 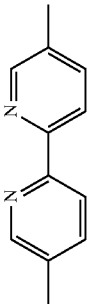 | PF$_6$ 2 |
| 229 | Ru | 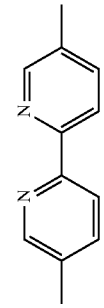 | 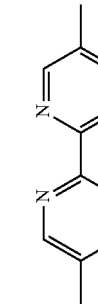 | PF$_6$ 2 |
| 230 | Ru | | 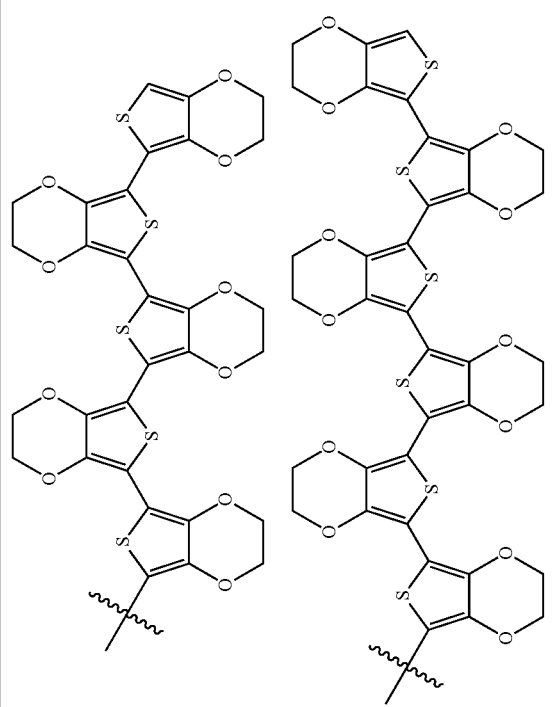 | PF$_6$ 2 |
| 231 | Ru | | 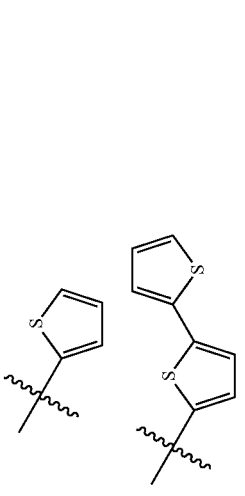 | PF$_6$ 2 |
| 232 | Ru | | 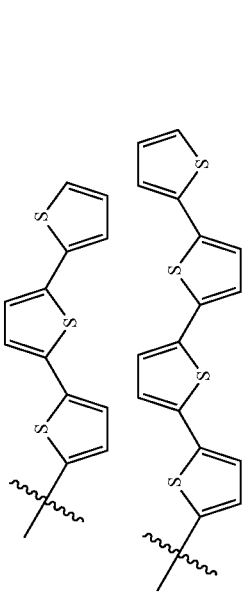 | PF$_6$ 2 |

TABLE 2-continued

| | | | | |
|---|---|---|---|---|
| 233 | Ru | [4,4'-dimethyl-2,2'-bipyridine] | [quinquethiophene] | PF$_6$ 2 |
| 234 | Ru | [4,4'-dimethyl-2,2'-bipyridine] | [sexithiophene] | PF$_6$ 2 |
| 235 | Ru | [4,4'-dimethyl-2,2'-bipyridine] | [EDOT] | PF$_6$ 2 |
| 236 | Ru | [4,4'-dimethyl-2,2'-bipyridine] | [bis-EDOT] | PF$_6$ 2 |
| 237 | Ru | [4,4'-dimethyl-2,2'-bipyridine] | [tris-EDOT] | PF$_6$ 2 |

TABLE 2-continued

| | | | | |
|---|---|---|---|---|
| 238 | Ru | (5,5'-dimethyl-2,2'-bipyridine) | (tri-EDOT) | PF₆ | 2 |
| 239 | Ru | (5,5'-dimethyl-2,2'-bipyridine) | (tri-EDOT) | PF₆ | 2 |
| 240 | Ru | (5,5'-dimethyl-2,2'-bipyridine) | (tri-EDOT) | PF₆ | 2 |
| 241 | Ru | (4,4'-dimethyl-2,2'-bipyridine) | (thiophene) | PF₆ | 2 |
| 242 | Ru | (4,4'-dimethyl-2,2'-bipyridine) | (bithiophene) | PF₆ | 2 |

TABLE 2-continued

| | | | | |
|---|---|---|---|---|
| 243 | Ru | (bipy-Me) | (terthiophene) | PF$_6$ 2 |
| 244 | Ru | (bipy-Me) | (tetrathiophene) | PF$_6$ 2 |
| 245 | Ru | (bipy-Me) | (tetrathiophene) | PF$_6$ 2 |
| 246 | Ru | (bipy-Me) | (pentathiophene) | PF$_6$ 2 |
| 247 | Ru | (bipy-Me) | (EDOT) | PF$_6$ 2 |
| 248 | Ru | (bipy-Me) | (bis-EDOT) | PF$_6$ 2 |

TABLE 2-continued

| | | | | |
|---|---|---|---|---|
| 249 | Ru | [4,4'-dimethyl-2,2'-bipyridine] | [bis-EDOT] | PF₆ 2 |
| 250 | Ru | [4,4'-dimethyl-2,2'-bipyridine] | [tri-EDOT] | PF₆ 2 |
| 251 | Ru | [4,4'-dimethyl-2,2'-bipyridine] | [tetra-EDOT] | PF₆ 2 |
| 252 | Ru | [4,4'-dimethyl-2,2'-bipyridine] | [penta-EDOT] | PF₆ 2 |

TABLE 2-continued

| | | | | |
|---|---|---|---|---|
| 253 | Ru | (3,3'-dimethyl-2,2'-bipyridine) | (thiophene) | PF$_6$ | 2 |
| 254 | Ru | (3,3'-dimethyl-2,2'-bipyridine) | (bithiophene) | PF$_6$ | 2 |
| 255 | Ru | (3,3'-dimethyl-2,2'-bipyridine) | (terthiophene) | PF$_6$ | 2 |
| 256 | Ru | (3,3'-dimethyl-2,2'-bipyridine) | (quaterthiophene) | PF$_6$ | 2 |
| 257 | Ru | (3,3'-dimethyl-2,2'-bipyridine) | (quinquethiophene) | PF$_6$ | 2 |
| 258 | Ru | (3,3'-dimethyl-2,2'-bipyridine) | (sexithiophene) | PF$_6$ | 2 |
| 259 | Ru | (3,3'-dimethyl-2,2'-bipyridine) | (EDOT) | PF$_6$ | 2 |

TABLE 2-continued
| | | | | |
|---|---|---|---|---|
| 260 | Ru | 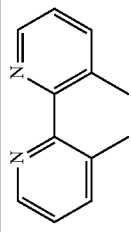 | 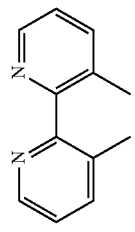 | PF$_6$ 2 |
| 261 | Ru | | | PF$_6$ 2 |
| 262 | Ru | | | PF$_6$ 2 |
| 263 | Ru | | | PF$_6$ 2 |

TABLE 2-continued

| | | | | |
|---|---|---|---|---|
| 264 | Ru | [3,3'-dimethyl-2,2'-bipyridine] | [tetra(EDOT)] | PF₆ | 2 |
| 265 | Ru | [4,4'-di-tert-butyl-2,2'-bipyridine] | [thiophene] | PF₆ | 2 |
| 266 | Ru | [4,4'-di-tert-butyl-2,2'-bipyridine] | [bithiophene] | PF₆ | 2 |
| 267 | Ru | [4,4'-di-tert-butyl-2,2'-bipyridine] | [terthiophene] | PF₆ | 2 |
| 268 | Ru | [4,4'-di-tert-butyl-2,2'-bipyridine] | [quaterthiophene] | PF₆ | 2 |
| 269 | Ru | [4,4'-di-tert-butyl-2,2'-bipyridine] | [quinquethiophene] | PF₆ | 2 |

TABLE 2-continued

| | | | | |
|---|---|---|---|---|
| 270 | Ru | [bpy-tBu structure] | [quinquethiophene structure] | PF$_6$ 2 |
| 271 | Ru | [bpy-tBu structure] | [EDOT structure] | PF$_6$ 2 |
| 272 | Ru | [bpy-tBu structure] | [bis-EDOT structure] | PF$_6$ 2 |
| 273 | Ru | [bpy-tBu structure] | [tris-EDOT structure] | PF$_6$ 2 |

TABLE 2-continued
| | | | | |
|---|---|---|---|---|
| 274 | Ru | 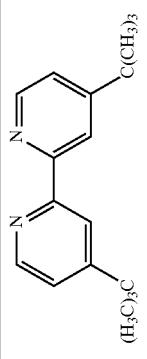 | 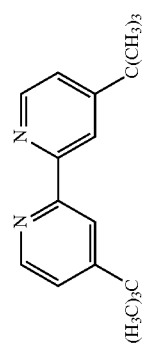 | PF$_6$ 2 |
| 275 | Ru | | | PF$_6$ 2 |
| 276 | Ru | | | PF$_6$ 2 |
| 277 | Ru | | | PF$_6$ 2 |
| 278 | Ru | | | PF$_6$ 2 |

TABLE 2-continued
| | | | | |
|---|---|---|---|---|
| 279 | Ru | 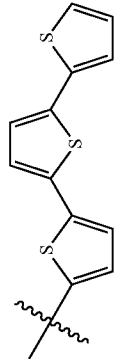 | 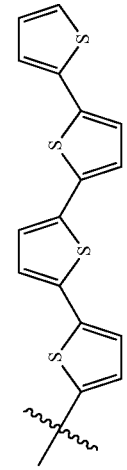 | PF$_6$ | 2 |
| 280 | Ru | | | PF$_6$ | 2 |
| 281 | Ru | | | PF$_6$ | 2 |
| 282 | Ru | | | PF$_6$ | 2 |
| 283 | Ru | | | PF$_6$ | 2 |
| 284 | Ru | | | PF$_6$ | 2 |

TABLE 2-continued
| | | | | |
|---|---|---|---|---|
| 285 | Ru | 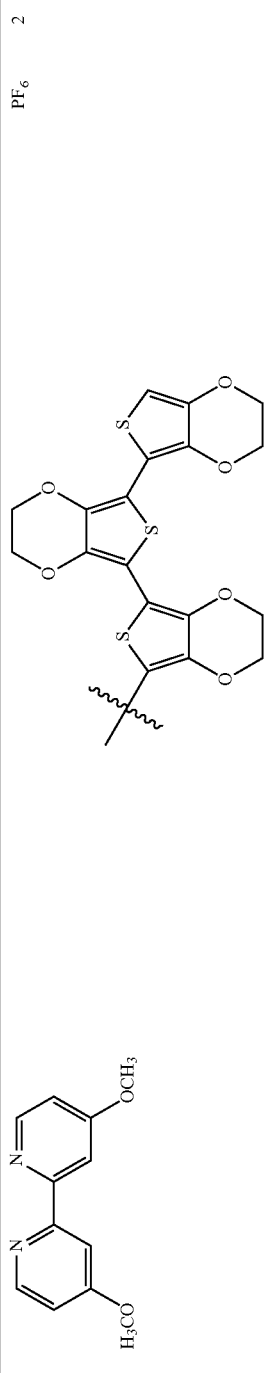 | 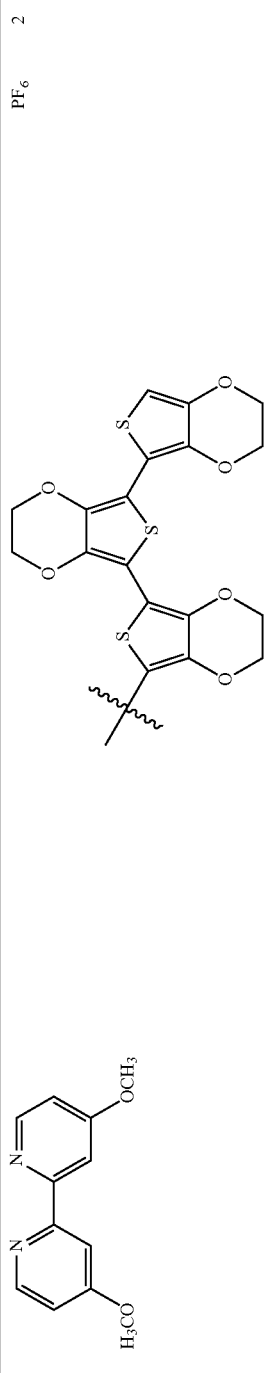 | PF$_6$ 2 |
| 286 | Ru | 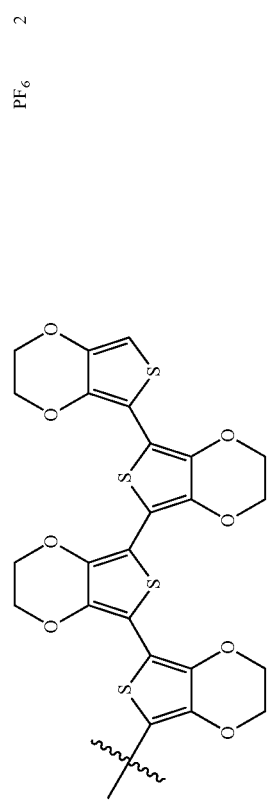 | 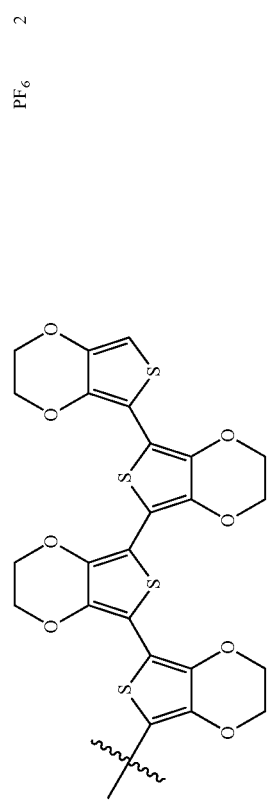 | PF$_6$ 2 |
| 287 | Ru | 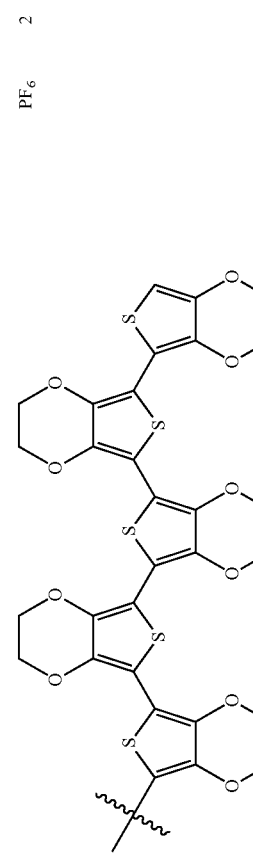 | 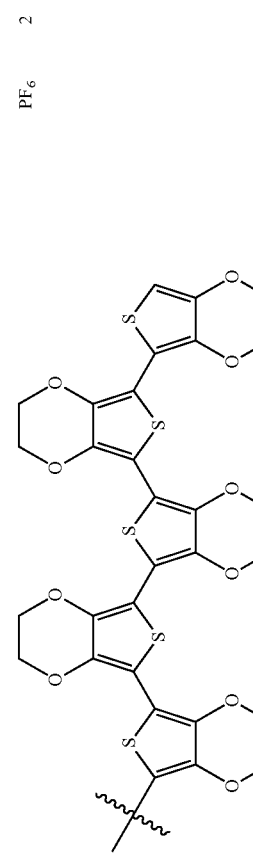 | PF$_6$ 2 |
| 288 | Ru | 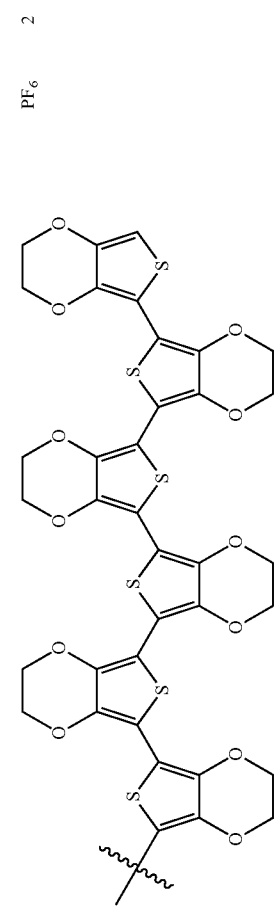 | 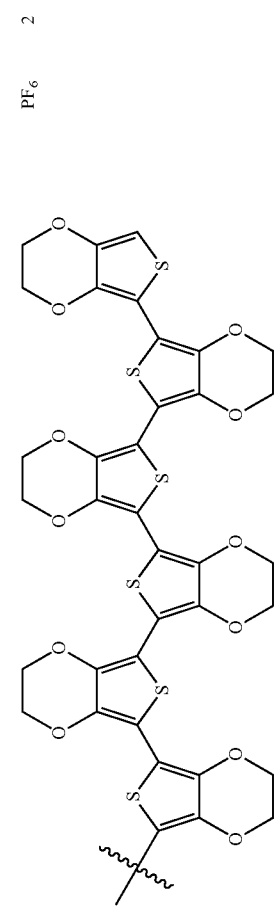 | PF$_6$ 2 |

TABLE 2-continued

| | | | | |
|---|---|---|---|---|
| 289 | Ru | bpy(CO2CH3)2 | thiophene | PF6 | 2 |
| 290 | Ru | bpy(CO2CH3)2 | bithiophene | PF6 | 2 |
| 291 | Ru | bpy(CO2CH3)2 | terthiophene | PF6 | 2 |
| 292 | Ru | bpy(CO2CH3)2 | quaterthiophene | PF6 | 2 |
| 293 | Ru | bpy(CO2CH3)2 | quinquethiophene | PF6 | 2 |
| 294 | Ru | bpy(CO2CH3)2 | sexithiophene | PF6 | 2 |
| 295 | Ru | bpy(CO2CH3)2 | EDOT | PF6 | 2 |

TABLE 2-continued

| | | | | |
|---|---|---|---|---|
| 296 | Ru | (bipyridine dicarboxylate methyl ester) | (EDOT-EDOT) | PF$_6$ 2 |
| 297 | Ru | (bipyridine dicarboxylate methyl ester) | (bis-EDOT substituted) | PF$_6$ 2 |
| 298 | Ru | (bipyridine dicarboxylate methyl ester) | (bis-EDOT substituted) | PF$_6$ 2 |
| 299 | Ru | (bipyridine dicarboxylate methyl ester) | (tetra-EDOT substituted) | PF$_6$ 2 |

TABLE 2-continued

| | | | | |
|---|---|---|---|---|
| 300 | Ru | (bipyridine with CO2CH3 and H3CO2C substituents) | (tetra-EDOT chain) | PF6 | 2 |
| 301 | Ru | (bipyridine with CF3 and F3C substituents) | (thiophene) | PF6 | 2 |
| 302 | Ru | (bipyridine with CF3 and F3C substituents) | (bithiophene) | PF6 | 2 |
| 303 | Ru | (bipyridine with CF3 and F3C substituents) | (terthiophene) | PF6 | 2 |
| 304 | Ru | (bipyridine with CF3 and F3C substituents) | (quaterthiophene) | PF6 | 2 |
| 305 | Ru | (bipyridine with CF3 and F3C substituents) | (quinquethiophene) | PF6 | 2 |

TABLE 2-continued
| | | | | |
|---|---|---|---|---|
| 306 | Ru |  |  | PF$_6$ 2 |
| 307 | Ru |  |  | PF$_6$ 2 |
| 308 | Ru |  | 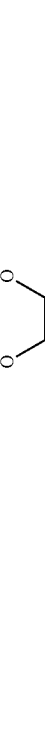 | PF$_6$ 2 |
| 309 | Ru |  |  | PF$_6$ 2 |

TABLE 2-continued

| | | | | |
|---|---|---|---|---|
| 310 | Ru | (4-CF₃, 3-CF₃ bipyridine) | (tris-EDOT) | PF₆ 2 |
| 311 | Ru | (4-CF₃, 3-CF₃ bipyridine) | (tris-EDOT) | PF₆ 2 |
| 312 | Ru | (4-CF₃, 3-CF₃ bipyridine) | (tris-EDOT) | PF₆ 2 |
| 313 | Ru | (bipyrimidine) | (thiophene) | PF₆ 2 |
| 314 | Ru | (bipyrimidine) | (bithiophene) | PF₆ 2 |

TABLE 2-continued

| | | | | |
|---|---|---|---|---|
| 315 | Ru | bipyridine | terthiophene | PF$_6$ | 2 |
| 316 | Ru | bipyridine | terthiophene | PF$_6$ | 2 |
| 317 | Ru | bipyridine | terthiophene | PF$_6$ | 2 |
| 318 | Ru | bipyridine | quaterthiophene | PF$_6$ | 2 |
| 319 | Ru | bipyridine | EDOT-thiophene | PF$_6$ | 2 |
| 320 | Ru | bipyridine | bis-EDOT-thiophene | PF$_6$ | 2 |

TABLE 2-continued

| | | | | |
|---|---|---|---|---|
| 321 | Ru | bpy | tri-EDOT | PF$_6$, 2 |
| 322 | Ru | bpy | tri-EDOT | PF$_6$, 2 |
| 323 | Ru | bpy | tetra-EDOT | PF$_6$, 2 |
| 324 | Ru | bpy | tetra-EDOT | PF$_6$, 2 |

TABLE 2-continued

| | | | | |
|---|---|---|---|---|
| 325 | Ru | bpy | thiophene | PF$_6$ 2 |
| 326 | Ru | bpy | bithiophene | PF$_6$ 2 |
| 327 | Ru | bpy | terthiophene | PF$_6$ 2 |
| 328 | Ru | bpy | quaterthiophene | PF$_6$ 2 |
| 329 | Ru | bpy | quinquethiophene | PF$_6$ 2 |
| 330 | Ru | bpy | sexithiophene | PF$_6$ 2 |
| 331 | Ru | bpy | EDOT | PF$_6$ 2 |

| | | | |
|---|---|---|---|
| 332 | Ru | ![pyrimidine-pyrimidine] | ![EDOT-EDOT] PF$_6$ 2 |
| 333 | Ru | ![pyrimidine-pyrimidine] | ![bis-EDOT branched] PF$_6$ 2 |
| 334 | Ru | ![pyrimidine-pyrimidine] | ![bis-EDOT branched] PF$_6$ 2 |
| 335 | Ru | ![pyrimidine-pyrimidine] | ![tris-EDOT branched] PF$_6$ 2 |

TABLE 2-continued
| | | | | |
|---|---|---|---|---|
| 336 | Ru | 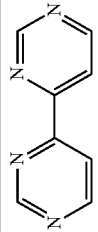 | 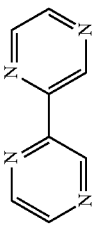 | PF$_6$ 2 |
| 337 | Ru | | | PF$_6$ 2 |
| 338 | Ru | | | PF$_6$ 2 |
| 339 | Ru | | | PF$_6$ 2 |
| 340 | Ru | | | PF$_6$ 2 |
| 341 | Ru | | | PF$_6$ 2 |
| 342 | Ru | | | PF$_6$ 2 |

TABLE 2-continued
| | | | | |
|---|---|---|---|---|
| 343 | Ru | 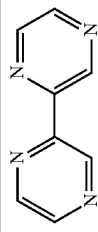 | 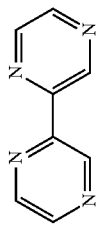 | PF$_6$ 2 |
| 344 | Ru | 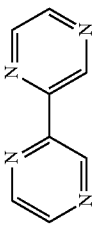 | 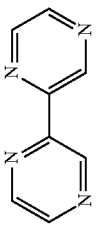 | PF$_6$ 2 |
| 345 | Ru |  | 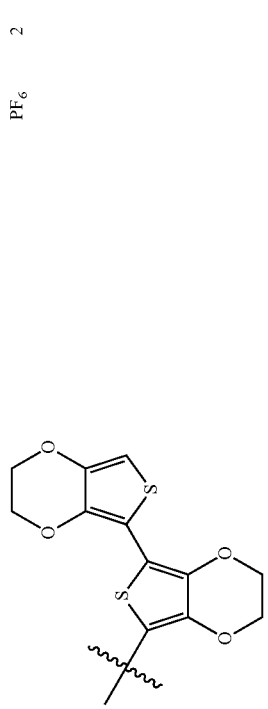 | PF$_6$ 2 |
| 346 | Ru | 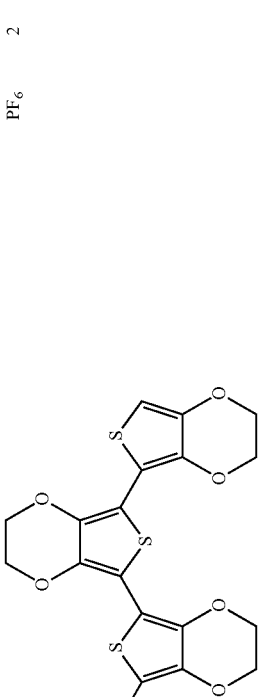 | 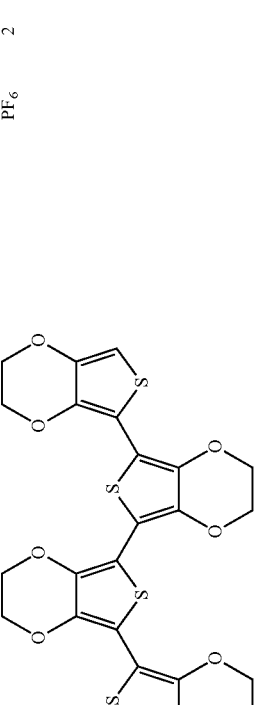 | PF$_6$ 2 |

TABLE 2-continued

| | | | | |
|---|---|---|---|---|
| 347 | Ru | (bipyrazine) | (tetra-EDOT) | PF$_6$ 2 |
| 348 | Ru | (bipyrazine) | (tetra-EDOT) | PF$_6$ 2 |
| 349 | Ru | (benzoquinoline) | (thiophene) | PF$_6$ 2 |
| 350 | Ru | (benzoquinoline) | (bithiophene) | PF$_6$ 2 |
| 351 | Ru | (benzoquinoline) | (terthiophene) | PF$_6$ 2 |
| 352 | Ru | (benzoquinoline) | (quaterthiophene) | PF$_6$ 2 |

TABLE 2-continued

| | | | | |
|---|---|---|---|---|
| 353 | Ru | | | PF₆ | 2 |
| 354 | Ru | | | PF₆ | 2 |
| 355 | Ru | | | PF₆ | 2 |
| 356 | Ru | | | PF₆ | 2 |
| 357 | Ru | | | PF₆ | 2 |

TABLE 2-continued
| | | | | |
|---|---|---|---|---|
| 358 | Ru | 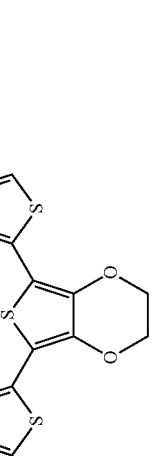 | 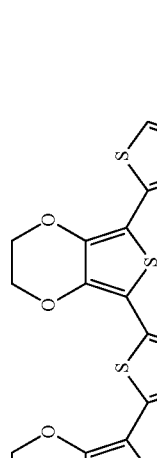 | PF$_6$ 2 |
| 359 | Ru | 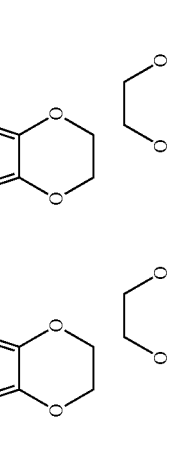 | 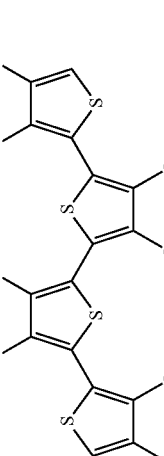 | PF$_6$ 2 |
| 360 | Ru | 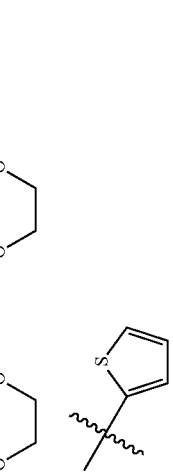 | 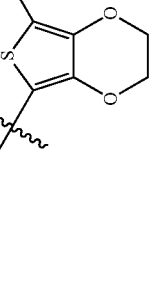 | PF$_6$ 2 |
| 361 | Ru | 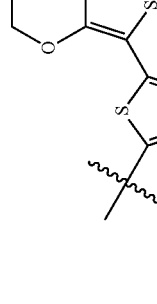 | 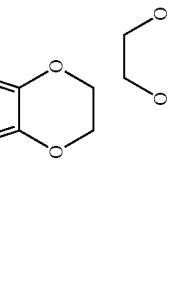 | PF$_6$ 2 |
| 362 | Ru | 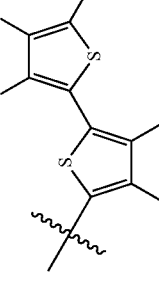 | 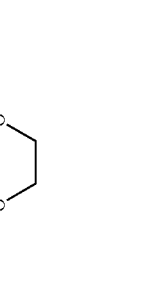 | PF$_6$ 2 |

TABLE 2-continued

| | | | | |
|---|---|---|---|---|
| 363 | Ru | [quinoline-fused structure] | [terthiophene] | PF₆ 2 |
| 364 | Ru | [quinoline-fused structure] | [terthiophene] | PF₆ 2 |
| 365 | Ru | [quinoline-fused structure] | [terthiophene] | PF₆ 2 |
| 366 | Ru | [quinoline-fused structure] | [quaterthiophene] | PF₆ 2 |
| 367 | Ru | [quinoline-fused structure] | [EDOT] | PF₆ 2 |
| 368 | Ru | [quinoline-fused structure] | [bis-EDOT] | PF₆ 2 |

TABLE 2-continued

| | | | | |
|---|---|---|---|---|
| 369 | Ru | [structure] | [structure] | PF$_6$ 2 |
| 370 | Ru | [structure] | [structure] | PF$_6$ 2 |
| 371 | Ru | [structure] | [structure] | PF$_6$ 2 |
| 372 | Ru | [structure] | [structure] | PF$_6$ 2 |

TABLE 2-continued
| | | | | |
|---|---|---|---|---|
| 373 | Ru |  |  | PF₆ 2 |
| 374 | Ru | | | PF₆ 2 |
| 375 | Ru | | | PF₆ 2 |
| 376 | Ru | | | PF₆ 2 |
| 377 | Ru | | | PF₆ 2 |
| 378 | Ru | | | PF₆ 2 |

TABLE 2-continued

| | | | | |
|---|---|---|---|---|
| 379 | Ru | (2,9-dimethyl-phen) | (EDOT) | PF₆ 2 |
| 380 | Ru | (2,9-dimethyl-phen) | (bi-EDOT) | PF₆ 2 |
| 381 | Ru | (2,9-dimethyl-phen) | (ter-EDOT) | PF₆ 2 |
| 382 | Ru | (2,9-dimethyl-phen) | (tetra-EDOT) | PF₆ 2 |

TABLE 2-continued
| | | | | |
|---|---|---|---|---|
| 383 | Ru | 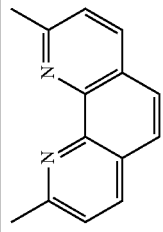 | 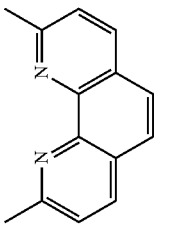 | PF$_6$ 2 |
| 384 | Ru | 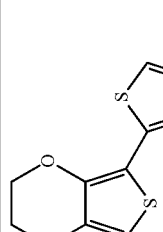 | 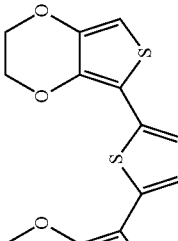 | PF$_6$ 2 |
| 385 | Ru |  | 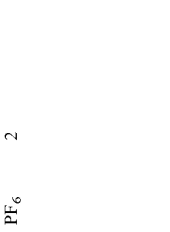 | PF$_6$ 2 |
| 386 | Ru | 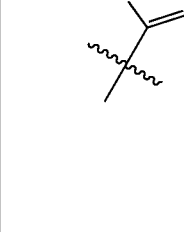 | 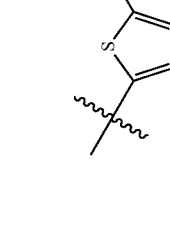 | PF$_6$ 2 |
| 387 | Ru | 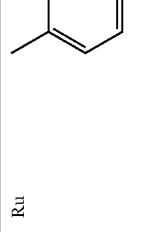 | 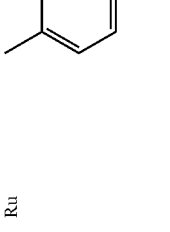 | PF$_6$ 2 |
| 388 | Ru | 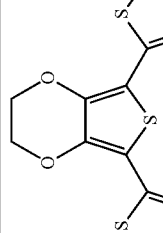 | 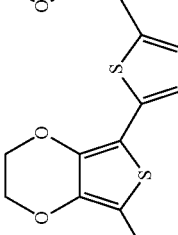 | PF$_6$ 2 |

TABLE 2-continued

| | | | | |
|---|---|---|---|---|
| 389 | Ru | | | PF$_6$ | 2 |
| 390 | Ru | | | PF$_6$ | 2 |
| 391 | Ru | | | PF$_6$ | 2 |
| 392 | Ru | | | PF$_6$ | 2 |
| 393 | Ru | | | PF$_6$ | 2 |

TABLE 2-continued

| | | | | |
|---|---|---|---|---|
| 394 | Ru | [bipyridine-Me] | [tri-EDOT] | PF₆ 2 |
| 395 | Ru | [bipyridine-Me] | [tri-EDOT] | PF₆ 2 |
| 396 | Ru | [bipyridine-Me] | [tri-EDOT] | PF₆ 2 |
| 397 | Ru | [Me-phenanthroline] | [thiophene] | PF₆ 2 |
| 398 | Ru | [Me-phenanthroline] | [bithiophene] | PF₆ 2 |

TABLE 2-continued

| | | | | |
|---|---|---|---|---|
| 399 | Ru | [phenanthroline-dimethyl] | [bithiophene] | PF$_6$ | 2 |
| 400 | Ru | [phenanthroline-dimethyl] | [terthiophene] | PF$_6$ | 2 |
| 401 | Ru | [phenanthroline-dimethyl] | [quaterthiophene] | PF$_6$ | 2 |
| 402 | Ru | [phenanthroline-dimethyl] | [quinquethiophene] | PF$_6$ | 2 |
| 403 | Ru | [phenanthroline-dimethyl] | [EDOT] | PF$_6$ | 2 |
| 404 | Ru | [phenanthroline-dimethyl] | [bis-EDOT-thiophene] | PF$_6$ | 2 |

TABLE 2-continued

| | | | | |
|---|---|---|---|---|
| 405 | Ru | (4,7-dimethyl-phenanthroline) | (bi-EDOT) | PF$_6$ 2 |
| 406 | Ru | (4,7-dimethyl-phenanthroline) | (tri-EDOT) | PF$_6$ 2 |
| 407 | Ru | (4,7-dimethyl-phenanthroline) | (tri-EDOT) | PF$_6$ 2 |
| 408 | Ru | (4,7-dimethyl-phenanthroline) | (tetra-EDOT) | PF$_6$ 2 |

Exemplary embodiments include compounds having the formula (VIII) or a pharmaceutically acceptable salt form thereof:
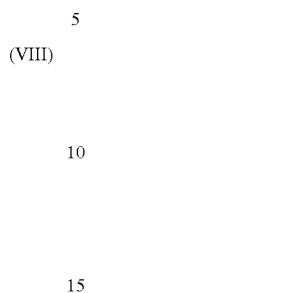
(VIII)
wherein non-limiting examples of M, $R^1$, X, and h are defined herein below in Table 3.
TABLE 3
| Entry | M | $R^1$ | X | h |
|---|---|---|---|---|
| 1 | Ru | thiophene | Cl | 2 |
| 2 | Ru | bithiophene | Cl | 2 |
| 3 | Ru | terthiophene | Cl | 2 |
| 4 | Ru | quaterthiophene | Cl | 2 |
| 5 | Ru | quinquethiophene | Cl | 2 |
| 6 | Ru | sexithiophene | Cl | 2 |
| 7 | Ru | EDOT | Cl | 2 |

TABLE 3-continued
| Entry | M | R¹ | X | h |
|---|---|---|---|---|
| 8 | Ru | 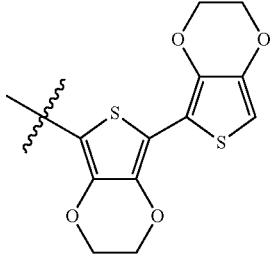 [SMILES: *c1sc(-c2scc3c2OCCO3)c2c1OCCO2] | Cl | 2 |
| 9 | Ru | 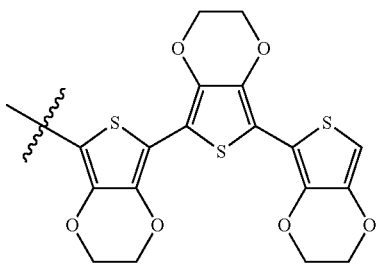 [SMILES: *c1sc(-c2sc(-c3scc4c3OCCO4)c3c2OCCO3)c2c1OCCO2] | Cl | 2 |
| 10 | Ru | 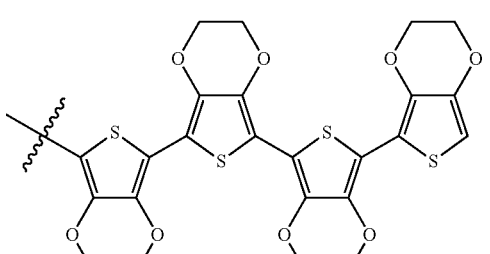 | Cl | 2 |
| 11 | Ru | 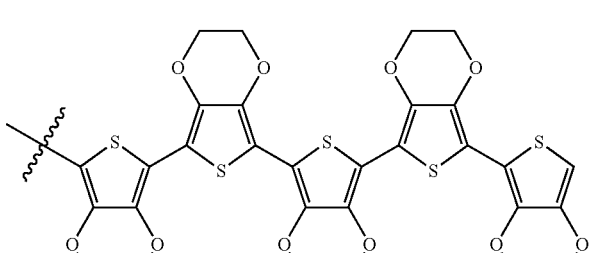 | Cl | 2 |
| 12 | Ru | 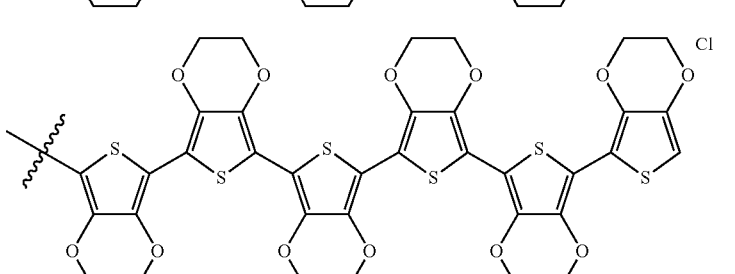 | Cl | 2 |
| 13 | Ru | 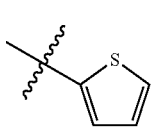 [SMILES: *c1cccs1] | Cl | 2 |
| 14 | Ru | 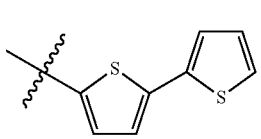 [SMILES: *c1ccc(-c2cccs2)s1] | Cl | 2 |

TABLE 3-continued

| Entry | M | R¹ | X | h |
|---|---|---|---|---|
| 15 | Ru | terthiophene | Cl | 2 |
| 16 | Ru | quaterthiophene | Cl | 2 |
| 17 | Ru | quinquethiophene | Cl | 2 |
| 18 | Ru | sexithiophene | Cl | 2 |
| 19 | Ru | EDOT | Cl | 2 |
| 20 | Ru | thiophene-EDOT | Cl | 2 |
| 21 | Ru | EDOT-thiophene-EDOT | Cl | 2 |
| 22 | Ru | bis(EDOT-thiophene) | Cl | 2 |

TABLE 3-continued

| Entry | M | R¹ | X | h |
|---|---|---|---|---|
| 23 | Ru | | Cl | 2 |
| 24 | Ru | | Cl | 2 |
| 25 | Ru | | Cl | 2 |
| 26 | Ru | | Cl | 2 |
| 27 | Ru | | Cl | 2 |
| 28 | Ru | | Cl | 2 |
| 29 | Ru | | Cl | 2 |
| 30 | Ru | | Cl | 2 |
| 31 | Ru | | Cl | 2 |

TABLE 3-continued

| Entry | M | R¹ | X | h |
|---|---|---|---|---|
| 32 | Ru | (EDOT-EDOT) | Cl | 2 |
| 33 | Ru | (EDOT-EDOT-EDOT) | Cl | 2 |
| 34 | Ru | (EDOT)₄ | Cl | 2 |
| 35 | Ru | (EDOT)₅ | Cl | 2 |
| 36 | Ru | (EDOT)₆ | Cl | 2 |
| 37 | Ru | (thienyl) | Cl | 2 |
| 38 | Ru | (bithienyl) | Cl | 2 |

TABLE 3-continued
| Entry | M | R¹ | X | h |
|---|---|---|---|---|
| 39 | Ru | 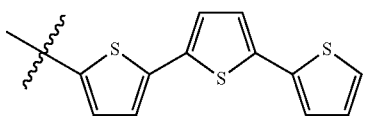 [SMILES: *c1ccc(-c2ccc(-c3cccs3)s2)s1] | Cl | 2 |
| 40 | Ru | 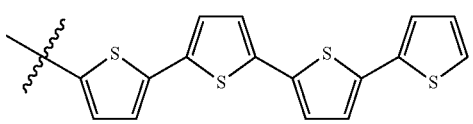 [SMILES: *c1ccc(-c2ccc(-c3ccc(-c4cccs4)s3)s2)s1] | Cl | 2 |
| 41 | Ru | 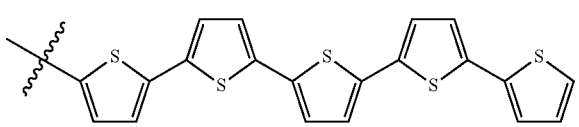 [SMILES: *c1ccc(-c2ccc(-c3ccc(-c4ccc(-c5cccs5)s4)s3)s2)s1] | Cl | 2 |
| 42 | Ru | 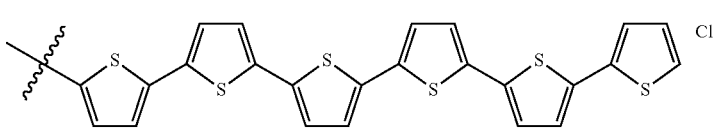 | Cl | 2 |
| 43 | Ru | 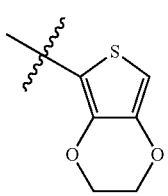 | Cl | 2 |
| 44 | Ru | 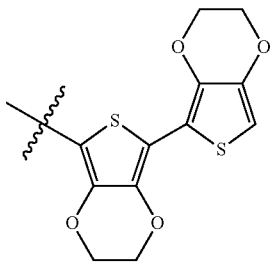 [SMILES: *c1sc(-c2scc3c2OCCO3)c2c1OCCO2] | Cl | 2 |
| 45 | Ru | 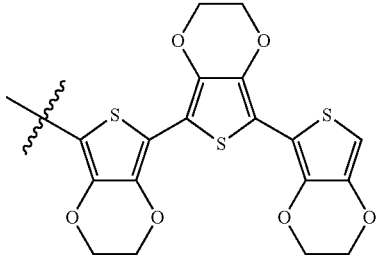 [SMILES: *c1sc(-c2sc(-c3scc4c3OCCO4)c3c2OCCO3)c2c1OCCO2] | Cl | 2 |
| 46 | Ru | 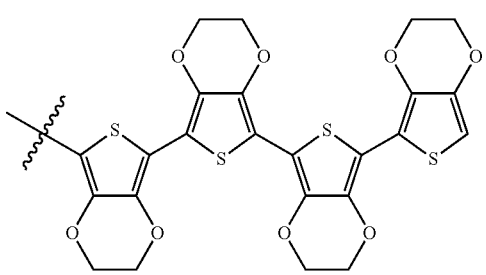 [SMILES: *c1sc(-c2sc(-c3sc(-c4scc5c4OCCO5)c4c3OCCO4)c3c2OCCO3)c2c1OCCO2] | Cl | 2 |

TABLE 3-continued
| Entry | M | R[1] | X | h |
|---|---|---|---|---|
| 47 | Ru | 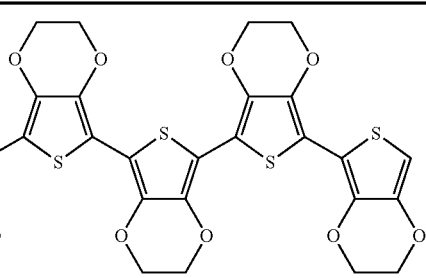 | Cl | 2 |
| 48 | Ru | 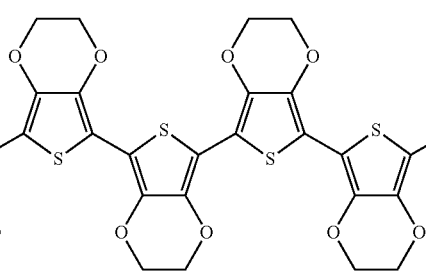 | Cl | 2 |
| 49 | Ru |  | Cl | 2 |
| 50 | Ru |  | Cl | 2 |
| 51 | Ru | 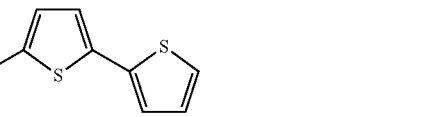 | Cl | 2 |
| 52 | Ru | 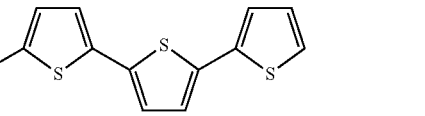 | Cl | 2 |
| 53 | Ru | 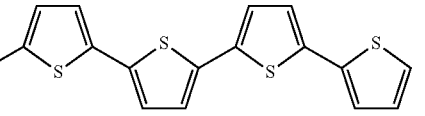 | Cl | 2 |
| 54 | Ru | 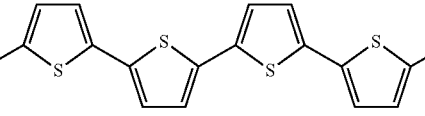 | Cl | 2 |
| 55 | Ru |  | Cl | 2 |

TABLE 3-continued
| Entry | M | R¹ | X | h |
|---|---|---|---|---|
| 56 | Ru | 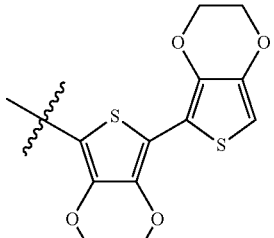 | Cl | 2 |
| 57 | Ru | 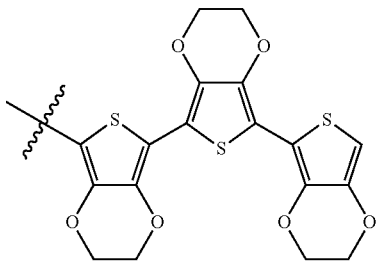 [SMILES: *c1sc(-c2sc(-c3scc4c3OCCO4)c3c2OCCO3)c2c1OCCO2] | Cl | 2 |
| 58 | Ru | 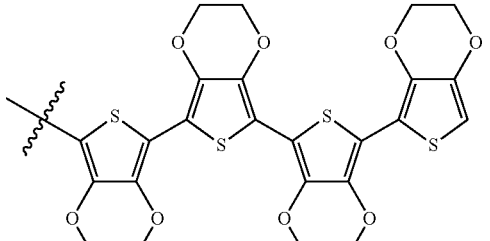 | Cl | 2 |
| 59 | Ru | 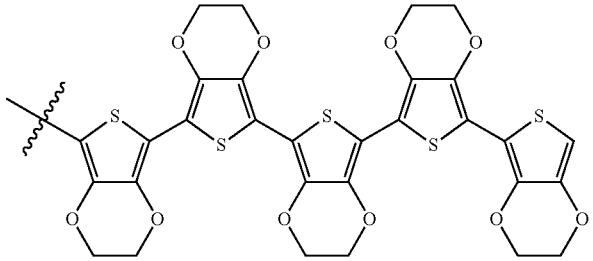 [SMILES: *c1sc(-c2sc(-c3sc(-c4sc(-c5scc6c5OCCO6)c5c4OCCO5)c4c3OCCO4)c3c2OCCO3)c2c1OCCO2] | Cl | 2 |
| 60 | Ru | 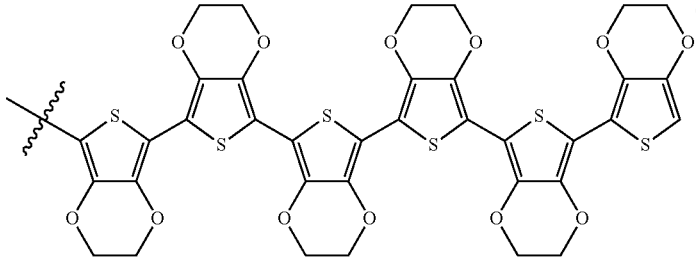 [SMILES: *c1sc(-c2sc(-c3sc(-c4sc(-c5sc(-c6scc7c6OCCO7)c6c5OCCO6)c5c4OCCO5)c4c3OCCO4)c3c2OCCO3)c2c1OCCO2] | Cl | 2 |
| 61 | Ru | 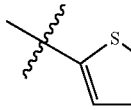 | Cl | 2 |
| 62 | Ru | 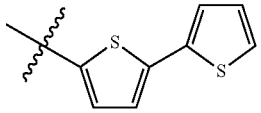 [SMILES: *c1ccc(-c2cccs2)s1] | Cl | 2 |

TABLE 3-continued

| Entry | M | R¹ | X | h |
|---|---|---|---|---|
| 63 | Ru | terthiophene | Cl | 2 |
| 64 | Ru | quaterthiophene | Cl | 2 |
| 65 | Ru | quinquethiophene | Cl | 2 |
| 66 | Ru | sexithiophene | Cl | 2 |
| 67 | Ru | EDOT (3,4-ethylenedioxythiophene) | Cl | 2 |
| 68 | Ru | bis-EDOT | Cl | 2 |
| 69 | Ru | ter-EDOT | Cl | 2 |
| 70 | Ru | quater-EDOT | Cl | 2 |

TABLE 3-continued

| Entry | M | R¹ | X | h |
|---|---|---|---|---|
| 71 | Ru | | Cl | 2 |
| 72 | Ru | | Cl | 2 |
| 73 | Ru | | Cl | 2 |
| 74 | Ru | | Cl | 2 |
| 75 | Ru | | Cl | 2 |
| 76 | Ru | | Cl | 2 |
| 77 | Ru | | Cl | 2 |
| 78 | Ru | | Cl | 2 |
| 79 | Ru | | Cl | 2 |

TABLE 3-continued
| Entry | M | R¹ | X | h |
|---|---|---|---|---|
| 80 | Ru | 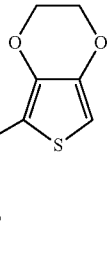 | Cl | 2 |
| 81 | Ru | 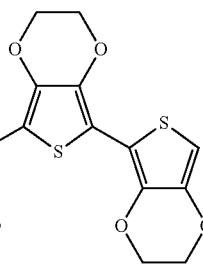 | Cl | 2 |
| 82 | Ru | 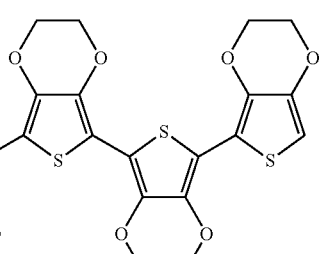 | Cl | 2 |
| 83 | Ru | 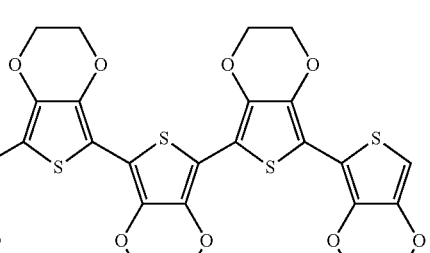 | Cl | 2 |
| 84 | Ru | 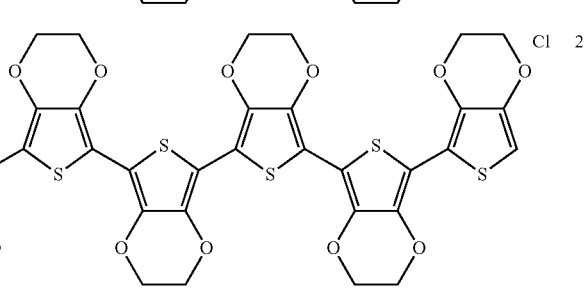 | Cl | 2 |
| 85 | Ru |  | Cl | 2 |
| 86 | Ru | 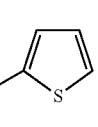 | Cl | 2 |

TABLE 3-continued

| Entry | M | R¹ | X | h |
|---|---|---|---|---|
| 87 | Ru | (terthiophene) | Cl | 2 |
| 88 | Ru | (quaterthiophene) | Cl | 2 |
| 89 | Ru | (quinquethiophene) | Cl | 2 |
| 90 | Ru | (sexithiophene) | Cl | 2 |
| 91 | Ru | (EDOT) | Cl | 2 |
| 92 | Ru | (thiophene-EDOT) | Cl | 2 |
| 93 | Ru | (EDOT-thiophene-EDOT) | Cl | 2 |
| 94 | Ru | (thiophene-EDOT-thiophene-EDOT) | Cl | 2 |

TABLE 3-continued

| Entry | M | R¹ | X | h |
|---|---|---|---|---|
| 95 | Ru | (structure) | Cl | 2 |
| 96 | Ru | (structure) | Cl | 2 |
| 97 | Ru | (structure) | Cl | 2 |
| 98 | Ru | (structure) | Cl | 2 |
| 99 | Ru | (structure) | Cl | 2 |
| 100 | Ru | (structure) | Cl | 2 |
| 101 | Ru | (structure) | Cl | 2 |
| 102 | Ru | (structure) | Cl | 2 |
| 103 | Ru | (structure) | Cl | 2 |

TABLE 3-continued
| Entry | M | R¹ | X | h |
|---|---|---|---|---|
| 104 | Ru | 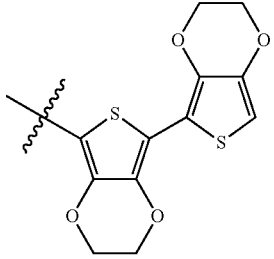 [SMILES: *c1sc(-c2scc3c2OCCO3)c2c1OCCO2] | Cl | 2 |
| 105 | Ru | 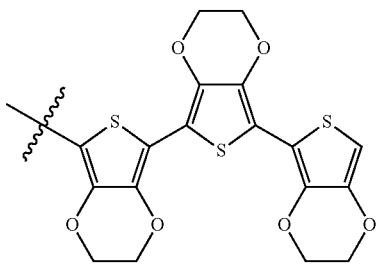 [SMILES: *c1sc(-c2sc(-c3scc4c3OCCO4)c3c2OCCO3)c2c1OCCO2] | Cl | 2 |
| 106 | Ru | 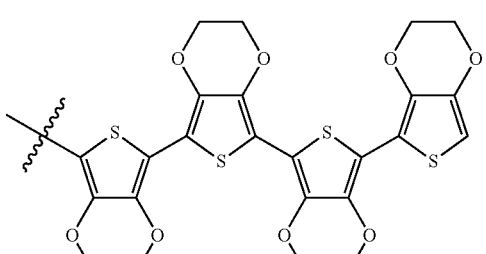 | Cl | 2 |
| 107 | Ru | 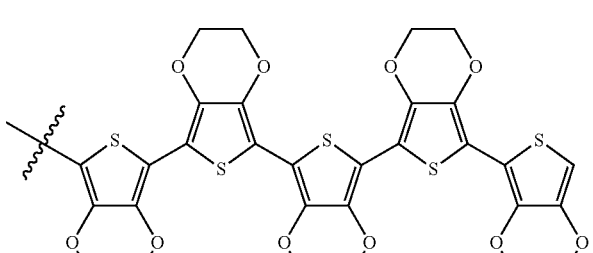 | Cl | 2 |
| 108 | Ru | 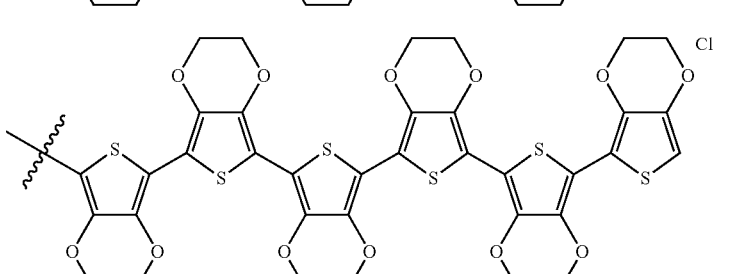 | Cl | 2 |
| 109 | Ru | 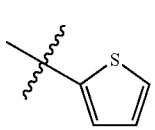 [SMILES: *c1cccs1] | Cl | 2 |
| 110 | Ru | 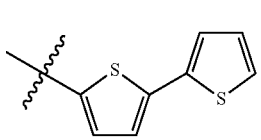 [SMILES: *c1ccc(-c2cccs2)s1] | Cl | 2 |

TABLE 3-continued
| Entry | M | R¹ | X | h |
|---|---|---|---|---|
| 111 | Ru | 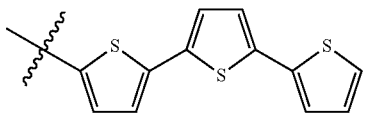 [SMILES: *c1ccc(-c2ccc(-c3cccs3)s2)s1] | Cl | 2 |
| 112 | Ru | 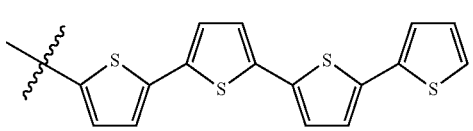 [SMILES: *c1ccc(-c2ccc(-c3ccc(-c4cccs4)s3)s2)s1] | Cl | 2 |
| 113 | Ru | 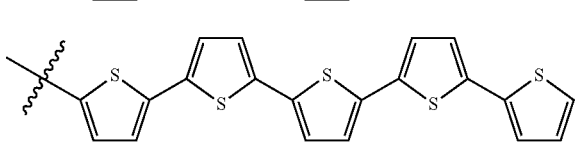 | Cl | 2 |
| 114 | Ru | 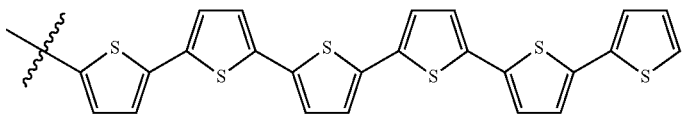 [SMILES: *c1ccc(-c2ccc(-c3ccc(-c4ccc(-c5ccc(-c6cccs6)s5)s4)s3)s2)s1] | Cl | 2 |
| 115 | Ru | 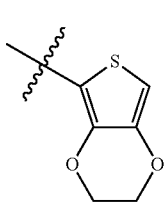 [SMILES: *c1scc2c1OCCO2] | Cl | 2 |
| 116 | Ru | 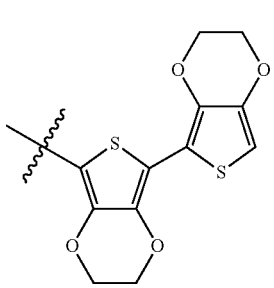 [SMILES: *c1sc(-c2scc3c2OCCO3)c2c1OCCO2] | Cl | 2 |
| 117 | Ru | 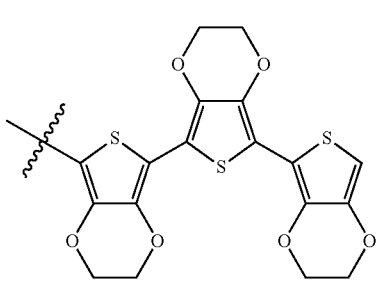 [SMILES: *c1sc(-c2sc(-c3scc4c3OCCO4)c3c2OCCO3)c2c1OCCO2] | Cl | 2 |
| 118 | Ru | 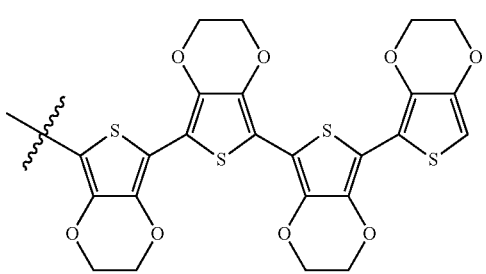 [SMILES: *c1sc(-c2sc(-c3sc(-c4scc5c4OCCO5)c4c3OCCO4)c3c2OCCO3)c2c1OCCO2] | Cl | 2 |

TABLE 3-continued

| Entry | M | R¹ | X | h |
|---|---|---|---|---|
| 119 | Ru | (structure) | Cl | 2 |
| 120 | Ru | (structure) | Cl | 2 |
| 121 | Ru | (structure) | Cl | 2 |
| 122 | Ru | (structure) | Cl | 2 |
| 123 | Ru | (structure) | Cl | 2 |
| 124 | Ru | (structure) | Cl | 2 |
| 125 | Ru | (structure) | Cl | 2 |
| 126 | Ru | (structure) | Cl | 2 |
| 127 | Ru | (structure) | Cl | 2 |

TABLE 3-continued

| Entry | M | R¹ | X | h |
|---|---|---|---|---|
| 128 | Ru | 5-(2,3-dihydrothieno[3,4-b][1,4]dioxin-5-yl)-2,3-dihydrothieno[3,4-b][1,4]dioxine | Cl | 2 |
| 129 | Ru | EDOT trimer | Cl | 2 |
| 130 | Ru | EDOT tetramer | Cl | 2 |
| 131 | Ru | EDOT pentamer | Cl | 2 |
| 132 | Ru | EDOT hexamer | Cl | 2 |
| 133 | Ru | thiophen-2-yl | Cl | 2 |
| 134 | Ru | 2,2'-bithiophen-5-yl | Cl | 2 |

TABLE 3-continued

| Entry | M | R¹ | X | h |
|---|---|---|---|---|
| 135 | Ru | terthiophene | Cl | 2 |
| 136 | Ru | quaterthiophene | Cl | 2 |
| 137 | Ru | quinquethiophene | Cl | 2 |
| 138 | Ru | sexithiophene | Cl | 2 |
| 139 | Ru | EDOT | Cl | 2 |
| 140 | Ru | bi-EDOT-thiophene | Cl | 2 |
| 141 | Ru | EDOT-thiophene-EDOT | Cl | 2 |
| 142 | Ru | bis(EDOT-thiophene) | Cl | 2 |

TABLE 3-continued

| Entry | M | R¹ | X | h |
|---|---|---|---|---|
| 143 | Ru | (bis-EDOT-thiophene-EDOT-EDOT-thiophene structure) | Cl | 2 |
| 144 | Ru | (hexameric EDOT/thiophene structure) | Cl | 2 |
| 145 | Ru | (thiophene) | Cl | 2 |
| 146 | Ru | (bithiophene) | Cl | 2 |
| 147 | Ru | (terthiophene) | Cl | 2 |
| 148 | Ru | (quaterthiophene) | Cl | 2 |
| 149 | Ru | (quinquethiophene) | Cl | 2 |
| 150 | Ru | (sexithiophene) | Cl | 2 |
| 151 | Ru | (EDOT) | Cl | 2 |

TABLE 3-continued
| Entry | M | R¹ | X | h |
|---|---|---|---|---|
| 152 | Ru | 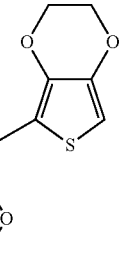 | Cl | 2 |
| 153 | Ru | 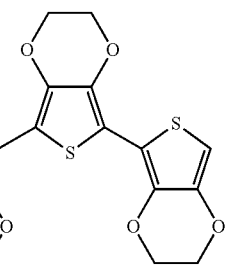 | Cl | 2 |
| 154 | Ru | 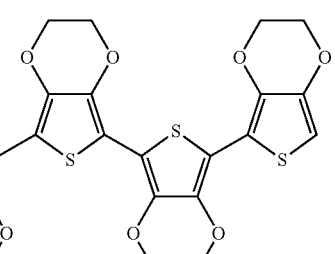 | Cl | 2 |
| 155 | Ru | 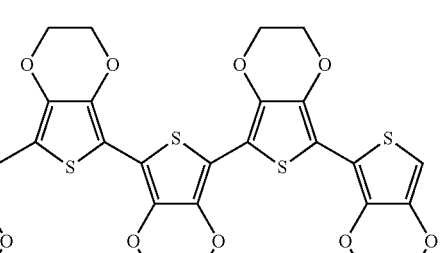 | Cl | 2 |
| 156 | Ru | 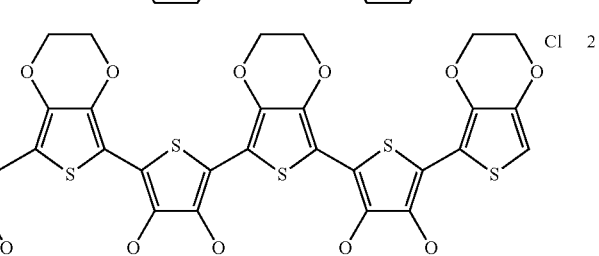 | Cl | 2 |
| 157 | Ru |  | Cl | 2 |
| 158 | Ru |  | Cl | 2 |

TABLE 3-continued

| Entry | M | R¹ | X | h |
|---|---|---|---|---|
| 159 | Ru | (terthiophene) | Cl | 2 |
| 160 | Ru | (quaterthiophene) | Cl | 2 |
| 161 | Ru | (quinquethiophene) | Cl | 2 |
| 162 | Ru | (sexithiophene) | Cl | 2 |
| 163 | Ru | (EDOT) | Cl | 2 |
| 164 | Ru | (thiophene-EDOT) | Cl | 2 |
| 165 | Ru | (EDOT-thiophene-EDOT) | Cl | 2 |
| 166 | Ru | (EDOT-thiophene-thiophene-EDOT) | Cl | 2 |

TABLE 3-continued

| Entry | M | R¹ | X | h |
|---|---|---|---|---|
| 167 | Ru | (structure: chain of 5 thiophene/EDOT units) | Cl | 2 |
| 168 | Ru | (structure: chain of 6 thiophene/EDOT units) | Cl | 2 |
| 169 | Ru | (structure: thiophene) | Cl | 2 |
| 170 | Ru | (structure: bithiophene) | Cl | 2 |
| 171 | Ru | (structure: terthiophene) | Cl | 2 |
| 172 | Ru | (structure: quaterthiophene) | Cl | 2 |
| 173 | Ru | (structure: quinquethiophene) | Cl | 2 |
| 174 | Ru | (structure: sexithiophene) | Cl | 2 |
| 175 | Ru | (structure: EDOT) | Cl | 2 |

TABLE 3-continued
| Entry | M | R¹ | X | h |
|---|---|---|---|---|
| 176 | Ru | 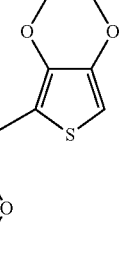 | Cl | 2 |
| 177 | Ru | 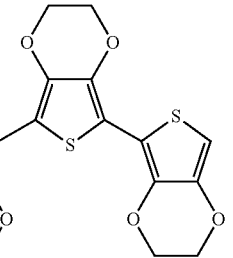 | Cl | 2 |
| 178 | Ru | 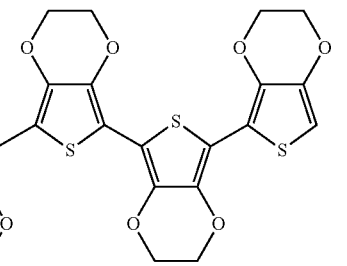 | Cl | 2 |
| 179 | Ru | 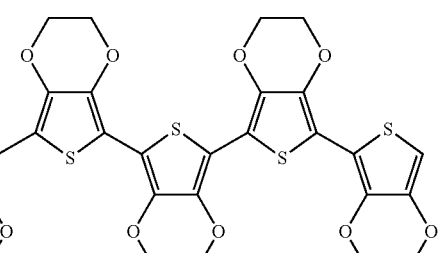 | Cl | 2 |
| 180 | Ru | 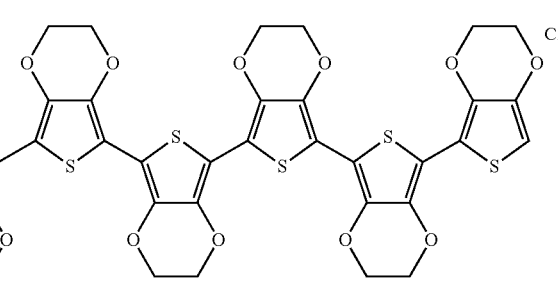 | Cl | 2 |
| 181 | Ru | 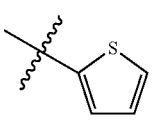 [SMILES: *c1cccs1] | Cl | 2 |
| 182 | Ru | 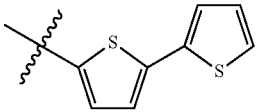 [SMILES: *c1ccc(-c2cccs2)s1] | Cl | 2 |

TABLE 3-continued

| Entry | M | R¹ | X | h |
|---|---|---|---|---|
| 183 | Ru | terthiophene | Cl | 2 |
| 184 | Ru | quaterthiophene | Cl | 2 |
| 185 | Ru | quinquethiophene | Cl | 2 |
| 186 | Ru | sexithiophene | Cl | 2 |
| 187 | Ru | EDOT | Cl | 2 |
| 188 | Ru | thiophene-EDOT | Cl | 2 |
| 189 | Ru | EDOT-thiophene-EDOT | Cl | 2 |
| 190 | Ru | thiophene-EDOT-thiophene-EDOT | Cl | 2 |

TABLE 3-continued

| Entry | M | R¹ | X | h |
|---|---|---|---|---|
| 191 | Ru | | Cl | 2 |
| 192 | Ru | | Cl | 2 |
| 193 | Ru | | PF₆ | 2 |
| 194 | Ru | | PF₆ | 2 |
| 195 | Ru | | PF₆ | 2 |
| 196 | Ru | | PF₆ | 2 |
| 197 | Ru | | PF₆ | 2 |
| 198 | Ru | | PF₆ | 2 |
| 199 | Ru | | PF₆ | 2 |

TABLE 3-continued
| Entry | M | R¹ | X | h |
|---|---|---|---|---|
| 200 | Ru | 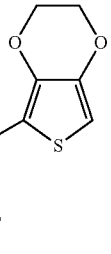 | PF₆ | 2 |
| 201 | Ru | 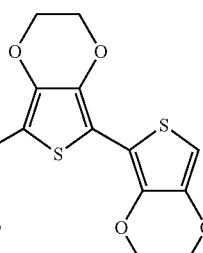 | PF₆ | 2 |
| 202 | Ru | 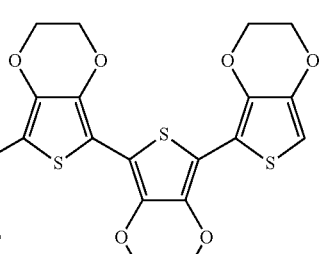 | PF₆ | 2 |
| 203 | Ru | 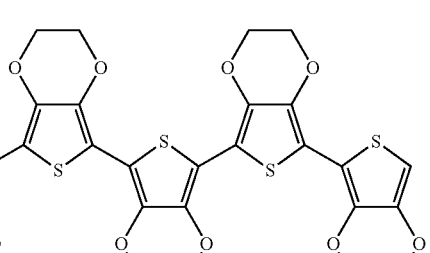 | PF₆ | 2 |
| 204 | Ru | 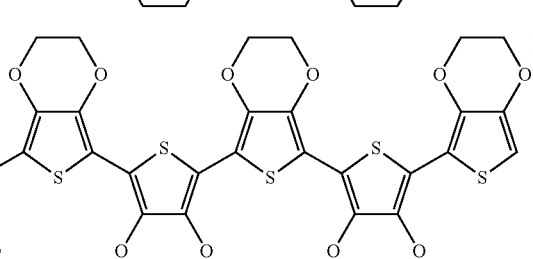 | PF₆ | 2 |
| 205 | Ru |  | PF₆ | 2 |
| 206 | Ru | 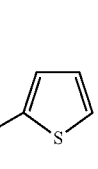 | PF₆ | 2 |

TABLE 3-continued
| Entry | M | R¹ | X | h |
|---|---|---|---|---|
| 207 | Ru | 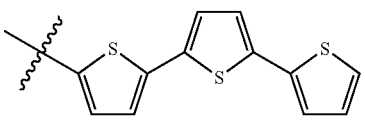 [SMILES: *c1ccc(-c2ccc(-c3cccs3)s2)s1] | PF$_6$ | 2 |
| 208 | Ru | 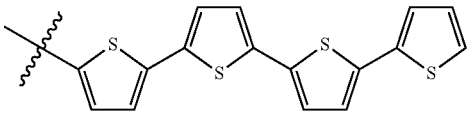 [SMILES: *c1ccc(-c2ccc(-c3ccc(-c4cccs4)s3)s2)s1] | PF$_6$ | 2 |
| 209 | Ru | 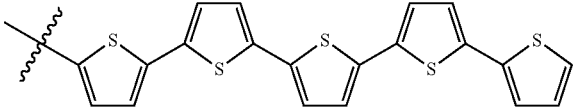 [SMILES: *c1ccc(-c2ccc(-c3ccc(-c4ccc(-c5cccs5)s4)s3)s2)s1] | PF$_6$ | 2 |
| 210 | Ru | 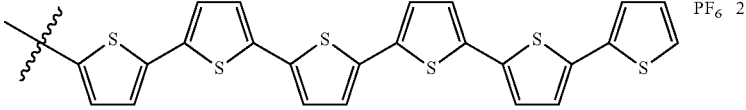 | PF$_6$ | 2 |
| 211 | Ru | 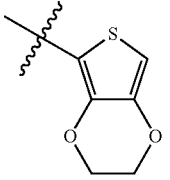 | PF$_6$ | 2 |
| 212 | Ru | 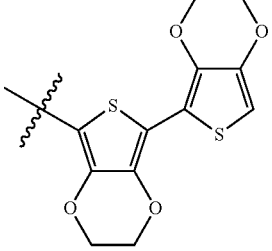 | PF$_6$ | 2 |
| 213 | Ru | 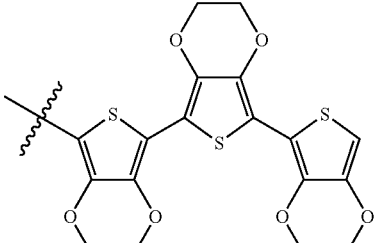 | PF$_6$ | 2 |
| 214 | Ru | 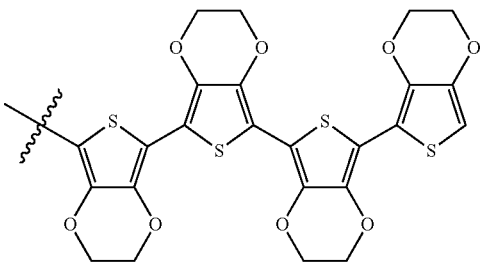 [SMILES: *c1sc(-c2sc(-c3sc(-c4scc5c4OCCO5)c4c3OCCO4)c3c2OCCO3)c2c1OCCO2] | PF$_6$ | 2 |

TABLE 3-continued

| Entry | M | R¹ | X | h |
|---|---|---|---|---|
| 215 | Ru | (EDOT-thiophene pentamer structure) | PF$_6$ | 2 |
| 216 | Ru | (EDOT-thiophene hexamer structure) | PF$_6$ | 2 |
| 217 | Ru | (thiophene) | PF$_6$ | 2 |
| 218 | Ru | (bithiophene) | PF$_6$ | 2 |
| 219 | Ru | (terthiophene) | PF$_6$ | 2 |
| 220 | Ru | (quaterthiophene) | PF$_6$ | 2 |
| 221 | Ru | (quinquethiophene) | PF$_6$ | 2 |
| 222 | Ru | (sexithiophene) | PF$_6$ | 2 |
| 223 | Ru | (EDOT-thiophene) | PF$_6$ | 2 |

TABLE 3-continued
| Entry | M | R¹ | X | h |
|---|---|---|---|---|
| 224 | Ru | 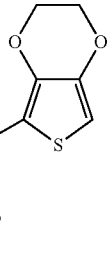 | PF$_6$ | 2 |
| 225 | Ru | 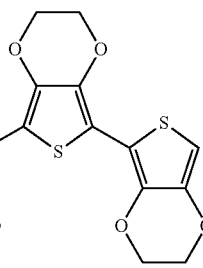 | PF$_6$ | 2 |
| 226 | Ru | 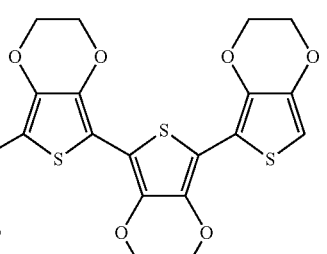 | PF$_6$ | 2 |
| 227 | Ru | 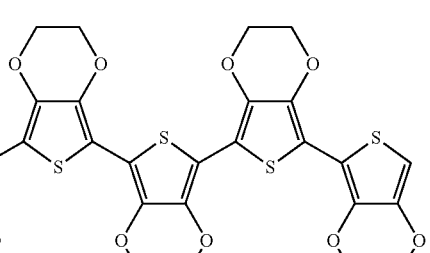 | PF$_6$ | 2 |
| 228 | Ru | 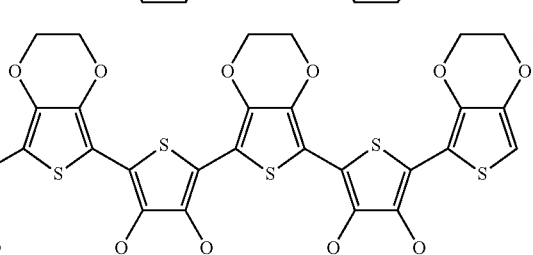 | PF$_6$ | 2 |
| 229 | Ru |  | PF$_6$ | 2 |
| 230 | Ru |  | PF$_6$ | 2 |

TABLE 3-continued

| Entry | M | R¹ | X | h |
|---|---|---|---|---|
| 231 | Ru | (terthiophene) | PF₆ | 2 |
| 232 | Ru | (quaterthiophene) | PF₆ | 2 |
| 233 | Ru | (quinquethiophene) | PF₆ | 2 |
| 234 | Ru | (sexithiophene) | PF₆ | 2 |
| 235 | Ru | (EDOT) | PF₆ | 2 |
| 236 | Ru | (bi-EDOT) | PF₆ | 2 |
| 237 | Ru | (EDOT-thiophene-EDOT) | PF₆ | 2 |
| 238 | Ru | (bis-EDOT-bithiophene) | PF₆ | 2 |

TABLE 3-continued

| Entry | M | R¹ | X | h |
|---|---|---|---|---|
| 239 | Ru | (bis-EDOT-thiophene-EDOT-thiophene chain) | PF$_6$ | 2 |
| 240 | Ru | (extended EDOT/thiophene hexamer chain) | PF$_6$ | 2 |
| 241 | Ru | (thiophene) | PF$_6$ | 2 |
| 242 | Ru | (bithiophene) | PF$_6$ | 2 |
| 243 | Ru | (terthiophene) | PF$_6$ | 2 |
| 244 | Ru | (quaterthiophene) | PF$_6$ | 2 |
| 245 | Ru | (quinquethiophene) | PF$_6$ | 2 |
| 246 | Ru | (sexithiophene) | PF$_6$ | 2 |
| 247 | Ru | (EDOT) | PF$_6$ | 2 |

TABLE 3-continued
| Entry | M | R¹ | X | h |
|---|---|---|---|---|
| 248 | Ru | 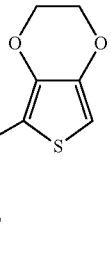 | PF$_6$ | 2 |
| 249 | Ru | 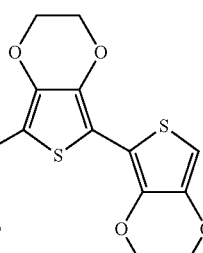 | PF$_6$ | 2 |
| 250 | Ru | 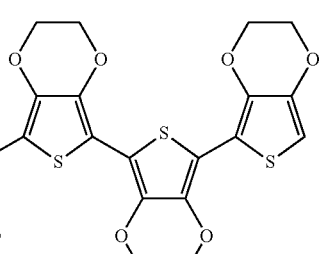 | PF$_6$ | 2 |
| 251 | Ru | 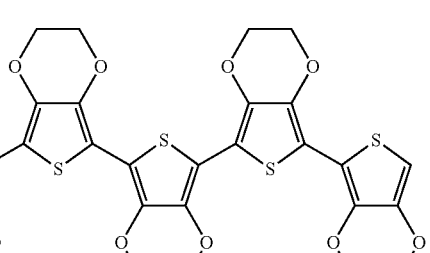 | PF$_6$ | 2 |
| 252 | Ru | 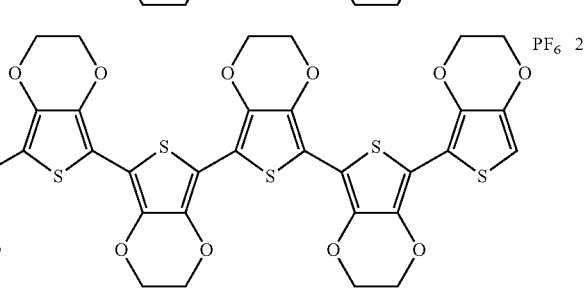 | PF$_6$ | 2 |
| 253 | Ru | 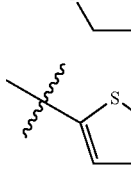 | PF$_6$ | 2 |
| 254 | Ru | 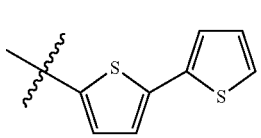 [SMILES: *c1ccc(-c2cccs2)s1] | PF$_6$ | 2 |

TABLE 3-continued

| Entry | M | R¹ | X | h |
|---|---|---|---|---|
| 255 | Ru | (terthiophene) | PF$_6$ | 2 |
| 256 | Ru | (quaterthiophene) | PF$_6$ | 2 |
| 257 | Ru | (quinquethiophene) | PF$_6$ | 2 |
| 258 | Ru | (sexithiophene) | PF$_6$ | 2 |
| 259 | Ru | (EDOT) | PF$_6$ | 2 |
| 260 | Ru | (bi-EDOT) | PF$_6$ | 2 |
| 261 | Ru | (EDOT-thiophene-EDOT) | PF$_6$ | 2 |
| 262 | Ru | (EDOT-thiophene-EDOT-thiophene) | PF$_6$ | 2 |

TABLE 3-continued

| Entry | M | R¹ | X | h |
|---|---|---|---|---|
| 263 | Ru | (thiophene-EDOT pentamer structure) | PF$_6$ | 2 |
| 264 | Ru | (thiophene-EDOT hexamer structure) | PF$_6$ | 2 |
| 265 | Ru | (thiophene) | PF$_6$ | 2 |
| 266 | Ru | (bithiophene) | PF$_6$ | 2 |
| 267 | Ru | (terthiophene) | PF$_6$ | 2 |
| 268 | Ru | (quaterthiophene) | PF$_6$ | 2 |
| 269 | Ru | (quinquethiophene) | PF$_6$ | 2 |
| 270 | Ru | (sexithiophene) | PF$_6$ | 2 |
| 271 | Ru | (thieno-dioxine) | PF$_6$ | 2 |

TABLE 3-continued
| Entry | M | R¹ | X | h |
|---|---|---|---|---|
| 272 | Ru | 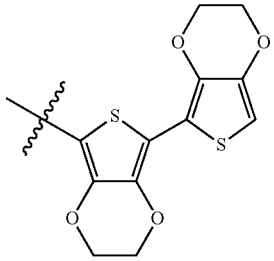 [SMILES: *c1sc(-c2scc3c2OCCO3)c2c1OCCO2] | PF$_6$ | 2 |
| 273 | Ru | 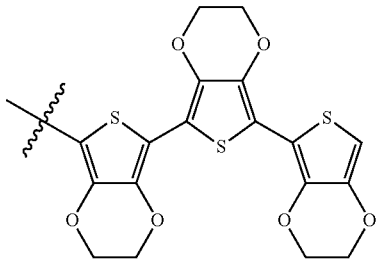 [SMILES: *c1sc(-c2sc(-c3scc4c3OCCO4)c3c2OCCO3)c2c1OCCO2] | PF$_6$ | 2 |
| 274 | Ru | 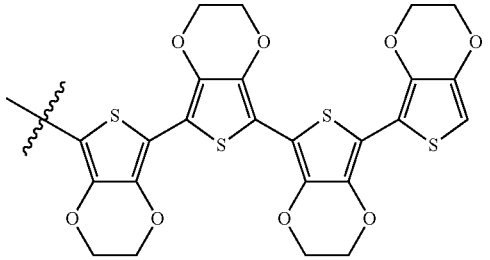 [SMILES: *c1sc(-c2sc(-c3sc(-c4scc5c4OCCO5)c4c3OCCO4)c3c2OCCO3)c2c1OCCO2] | PF$_6$ | 2 |
| 275 | Ru | 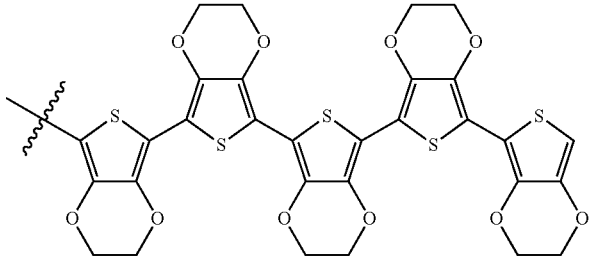 [SMILES: *c1sc(-c2sc(-c3sc(-c4sc(-c5scc6c5OCCO6)c5c4OCCO5)c4c3OCCO4)c3c2OCCO3)c2c1OCCO2] | PF$_6$ | 2 |
| 276 | Ru | 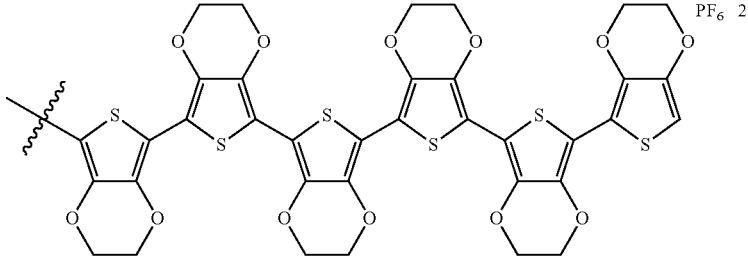 | PF$_6$ | 2 |
| 277 | Ru | 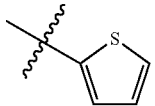 [SMILES: *c1cccs1] | PF$_6$ | 2 |
| 278 | Ru | 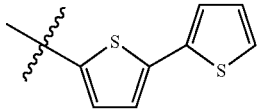 [SMILES: *c1ccc(-c2cccs2)s1] | PF$_6$ | 2 |

TABLE 3-continued

| Entry | M | R¹ | X | h |
|---|---|---|---|---|
| 279 | Ru | [terthiophene] | PF₆ | 2 |
| 280 | Ru | [quaterthiophene] | PF₆ | 2 |
| 281 | Ru | [quinquethiophene] | PF₆ | 2 |
| 282 | Ru | [sexithiophene] | PF₆ | 2 |
| 283 | Ru | [EDOT] | PF₆ | 2 |
| 284 | Ru | [thiophene-EDOT] | PF₆ | 2 |
| 285 | Ru | [EDOT-thiophene-EDOT] | PF₆ | 2 |
| 286 | Ru | [bis(EDOT)-bithiophene] | PF₆ | 2 |

TABLE 3-continued

| Entry | M | R¹ | X | h |
|---|---|---|---|---|
| 287 | Ru | | PF₆ | 2 |
| 288 | Ru | | PF₆ | 2 |
| 289 | Ru | | PF₆ | 2 |
| 290 | Ru | | PF₆ | 2 |
| 291 | Ru | | PF₆ | 2 |
| 292 | Ru | | PF₆ | 2 |
| 293 | Ru | | PF₆ | 2 |
| 294 | Ru | | PF₆ | 2 |
| 295 | Ru | | PF₆ | 2 |

TABLE 3-continued
| Entry | M | R¹ | X | h |
|---|---|---|---|---|
| 296 | Ru | 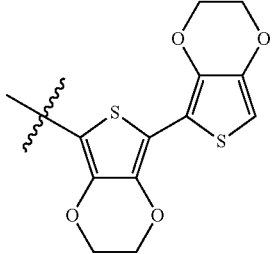 [SMILES: *c1sc(-c2scc3c2OCCO3)c2c1OCCO2] | PF$_6$ | 2 |
| 297 | Ru | 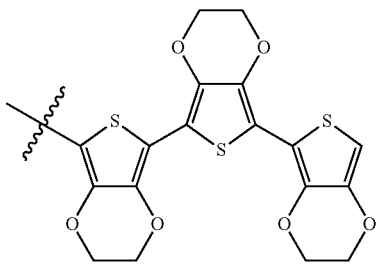 [SMILES: *c1sc(-c2sc(-c3scc4c3OCCO4)c3c2OCCO3)c2c1OCCO2] | PF$_6$ | 2 |
| 298 | Ru | 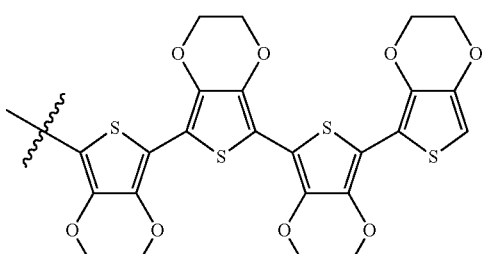 | PF$_6$ | 2 |
| 299 | Ru | 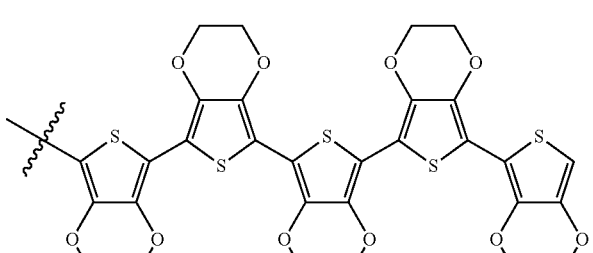 | PF$_6$ | 2 |
| 300 | Ru | 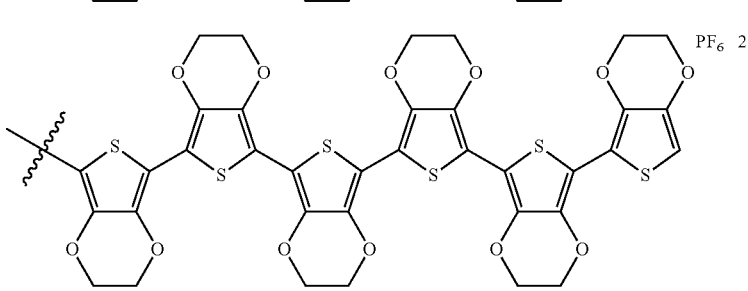 | PF$_6$ | 2 |
| 301 | Ru | 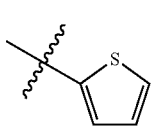 [SMILES: *c1cccs1] | PF$_6$ | 2 |
| 302 | Ru | 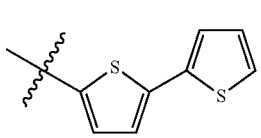 [SMILES: *c1ccc(-c2cccs2)s1] | PF$_6$ | 2 |

TABLE 3-continued

| Entry | M | R¹ | X | h |
|---|---|---|---|---|
| 303 | Ru | terthiophene | PF$_6$ | 2 |
| 304 | Ru | quaterthiophene | PF$_6$ | 2 |
| 305 | Ru | quinquethiophene | PF$_6$ | 2 |
| 306 | Ru | sexithiophene | PF$_6$ | 2 |
| 307 | Ru | EDOT | PF$_6$ | 2 |
| 308 | Ru | bis-EDOT | PF$_6$ | 2 |
| 309 | Ru | EDOT-thiophene-EDOT | PF$_6$ | 2 |
| 310 | Ru | bis(EDOT-thiophene) | PF$_6$ | 2 |

TABLE 3-continued

| Entry | M | R¹ | X | h |
|---|---|---|---|---|
| 311 | Ru | (EDOT)₅ structure | PF₆ | 2 |
| 312 | Ru | (EDOT)₆ structure | PF₆ | 2 |
| 313 | Ru | thiophene | PF₆ | 2 |
| 314 | Ru | bithiophene | PF₆ | 2 |
| 315 | Ru | terthiophene | PF₆ | 2 |
| 316 | Ru | quaterthiophene | PF₆ | 2 |
| 317 | Ru | quinquethiophene | PF₆ | 2 |
| 318 | Ru | sexithiophene | PF₆ | 2 |
| 319 | Ru | EDOT | PF₆ | 2 |

TABLE 3-continued
| Entry | M | R¹ | X | h |
|---|---|---|---|---|
| 320 | Ru | 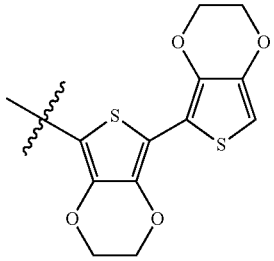 [SMILES: *c1sc(-c2scc3c2OCCO3)c2c1OCCO2] | PF$_6$ | 2 |
| 321 | Ru | 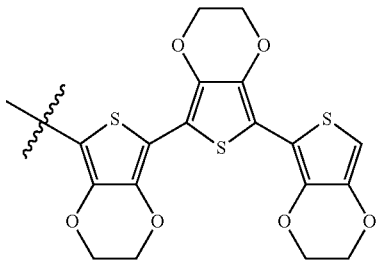 [SMILES: *c1sc(-c2sc(-c3scc4c3OCCO4)c3c2OCCO3)c2c1OCCO2] | PF$_6$ | 2 |
| 322 | Ru | 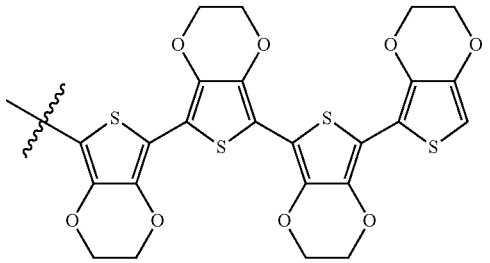 [SMILES: *c1sc(-c2sc(-c3sc(-c4scc5c4OCCO5)c4c3OCCO4)c3c2OCCO3)c2c1OCCO2] | PF$_6$ | 2 |
| 323 | Ru | 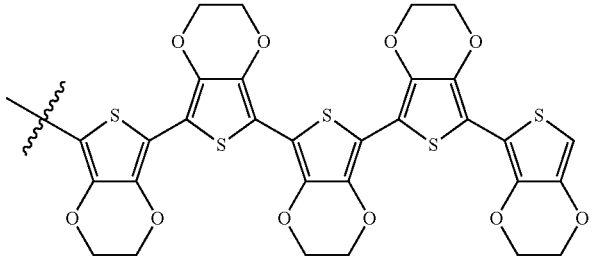 [SMILES: *c1sc(-c2sc(-c3sc(-c4sc(-c5scc6c5OCCO6)c5c4OCCO5)c4c3OCCO4)c3c2OCCO3)c2c1OCCO2] | PF$_6$ | 2 |
| 324 | Ru | 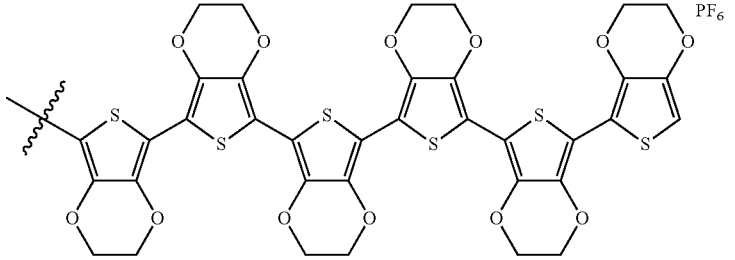 | PF$_6$ | 2 |
| 325 | Ru | 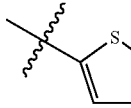 | PF$_6$ | 2 |
| 326 | Ru | 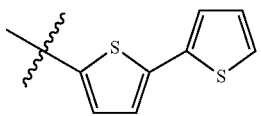 [SMILES: *c1ccc(-c2cccs2)s1] | PF$_6$ | 2 |

TABLE 3-continued
| Entry | M | R¹ | X | h |
|---|---|---|---|---|
| 327 | Ru | 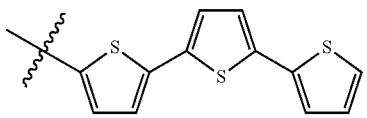 | PF₆ | 2 |
| 328 | Ru | 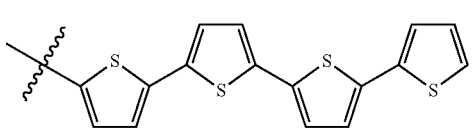 [SMILES: *c1ccc(-c2ccc(-c3ccc(-c4cccs4)s3)s2)s1] | PF₆ | 2 |
| 329 | Ru | 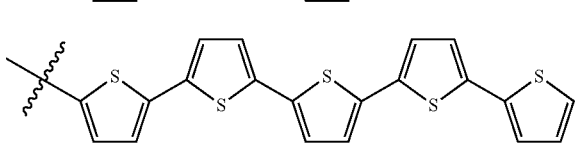 | PF₆ | 2 |
| 330 | Ru | 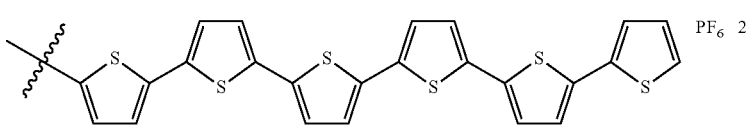 | PF₆ | 2 |
| 331 | Ru | 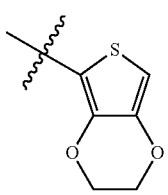 | PF₆ | 2 |
| 332 | Ru | 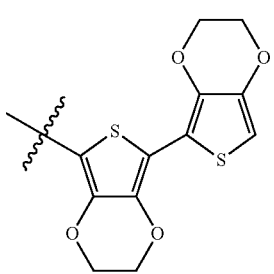 [SMILES: *c1sc(-c2scc3c2OCCO3)c2c1OCCO2] | PF₆ | 2 |
| 333 | Ru | 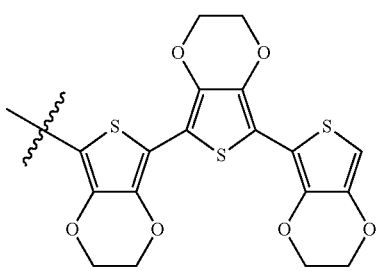 [SMILES: *c1sc(-c2sc(-c3scc4c3OCCO4)c3c2OCCO3)c2c1OCCO2] | PF₆ | 2 |
| 334 | Ru | 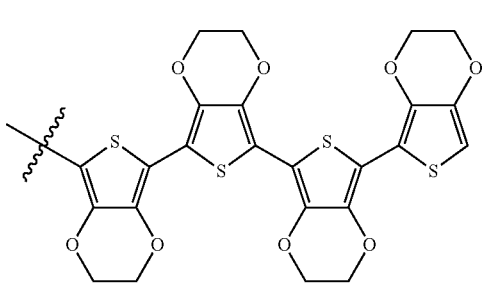 [SMILES: *c1sc(-c2sc(-c3sc(-c4scc5c4OCCO5)c4c3OCCO4)c3c2OCCO3)c2c1OCCO2] | PF₆ | 2 |

TABLE 3-continued

| Entry | M | R¹ | X | h |
|---|---|---|---|---|
| 335 | Ru | (structure) | PF$_6$ | 2 |
| 336 | Ru | (structure) | PF$_6$ | 2 |
| 337 | Ru | (structure) | PF$_6$ | 2 |
| 338 | Ru | (structure) | PF$_6$ | 2 |
| 339 | Ru | (structure) | PF$_6$ | 2 |
| 340 | Ru | (structure) | PF$_6$ | 2 |
| 341 | Ru | (structure) | PF$_6$ | 2 |
| 342 | Ru | (structure) | PF$_6$ | 2 |
| 343 | Ru | (structure) | PF$_6$ | 2 |

TABLE 3-continued

| Entry | M | R¹ | X | h |
|---|---|---|---|---|
| 344 | Ru | | PF₆ | 2 |
| 345 | Ru | | PF₆ | 2 |
| 346 | Ru | | PF₆ | 2 |
| 347 | Ru | | PF₆ | 2 |
| 348 | Ru | | PF₆ | 2 |
| 349 | Ru | | PF₆ | 2 |
| 350 | Ru | | PF₆ | 2 |

TABLE 3-continued

| Entry | M | R¹ | X | h |
|---|---|---|---|---|
| 351 | Ru | [terthiophene] | PF₆ | 2 |
| 352 | Ru | [quaterthiophene] | PF₆ | 2 |
| 353 | Ru | [quinquethiophene] | PF₆ | 2 |
| 354 | Ru | [sexithiophene] | PF₆ | 2 |
| 355 | Ru | [EDOT] | PF₆ | 2 |
| 356 | Ru | [bi-EDOT] | PF₆ | 2 |
| 357 | Ru | [EDOT-thiophene-EDOT] | PF₆ | 2 |
| 358 | Ru | [EDOT-thiophene-thiophene-EDOT] | PF₆ | 2 |

TABLE 3-continued

| Entry | M | R¹ | X | h |
|---|---|---|---|---|
| 359 | Ru | [3,4-ethylenedioxythiophene pentamer structure] | PF$_6$ | 2 |
| 360 | Ru | [3,4-ethylenedioxythiophene hexamer structure] | PF$_6$ | 2 |
| 361 | Ru | [thiophene] | PF$_6$ | 2 |
| 362 | Ru | [bithiophene] | PF$_6$ | 2 |
| 363 | Ru | [terthiophene] | PF$_6$ | 2 |
| 364 | Ru | [quaterthiophene] | PF$_6$ | 2 |
| 365 | Ru | [quinquethiophene] | PF$_6$ | 2 |
| 366 | Ru | [sexithiophene] | PF$_6$ | 2 |
| 367 | Ru | [EDOT monomer] | PF$_6$ | 2 |

TABLE 3-continued
| Entry | M | R¹ | X | h |
|---|---|---|---|---|
| 368 | Ru | 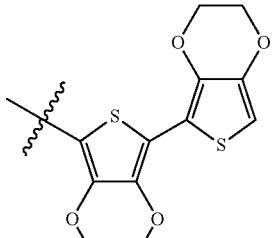 | PF₆ | 2 |
| 369 | Ru | 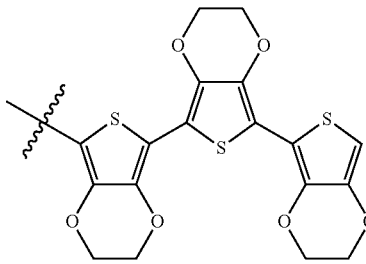 | PF₆ | 2 |
| 370 | Ru | 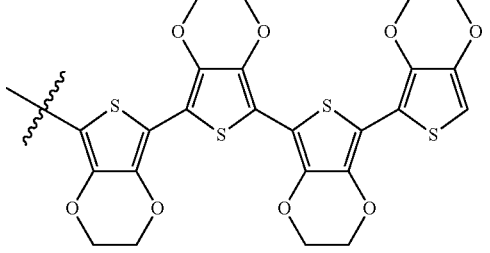 | PF₆ | 2 |
| 371 | Ru | 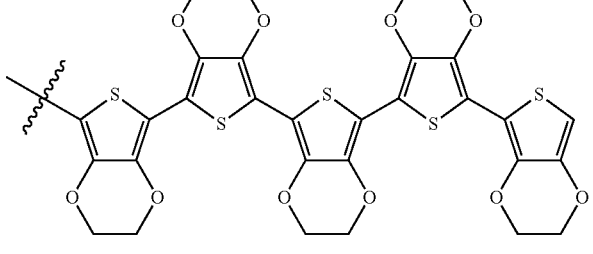 | PF₆ | 2 |
| 372 | Ru | 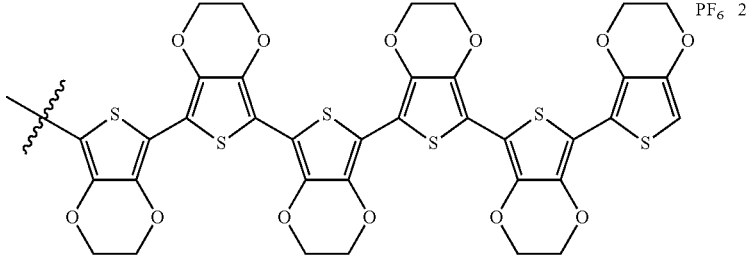 | PF₆ | 2 |
| 373 | Ru | 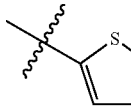 | PF₆ | 2 |
| 374 | Ru | 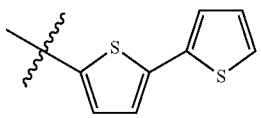 [SMILES: *c1ccc(-c2cccs2)s1] | PF₆ | 2 |

TABLE 3-continued

| Entry | M | R¹ | X | h |
|---|---|---|---|---|
| 375 | Ru | terthiophene | PF₆ | 2 |
| 376 | Ru | quaterthiophene | PF₆ | 2 |
| 377 | Ru | quinquethiophene | PF₆ | 2 |
| 378 | Ru | sexithiophene | PF₆ | 2 |
| 379 | Ru | EDOT | PF₆ | 2 |
| 380 | Ru | thiophene-EDOT | PF₆ | 2 |
| 381 | Ru | thiophene-EDOT-thiophene (with EDOT center) | PF₆ | 2 |
| 382 | Ru | EDOT-thiophene-thiophene-EDOT | PF₆ | 2 |

TABLE 3-continued
| Entry | M | R[1] | X | h |
|---|---|---|---|---|
| 383 | Ru | | PF_6 | 2 |
| 384 | Ru | | PF_6 | 2 |
Exemplary embodiments include compounds having the formula (IX) or a pharmaceutically acceptable salt form thereof:
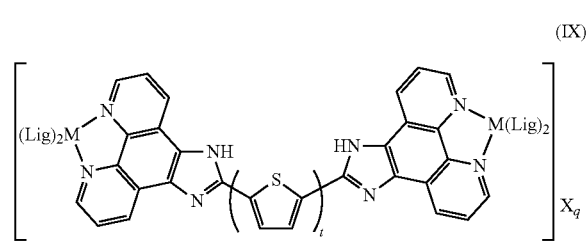
(IX)
wherein non-limiting examples of M, Lig, t, X, and q are defined herein below in Table 4.
TABLE 4
| Entry | M | Lig | t | X | q |
|---|---|---|---|---|---|
| 1 | Ru | bpy | 1 | Cl | 4 |
| 2 | Ru | bpy | 2 | Cl | 4 |
| 3 | Ru | bpy | 3 | Cl | 4 |
| 4 | Ru | bpy | 4 | Cl | 4 |
| 5 | Ru | bpy | 5 | Cl | 4 |
| 6 | Ru | bpy | 6 | Cl | 4 |
| 7 | Ru | bpy | 1 | PF_6 | 4 |
| 8 | Ru | bpy | 2 | PF_6 | 4 |
| 9 | Ru | bpy | 3 | PF_6 | 4 |
| 10 | Ru | bpy | 4 | PF_6 | 4 |
| 11 | Ru | bpy | 5 | PF_6 | 4 |
| 12 | Ru | bpy | 6 | PF_6 | 4 |

TABLE 4-continued

| Entry | M | Lig | t | X | q |
|---|---|---|---|---|---|
| 13 | Ru | 6,6'-dimethyl-2,2'-bipyridine | 1 | Cl | 4 |
| 14 | Ru | 6,6'-dimethyl-2,2'-bipyridine | 2 | Cl | 4 |
| 15 | Ru | 6,6'-dimethyl-2,2'-bipyridine | 3 | Cl | 4 |
| 16 | Ru | 6,6'-dimethyl-2,2'-bipyridine | 4 | Cl | 4 |
| 17 | Ru | 6,6'-dimethyl-2,2'-bipyridine | 5 | Cl | 4 |
| 18 | Ru | 6,6'-dimethyl-2,2'-bipyridine | 6 | Cl | 4 |
| 19 | Ru | 6,6'-dimethyl-2,2'-bipyridine | 1 | PF$_6$ | 4 |
| 20 | Ru | 6,6'-dimethyl-2,2'-bipyridine | 2 | PF$_6$ | 4 |
| 21 | Ru | 6,6'-dimethyl-2,2'-bipyridine | 3 | PF$_6$ | 4 |
| 22 | Ru | 6,6'-dimethyl-2,2'-bipyridine | 4 | PF$_6$ | 4 |
| 23 | Ru | 6,6'-dimethyl-2,2'-bipyridine | 5 | PF$_6$ | 4 |
| 24 | Ru | 6,6'-dimethyl-2,2'-bipyridine | 6 | PF$_6$ | 4 |
| 25 | Ru | 5,5'-dimethyl-2,2'-bipyridine | 1 | Cl | 4 |
| 26 | Ru | 5,5'-dimethyl-2,2'-bipyridine | 2 | Cl | 4 |
| 27 | Ru | 5,5'-dimethyl-2,2'-bipyridine | 3 | Cl | 4 |
| 28 | Ru | 5,5'-dimethyl-2,2'-bipyridine | 4 | Cl | 4 |
| 29 | Ru | 5,5'-dimethyl-2,2'-bipyridine | 5 | Cl | 4 |
| 30 | Ru | 5,5'-dimethyl-2,2'-bipyridine | 6 | Cl | 4 |
| 31 | Ru | 5,5'-dimethyl-2,2'-bipyridine | 1 | PF$_6$ | 4 |
| 32 | Ru | 5,5'-dimethyl-2,2'-bipyridine | 2 | PF$_6$ | 4 |
| 33 | Ru | 5,5'-dimethyl-2,2'-bipyridine | 3 | PF$_6$ | 4 |
| 34 | Ru | 5,5'-dimethyl-2,2'-bipyridine | 4 | PF$_6$ | 4 |
| 35 | Ru | 5,5'-dimethyl-2,2'-bipyridine | 5 | PF$_6$ | 4 |
| 36 | Ru | 5,5'-dimethyl-2,2'-bipyridine | 6 | PF$_6$ | 4 |
| 37 | Ru | 4,4'-dimethyl-2,2'-bipyridine | 1 | Cl | 4 |

TABLE 4-continued

| Entry | M | Lig | t | X | q |
|---|---|---|---|---|---|
| 38 | Ru | 4,4'-dimethyl-2,2'-bipyridine | 2 | Cl | 4 |
| 39 | Ru | 4,4'-dimethyl-2,2'-bipyridine | 3 | Cl | 4 |
| 40 | Ru | 4,4'-dimethyl-2,2'-bipyridine | 4 | Cl | 4 |
| 41 | Ru | 4,4'-dimethyl-2,2'-bipyridine | 5 | Cl | 4 |
| 42 | Ru | 4,4'-dimethyl-2,2'-bipyridine | 6 | Cl | 4 |
| 43 | Ru | 4,4'-dimethyl-2,2'-bipyridine | 1 | $PF_6$ | 4 |
| 44 | Ru | 4,4'-dimethyl-2,2'-bipyridine | 2 | $PF_6$ | 4 |
| 45 | Ru | 4,4'-dimethyl-2,2'-bipyridine | 3 | $PF_6$ | 4 |
| 46 | Ru | 4,4'-dimethyl-2,2'-bipyridine | 4 | $PF_6$ | 4 |
| 47 | Ru | 4,4'-dimethyl-2,2'-bipyridine | 5 | $PF_6$ | 4 |
| 48 | Ru | 4,4'-dimethyl-2,2'-bipyridine | 6 | $PF_6$ | 4 |
| 49 | Ru | 3,3'-dimethyl-2,2'-bipyridine | 1 | Cl | 4 |
| 50 | Ru | 3,3'-dimethyl-2,2'-bipyridine | 2 | Cl | 4 |
| 51 | Ru | 3,3'-dimethyl-2,2'-bipyridine | 3 | Cl | 4 |
| 52 | Ru | 3,3'-dimethyl-2,2'-bipyridine | 4 | Cl | 4 |
| 53 | Ru | 3,3'-dimethyl-2,2'-bipyridine | 5 | Cl | 4 |
| 54 | Ru | 3,3'-dimethyl-2,2'-bipyridine | 6 | Cl | 4 |
| 55 | Ru | 3,3'-dimethyl-2,2'-bipyridine | 1 | $PF_6$ | 4 |
| 56 | Ru | 3,3'-dimethyl-2,2'-bipyridine | 2 | $PF_6$ | 4 |
| 57 | Ru | 3,3'-dimethyl-2,2'-bipyridine | 3 | $PF_6$ | 4 |
| 58 | Ru | 3,3'-dimethyl-2,2'-bipyridine | 4 | $PF_6$ | 4 |
| 59 | Ru | 3,3'-dimethyl-2,2'-bipyridine | 5 | $PF_6$ | 4 |

TABLE 4-continued

| Entry | M | Lig | t | X | q |
|---|---|---|---|---|---|
| 60 | Ru | 3,3'-dimethyl-2,2'-bipyridine | 6 | PF$_6$ | 4 |
| 61 | Ru | 4,4'-di-tert-butyl-2,2'-bipyridine | 1 | Cl | 4 |
| 62 | Ru | 4,4'-di-tert-butyl-2,2'-bipyridine | 2 | Cl | 4 |
| 63 | Ru | 4,4'-di-tert-butyl-2,2'-bipyridine | 3 | Cl | 4 |
| 64 | Ru | 4,4'-di-tert-butyl-2,2'-bipyridine | 4 | Cl | 4 |
| 65 | Ru | 4,4'-di-tert-butyl-2,2'-bipyridine | 5 | Cl | 4 |
| 66 | Ru | 4,4'-di-tert-butyl-2,2'-bipyridine | 6 | Cl | 4 |
| 67 | Ru | 4,4'-di-tert-butyl-2,2'-bipyridine | 1 | PF$_6$ | 4 |
| 68 | Ru | 4,4'-di-tert-butyl-2,2'-bipyridine | 2 | PF$_6$ | 4 |
| 69 | Ru | 4,4'-di-tert-butyl-2,2'-bipyridine | 3 | PF$_6$ | 4 |
| 70 | Ru | 4,4'-di-tert-butyl-2,2'-bipyridine | 4 | PF$_6$ | 4 |
| 71 | Ru | 4,4'-di-tert-butyl-2,2'-bipyridine | 5 | PF$_6$ | 4 |
| 72 | Ru | 4,4'-di-tert-butyl-2,2'-bipyridine | 6 | PF$_6$ | 4 |
| 73 | Ru | 4,4'-dimethoxy-2,2'-bipyridine | 1 | Cl | 4 |
| 74 | Ru | 4,4'-dimethoxy-2,2'-bipyridine | 2 | Cl | 4 |
| 75 | Ru | 4,4'-dimethoxy-2,2'-bipyridine | 3 | Cl | 4 |
| 76 | Ru | 4,4'-dimethoxy-2,2'-bipyridine | 4 | Cl | 4 |
| 77 | Ru | 4,4'-dimethoxy-2,2'-bipyridine | 5 | Cl | 4 |
| 78 | Ru | 4,4'-dimethoxy-2,2'-bipyridine | 6 | Cl | 4 |
| 79 | Ru | 4,4'-dimethoxy-2,2'-bipyridine | 1 | PF$_6$ | 4 |

TABLE 4-continued

| Entry | M | Lig | t | X | q |
|---|---|---|---|---|---|
| 80 | Ru | 4,4'-dimethoxy-2,2'-bipyridine | 2 | $PF_6$ | 4 |
| 81 | Ru | 4,4'-dimethoxy-2,2'-bipyridine | 3 | $PF_6$ | 4 |
| 82 | Ru | 4,4'-dimethoxy-2,2'-bipyridine | 4 | $PF_6$ | 4 |
| 83 | Ru | 4,4'-dimethoxy-2,2'-bipyridine | 5 | $PF_6$ | 4 |
| 84 | Ru | 4,4'-dimethoxy-2,2'-bipyridine | 6 | $PF_6$ | 4 |
| 85 | Ru | dimethyl 2,2'-bipyridine-4,4'-dicarboxylate | 1 | Cl | 4 |
| 86 | Ru | dimethyl 2,2'-bipyridine-4,4'-dicarboxylate | 2 | Cl | 4 |
| 87 | Ru | dimethyl 2,2'-bipyridine-4,4'-dicarboxylate | 3 | Cl | 4 |
| 88 | Ru | dimethyl 2,2'-bipyridine-4,4'-dicarboxylate | 4 | Cl | 4 |
| 89 | Ru | dimethyl 2,2'-bipyridine-4,4'-dicarboxylate | 5 | Cl | 4 |
| 90 | Ru | dimethyl 2,2'-bipyridine-4,4'-dicarboxylate | 6 | Cl | 4 |
| 91 | Ru | dimethyl 2,2'-bipyridine-4,4'-dicarboxylate | 1 | $PF_6$ | 4 |
| 92 | Ru | dimethyl 2,2'-bipyridine-4,4'-dicarboxylate | 2 | $PF_6$ | 4 |
| 93 | Ru | dimethyl 2,2'-bipyridine-4,4'-dicarboxylate | 3 | $PF_6$ | 4 |
| 94 | Ru | dimethyl 2,2'-bipyridine-4,4'-dicarboxylate | 4 | $PF_6$ | 4 |
| 95 | Ru | dimethyl 2,2'-bipyridine-4,4'-dicarboxylate | 5 | $PF_6$ | 4 |
| 96 | Ru | dimethyl 2,2'-bipyridine-4,4'-dicarboxylate | 6 | $PF_6$ | 4 |
| 97 | Ru | 4,4'-bis(trifluoromethyl)-2,2'-bipyridine | 1 | Cl | 4 |
| 98 | Ru | 4,4'-bis(trifluoromethyl)-2,2'-bipyridine | 2 | Cl | 4 |
| 99 | Ru | 4,4'-bis(trifluoromethyl)-2,2'-bipyridine | 3 | Cl | 4 |

TABLE 4-continued

| Entry | M | Lig | t | X | q |
|---|---|---|---|---|---|
| 100 | Ru | 4,4'-bis(CF3)-2,2'-bipyridine | 4 | Cl | 4 |
| 101 | Ru | 4,4'-bis(CF3)-2,2'-bipyridine | 5 | Cl | 4 |
| 102 | Ru | 4,4'-bis(CF3)-2,2'-bipyridine | 6 | Cl | 4 |
| 103 | Ru | 4,4'-bis(CF3)-2,2'-bipyridine | 1 | PF6 | 4 |
| 104 | Ru | 4,4'-bis(CF3)-2,2'-bipyridine | 2 | PF6 | 4 |
| 105 | Ru | 4,4'-bis(CF3)-2,2'-bipyridine | 3 | PF6 | 4 |
| 106 | Ru | 4,4'-bis(CF3)-2,2'-bipyridine | 4 | PF6 | 4 |
| 107 | Ru | 4,4'-bis(CF3)-2,2'-bipyridine | 5 | PF6 | 4 |
| 108 | Ru | 4,4'-bis(CF3)-2,2'-bipyridine | 6 | PF6 | 4 |
| 109 | Ru | 4,4'-bipyrimidine | 1 | Cl | 4 |
| 110 | Ru | 4,4'-bipyrimidine | 2 | Cl | 4 |
| 111 | Ru | 4,4'-bipyrimidine | 3 | Cl | 4 |
| 112 | Ru | 4,4'-bipyrimidine | 4 | Cl | 4 |
| 113 | Ru | 4,4'-bipyrimidine | 5 | Cl | 4 |
| 114 | Ru | 4,4'-bipyrimidine | 6 | Cl | 4 |
| 115 | Ru | 4,4'-bipyrimidine | 1 | PF6 | 4 |
| 116 | Ru | 4,4'-bipyrimidine | 2 | PF6 | 4 |
| 117 | Ru | 4,4'-bipyrimidine | 3 | PF6 | 4 |
| 118 | Ru | 4,4'-bipyrimidine | 4 | PF6 | 4 |
| 119 | Ru | 4,4'-bipyrimidine | 5 | PF6 | 4 |
| 120 | Ru | 4,4'-bipyrimidine | 6 | PF6 | 4 |
| 121 | Ru | 2,2'-bipyrazine | 1 | Cl | 4 |
| 122 | Ru | 2,2'-bipyrazine | 2 | Cl | 4 |
| 123 | Ru | 2,2'-bipyrazine | 3 | Cl | 4 |
| 124 | Ru | 2,2'-bipyrazine | 4 | Cl | 4 |
| 125 | Ru | 2,2'-bipyrazine | 5 | Cl | 4 |

TABLE 4-continued

| Entry | M | Lig | t | X | q |
|---|---|---|---|---|---|
| 126 | Ru | 2,2'-bipyrazine | 6 | Cl | 4 |
| 127 | Ru | 2,2'-bipyrazine | 1 | PF$_6$ | 4 |
| 128 | Ru | 2,2'-bipyrazine | 2 | PF$_6$ | 4 |
| 129 | Ru | 2,2'-bipyrazine | 3 | PF$_6$ | 4 |
| 130 | Ru | 2,2'-bipyrazine | 4 | PF$_6$ | 4 |
| 131 | Ru | 2,2'-bipyrazine | 5 | PF$_6$ | 4 |
| 132 | Ru | 2,2'-bipyrazine | 6 | PF$_6$ | 4 |
| 133 | Ru | 1,10-phenanthroline | 1 | Cl | 4 |
| 134 | Ru | 1,10-phenanthroline | 2 | Cl | 4 |
| 135 | Ru | 1,10-phenanthroline | 3 | Cl | 4 |
| 136 | Ru | 1,10-phenanthroline | 4 | Cl | 4 |
| 137 | Ru | 1,10-phenanthroline | 5 | Cl | 4 |

TABLE 4-continued

| Entry | M | Lig | t | X | q |
|---|---|---|---|---|---|
| 138 | Ru | 1,10-phenanthroline | 6 | Cl | 4 |
| 139 | Ru | 1,10-phenanthroline | 1 | PF$_6$ | 4 |
| 140 | Ru | 1,10-phenanthroline | 2 | PF$_6$ | 4 |
| 141 | Ru | 1,10-phenanthroline | 3 | PF$_6$ | 4 |
| 142 | Ru | 1,10-phenanthroline | 4 | PF$_6$ | 4 |
| 143 | Ru | 1,10-phenanthroline | 5 | PF$_6$ | 4 |
| 144 | Ru | 1,10-phenanthroline | 6 | PF$_6$ | 4 |
| 145 | Ru | dihydrophenanthroline | 1 | Cl | 4 |
| 146 | Ru | dihydrophenanthroline | 2 | Cl | 4 |
| 147 | Ru | dihydrophenanthroline | 3 | Cl | 4 |
| 148 | Ru | dihydrophenanthroline | 4 | Cl | 4 |

TABLE 4-continued

| Entry | M | Lig | t | X | q |
|---|---|---|---|---|---|
| 149 | Ru | 5,6-dihydro-1,10-phenanthroline | 5 | Cl | 4 |
| 150 | Ru | 5,6-dihydro-1,10-phenanthroline | 6 | Cl | 4 |
| 151 | Ru | 5,6-dihydro-1,10-phenanthroline | 1 | PF$_6$ | 4 |
| 152 | Ru | 5,6-dihydro-1,10-phenanthroline | 2 | PF$_6$ | 4 |
| 153 | Ru | 5,6-dihydro-1,10-phenanthroline | 3 | PF$_6$ | 4 |
| 154 | Ru | 5,6-dihydro-1,10-phenanthroline | 4 | PF$_6$ | 4 |
| 155 | Ru | 5,6-dihydro-1,10-phenanthroline | 5 | PF$_6$ | 4 |
| 156 | Ru | 5,6-dihydro-1,10-phenanthroline | 6 | PF$_6$ | 4 |
| 157 | Ru | 2,9-dimethyl-1,10-phenanthroline | 1 | Cl | 4 |
| 158 | Ru | 2,9-dimethyl-1,10-phenanthroline | 2 | Cl | 4 |
| 159 | Ru | 2,9-dimethyl-1,10-phenanthroline | 3 | Cl | 4 |
| 160 | Ru | 2,9-dimethyl-1,10-phenanthroline | 4 | Cl | 4 |
| 161 | Ru | 2,9-dimethyl-1,10-phenanthroline | 5 | Cl | 4 |
| 162 | Ru | 2,9-dimethyl-1,10-phenanthroline | 6 | Cl | 4 |
| 163 | Ru | 2,9-dimethyl-1,10-phenanthroline | 1 | PF$_6$ | 4 |
| 164 | Ru | 2,9-dimethyl-1,10-phenanthroline | 2 | PF$_6$ | 4 |
| 165 | Ru | 2,9-dimethyl-1,10-phenanthroline | 3 | PF$_6$ | 4 |
| 166 | Ru | 2,9-dimethyl-1,10-phenanthroline | 4 | PF$_6$ | 4 |
| 167 | Ru | 2,9-dimethyl-1,10-phenanthroline | 5 | PF$_6$ | 4 |

TABLE 4-continued

| Entry | M | Lig | t | X | q |
|---|---|---|---|---|---|
| 168 | Ru | 2,9-dimethyl-1,10-phenanthroline | 6 | PF$_6$ | 4 |
| 169 | Ru | 3,8-dimethyl-1,10-phenanthroline | 1 | Cl | 4 |
| 170 | Ru | 3,8-dimethyl-1,10-phenanthroline | 2 | Cl | 4 |
| 171 | Ru | 3,8-dimethyl-1,10-phenanthroline | 3 | Cl | 4 |
| 172 | Ru | 3,8-dimethyl-1,10-phenanthroline | 4 | Cl | 4 |
| 173 | Ru | 3,8-dimethyl-1,10-phenanthroline | 5 | Cl | 4 |
| 174 | Ru | 3,8-dimethyl-1,10-phenanthroline | 6 | Cl | 4 |
| 175 | Ru | 3,8-dimethyl-1,10-phenanthroline | 1 | PF$_6$ | 4 |
| 176 | Ru | 3,8-dimethyl-1,10-phenanthroline | 2 | PF$_6$ | 4 |
| 177 | Ru | 3,8-dimethyl-1,10-phenanthroline | 3 | PF$_6$ | 4 |
| 178 | Ru | 3,8-dimethyl-1,10-phenanthroline | 4 | PF$_6$ | 4 |

TABLE 4-continued

| Entry | M | Lig | t | X | q |
|---|---|---|---|---|---|
| 179 | Ru | 3,8-dimethyl-1,10-phenanthroline | 5 | PF$_6$ | 4 |
| 180 | Ru | 3,8-dimethyl-1,10-phenanthroline | 6 | PF$_6$ | 4 |
| 181 | Ru | 4,7-dimethyl-1,10-phenanthroline | 1 | Cl | 4 |
| 182 | Ru | 4,7-dimethyl-1,10-phenanthroline | 2 | Cl | 4 |
| 183 | Ru | 4,7-dimethyl-1,10-phenanthroline | 3 | Cl | 4 |
| 184 | Ru | 4,7-dimethyl-1,10-phenanthroline | 4 | Cl | 4 |
| 185 | Ru | 4,7-dimethyl-1,10-phenanthroline | 5 | Cl | 4 |
| 186 | Ru | 4,7-dimethyl-1,10-phenanthroline | 6 | Cl | 4 |
| 187 | Ru | 4,7-dimethyl-1,10-phenanthroline | 1 | PF$_6$ | 4 |
| 188 | Ru | 4,7-dimethyl-1,10-phenanthroline | 2 | PF$_6$ | 4 |
| 189 | Ru | 4,7-dimethyl-1,10-phenanthroline | 3 | PF$_6$ | 4 |

TABLE 4-continued

| Entry | M | Lig | t | X | q |
|---|---|---|---|---|---|
| 190 | Ru | 4,7-dimethyl-1,10-phenanthroline | 4 | PF$_6$ | 4 |
| 191 | Ru | 4,7-dimethyl-1,10-phenanthroline | 5 | PF$_6$ | 4 |
| 192 | Ru | 4,7-dimethyl-1,10-phenanthroline | 6 | PF$_6$ | 4 |
| 193 | Ru | 2,2'-bipyrimidine | 1 | Cl | 4 |
| 194 | Ru | 2,2'-bipyrimidine | 2 | Cl | 4 |
| 195 | Ru | 2,2'-bipyrimidine | 3 | Cl | 4 |
| 196 | Ru | 2,2'-bipyrimidine | 4 | Cl | 4 |
| 197 | Ru | 2,2'-bipyrimidine | 5 | Cl | 4 |
| 198 | Ru | 2,2'-bipyrimidine | 6 | Cl | 4 |
| 199 | Ru | 2,2'-bipyrimidine | 1 | PF$_6$ | 4 |
| 200 | Ru | 2,2'-bipyrimidine | 2 | PF$_6$ | 4 |
| 201 | Ru | 2,2'-bipyrimidine | 3 | PF$_6$ | 4 |
| 202 | Ru | 2,2'-bipyrimidine | 4 | PF$_6$ | 4 |
| 203 | Ru | 2,2'-bipyrimidine | 5 | PF$_6$ | 4 |
| 204 | Ru | 2,2'-bipyrimidine | 6 | PF$_6$ | 4 |

Exemplary embodiments include compounds having the formula (X) or a pharmaceutically acceptable salt form thereof:

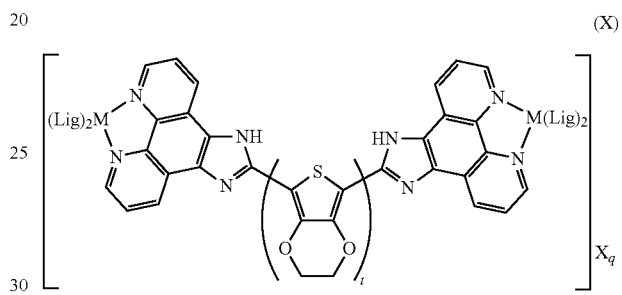

(X)

wherein non-limiting examples of M, Lig, t, X, and q are defined herein below in Table 5.

TABLE 5

| Entry | M | Lig | t | X | q |
|---|---|---|---|---|---|
| 1 | Ru | 2,2'-bipyridine | 1 | Cl | 4 |
| 2 | Ru | 2,2'-bipyridine | 2 | Cl | 4 |
| 3 | Ru | 2,2'-bipyridine | 3 | Cl | 4 |
| 4 | Ru | 2,2'-bipyridine | 4 | Cl | 4 |
| 5 | Ru | 2,2'-bipyridine | 5 | Cl | 4 |
| 6 | Ru | 2,2'-bipyridine | 6 | Cl | 4 |
| 7 | Ru | 2,2'-bipyridine | 1 | PF$_6$ | 4 |

TABLE 5-continued

| Entry | M | Lig | t | X | q |
|---|---|---|---|---|---|
| 8 | Ru | 2,2'-bipyridine | 2 | PF$_6$ | 4 |
| 9 | Ru | 2,2'-bipyridine | 3 | PF$_6$ | 4 |
| 10 | Ru | 2,2'-bipyridine | 4 | PF$_6$ | 4 |
| 11 | Ru | 2,2'-bipyridine | 5 | PF$_6$ | 4 |
| 12 | Ru | 2,2'-bipyridine | 6 | PF$_6$ | 4 |
| 13 | Ru | 6,6'-dimethyl-2,2'-bipyridine | 1 | Cl | 4 |
| 14 | Ru | 6,6'-dimethyl-2,2'-bipyridine | 2 | Cl | 4 |
| 15 | Ru | 6,6'-dimethyl-2,2'-bipyridine | 3 | Cl | 4 |
| 16 | Ru | 6,6'-dimethyl-2,2'-bipyridine | 4 | Cl | 4 |
| 17 | Ru | 6,6'-dimethyl-2,2'-bipyridine | 5 | Cl | 4 |
| 18 | Ru | 6,6'-dimethyl-2,2'-bipyridine | 6 | Cl | 4 |
| 19 | Ru | 6,6'-dimethyl-2,2'-bipyridine | 1 | PF$_6$ | 4 |
| 20 | Ru | 6,6'-dimethyl-2,2'-bipyridine | 2 | PF$_6$ | 4 |
| 21 | Ru | 6,6'-dimethyl-2,2'-bipyridine | 3 | PF$_6$ | 4 |
| 22 | Ru | 6,6'-dimethyl-2,2'-bipyridine | 4 | PF$_6$ | 4 |
| 23 | Ru | 6,6'-dimethyl-2,2'-bipyridine | 5 | PF$_6$ | 4 |
| 24 | Ru | 6,6'-dimethyl-2,2'-bipyridine | 6 | PF$_6$ | 4 |
| 25 | Ru | 5,5'-dimethyl-2,2'-bipyridine | 1 | Cl | 4 |
| 26 | Ru | 5,5'-dimethyl-2,2'-bipyridine | 2 | Cl | 4 |
| 27 | Ru | 5,5'-dimethyl-2,2'-bipyridine | 3 | Cl | 4 |
| 28 | Ru | 5,5'-dimethyl-2,2'-bipyridine | 4 | Cl | 4 |
| 29 | Ru | 5,5'-dimethyl-2,2'-bipyridine | 5 | Cl | 4 |
| 30 | Ru | 5,5'-dimethyl-2,2'-bipyridine | 6 | Cl | 4 |
| 31 | Ru | 5,5'-dimethyl-2,2'-bipyridine | 1 | PF$_6$ | 4 |
| 32 | Ru | 5,5'-dimethyl-2,2'-bipyridine | 2 | PF$_6$ | 4 |
| 33 | Ru | 5,5'-dimethyl-2,2'-bipyridine | 3 | PF$_6$ | 4 |
| 34 | Ru | 5,5'-dimethyl-2,2'-bipyridine | 4 | PF$_6$ | 4 |

TABLE 5-continued

| Entry | M | Lig | t | X | q |
|---|---|---|---|---|---|
| 35 | Ru | 5,5'-dimethyl-2,2'-bipyridine | 5 | PF$_6$ | 4 |
| 36 | Ru | 5,5'-dimethyl-2,2'-bipyridine | 6 | PF$_6$ | 4 |
| 37 | Ru | 4,4'-dimethyl-2,2'-bipyridine | 1 | Cl | 4 |
| 38 | Ru | 4,4'-dimethyl-2,2'-bipyridine | 2 | Cl | 4 |
| 39 | Ru | 4,4'-dimethyl-2,2'-bipyridine | 3 | Cl | 4 |
| 40 | Ru | 4,4'-dimethyl-2,2'-bipyridine | 4 | Cl | 4 |
| 41 | Ru | 4,4'-dimethyl-2,2'-bipyridine | 5 | Cl | 4 |
| 42 | Ru | 4,4'-dimethyl-2,2'-bipyridine | 6 | Cl | 4 |
| 43 | Ru | 4,4'-dimethyl-2,2'-bipyridine | 1 | PF$_6$ | 4 |
| 44 | Ru | 4,4'-dimethyl-2,2'-bipyridine | 2 | PF$_6$ | 4 |
| 45 | Ru | 4,4'-dimethyl-2,2'-bipyridine | 3 | PF$_6$ | 4 |
| 46 | Ru | 4,4'-dimethyl-2,2'-bipyridine | 4 | PF$_6$ | 4 |
| 47 | Ru | 4,4'-dimethyl-2,2'-bipyridine | 5 | PF$_6$ | 4 |
| 48 | Ru | 4,4'-dimethyl-2,2'-bipyridine | 6 | PF$_6$ | 4 |
| 49 | Ru | 3,3'-dimethyl-2,2'-bipyridine | 1 | Cl | 4 |
| 50 | Ru | 3,3'-dimethyl-2,2'-bipyridine | 2 | Cl | 4 |
| 51 | Ru | 3,3'-dimethyl-2,2'-bipyridine | 3 | Cl | 4 |
| 52 | Ru | 3,3'-dimethyl-2,2'-bipyridine | 4 | Cl | 4 |
| 53 | Ru | 3,3'-dimethyl-2,2'-bipyridine | 5 | Cl | 4 |
| 54 | Ru | 3,3'-dimethyl-2,2'-bipyridine | 6 | Cl | 4 |
| 55 | Ru | 3,3'-dimethyl-2,2'-bipyridine | 1 | PF$_6$ | 4 |
| 56 | Ru | 3,3'-dimethyl-2,2'-bipyridine | 2 | PF$_6$ | 4 |

TABLE 5-continued
| Entry | M | Lig | t | X | q |
|---|---|---|---|---|---|
| 57 | Ru | 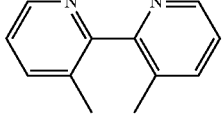 | 3 | PF$_6$ | 4 |
| 58 | Ru | 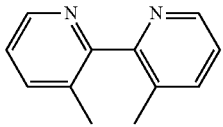 | 4 | PF$_6$ | 4 |
| 59 | Ru | 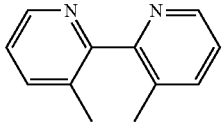 | 5 | PF$_6$ | 4 |
| 60 | Ru | 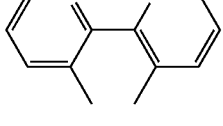 | 6 | PF$_6$ | 4 |
| 61 | Ru | 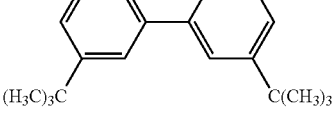 | 1 | Cl | 4 |
| 62 | Ru | 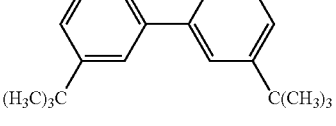 | 2 | Cl | 4 |
| 63 | Ru | 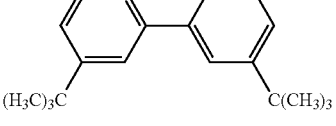 | 3 | Cl | 4 |
| 64 | Ru | 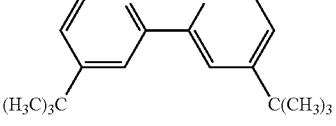 | 4 | Cl | 4 |
| 65 | Ru | 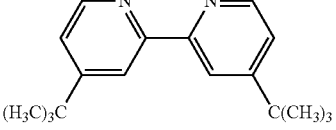 | 5 | Cl | 4 |
| 66 | Ru | 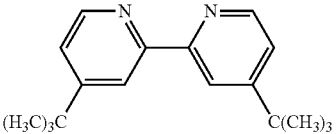 | 6 | Cl | 4 |
| 67 | Ru | 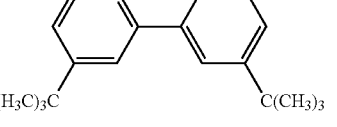 | 1 | PF$_6$ | 4 |
| 68 | Ru | 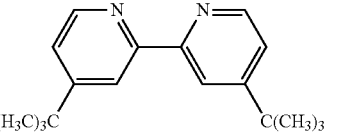 | 2 | PF$_6$ | 4 |
| 69 | Ru | 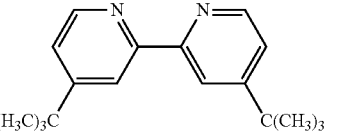 | 3 | PF$_6$ | 4 |
| 70 | Ru | 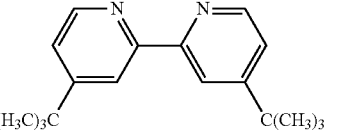 | 4 | PF$_6$ | 4 |
| 71 | Ru | 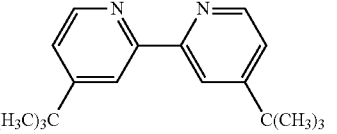 | 5 | PF$_6$ | 4 |
| 72 | Ru | 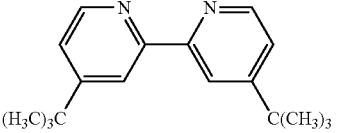 [SMILES: CC(C)(C)c1ccnc(-c2cc(C(C)(C)C)ccn2)c1] | 6 | PF$_6$ | 4 |
| 73 | Ru | 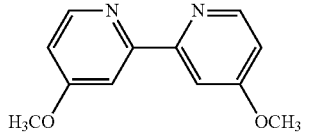 | 1 | Cl | 4 |
| 74 | Ru | 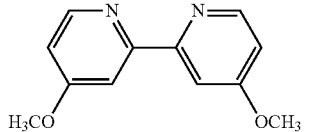 | 2 | Cl | 4 |
| 75 | Ru | 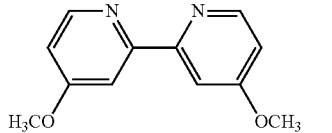 [SMILES: COc1ccnc(-c2cc(OC)ccn2)c1] | 3 | Cl | 4 |
| 76 | Ru | 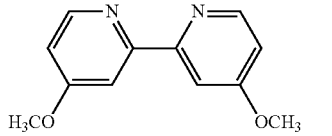 [SMILES: COc1ccnc(-c2cc(OC)ccn2)c1] | 4 | Cl | 4 |

TABLE 5-continued

| Entry | M | Lig | t | X | q |
|---|---|---|---|---|---|
| 77 | Ru | 4,4'-dimethoxy-2,2'-bipyridine | 5 | Cl | 4 |
| 78 | Ru | 4,4'-dimethoxy-2,2'-bipyridine | 6 | Cl | 4 |
| 79 | Ru | 4,4'-dimethoxy-2,2'-bipyridine | 1 | $PF_6$ | 4 |
| 80 | Ru | 4,4'-dimethoxy-2,2'-bipyridine | 2 | $PF_6$ | 4 |
| 81 | Ru | 4,4'-dimethoxy-2,2'-bipyridine | 3 | $PF_6$ | 4 |
| 82 | Ru | 4,4'-dimethoxy-2,2'-bipyridine | 4 | $PF_6$ | 4 |
| 83 | Ru | 4,4'-dimethoxy-2,2'-bipyridine | 5 | $PF_6$ | 4 |
| 84 | Ru | 4,4'-dimethoxy-2,2'-bipyridine | 6 | $PF_6$ | 4 |
| 85 | Ru | dimethyl 2,2'-bipyridine-4,4'-dicarboxylate | 1 | Cl | 4 |
| 86 | Ru | dimethyl 2,2'-bipyridine-4,4'-dicarboxylate | 2 | Cl | 4 |
| 87 | Ru | dimethyl 2,2'-bipyridine-4,4'-dicarboxylate | 3 | Cl | 4 |
| 88 | Ru | dimethyl 2,2'-bipyridine-4,4'-dicarboxylate | 4 | Cl | 4 |
| 89 | Ru | dimethyl 2,2'-bipyridine-4,4'-dicarboxylate | 5 | Cl | 4 |
| 90 | Ru | dimethyl 2,2'-bipyridine-4,4'-dicarboxylate | 6 | Cl | 4 |
| 91 | Ru | dimethyl 2,2'-bipyridine-4,4'-dicarboxylate | 1 | $PF_6$ | 4 |
| 92 | Ru | dimethyl 2,2'-bipyridine-4,4'-dicarboxylate | 2 | $PF_6$ | 4 |
| 93 | Ru | dimethyl 2,2'-bipyridine-4,4'-dicarboxylate | 3 | $PF_6$ | 4 |
| 94 | Ru | dimethyl 2,2'-bipyridine-4,4'-dicarboxylate | 4 | $PF_6$ | 4 |
| 95 | Ru | dimethyl 2,2'-bipyridine-4,4'-dicarboxylate | 5 | $PF_6$ | 4 |
| 96 | Ru | dimethyl 2,2'-bipyridine-4,4'-dicarboxylate | 6 | $PF_6$ | 4 |

TABLE 5-continued
| Entry | M | Lig | t | X | q |
|---|---|---|---|---|---|
| 97 | Ru | 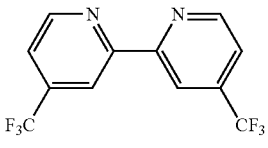 [SMILES: FC(F)(F)c1ccnc(-c2cc(C(F)(F)F)ccn2)c1] | 1 | Cl | 4 |
| 98 | Ru | 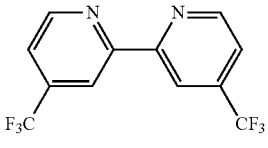 | 2 | Cl | 4 |
| 99 | Ru | 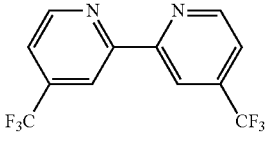 [SMILES: FC(F)(F)c1ccnc(-c2cc(C(F)(F)F)ccn2)c1] | 3 | Cl | 4 |
| 100 | Ru | 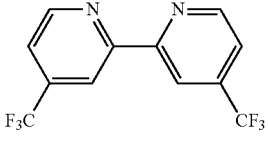 | 4 | Cl | 4 |
| 101 | Ru | 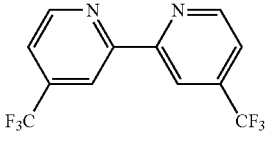 [SMILES: FC(F)(F)c1ccnc(-c2cc(C(F)(F)F)ccn2)c1] | 5 | Cl | 4 |
| 102 | Ru | 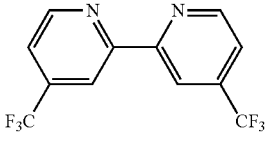 [SMILES: FC(F)(F)c1ccnc(-c2cc(C(F)(F)F)ccn2)c1] | 6 | Cl | 4 |
| 103 | Ru | 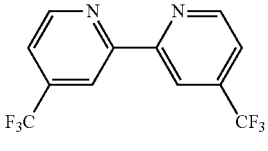 [SMILES: FC(F)(F)c1ccnc(-c2cc(C(F)(F)F)ccn2)c1] | 1 | $PF_6$ | 4 |
| 104 | Ru | 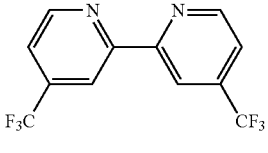 [SMILES: FC(F)(F)c1ccnc(-c2cc(C(F)(F)F)ccn2)c1] | 2 | $PF_6$ | 4 |
| 105 | Ru | 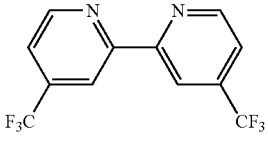 [SMILES: FC(F)(F)c1ccnc(-c2cc(C(F)(F)F)ccn2)c1] | 3 | $PF_6$ | 4 |
| 106 | Ru | 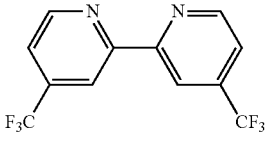 | 4 | $PF_6$ | 4 |
| 107 | Ru | 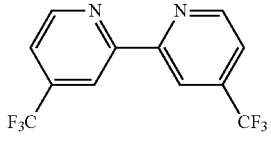 | 5 | $PF_6$ | 4 |
| 108 | Ru | 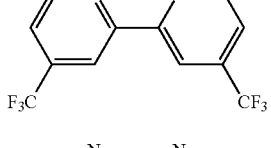 | 6 | $PF_6$ | 4 |
| 109 | Ru | 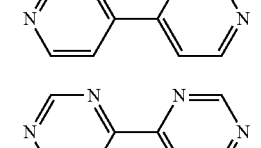 | 1 | Cl | 4 |
| 110 | Ru | 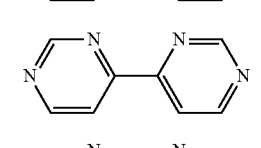 | 2 | Cl | 4 |
| 111 | Ru | 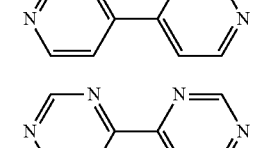 | 3 | Cl | 4 |
| 112 | Ru | 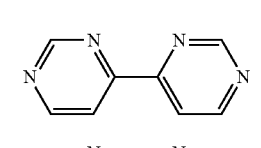 | 4 | Cl | 4 |
| 113 | Ru | 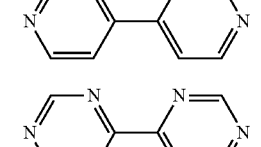 | 5 | Cl | 4 |
| 114 | Ru | 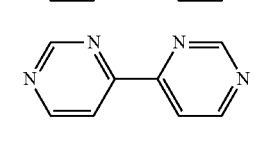 | 6 | Cl | 4 |
| 115 | Ru | 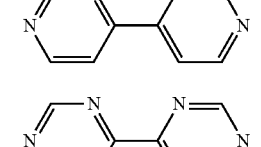 | 1 | $PF_6$ | 4 |
| 116 | Ru | 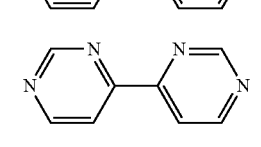 | 2 | $PF_6$ | 4 |
| 117 | Ru | 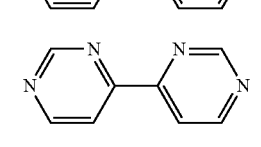 | 3 | $PF_6$ | 4 |
| 118 | Ru | 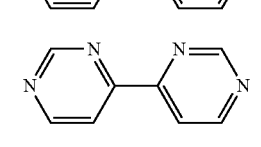 | 4 | $PF_6$ | 4 |
| 119 | Ru | 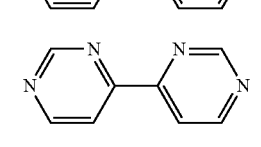 | 5 | $PF_6$ | 4 |
| 120 | Ru | 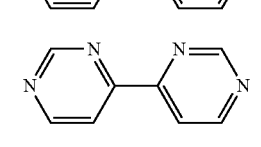 | 6 | $PF_6$ | 4 |

TABLE 5-continued

| Entry | M | Lig | t | X | q |
|---|---|---|---|---|---|
| 121 | Ru | 2,2'-bipyrazine | 1 | Cl | 4 |
| 122 | Ru | 2,2'-bipyrazine | 2 | Cl | 4 |
| 123 | Ru | 2,2'-bipyrazine | 3 | Cl | 4 |
| 124 | Ru | 2,2'-bipyrazine | 4 | Cl | 4 |
| 125 | Ru | 2,2'-bipyrazine | 5 | Cl | 4 |
| 126 | Ru | 2,2'-bipyrazine | 6 | Cl | 4 |
| 127 | Ru | 2,2'-bipyrazine | 1 | PF$_6$ | 4 |
| 128 | Ru | 2,2'-bipyrazine | 2 | PF$_6$ | 4 |
| 129 | Ru | 2,2'-bipyrazine | 3 | PF$_6$ | 4 |
| 130 | Ru | 2,2'-bipyrazine | 4 | PF$_6$ | 4 |
| 131 | Ru | 2,2'-bipyrazine | 5 | PF$_6$ | 4 |
| 132 | Ru | 2,2'-bipyrazine | 6 | PF$_6$ | 4 |
| 133 | Ru | 1,10-phenanthroline | 1 | Cl | 4 |
| 134 | Ru | 1,10-phenanthroline | 2 | Cl | 4 |
| 135 | Ru | 1,10-phenanthroline | 3 | Cl | 4 |
| 136 | Ru | 1,10-phenanthroline | 4 | Cl | 4 |
| 137 | Ru | 1,10-phenanthroline | 5 | Cl | 4 |
| 138 | Ru | 1,10-phenanthroline | 6 | Cl | 4 |
| 139 | Ru | 1,10-phenanthroline | 1 | PF$_6$ | 4 |
| 140 | Ru | 1,10-phenanthroline | 2 | PF$_6$ | 4 |
| 141 | Ru | 1,10-phenanthroline | 3 | PF$_6$ | 4 |
| 142 | Ru | 1,10-phenanthroline | 4 | PF$_6$ | 4 |
| 143 | Ru | 1,10-phenanthroline | 5 | PF$_6$ | 4 |
| 144 | Ru | 1,10-phenanthroline | 6 | PF$_6$ | 4 |

TABLE 5-continued

| Entry | M | Lig | t | X | q |
|---|---|---|---|---|---|
| 145 | Ru | (phenanthroline-like) | 1 | Cl | 4 |
| 146 | Ru | (phenanthroline-like) | 2 | Cl | 4 |
| 147 | Ru | (phenanthroline-like) | 3 | Cl | 4 |
| 148 | Ru | (phenanthroline-like) | 4 | Cl | 4 |
| 149 | Ru | (phenanthroline-like) | 5 | Cl | 4 |
| 150 | Ru | (phenanthroline-like) | 6 | Cl | 4 |
| 151 | Ru | (phenanthroline-like) | 1 | $PF_6$ | 4 |
| 152 | Ru | (phenanthroline-like) | 2 | $PF_6$ | 4 |
| 153 | Ru | (phenanthroline-like) | 3 | $PF_6$ | 4 |
| 154 | Ru | (phenanthroline-like) | 4 | $PF_6$ | 4 |
| 155 | Ru | (phenanthroline-like) | 5 | $PF_6$ | 4 |
| 156 | Ru | (phenanthroline-like) | 6 | $PF_6$ | 4 |
| 157 | Ru | (dimethyl-phenanthroline) | 1 | Cl | 4 |
| 158 | Ru | (dimethyl-phenanthroline) | 2 | Cl | 4 |
| 159 | Ru | (dimethyl-phenanthroline) | 3 | Cl | 4 |
| 160 | Ru | (dimethyl-phenanthroline) | 4 | Cl | 4 |
| 161 | Ru | (dimethyl-phenanthroline) | 5 | Cl | 4 |
| 162 | Ru | (dimethyl-phenanthroline) | 6 | Cl | 4 |
| 163 | Ru | (dimethyl-phenanthroline) | 1 | $PF_6$ | 4 |
| 164 | Ru | (dimethyl-phenanthroline) | 2 | $PF_6$ | 4 |

TABLE 5-continued
| Entry | M | Lig | t | X | q |
|---|---|---|---|---|---|
| 165 | Ru | 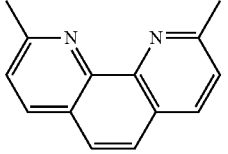 [SMILES: Cc1ccc2ccc3ccc(C)nc3c2n1] | 3 | PF$_6$ | 4 |
| 166 | Ru | 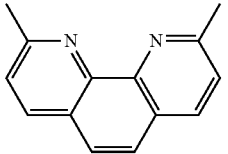 [SMILES: Cc1ccc2ccc3ccc(C)nc3c2n1] | 4 | PF$_6$ | 4 |
| 167 | Ru | 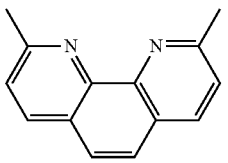 [SMILES: Cc1ccc2ccc3ccc(C)nc3c2n1] | 5 | PF$_6$ | 4 |
| 168 | Ru | 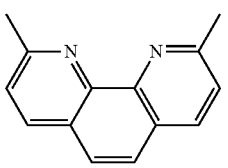 [SMILES: Cc1ccc2ccc3ccc(C)nc3c2n1] | 6 | PF$_6$ | 4 |
| 169 | Ru | 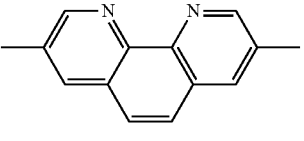 | 1 | Cl | 4 |
| 170 | Ru | 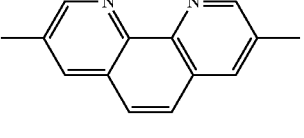 | 2 | Cl | 4 |
| 171 | Ru | 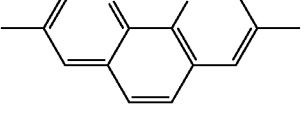 | 3 | Cl | 4 |
| 172 | Ru | 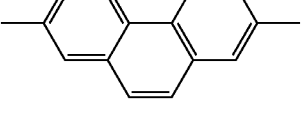 | 4 | Cl | 4 |
| 173 | Ru | 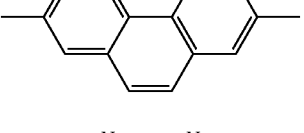 | 5 | Cl | 4 |
| 174 | Ru | 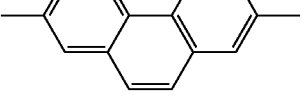 | 6 | Cl | 4 |
| 175 | Ru | 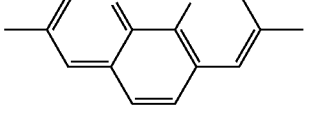 | 1 | PF$_6$ | 4 |
| 176 | Ru | 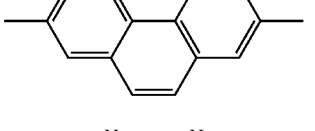 | 2 | PF$_6$ | 4 |
| 177 | Ru | 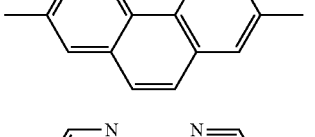 | 3 | PF$_6$ | 4 |
| 178 | Ru | 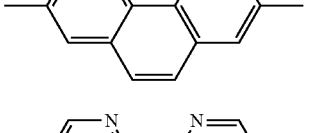 | 4 | PF$_6$ | 4 |
| 179 | Ru | 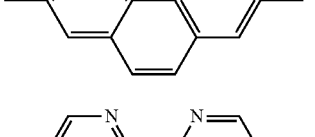 | 5 | PF$_6$ | 4 |
| 180 | Ru | 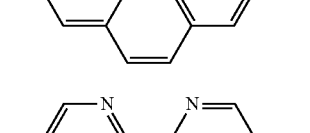 | 6 | PF$_6$ | 4 |
| 181 | Ru | 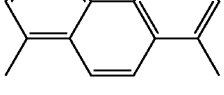 | 1 | Cl | 4 |
| 182 | Ru | 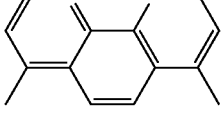 | 2 | Cl | 4 |
| 183 | Ru | 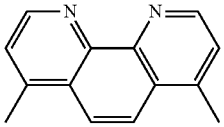 [SMILES: Cc1ccnc2c1ccc1c(C)ccnc12] | 3 | Cl | 4 |
| 184 | Ru | 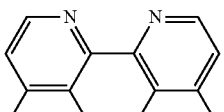 | 4 | Cl | 4 |
| 185 | Ru | 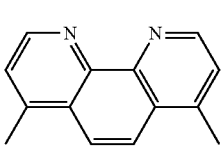 [SMILES: Cc1ccnc2c1ccc1c(C)ccnc12] | 5 | Cl | 4 |

TABLE 5-continued

| Entry | M | Lig | t | X | q |
|---|---|---|---|---|---|
| 186 | Ru | 4,7-dimethyl-1,10-phenanthroline | 6 | Cl | 4 |
| 187 | Ru | 4,7-dimethyl-1,10-phenanthroline | 1 | PF$_6$ | 4 |
| 188 | Ru | 4,7-dimethyl-1,10-phenanthroline | 2 | PF$_6$ | 4 |
| 189 | Ru | 4,7-dimethyl-1,10-phenanthroline | 3 | PF$_6$ | 4 |
| 190 | Ru | 4,7-dimethyl-1,10-phenanthroline | 4 | PF$_6$ | 4 |
| 191 | Ru | 4,7-dimethyl-1,10-phenanthroline | 5 | PF$_6$ | 4 |
| 192 | Ru | 4,7-dimethyl-1,10-phenanthroline | 6 | PF$_6$ | 4 |
| 193 | Ru | 2,2'-bipyrimidine | 1 | Cl | 4 |
| 194 | Ru | 2,2'-bipyrimidine | 2 | Cl | 4 |
| 195 | Ru | 2,2'-bipyrimidine | 3 | Cl | 4 |
| 196 | Ru | 2,2'-bipyrimidine | 4 | Cl | 4 |
| 197 | Ru | 2,2'-bipyrimidine | 5 | Cl | 4 |
| 198 | Ru | 2,2'-bipyrimidine | 6 | Cl | 4 |
| 199 | Ru | 2,2'-bipyrimidine | 1 | PF$_6$ | 4 |
| 200 | Ru | 2,2'-bipyrimidine | 2 | PF$_6$ | 4 |
| 201 | Ru | 2,2'-bipyrimidine | 3 | PF$_6$ | 4 |
| 202 | Ru | 2,2'-bipyrimidine | 4 | PF$_6$ | 4 |
| 203 | Ru | 2,2'-bipyrimidine | 5 | PF$_6$ | 4 |
| 204 | Ru | 2,2'-bipyrimidine | 6 | PF$_6$ | 4 |

For the purposes of the present invention, a compound depicted by the racemic formula will stand equally well for either of the two enantiomers or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Figure 2:
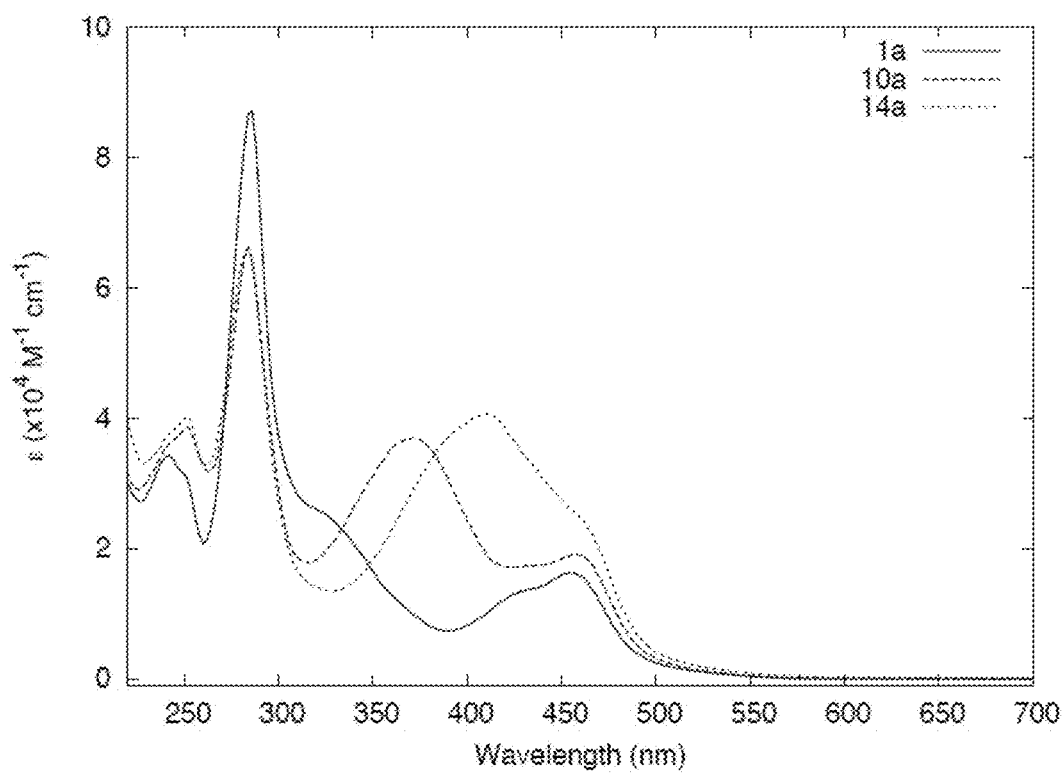
FIG. 2 is a graph of the UV-Vis absorption spectra of 1a, 10a, and 14a in MeCN. The integrated absorption profiles for 1a, 10a, and 14a in the visible range (25,000-15,000 cm$^{-1}$) are 5841, 8190 and 14,100, respectively.

Photophysical properties of the compounds of the invention:

The modular nature of compounds of the disclosure enables fine-tuning of their photophysical properties through minor changes to the molecular scaffold. For example, in the series 1a, 10a, and 14a (FIG. 2), the absorption spectra systematically shift to longer wavelengths, leading to corresponding increases in the extinction coefficients in the visible region (Table 6). When R is a single thiophene as in 1a, the integrated absorption of visible light ($\epsilon$ vs. cm$^{-1}$) is approximately 5841 (FIG. 2). Incorporation of additional thiophene units in the pendant R group increases this absorption cross-section; for 10a and 14a, these enhancements are 40% and 141%, respectively (Table 7). According to this progression, the absorption of visible light will be increase systematically in the corresponding homoleptic complexes as the number of thiophene linkers is increased. Such improvements in visible light absorption are critical to the optimization of PDCs for applications such as PDT.

TABLE 6

Electronic absorption and emission maxima for PDCs and the reference compounds

| Complex | λmax Absorption (log ε), nm | $\lambda_{em}$, nm |
|---|---|---|
| 1a | 242 (4.54), 286 (5.00), 326 (4.42), 426 (4.10), 458 (4.21), 500 (3.37) | 616 |
| 1b | 220 (4.91), 260 (5.04), 286 (4.83), 326 (4.37), 424 (4.25), 454 (4.31), 500 (3.47) | 604 |
| 2a | 244 (4.90), 250 (4.91), 284 (5.20), 378 (4.76), 396 (4.79), 430 (4.66), 460 (4.70), 500 (3.89) | 617 |
| 2b | 220 (5.15), 260 (5.29), 284 (4.81), 298 (4.63), 374 (4.70), 396 (4.78), 458 (4.63), 500 (3.86) | 605 |
| 3a | 252 (4.86), 282 (5.13), 422 (4.79), 464 (4.75) 500 (3.94) | 619 |
| 3b | 220 (4.96), 260 (5.10), 284 (4.59), 298 (4.29), 420 (4.61), 462 (4.55), 500 (3.87) | 613 |
| 10a | 252 (4.59), 284 (4.87), 370 (4.60), 458 (4.28), 500 (3.46) | 618 |
| 10b | 220 (4.95), 260 (5.07), 286 (4.58), 294 (4.52) 378 (4.69), 456 (4.41), 500 (3.62) | 618 |
| 14a | 252 (4.61), 282 (4.83), 408 (4.62), 464 (4.37), 500 (3.60) | 620 |
| 14b | 220 (4.81), 260 (4.92), 286 (4.45), 410 (4.59) 458 (4.37), 500 (3.53) | 618 |

TABLE 7

Integrated absorption profiles for PDCs in the visible range (25,000-15,000 cm$^{-1}$).

| Complex | Abs. (400-700 nm) | increase |
|---|---|---|
| 1a | 5841 | |
| 10a | 8190 | 40% (1.4X) |
| 14a | 14,100 | 141% (2.4X) |

Figure 3:
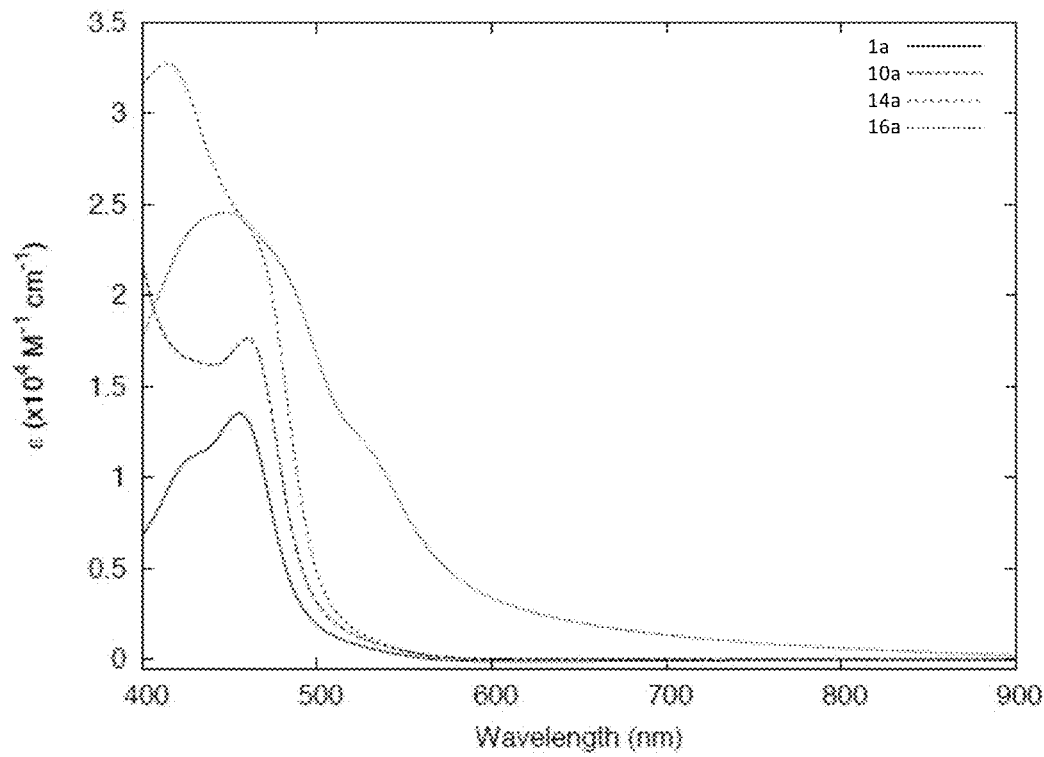
FIG. 3: Light absorption by PDCs 1a, 10a, 14a, and 16a dissolved at 20 μM in water.

The modular nature of the compounds of the disclosure enables fine-tuning of their photophysical properties through systematic changes to the molecular scaffold. For example, In the series 1a, 10a, 14a, and 16a, the absorption spectra extend to longer wavelengths as the number of thiophene rings is increased, leading to absorption in the near infrared region when 4 thiophenes are present (16a). Also, the integrated absorption from 400-900 nm is almost 4 times greater for 16a versus 1a (Table 8 and FIG. 3).

TABLE 8

Integrated absorption profiles for PDCs 1a, 10a, 14a, and 16a in the visible and NIR region.

| Compound | Integrated absorption relative increase (400-900 nm) | Increase relative to 1a |
|---|---|---|
| 1a | 19 | 1 |
| 10a | 33 | 1.74 |
| 14a | 50 | 2.63 |
| 16a | 69 | 3.63 |

Figure 1:
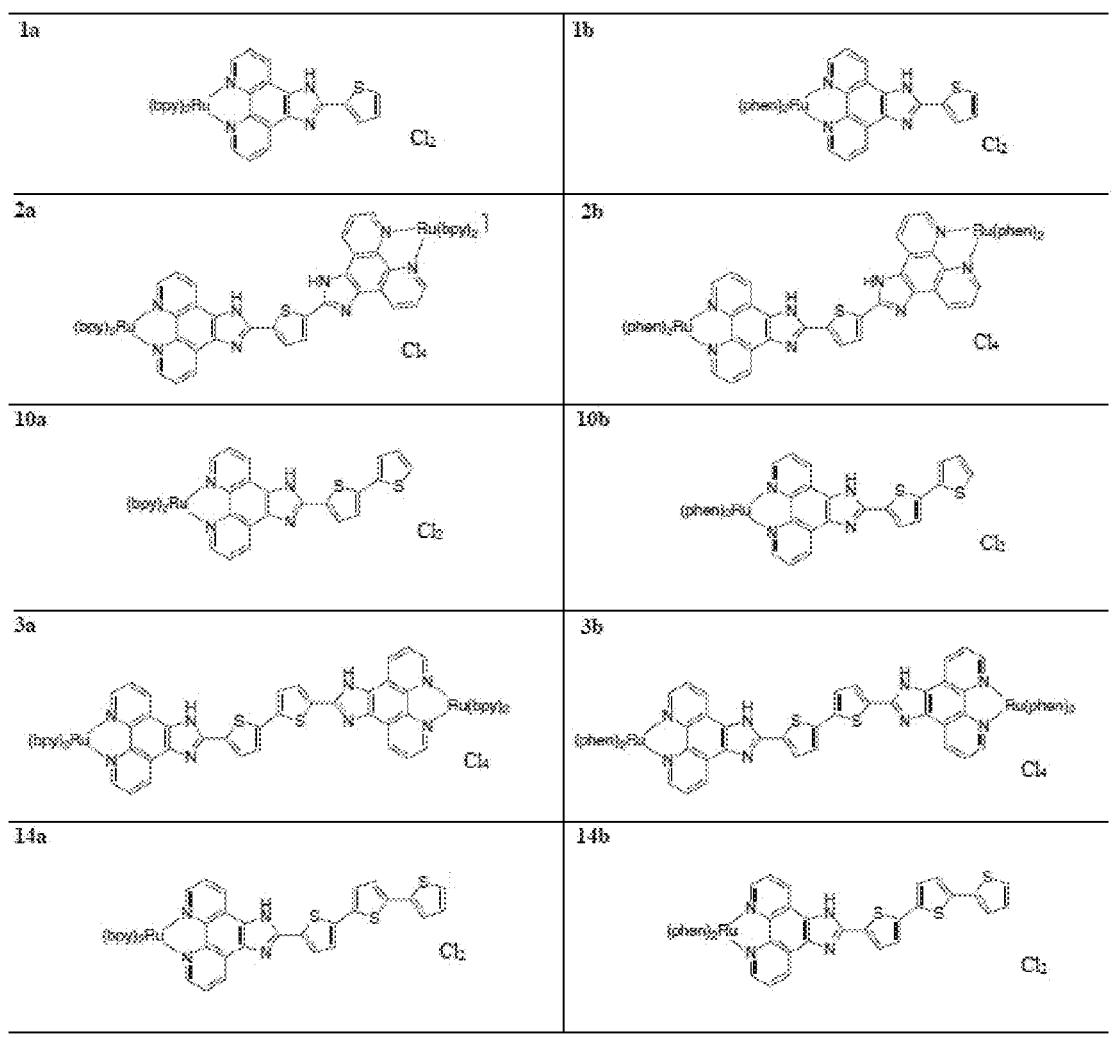
FIG. 1 shows a set of representative compounds of the disclosure (compounds 1a, 2a, 10a, 10b, 3a, 3b, 14a and 14b).
Figure 4:
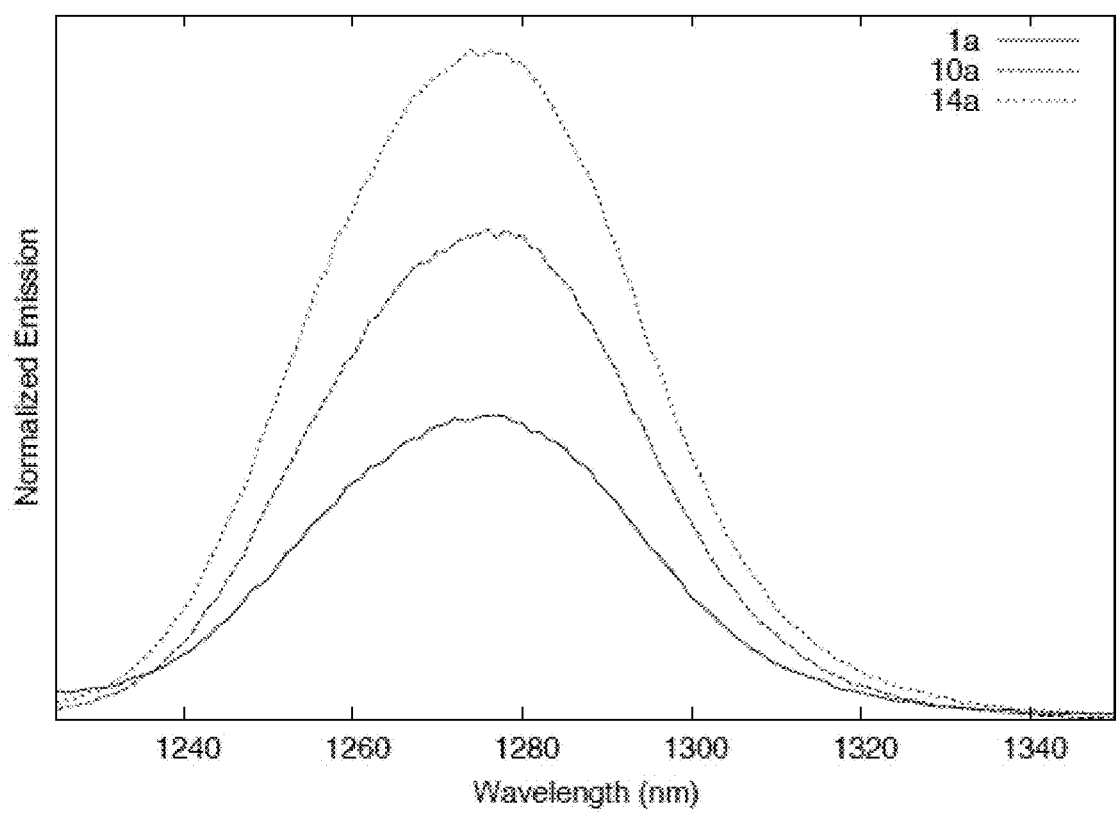
FIG. 4: is a graph of the $^1O_2$ emission sensitized by PDCs 1a, 10a, and 14a in MeCN. The $^1O_2$ quantum yields for 1a, 10a, and 14a are 0.47, 0.74, and 1.0, respectively.

Current sensitizers for PDT rely on $^1O_2$ generation for photodynamic action toward target cells. Similar to the trend in visible absorption, the quantum yields for $^1O_2$ production for these compounds also increase with the number of thiophene units (FIG. 4). The measured $\Phi^1O_2$ for 1a is 0.47 while 10a and 14a yield 0.74 and 1.0, respectively (Table 9). Two additional compounds in this family including 14a (FIGS. 1, 3a and 3b) have been shown to exhibit 100% efficiency for $^1O_2$ sensitization, exceeding the PDT drug PHOTOFRIN ($\Phi^1O_2$=0.75, ethanol). Interestingly, despite remarkable $^1O_2$ quantum yields, compounds of the disclosure have a quantum yield for emission less than 1% in deoxygenated solution (e.g. 14a, $\Phi^1O_2$<0.15%). Therefore, another nonradiative pathway becomes important in the absence of $O_2$ and may predominate under hypoxic conditions, imparting $O_2$ independence to the compounds of the disclosure as a PDT agent. The fact that compounds of the disclosure photodamage DNA under hypoxic conditions is evidence for potential $O_2$ independence in terms of photobiological activity.

TABLE 9

Photophysical properties for PDCs

| Complex | $\Phi_{em}$ (air) | $\Phi_{em}$ (Ar)* | $\tau_{em}$, ns (air) | $\tau_{em}$, ns (Ar)* | $\Phi^1O_2$ |
|---|---|---|---|---|---|
| 1a | 1.27 × 10$^{-2}$ | 1.08 × 10$^{-1}$ | 150 | 1040 | 0.467 |
| 1b | 8.92 × 10$^{-3}$ | 7.40 × 10$^{-2}$ | 112 | 700 | 0.422 |
| 2a | 4.02 × 10$^{-3}$ | 5.51 × 10$^{-2}$ | 188 | 2810 | 0.741 |
| 2b | 2.15 × 10$^{-3}$ | 5.19 × 10$^{-2}$ | 194 | 4400 | 0.677 |
| 3a | 3.60 × 10$^{-4}$ | 1.96 × 10$^{-3}$ | 159 | 1520 | 1 |
| 3b | 5.40 × 10$^{-4}$ | 2.06 × 10$^{-3}$ | 129 | 1240 | 1 |
| 10a | 4.59 × 10$^{-4}$ | 3.37 × 10$^{-2}$ | 151 | 1290 | 0.738 |
| 10b | 3.83 × 10$^{-4}$ | 1.14 × 10$^{-2}$ | 133 | 741 | 0.790 |
| 14a | 3.30 × 10$^{-4}$ | 1.34 × 10$^{-3}$ | 154 | 575 | 1 |
| 14b | 4.70 × 10$^{-4}$ | 1.88 × 10$^{-3}$ | 140 | 908 | 0.496 |

*Argon purge, 30 min. at 30 ± 5 mm Hg.

Figure 5:
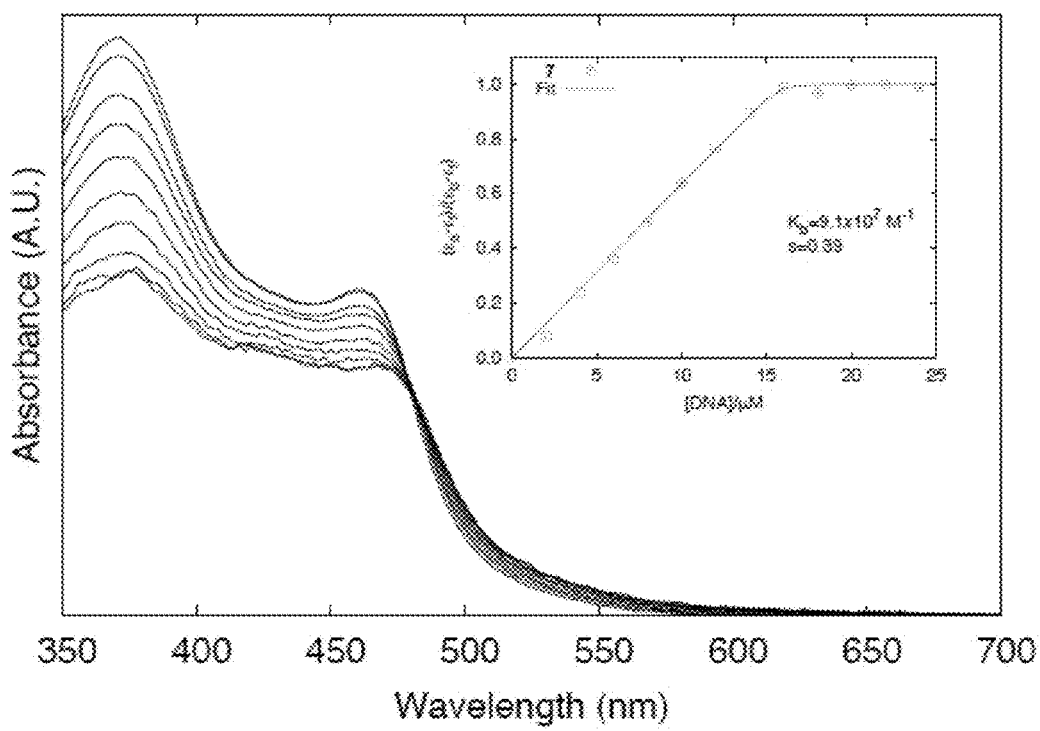
FIG. 5: (a) Titration of 10a (20 μM) with CT DNA (10 mM Tris·100 mM NaCl, pH 7.5). Inset: binding isotherm at 372 nm. (b) Titration of 10b (50 μM) with CT DNA (10 mM Tris·100 mM NaCl, pH 7.5). Inset: binding isotherm at 380 nm.
Figure 5:
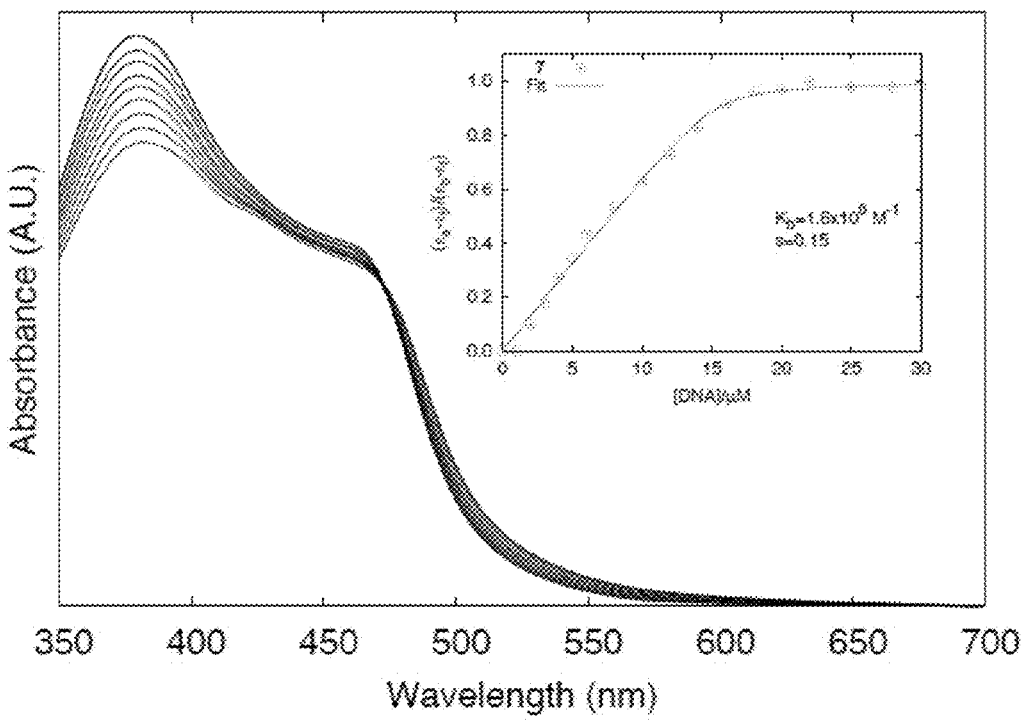
Figure 6:
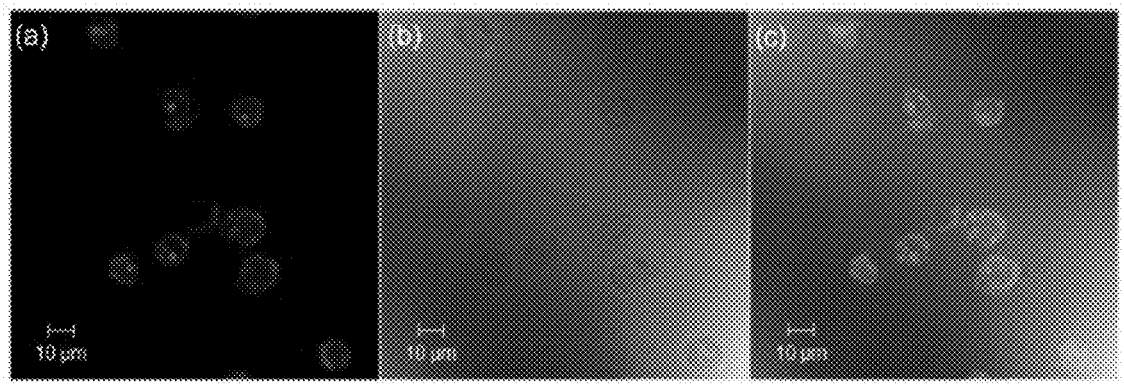
FIG. 6: HL60 cells loaded with 14a viewed by laser scanning confocal microscopy. Excitation of the PDC at 458/488 nm produced red emission that was collected through a LP510 filter. Images were collected by a laser scanning confocal microscope (Zeiss LSM510 with ZEN operating system) by using 40×/NA1.3, oil or 63×/NA1.4, oil objectives. Excitation were 458/488 nm of argon/krypton and signals were collected through a LP510 filter. (a) Emission from the PDC 14a, (b) Differential interference contract (DIC), and (c) emission/DIC overlay.

DNA Binding Properties of the Compounds of the Disclosure:

As shown in FIG. 5, 10a binds DNA very strongly, having one of the largest known binding constants for this type of interaction ($K_b$=9.1×10$^7$ at 372 nm; 4.4×10$^7$ at 460 nm) determined by UV-Vis absorption. The magnitude of this binding interaction is further supported by emission measurements ($K_b$=4.2×10$^7$ at 625 nm) and is also observed for other PDCs of the disclosure such as 14a. This binding occurs in cells and can be seen as diffuse nuclear staining by the PDC 14a in HL60 cells when viewed by laser scanning confocal microscopy (FIG. 6).

Changes in the identity of the ancillary ligands (10b) or a reduction in the number of thiophenes in the C2-substituted ligand (1a) attenuates the binding affinity by an order of magnitude, indicating that subtle modifications lead to profound effects within a single family of structurally related PDCs of the disclosure (Table 10).

TABLE 10

DNA binding constants from absorption and emission optical titrations

| Complex | $K_b$, s (Abs.) | $K_b$, s (Em.) |
|---|---|---|
| 1a | 2.4 × 10$^6$, 0.73 (456 nm) | 3.2 × 10$^6$, 4.7 (627 nm) |
| 10a | 4.4 × 10$^7$, 0.4 (460 nm) | 4.2 × 10$^7$, 7.6 (625 nm) |
| 10b | 3.3 × 10$^6$, 0.19 (462 nm) | 3.6 × 10$^7$, 7.1 (619 nm) |
| 14a | 1.6 × 10$^7$, 0.30 (452 nm) | 1.4 × 10$^7$, 5.1 (626 nm) |

Figure 7:
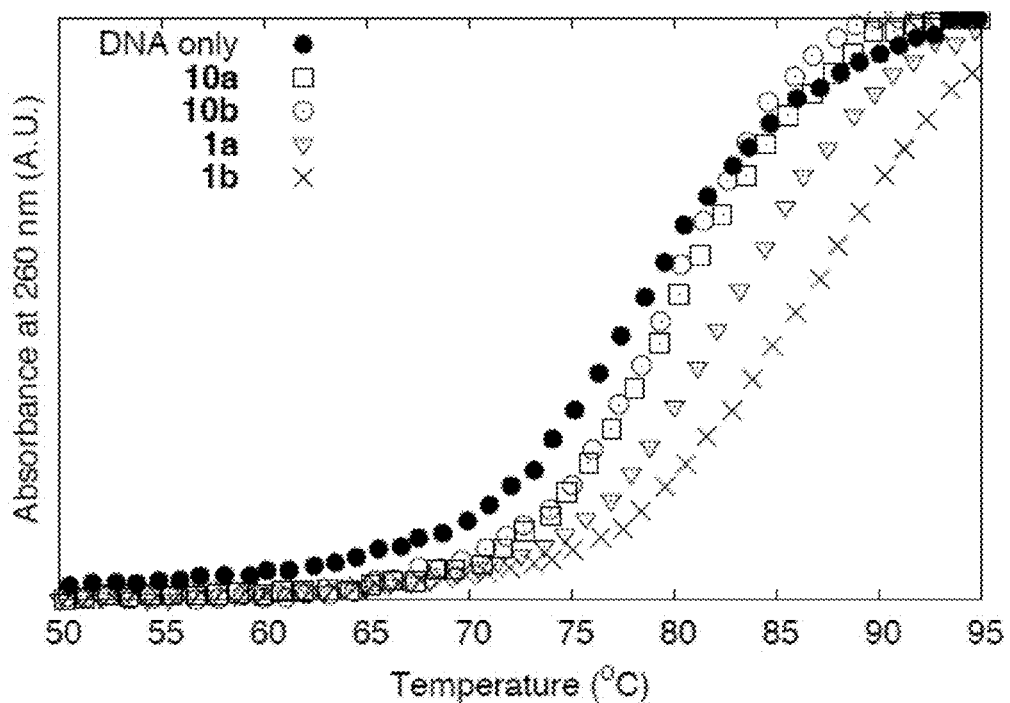
FIG. 7: Thermal denaturation of calf-thymus DNA (50 μM, NP) in 5 mM Tris with 50 mM NaCl, pH 7.4) alone and in the presence of 1a, 1b, 10a, and 10b (5 μM, [PDC]/[NP]=0.1).

The PDCs of the disclosure also differ in the extent to which they stabilize a DNA helix when they bind (FIG. 7, Table 11). Even though 1a exhibits weaker binding to DNA relative to 10a, the additional thiophene moiety in 10a leads to less stabilization of the helix upon DNA binding as observed by only a slight increase in $T_m$ of 1° C. In fact, gel electrophoretic analysis indicates that 10a substantially destabilizes the native DNA structure, evidenced by the inability of the intercalator ethidium bromide to stain DNA effectively at [10a]:[DNA]>0.4 (FIG. 14, (b) Lanes 8-14); in contrast, 1a does not interfere with ethidium bromide intercalation, and the gel bands produced by ethidium bromide staining remain visible with increasing PDC concentration (FIG. 14, (a) Lanes 8-14).

TABLE 11

Thermal denaturation parameters for CT-DNA with added 1a, 1b, 10a, and 10b ([PDC]/[NP] = 0.1). $T_m$ for CT-DNA in the absence of a PDC was 78.6° C.

| Complex | $T_m$, ° C. | $\Delta T_m$ |
|---|---|---|
| 1a | 82.7 | 4.1 |
| 1b | 86.0 | 7.4 |
| 10a | 79.9 | 1.3 |
| 10b | 79.9 | 1.3 |

DNA Light Switch Effects of the Compounds of the Invention

Figure 8:
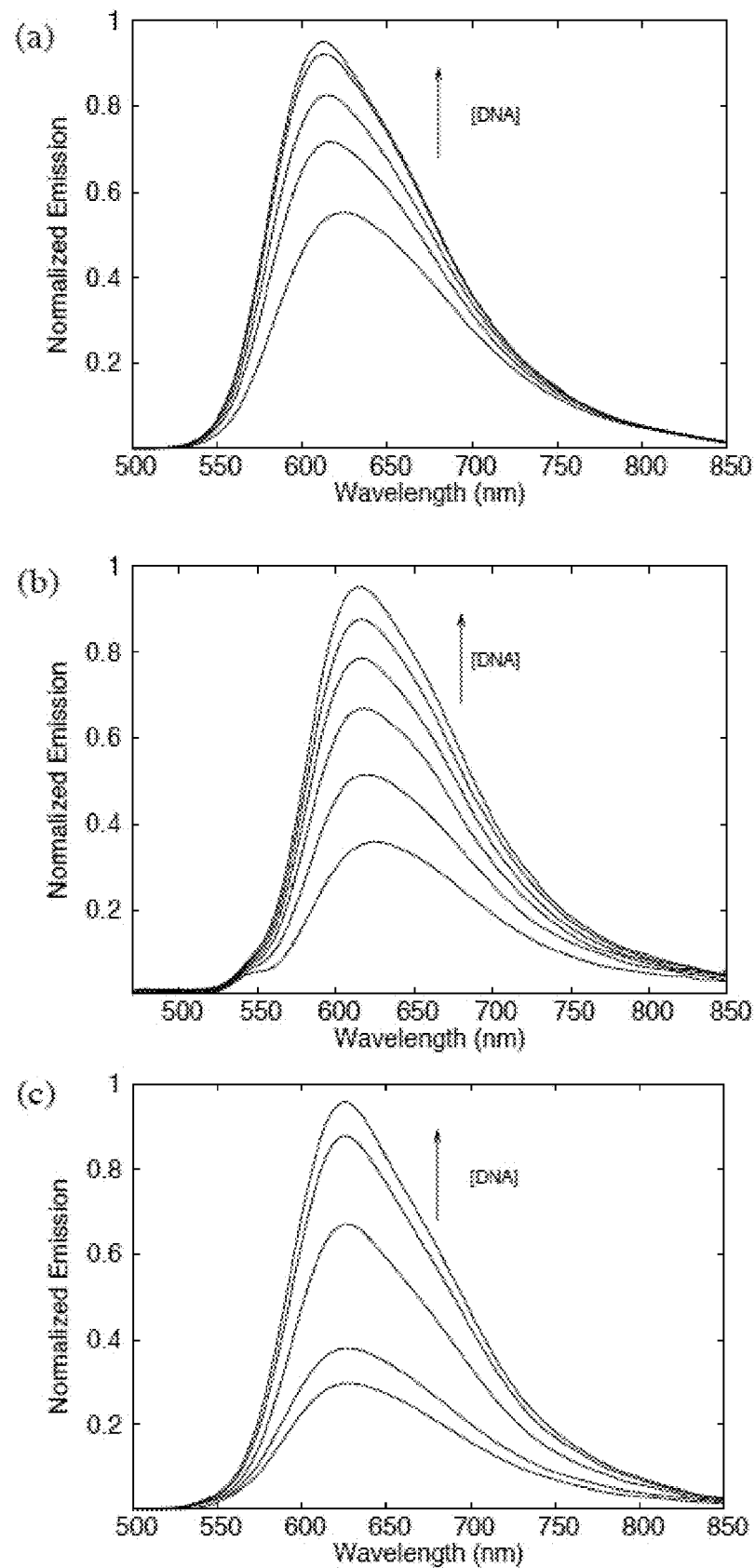
Figure 9:
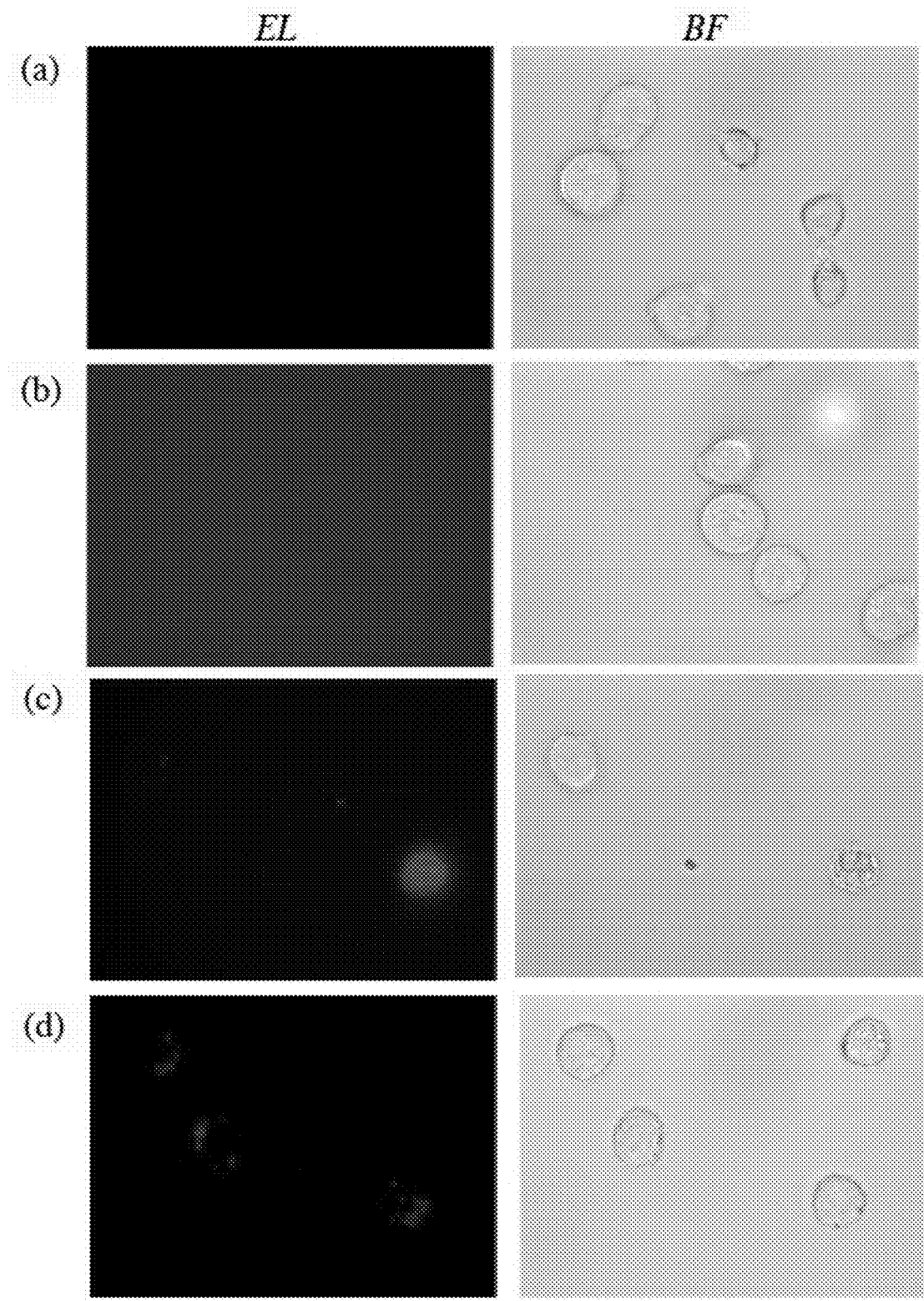
FIG. 9: Epi-luminescence (EL) and bright field (BF) images of PDC-treated HL-60 cells: a) untreated control, (b)

While the PDCs of the disclosure, excluding 1a and 1b, have a quantum yield for emission of less than 1% in air, they become measurably emissive in the absence of oxygen (Table 9) or in the presence of DNA (FIG. 8), the latter of which is known as the DNA light-switch effect. This effect increases with the number of thiophene units in the pendant R group: approximately 2-, 3-, and 4-fold for 1a, 10a, and 14a, respectively (Table 12).

TABLE 12

Measured enhancement for DNA light-switch effect produced by PDCs 1a, 10a, and 14a

| Complex | Enhancement |
|---|---|
| 1a | 76% (1.8x) |
| 10a | 160% (2.6x) |
| 14a | 260% (3.6x) |

The enhancement in luminescence can be exploited to detect the PDCs of the disclosure in the presence of biomolecules and/or hypoxic environments or to ascertain subcellular localization. For example, 10a localizes outside of the nucleus in non-irradiated cells (FIG. 10c) while 14a appears to stain chromatin (FIG. 12c). In irradiated cells, both 10a and 14a are distributed throughout the cytoplasm and nucleus (FIGS. 10d and 12d). Interestingly, 10a and 10b stain nonviable cells in the dark at 5 minutes (FIGS. 10b and 11b). 1a, being 1-2 orders of magnitude more emissive than 10a or 14a in air or argon, can be used as a stain at much lower concentration.

DNA photo cleavage properties of the compounds of the disclosure:

Perhaps due, in part, to very strong binding interactions with DNA, PDCs of the disclosure cause extensive DNA damage in the form of single-strand breaks upon irradiation with visible light. The observation that no strand breaks occur at similar concentrations of PDC without light activation is very promising as a mechanism for cellular destruction based on photodynamic action (FIGS. 13 and 14). Given that DNA is the blueprint for all cellular function, photo dynamic action targeted at this biomolecule will initiate apoptotic pathways that selectively destroy irradiated cells that have taken up the PDC of the disclosure. The mechanism for DNA damage is not confirmed, but with $^1O_2$ quantum yields of unity for PDCs such as 14a, it is likely that $^1O_2$-mediated photodamage plays a significant role in oxygenated conditions. Under hypoxic conditions, DNA photodamage by these compounds remains significant (FIGS. 15 and 16, Tables 12 and 13), indicating that oxygen-deficient cells are susceptible to photodynamic action by PDCs such as 10a and 14a. This oxygen-independent DNA damage is further corroborated by the fact that the quantum yield for emission for a compound such as 14a remains very low (0.13%) in the absence of oxygen. Therefore, intra- or intermolecular electron transfer, which is common to thiophene photophysics, contribute to non-radiative decay in these systems as well. Such electron transfer pathways may become important in the absence of molecular oxygen, giving rise to Type I photoprocesses with biomolecules. Preliminary experiments indicate that energy versus electron transfer is governed by environment. In other words, there may not be a partitioning of excited state energy between numerous pathways; rather, the presence of oxygen serves to switch between two major non-radiative pathways: electron transfer and energy transfer, both of which are extremely efficient at invoking DNA damage. This photodynamic switch between Type I and Type II photoprocesses ensures that photodynamic action is optimal regardless of oxygen concentration. Such a versatile PDC eliminates the need for distinct Type I and Type II photosensitizers for maximizing photodynamic action according to oxygen levels in target cells.

TABLE 12

Calculated percentages of DNA forms observed for PDC-mediated pUC19 photocleavage in air-saturated and deoxygenated solution with 420-nm irradiation, FIG. 15.

| Lane | PDC | Treatment | Form I | Form II | Form III |
|---|---|---|---|---|---|
| 1 | None | Air, dark | 76 | 24 | |
| 2 | $[Ru(bpy)^3]^{2+}$ | Air, dark | 71 | 29 | |
| 3 | $[Ru(bpy)^3]^{2+}$ | Air, +hv | 33 | 67 | |
| 4 | $[Ru(bpy)^3]^{2+}$ | Ar, +hv | 71 | 29 | |
| 5 | 10a | Air, dark | 78 | 22 | |
| 6 | 10a | Air, +hv | 14 | 86 | |
| 7 | 10a | Ar, +hv | 34 | 66 | |
| 8 | 10b | Air, dark | 71 | 29 | |
| 9 | 10b | Air, +hv | 15 | 85 | |
| 10 | 10b | Ar, +hv | 27 | 73 | |
| 11 | 14a | Air, dark | 50 | 23 | 27 |
| 12 | 14a | Air, +hv | 21 | 79 | |
| 13 | 14a | Ar, +hv | 30 | 39 | 31 |

TABLE 13

Calculated percentages of DNA forms observed for PDC-mediated pUC19 photocleavage in air-saturated and deoxygenated solution with visible irradiation, FIG. 16.

| Lane | Complex | Treatment | Form I | Form II |
|---|---|---|---|---|
| 1 | None | Air, dark | 77 | 23 |
| 2 | $[Ru(bpy)^3]^{2+}$ | Air, dark | 72 | 28 |
| 3 | $[Ru(bpy)^3]^{2+}$ | Air, +hv | 37 | 63 |
| 4 | $[Ru(bpy)^3]^{2+}$ | Ar, +hv | 57 | 43 |
| 5 | 10a | Air, dark | 80 | 20 |
| 6 | 10a | Air, +hv | 14 | 86 |
| 7 | 10a | Ar, +hv | 38 | 62 |

Cytotoxicity and Photocytotoxicity of the Compounds of the Invention

A host of PDCs of the disclosure exhibit marked photocytotoxicity with no substantial dark toxicity even at concentrations as high as 100 μM (checked at 12, 18, 24, 36, and 48 hr. post-irradiation). As observed for 1a, 10a, and 14a in terms of integrated visible absorption, $\Phi^1O_2$, DNA binding, and DNA photodamage, there exists a profound effect of overall structure on the photocytotoxicity toward HL-60 cells. To illustrate, 10a, which differs from 10b only in that Lig=[2,2'] bipyridine instead of [1,10]phenanthroline, is phototoxic toward cells at 20 µM, whereas 10b displays no photocytotoxicity even at 100 µM (FIG. 17). For the series 1a, 10a, and 14a, where Lig=[2,2']bipyridine and $R^1$ differs by the number of thiophenes that make up the pendant C2 unit, there is a drastic difference in the photocytotoxicity toward HL-60 cells, whereby photodynamic action is 100% at less than 10 µM for 14a and virtually zero at similar concentrations of 1a (FIG. 18). Interestingly, as the number of thiophenes that make up $R^1$ increases, so does the photodynamic action toward HL-60 cells. This progression was confirmed through viability staining with Trypan Blue using a commercial cell counting system as well as AO-EB viability staining using epi-fluorescence microscopy (FIG. 19). This activity parallels the trends observed for integrated visible absorption, $\Phi^1 O_2$, and DNA photodamage, which together determine the overall photocytotoxicity for a given PDC toward a particular cell.

To discern whether batch-to-batch variability in photodynamic action exists for the PDCs of the disclosure, 1a, 10a, and 14a were synthesized using a novel method for preparing compounds of the disclosure using microwave irradiation. Their molecular structures were confirmed by $^1$H NMR, HRMS, and elemental analysis and are identical to structures obtained via standard methodology. The photocytotoxicity observed for the PDCs 1a, 10a, and 14a prepared by microwave irradiation exhibits the same trend that was documented for PDCs 1a, 10a, and 14a prepared according to standard methods: namely, 14a>10a>1a (FIG. 20). Likewise, the effective concentrations at which photocytotoxicity is observed for each PDC does not vary substantially between the two independently prepared batches for the post-irradiation times employed (18 hr., FIG. 21 and 40 hr., FIG. 22). The photodynamic action of 14a is best illustrated in FIGS. 23-25, where 100% photocytotoxicity occurs in the 5-10 µM range.

Activation of Apoptotic Pathways by Compounds of the Disclosure

Both 10a and 14a exert their photocytotoxicity by activating apoptotic pathways. Nuclear condensation and the formation of apoptotic bodies can be seen clearly with AO-EB nuclear morphology staining at 18 and 40 hr. post-irradiation by epi-fluorescence microscopy of cells treated with 10a (FIG. 26, Panel C). AO stains viable nuclei and fluoresces intense green (FIG. 26, Panel B, upper right cell) while EB stains nonviable nuclei and fluoresces intense red (FIG. 26, Panel C, lower left cell). Likewise nuclear condensation and the formation of apoptotic bodies are evident in AO-EB stained cells treated with 14a at 18 (FIG. 27) and 40 hr. (FIG. 28) post-irradiation.

Further support for apoptosis as the primary mechanism for cellular destruction is based on the large changes in cell diameter that take place upon irradiation of cells that have been treated with 10a or 14a. It is well-known that apoptotic cell diameters are significantly smaller than either normal or necrotic cells. Healthy HL-60 cells can range from 9-25 µm in diameter, although 13 µm is typical. The HL-60 cells used in these cytotoxicity studies average 11-13 µm in diameter. In the presence of 50 µM 10a, 70% of the irradiated HL-60 cells that remain at 40 hr. are roughly half their original size (mean diameter <6 µm) while the same concentration of 10b has little effect on the mean cell diameter (FIG. 29). The same trend exists for 14a while 1a, which exhibits no significant photocytotoxicity, does not notably alter the irradiated HL-60 cell diameter distribution (FIG. 30). Interestingly, 1a does produce a small population (<30% at 40 hr.) of HL-60 cells with diameters less than 6 µm in the dark. This finding is corroborated by the slight dark toxicity observed for 1a (FIG. 18a). Together, these changes in size distribution upon irradiation of PDC treated cells further underscore that the structure of compounds of the disclosure has an important and distinct effect on the photobiology of these PDCs of the disclosure. The systematic variation that can be achieved in terms of their photophysical, photochemical, and photobiological properties offers an avenue to rational PDC design and optimization of compounds of the disclosure.

PDCs of the Disclosure as Excited-State Oxidants and Reductants:

Compounds of the disclosure are capable of acting as excited-state oxidants and reductants. For example, The excited-state reduction and oxidation potentials of 14a are estimated at 1.31 and −0.87 V, respectively, making both guanine oxidation and cystosine or thymine reduction feasible upon photoactivation (Table 14, FIGS. 31 and 32). Compounds of the disclosure act as photoreductants for DNA, supported by the observation that endogenous reductants such as glutathione (GSH) and ascorbic acid (AA) facilitate DNA photodamage by compounds of the disclosure.

TABLE 14

Ground state and excited-state redox potentials of 14a

| Entry | $E_{ox}$(V) | $E_{red}$(V) | $E_{0-0}$(eV) | $E^*_{red}$(V) | $E^{*ox}$(V) |
|---|---|---|---|---|---|
| 14a | 1.56 | −1.13 | 2.43 | 1.31 | −0.87 |
|  |  | −1.33 |  | 1.10 |  |
|  |  | −1.68 |  | 0.75 |  |

The DNA photocleavage produced by 14a is greatly enhanced by endogenous reductants such as glutathione (GSH). At submicromolar concentrations of 14a, 4 mM GSH results in detectable double-strand breaks while DNA exposed to the PDC alone is mostly undamaged (FIG. 33, Lane 1). At 3 µM 14a, the presence of GSH results in total DNA degradation (FIG. 33 Lane 6). It is well-known that GSH concentraion is high in human tumour cells, decreasing the cytotoxic effects of electrophilic alkylating agents (such as cisplatin) and radiation and also diminishing the effects of PDT. Herein we disclose a family of PDT agents that is preferentially activated by GSH.

The ability of GSH to facilitate DNA damage is broad in scope and holds for additional compounds of the disclosure (e.g., 14c and 16c), and for other reductants (ascorbate, DTT, NADH, etc.). FIG. 34 (Lanes 7-16) illustrates that for 1a, the addition of GSH (0.5-7 mM) has no effect on DNA photocleavage, and the predominant form of DNA is supercoiled (Form I). For 10a, GSH promotes the formation of both single- and double-strand DNA breaks, and for 14a, GSH promotes total degradation of the DNA. For all 3 complexes, Lane 17 shows the amount of DNA damage to pBR322 that results with photoactivation of 2 µM PDC in the absence of GSH. For comparison, Lane 14 shows the effect of 6 mM GSH on DNA photodamage by the PDCs: (a) there is no effect on DNA photocleavage by 1a; (b) GSH facilitates the formation of double-strand breaks by 10a; and (c) GSH facilitates total DNA degradation by 14a. FIG. 35 demonstrates the facilitation of DNA photodamage by 14a for another reductant, ascorbic acid (AA). A comparison between Lanes 13 and 14 clearly shows that the presence of AA turns a predominantly single-strand DNA photocleaver into a very powerful DNA degrader (note smear in Lanes 9-13).

Destruction of Cancer Cells by Compounds of the Invention

Compounds of the disclosure with low dark toxicity are able to effectively destroy cancer cells by PDT at very low concentrations ex vivo (i.e., in a cell outside of an animal). An ideal PDC should exhibit PDT effects at low PDC concentrations while having a low dark toxicity, i.e., the cell kill of the PDC alone with no light exposure. Dark toxicity and PDT effects on cell kill for PDCs 10A, 14A, and 16A were tested ex vivo on the following cell lines: CT26.WT (murine colon carcinoma), U87 (human glioblastoma), F98 (rat glioma). Irradiation was conducted at 45 J/cm$^2$ (TLC-3000 light source, λ=530 nm, 4-6 hours PS-light interval) and cell viability was measured 24 hours post-irradiation using the Presto Blue cell viability assay. FIG. 39 shows that neither 10A, 14A, nor 16A alone (without light) demonstrated significant cell kill. However, a strong photodynamic effect (PDC plus light) was observed with 10A, 14A, and 16A; 60-100% cell kill in all three cell lines, depending on the PDC concentration. The best effect on cell kill was shown for 14A and 16A, followed by 10A.

In Vivo Efficacy of Compounds of the Disclosure:

Compounds of the disclosure have comparable effective in vivo PDT doses as FDA approved PHOTOFRIN and Aminolevulinic Acid (ALA). The mean toxic dose that causes death in 50% of animals tested ($MTD_{50}$) was determined for PDCs 14A and 14C. $MTD_{50}$ was identified by administering a series of increasing and decreasing drug doses, starting at a concentration $10^2$ lower in magnitude to the presumed $MTD_{50}$ from in vitro studies. $MTD_{50}$s for PDCs 14A and 14C are the effective doses that are used in further PDT studies. As shown in FIG. 40, the effective PDT doses for 14A and 14C fall between the range of PHOTOFRIN and ALA, i.e., 36 mg/kg for 14A, 98 mg/kg for 14C, 10 mg/kg for PHOTOFRIN, and 250 mg/kg for ALA. Note: the effective dose of protoporphyrin IX (PPIX, the photoactive metabolite of ALA), is ¼ the administrative dose of ALA.

Compounds of the Disclosure Ex Vivo Potency

Compounds of the disclosure are more effective at killing cancer cells ex vivo as compared to ALA. For example, 14A is more effective at killing cancer cells ex vivo compared to ALA. ALA is an FDA approved PDC currently used to treat skin, bladder, and brain cancers. As shown in FIG. 41, dark toxicity of 14A (PDC alone and without light) was weak or negligible in all three cancer cell lines (CT26.WT, U87, F980) which was comparable to the level of dark toxicity of ALA at the same concentrations. The efficiency of 14A plus light (TLC-3000 light source, 530 nm, 45 J/cm$^2$) in killing cells was also much higher compared to the efficacy of ALA. 14A resulted in 100% cell kill at very low concentrations, whereas ALA produced no, or very little, cell kill.

Tissue Penetration of Compounds of the Disclosure

PDCs should absorb light at longer wavelengths in order to effectively penetrate tissue. Absorbance at shorter wavelengths will achieve less tissue penetration and may lead to skin photosensitivity. To measure the absorbance for each PDC, PDC stock solutions were diluted with the same solvent to achieve an optical density (OD) of 0.2 at 525 nm (6.7 µM for 14C, 1.2 µM for PPIX). Optical densities were measured from 300 nm to 800 nm. As shown in FIG. 42, both 14C and PPIX have similar and relatively low absorption at 525 nm. PDT irradiation at wavelengths of 525 nm or longer, as seen with compounds of the disclosure, are clinically warranted, while the use of shorter wavelengths is not clinically justified.

Photostability of Compounds of the Disclosure

Compounds of the disclosure exhibit greater photostability compared to PPIX. An effective PDC should maintain high photochemical stability, allowing for a long shelf-life. To measure photostability, each PDC was irradiated and the OD at the wavelengths corresponding to the maximal absorbance (423 nm for 14C, 411 nm for PPIX), was measured every 5 minutes for 60 minutes of total irradiation time. FIG. 43 shows that PDC 14C is photobleached by approximately 50%. PPIX underwent considerable photobleaching by 60 minutes of irradiation (approximately 70%). 14C is, therefore, more photostable than PPIX.

Will the subcutaneous tumor data be inserted here?

Process

The present invention further relates to a process for preparing the photodynamic compounds of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and coordination complexes and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic and inorganic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., 1H or 13C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic and inorganic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic and inorganic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the process outlined in the following schemes.

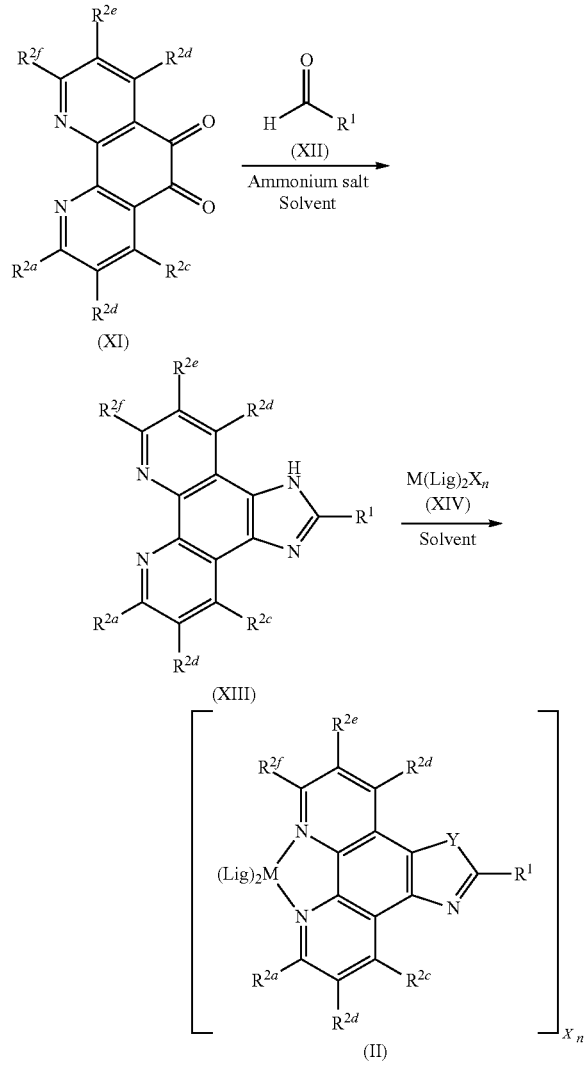

Accordingly, a suitably substituted compound of the formula (XI), a known compound or compound prepared by known methods, is reacted with a suitably substituted compound of the formula (XII) in the presence of an ammonium salt such as ammonium acetate, ammonium formate, ammonium chloride, ammonium bromide, ammonium sulfate and the like in a solvent such as acetic acid, formic acid, propionic acid and the like, optionally in the presence of methanol, ethanol, N,N-dimethylformamide and the like, optionally heated, optionally heated with microwave irradiation, to provide a compound of the formula (XIII) A compound of the formula (XIII) was then reacted with a compound of the formula (XIV) in a solvent such as methanol, ethanol, isopropanol, ethylene glycol, glycerol, water, 1,4-dioxane, dimethyl formamide, mixtures of the aforementioned solvents, and the like, optionally heated, optionally heated with microwave irradiation, to provide a compound of the formula (II). Compounds of the formula (II) may be converted to alternative salt forms by conventional methods known to those skilled in the art.

Compounds of formula (III) may be prepared according to the process outlined in Scheme 2.

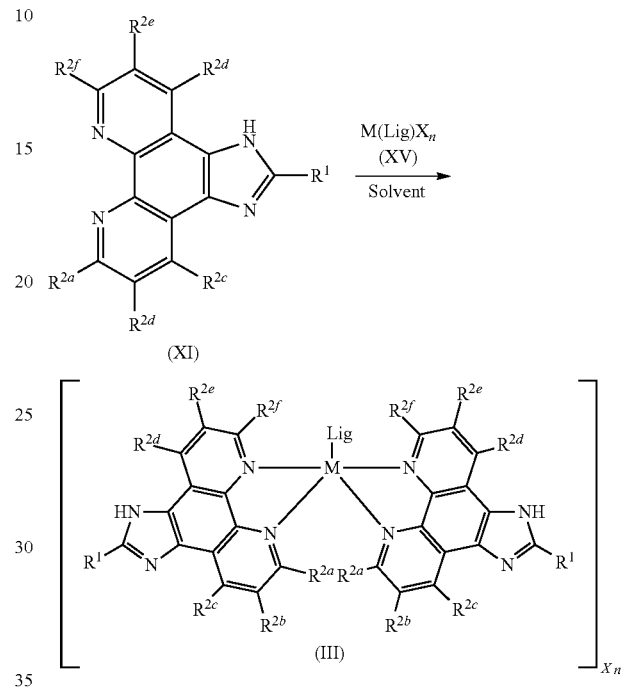

Accordingly, a suitably substituted compound of the formula (XI) is reacted with a compound of the formula (XV) in an a solvent such as methanol, ethanol, isopropanol, ethylene glycol, glycerol, water, 1,4-dioxane, dimethyl formamide, mixtures of the aforementioned solvents, and the like, optionally heated, optionally heated with microwave irradiation, to provide a compound of the formula (III). Compounds of the formula (III) may be converted to alternative salt forms by conventional methods known to those skilled in the art.

Compounds of formula (IV) may be prepared according to the process outlined in Scheme 3.

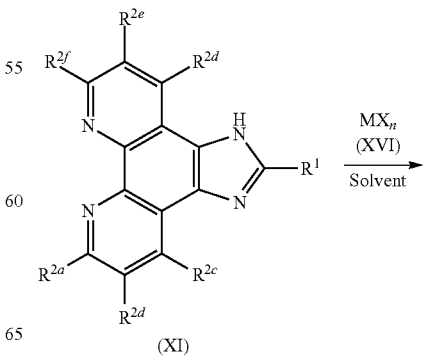

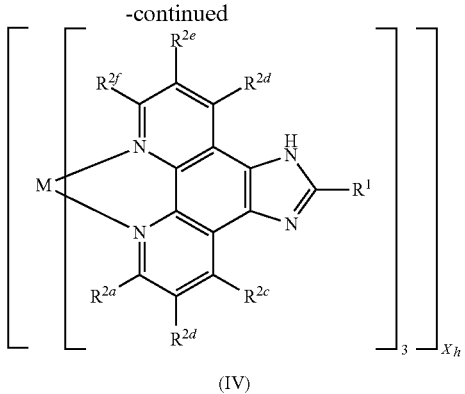

(IV)

Accordingly, a suitably substituted compound of the formula (XI) is reacted with a compound of the formula (XVI) in a solvent such as methanol, ethanol, isopropanol, ethylene glycol, glycerol, water, 1,4-dioxane, dimethyl formamide, mixtures of the aforementioned solvents, and the like, optionally heated, optionally heated with microwave irradiation, to provide a compound of the formula (IV). Compounds of the formula (IV) may be converted to alternative salt forms by conventional methods known to those skilled in the art.

Compounds of formula (V) may be prepared according to the process outlined in Scheme 4.

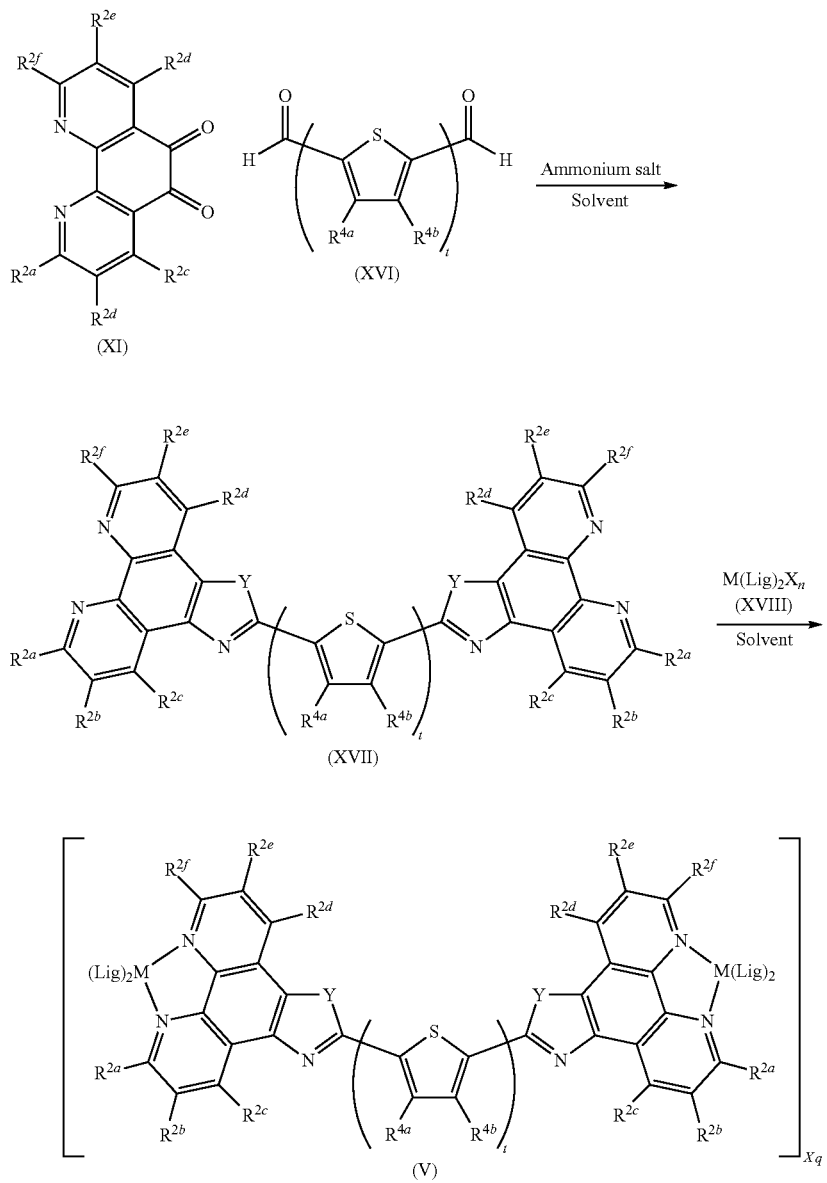

Accordingly, a suitably substituted compound of the formula (XI), a known compound or compound prepared by known methods, is reacted with a suitably substituted compound of the formula (XVI) in the presence of an ammonium salt such as ammonium acetate, ammonium formate, ammonium chloride, ammonium bromide, ammonium sulfate and the like in a solvent such as acetic acid, formic acid, acid, propionic acid and the like, optionally in the presence methanol, ethanol, N,N-dimethylformamide and the like, optionally heated, optionally heated with microwave irradiation, to provide a compound of the formula (XVII). A compound of the formula (XVII) was then reacted with a compound of the formula (XVIII) in a solvent such as methanol, ethanol, isopropanol ethylene glycol, glycerol, water, 1,4-dioxane and the like, optionally heated, optionally heated with microwave irradiation, to provide a compound of the formula (V). Compounds of the formula (V) may be converted to alternative salt forms by conventional methods known to those skilled in the art.

The invention will be illustrated in more detail with reference to the following Examples, but it should be understood that the present invention is not deemed to be limited thereto.

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

$^1$H-NMR spectra were obtained on a Bruker Avance 300-MHz NMR. Low and high resolution mass spectral data were determined with a Bruker Daltonics micrOTOF instrument.

EXAMPLES

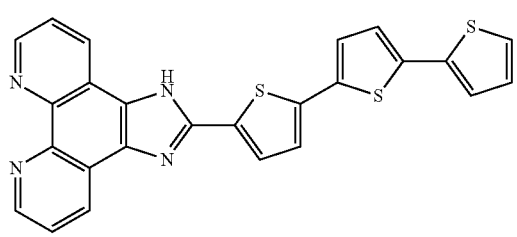

14L

Preparation of 14L: 10-Phenanthroline-5,6-dione (166.6 mg, 0.800 mmol), ammonium acetate (616 mg, 8.00 mmol), and 5-formyl-2,2':5',2''-terthiophene (221.12, 0.800 mmol) were combined with glacial acetic acid (4.0 mL) in a microwave reaction chamber and reacted with 300 W at 180° C. for 10 minutes. The solution changed from a light yellow colour to a deep red colour and was allowed to cool to room temperature. The solution was neutralized by drop-wise addition of aqueous NH$_4$OH (6 mL) until the product precipitated out as a yellow/brown solid. The solid was collected using a fine glass-sintered frit filter and washed with H$_2$O (15 mL). The product was dried under vacuum to give a tan powder. (256 mg, 69%). R$_f$=(2% H$_2$O, 43% CHCl$_3$, 25% Acetone, 30% MeOH+1% NH$_4$OH). $^1$H NMR (DMSO-d$_6$) 7.14 (dd; 1H; J=4.37 Hz), 7.33-7.43 (m; 4H), 7.55 (m; 1H), 7.75-7.79 (m; 3H), 8.82 (d; 2H; J=8.01 Hz), 8.97 (d; 2H; J=3.00 Hz).

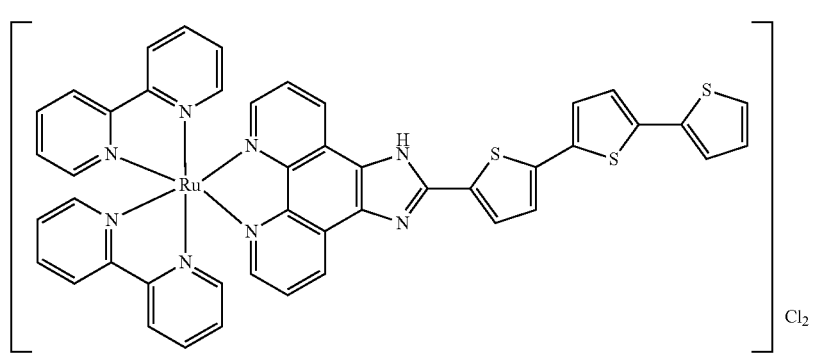

14a

Preparation of 14a: Ru(2,2'-bipyridine)$_2$Cl$_2$.2H$_2$O (156.1 mg, 0.300 mmol) and 14L (140.0 mg, 0.300 mmol) and 100% ethanol (6.0 mL) were combined in a microwave tube and argon purged for 10 minutes by running argon through a needle in the cap of the tube. The cap was switched with a new one before being put in the microwave. The solution was reacted with 300 W at 180° C. for 10 minutes. The resulting solution was a deep, dark red colour. Saturated KPF$_6$ was added drop-wise to the aqueous solution until no additional product precipitated (2-4 mL). The crude product was isolated by filtration through a fine glass-sintered frit filter yielding a bright red/orange solid (307.8 mg, 88%). Purification was done on a silica column, eluting with a 10% H$_2$O:MeCN solution containing 2.5% KNO$_3$, and the principle red spot was collected (R$_f$=0.46). The fractions containing the desired product were combined, evaporated under reduced pressure, and further dried under vacuum to give the corresponding NO$_3^-$ complex and excess KNO$_3$. To remove the unwanted salt, the product was dissolved in H$_2$O with sonication. Saturated KPF$_6$ was added (3-4 mL), and the product precipitated out of solution. The desired PF6$^-$ complex was extracted using CH$_2$Cl$_2$ (3×75 mL). The organic layer was separated, concentrated under reduced pressure, and dried under vacuum to give the final pure product as a red-orange solid (169 mg, 48%). R$_f$=0.41 (10% H$_2$O:MeCN+2.5% KNO$_3$). $^1$H NMR (CD$_3$CN): 8.65 (d; 2H; J=7.89 Hz), 8.51-8.55 (m; 4H), 8.11-7.96 (m; 6H), 7.85 (d; 2H; J=5.49 Hz), 7.72 (d; 1H; J=3.81 Hz), 7.61-7.67 (m; 4H), 7.46 (t; 2H; J=6.93 Hz), 7.37 (d; 1H; J=5.10 Hz), 7.06-7.30 (m; 7H). MS (ESI+) m/z: 440.0 [M-2PF$_6$]$^{2+,}$ $^{879.1}$ [M-2PF$_6$-1H]$^+$. HRMS (ESI+) m/z for C$_{45}$H$_{30}$N$_8$RuS$_3$; calcd 440.0399. found 440.0382.

The PF$^{6-}$ complex was dissolved in a 1:1 solution of MeCN/MeOH and converted to its corresponding C$^{1-}$ salt on Amberlite IRA-410 ion exchange resin (30 cm×1.5 cm, 30 g of resin) eluting with MeOH. Anal. Calc. C$_{45}$H$_{30}$C$_{12}$N$_8$RuS$_3$.4.065 (H$_2$O): C, 52.77%; H, 3.75%; N, 10.94%. Found: C, 51.78%; H, 4.25%; N, 10.20%.

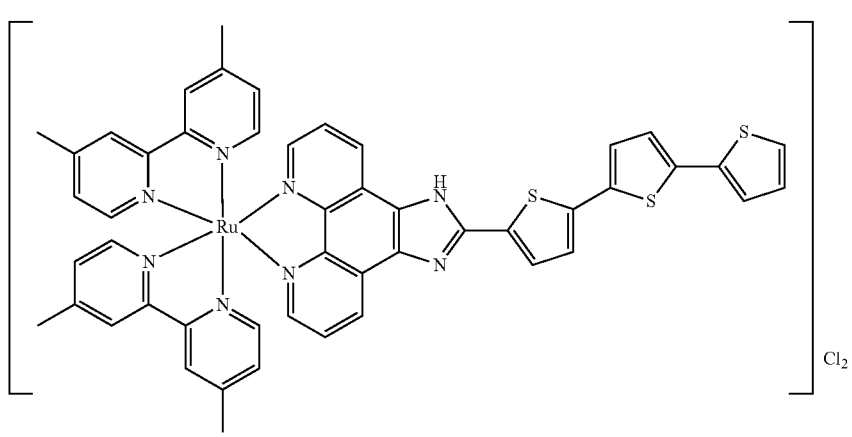

Preparation of 14C: Ru(4,4'-dimethyl-2,2'-bipyridine)$_2$Cl$_2$·2H$_2$O (60.2 mg, 0.104 mmol) and 14L (48.5 mg, 0.104 mmol) and 100% ethanol (2.0 mL) were combined in a microwave tube and argon purged for 15 minutes by running argon through a needle in the cap of the tube. The cap was switched with a new one before being put in the microwave. The solution was reacted with 300 W at 180° C. for 10 minutes. The resulting solution was a deep, dark red colour. Saturated KPF$_6$ was added drop-wise to the aqueous solution until no additional product precipitated (2-3 mL). The crude product was isolated by filtration through a fine glass-sintered frit filter yielding a red/brown solid (112.6 mg, 88%). Purification was done on a silica column, eluting with a 10% H$_2$O: MeCN solution containing 2.5% KNO$_3$, and the principle red spot was collected (R$_f$=0.54). The fractions containing the desired product were combined, evaporated under reduced pressure, and further dried under vacuum to give the corresponding NO$_3^-$ complex and excess KNO$_3$. To remove the unwanted salt, the product was dissolved in H$_2$O with sonication. Saturated KPF$_6$ was added (3-4 mL), and the product precipitated out of solution. The desired PF6$^-$ complex was extracted using CH$_2$Cl$_2$ (3×50 mL). The organic layer was separated, concentrated under reduced pressure, and dried under vacuum to give the final pure product as a red-orange solid (76.0 mg, 59%). R$_f$=0.54 (10% H$_2$O:MeCN+2.5% KNO$_3$). $^1$H NMR (CD$_3$CN): 8.87 (d; 2H; J=6.60 Hz), 8.38 (d; 4H; J=10.1 Hz), 8.02 (m; 2H; J=4.50 Hz), 7.84 (d; 2H; J=4.02 Hz), 7.74 (br; 2H), 7.67 (d; 2H; J=5.67 Hz), 7.53 (d; 1H; J=6.42 Hz), 7.42 (d; 2H; J=5.67 Hz), 7.25-7.31 (m; 6H), 7.07-7.14 (m; 3H). MS (ESI+) m/z: 468.1 [M-2PF$_6$]$^{2+}$, 1081.2 [M-PF$_6$]$^+$. HRMS (ESI+) m/z for C$_{49}$H$_{38}$N$_8$RuS$_3$; calcd 468.0707. found 468.0697.

The PF6$^-$ complex was dissolved in a 1:1 solution of MeCN/MeOH and converted to its corresponding Cl$^-$ salt on Amberlite IRA-410 ion exchange resin (30 cm×1.5 cm, 30 g of resin) eluting with MeOH.

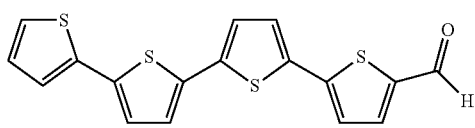

Preparation of 16x: 2,2'-5,2"-Terthiophene-5-boronic acid pinicolester (236.1 mg, 0.780 mmol), 5-bromo-2-thiophene carboxaldyde (57.4 uL, 0.59 mmol), and Pd(PPh$_3$)$_4$ (55 mg) were combined in an argon purged microwave tube. The microwave tube was again argon purged and DME (5.66 mL) and 2M Na$_2$CO$_3$ aqueous solution (0.4 mL) were then added separately by syringe. The solution was reacted at 200 W and 175° C. for 1 hour. The dark green solution was filtered on a fine frit to remove the catalyst and washed with tiny amounts of ethyl acetate. The filtrate was diluted with additional EtOAc, transferred to a 125-mL reparatory, and washed with saturated aqueous NaCl (3×50 mL). The organic layer was concentrated under reduced pressure, and dried under vacuum to give the crude product (130.9 mg, 62%). Purification was done on a silica column, eluting with 1:1 DCM: hexanes. A slow moving spot that stained positive to have aldehyde by Dinitrophenylhydrazine was collected, concentrated under reduced pressure, and dried under vacuum to give the pure product (14.1 mg, 6.7%). R$_f$=0.20 (1:1 DCM: hexanes). $^1$H NMR (CDCl$_3$) 9.86 (s; 1H), 7.67 (d; 1H; J=3.96 Hz), 7.21-7.29 (m; 3H), 7.20 (d; 1H; J=3.54 Hz), 7.11-7.14 (m; 3H), 7.04 (t; 1H; J=4.89 Hz).

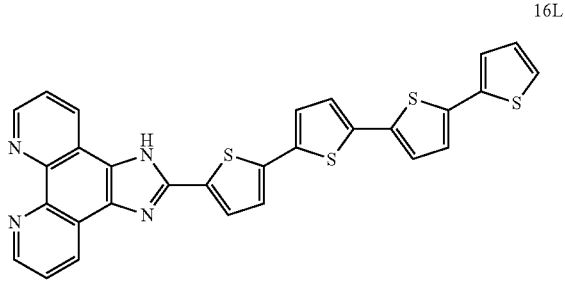 [SMILES: c1csc(-c2ccc(-c3ccc(-c4ccc(-c5nc6c7cccnc7c7ncccc7c6[nH]5)s4)s3)s2)c1]

Preparation of 16L: 1,10-Phenanthroline-5,6-dione (41.6 mg, 0.200 mmol), ammonium acetate (154 mg, 2.00 mmol), and 16x (71.7 mg, 0.200 mmol) were combined with glacial acetic acid (1.0 mL) in a microwave reaction chamber and reacted at 300 W at 180° C. for 10 minutes. The solution was allowed to cool to room temperature followed by neutralization by dropwise addition of aqueous NH$_4$OH (2-4 mL) until the product precipitated out as a brown solid. The solid was collected using a fine glass-sintered frit filter and washed with H$_2$O (15 mL). The product was dried under vacuum to give the crude product as a brown powder (105.9 mg, 96%). Purification was done by recrystallization from hot MeOH to give the pure product (31.1 mg, 28%). $^1$H NMR (DMSO-$d_6$) 9.04 (br; 2H), 8.84 (d; 2H; J=7.35 Hz), 7.86 (br; 2H), 7.33-7.57 (m; 8H); 7.11 (br; 1H). MS (ESI+) m/z: 549.0 [M+1H]$^+$. HRMS (ESI+) m/z for $C_{29}H_{17}N_4S_4$; calcd 549.0331. found 549.0307.

rated KPF$_6$ was added (3-4 mL), and the product precipitated out of solution. The desired PF6$^-$ complex was extracted using CH$_2$Cl$_2$ (3×75 mL). The organic layer was separated, concentrated under reduced pressure, and dried under

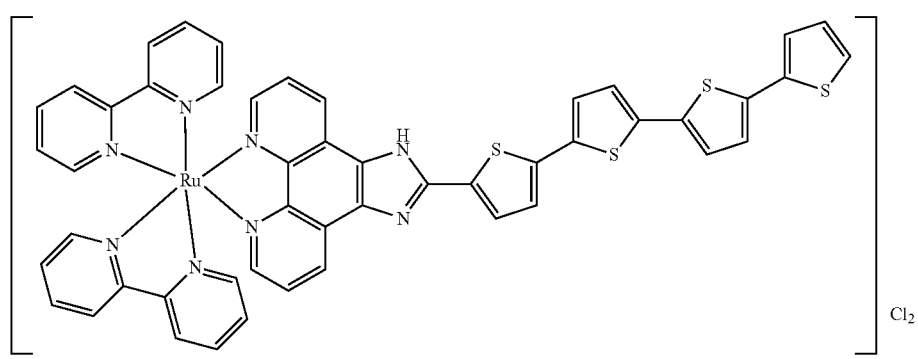

16a

Preparation of 16a: Ru(2,2'-bipyridine)$_2$Cl$_2$.2H$_2$O (81.2 mg, 0.156 mmol) and 16L (85.7 mg, 0.156 mmol) and 100% ethanol (3.0 mL) were combined in a microwave tube and argon purged for 10 minutes by running argon through a needle in the cap of the tube. The cap was switched with a new one before being put in the microwave. The solution was reacted with 300 W at 180° C. for 10 minutes. The resulting solution was a deep, dark red colour. Saturated KPF$_6$ was added drop-wise to the aqueous solution until no additional product precipitated (2-4 mL). The crude product was isolated by filtration through a fine glass-sintered frit filter yielding a dark red/orange solid (155.2 mg, 64%). Purification was done on a silica column, eluting with a 7% H$_2$O:MeCN solution containing 2.5% KNO$_3$, and the principle red spot was collected (R$_f$=0.46). The fractions containing the desired product were combined, evaporated under reduced pressure, and further dried under vacuum to give the corresponding NO$_3^-$ complex and excess KNO$_3$. To remove the unwanted salt, the product was dissolved in H$_2$O with sonication. Satuvacuum to give the product as a red-orange solid (169 mg, 48%). The PF6$^-$ complex was dissolved in a 1:1 solution of MeCN/MeOH and converted to its corresponding Cl$^-$ salt on Amberlite IRA-410 ion exchange resin (30 cm×1.5 cm, 30 g of resin) eluting with MeOH. The product was further purified on Sephadex LH-50 in methanol and the principal red spot was collected. The fractions containing the desired product were combined, evaporated under reduced pressure, and further dried under vacuum to give the final product (12.7 mg, 6.5%) R$_f$=0.35 (10% H$_2$O:MeCN+2.5% KNO$_3$). $^1$H NMR (CD$_3$CN): 8.91 (d; 2H; J=7.32 Hz), 8.50 (t; 4H; J=7.92 Hz), 8.08 (t; 2H; J=7.74 Hz), 7.99 (br; 4H), 7.84 (br; 3H), 7.74 (br; 4H), 7.60 (br; 2H), 7.44 (t; 2H; J=5.55 Hz), 7.37 (br; 1H) 7.08-7.27 (m; 9H). MS (ESI+) m/z: 498.1 [M-2PF$_6$]$^{2+}$. HRMS (ESI+) m/z for $C_{49}H_{32}N_8RuS_4$; calcd 481.0333. found 481.0341.

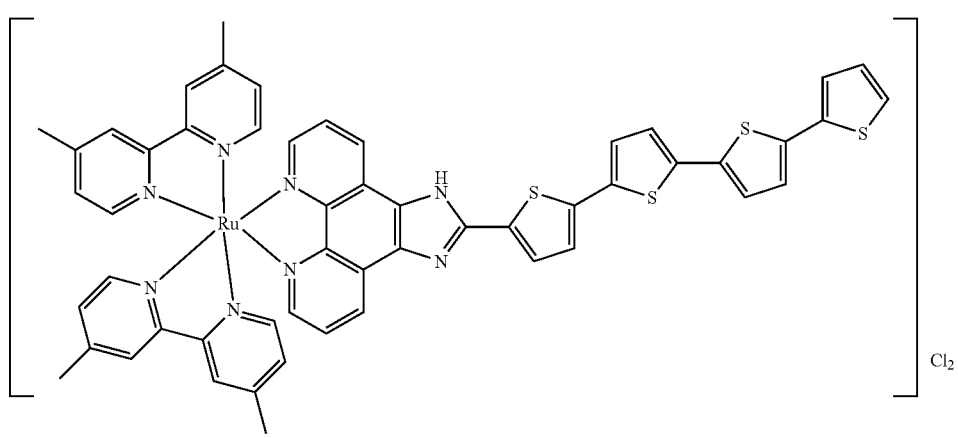

16c

Preparation of 16c: Ru(dmb)$_2$Cl$_2$.2H$_2$O (88.93 mg, 0.156 mmol) and 16L (85.7 mg, 0.156 mmol) and 100% ethanol (3.0 mL) were combined in a microwave tube and argon purged for 10 minutes by running argon through a needle in the cap of the tube. The cap was switched with a new one before being put in the microwave. The solution was reacted with 300 W at 180° C. for 10 minutes. The resulting solution was a deep, dark red colour. Saturated KPF$_6$ was added drop-wise to the aqueous solution until no additional product precipitated (1-2 mL). The crude product was isolated by filtration through a fine glass-sintered frit filter yielding a dark red (156.7 mg, 92%). Purification was done on a silica column, eluting with a 7% H$_2$O:MeCN solution containing 2.5% KNO$_3$, and the principle red spot was collected. The fractions containing the desired product were combined, evaporated under reduced pressure, and further dried under vacuum to give the corresponding NO$_3^-$ complex and excess KNO$_3$. To remove the unwanted salt, the product was dissolved in H$_2$O with sonication. Saturated KPF$_6$ was added (3-4 mL), and the product precipitated out of solution. The desired PF6$^-$ complex was extracted using CH$_2$Cl$_2$ (3×75 mL). The organic layer was separated, concentrated under reduced pressure, and dried under vacuum to give the product as a red solid (69.9 mg, 41%). The PF6$^-$ complex was dissolved in a 1:1 solution of MeCN/MeOH and converted to its corresponding Cl$^-$ salt on Amberlite IRA-410 ion exchange resin (30 cm×1.5 cm, 30 g of resin) eluting with MeOH. The product was further purified on Sephadex LH-50 in methanol and the principal red spot was collected. The fractions containing the desired product were combined, evaporated under reduced pressure, and further dried under vacuum to give the final product (23.0 mg, 13%) R$_f$=0.33 (10% H$_2$O:MeCN+2.5% KNO$_3$). $^1$H NMR (CD$_3$CN): 8.92 (br; 2H), 8.34 (s; 4H), 7.97 (br; 2H), 7.87 (br; 1H), 7.62-7.65 (m; 4H), 6.92-7.42 (m; 14H), 2.54, (s; 6H), 2.46 (s; 6H). MS (ESI+) m/z: 509.1 [M-2PF$_6$]$^{2+}$, 1163.1 [M-PF$_6$]$^+$. HRMS (ESI+) m/z for C$_{53}$H$_{40}$N$_8$RuS$_4$; calcd 509.0646. found 509.0663.

pure product as a light orange powder. No purification was needed. (90.7 mg, 31.3%). R$_f$=streak to 0.60 (2% H$_2$O, 43% CHCl$_3$, 25% Acetone, 30% MeOH+1% NH$_4$OH). $^1$H NMR (300 MHz) [(CD$_3$)$_2$SO]: 9.07 (d; 4H; J=3.03 Hz), 8.90 (d; 4H; J=8.22 Hz), 8.04 (s; 2H), 7.86-7.90 (br; 4H). MS (ESI+) m/z: 521.1 [M+H]$^+$. HRMS (ESI+) m/z for C$_{30}$H$_{17}$N$_8$S; calcd 521.1291. found 521.1265.

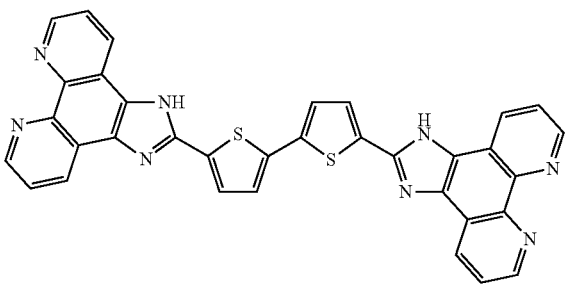

3L

Preparation of 3L: 1,10-Phenanthroline-5,6-dione (18.9 mg, 0.0900 mmol), ammonium acetate (138.7 mg, 1.80 mmol), and 2,2'-bithiophene-5,5'-dicarbaldehyde (10 mg, 0.0450 mmol) were combined in glacial acetic acid (5 mL) and refluxed in air at 135° C. for 6 hours. The solution changed from a light yellow colour to a deep red colour and the product precipitated as a light orange precipitate powder. The reaction was cooled to room temperature. The solution was neutralized by drop-wise addition of aqueous NH$_4$OH (5 mL) until more desired product finished precipitating out as an orange solid. The orange precipitate was collected using a fine glass-sintered frit filter and washed with H$_2$O (10 mL). The product was dried under vacuum to give an orange powder which showed the product and contaminant by NMR. (12.6 mg, 47%). An alternate microwave synthesis was also performed involving 1,10-Phenanthroline-5,6-dione (18.9 mg, 0.0900 mmol), ammonium acetate (138.7 mg, 1.80 mmol), and 2,2'-bithiophene-5,5'-dicarbaldehyde (10 mg, 0.0450 mmol) being combined in glacial acetic acid (1.0 mL) in a microwave reaction chamber and reacted with 300 W at 180° C. for 10 minutes. The solution changed from a light yellow colour to a deep red colour and was allowed to cool to room temperature. An orange precipitate of the product was seen. The solution was neutralized by drop-wise addition of aqueous NH$_4$OH (1 mL) until more desired product finished precipitating out as an orange solid. The solid was collected using a fine glass-sintered frit filter and washed with H$_2$O (10 mL). The product was dried under vacuum to give an orange powder which showed the product and contaminant by NMR. (25.3 mg, 93%) R$_f$=streak to 0.68 (2% H$_2$O, 43% CHCl$_3$, 25% Acetone, 30% MeOH+1% NH$_4$OH). $^1$H NMR (300 MHz) [(CD$_3$)$_2$SO]: 9.02 (br), 8.85 (br; 4H), 7.84 (m; 2H), 7.70 (br).

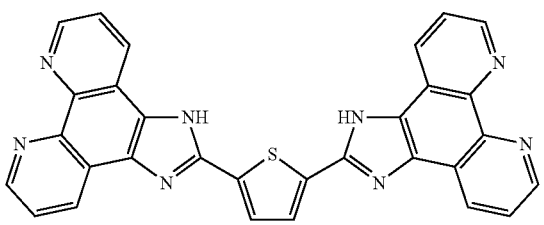

2L

Preparation of 2L: 1,10-Phenanthroline-5,6-dione (234.1 mg, 1.11 mmol), ammonium acetate (1.77 g, 23.0 mmol), and 2,5-thiophene dicarboxaldehyde (77.9 mg, 0.556 mmol) were combined in glacial acetic acid (20 mL) and refluxed in air at 135° C. for 6 hours. The solution changed from a light yellow colour to a deep red colour and the product precipitated as a light orange stringy precipitate. The reaction was cooled to room temperature. The orange precipitate was collected using a medium glass-sintered frit filter and washed with H$_2$O (10 mL). The product was dried under vacuum to give the final

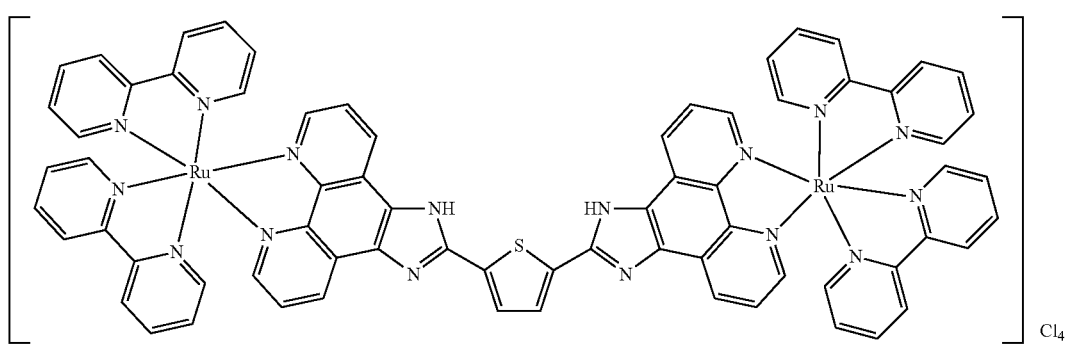

2a

Preparation of 2a: Ru(bpy)$_2$Cl$_2$·2H$_2$O (60 mg, 0.115 mmol) and 2L (30 mg, 0.0576 mmol) were combined in glycerol (3 mL) and refluxed in argon for 16 hours at 100° C. The glycerol was first added to a dry reaction flask which was attached to a Schlenk line. The reaction flask was evacuated until bubbling in the glycerol occurred and then was filled with dry argon. The evacuation and argon purging was repeated two more times. Ru(bpy)$_2$Cl$_2$·2H$_2$O was added to the glycerol and the reaction flask was evacuated and argon filled three more times. The resulting glycerol and Ru(bpy)$_2$Cl$_2$·2H$_2$O solution was heated to 100° C. for 30 minutes. After heating the 2L was added to the solution and the reaction flask was evacuated and filled with argon three more times. The dark purple solution was put under argon using a filled balloon and reacted for 16 hours at 100° C. The resulting solution was a deep dark red/purple colour and cooled to room temperature. 12 mL of H$_2$O was added to solution and filtered over a medium glass-sintered frit. Saturated KPF$_6$ was added drop-wise to the aqueous solution until no additional product precipitated (1-2 mL). The crude product was isolated by filtration through a fine glass-sintered frit filter yielding a dark red/brown solid (106.1 mg, 0.0550 mmol). Purification was done on a silica column, eluting with a 20% H$_2$O:MeCN solution containing 2.5% KNO$_3$, and the principle red spot was collected. The fractions containing the desired product were combined, evaporated under reduced pressure, and further dried under vacuum to give the product and excess KNO$_3$. To remove the unwanted salt, the product was dissolved in H$_2$O with sonication. The product did not dissolve in H$_2$O, a quantity of H$_2$O (approximately 50-100 mL) was added to ensure the excess KNO$_3$ would dissolve in the solution followed by the addition of copious amounts of saturated KPF$_6$ (10-12 mL). The desired PF6 complex was extracted using CH$_2$Cl$_2$ (3×50-150 mL). The organic layer was separated, concentrated under reduced pressure, and dried under vacuum to give the final pure product as a red-orange solid (38.8 mg, 35%). R$_f$=0.19 (20% H$_2$O:MeCN+ 2.5% KNO3). $^1$H NMR (300 MHz) [(CD$_3$)$_2$SO]: 9.02-9.10 (dd; 4H; J=9.06 Hz), 8.88 (t; 8H; J=8.52 Hz), 8.24 (t; 4H; J=6.60 Hz), 8.09-8.15 (m; 10H), 7.97 (br; 4H), 7.85 (d; 4H; J=4.14 Hz), 7.61 (m; 8H), 7.36 (t; 4H; J=4.68 Hz). 13C NMR [(CD3CN] 158.0, 157.8, 152.8, 151.3, 148.3, 146.7, 138.7, 138.2, 135.6, 135.6, 131.2, 129.0, 128.3, 126.8, 125.1, 122.1. Anal. Calc C$_{70}$H$_{48}$F$_{24}$N$_{16}$P$_4$Ru$_2$S·6 (H$_2$O)·0.5 (C$_3$H$_6$O): C, 41.60%; H, 3.08%; N, 10.86%. Found: C, 41.74%; H, 2.72%; N, 10.16%.

The PF$_6^-$ complex was dissolved in a 1:1 solution of MeCN/MeOH and converted to its corresponding Cl$^-$ salt on Amberlite IRA-410 ion exchange resin (30 cm×1.5 cm, 30 g of resin) eluting with MeOH. MS (ESI+) m/z: 673.1 [M-4Cl-2H]$^{2+}$, 449.1 [M-4Cl-H]$^{3+}$. HRMS (ESI+) m/z for C$_{70}$H$_{46}$N$_{16}$Ru$_2$S; calcd 673.0944. found 673.0945.

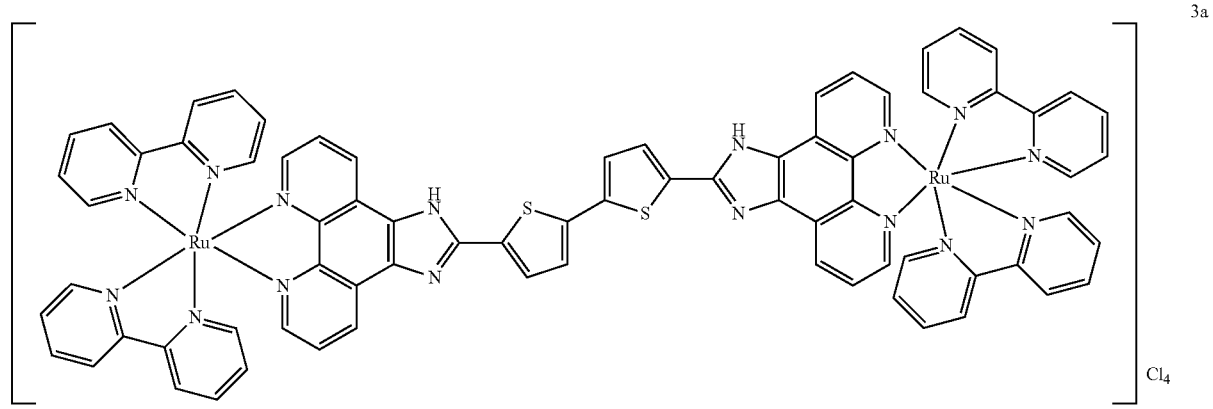

3a

Preparation of 3a: Ru(bpy)$_2$Cl$_2$·2H$_2$O (50.0 mg, 0.0960 mmol) and 3L (30.0 mg, 0.0500 mmol) were combined in glycerol (3 mL) and refluxed in argon for 16 hours at 100° C. The glycerol was first added to a dry reaction flask which was attached to a Schlenk line. The reaction flask was evacuated until bubbling in the glycerol occurred and then was filled with dry argon. The evacuation and argon filling was repeated two more times. Ru(bpy)$_2$Cl$_2$·2H$_2$O was added to the glycerol and the reaction flask was evacuated and argon filled three more times. The resulting glycerol and Ru(bpy)$_2$Cl$_2$·2H$_2$O solution was heated to 100° C. for 30 minutes. After heating the glycerol the 3L was added to the solution and the reaction flask was evacuated and filled with argon three more times. The dark purple solution was put under argon using a filled balloon and reacted for 16 hours at 100° C. The resulting solution was a deep dark red/purple colour and cooled top room temperature. 12 mL of $H_2O$ was added to solution and filtered over a medium glass-sintered frit. Saturated $KPF_6$ was added drop wise to the filtrate until the product completely precipitated out of solution. The crude product was obtained through filtration and washed with $H_2O$ (5 mL). The crude product was dark red/black in colour (78.1 mg, 0.0389 mmol). Purification was done on a silica column, eluting with a 20% $H_2O$:MeCN solution containing 2.5% $KNO_3$, and the principle red spot was collected. The fractions containing the desired product were combined, evaporated under reduced pressure, and further dried under vacuum to give the product and excess $KNO_3$. To remove the unwanted salt, the product was attempted to be dissolved in $H_2O$ with sonication. The product did not dissolve in $H_2O$ and a quantity of $H_2O$ (approximately 50 mL) was added to ensure the excess $KNO_3$ would dissolve in the solution followed by the addition of copious amounts of $KPF_6$ (10-12 mL). The desired $PF_6^-$ complex was extracted using $CH_2Cl_2$ (3×50-150 mL). The organic layer was separated, concentrated under reduced pressure, and dried under vacuum to give the final pure product as a red-orange solid (19.4 mg, 19%). $R_f$=0.27 (20% $H_2O$:MeCN+2.5% $KNO_3$). $^1H$ NMR (300 MHz) [$(CD_3)_2SO$]: 9.04 (dd; 4H; J=11.25 Hz), 8.87 (t; 8H; J=10.41 Hz), 8.23 (t; 4H; J=6.57 Hz), 8.07-8.15 (m; 8H), 7.93-8.03 (m; 6H), 7.84 (br; 4H), 7.74 (br; 2H), 7.60 (br; 8H), 7.36 (t; 4H; J=6.30 Hz). Anal. Calc. $C_{74}H_{50}F_{24}N_{16}P_4Ru_2S_2.8(H_2O).2(C_6H_{14})$: C, 44.41%; H, 4.07%; N, 9.64%. Found: C, 44.76%; H, 3.61%; N, 8.52%. MS (ESI+) m/z: 714.1 [M-4$PF_6$.2H]$^{2+}$, 476.4 [M-4$PF_6$-1H]$^{3+}$. HRMS (ESI+) m/z for $C_{74}H_{49}N_{16}Ru_2S_2$; calcd 476.3946. found 476.3941. The PF6 complex was dissolved in a 1:1 solution of MeCN/MeOH and converted to its corresponding $Cl^-$ salt on Amberlite IRA-410 ion exchange resin (30 cm×1.5 cm, 30 g of resin) eluting with MeOH.

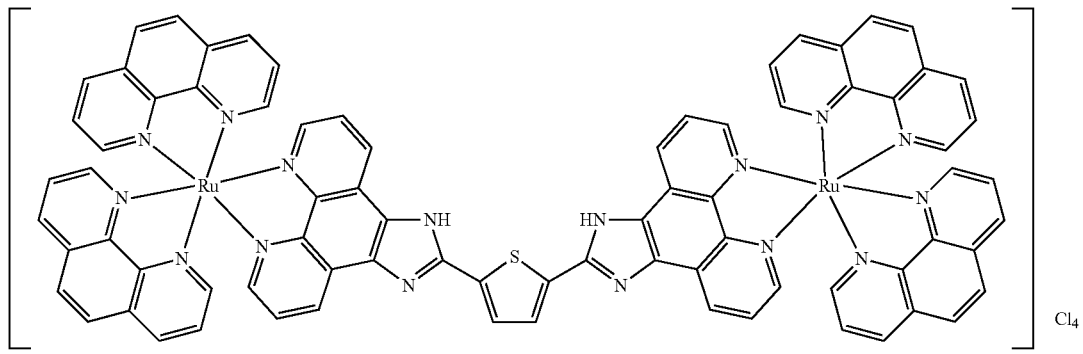

2b

Preparation of 2b: Compound 2b was prepared by the same procedure as 2a using $Ru(phen)_2Cl_2$. $^1H$ NMR (300 MHz) [($CD_3CN$]: 9.01 (d; 2H; J=10.17 Hz), 8.86 (d; 2H; J=7.68 Hz), 8.63 (d; 8H; J=7.98 Hz), 8.29 (s; 8H), 8.13 (br; 4H), 8.00-8.04 (m; 10H), 7.66 (m; 12H). Anal. Calc. $C_{37}H_{26}F_{12}N_8P_2RuS.0.5 (H_2O)$: C, 43.79%; H, 2.68%; N, 11.04%. Found: C, 44.66%; H, 2.98%; N, 10.16%. The $PF_6^-$ complex was dissolved in a 1:1 solution of MeCN/MeOH and converted to its corresponding $Cl^-$ salt on Amberlite IRA-410 ion exchange resin (30 cm×1.5 cm, 30 g of resin) eluting MeOH. MS (ESI+) m/z: 721.1 [M-4Cl-2H]$^{2+}$, 481.1 [M-4Cl-H]$^{3+}$. HRMS (ESI+) m/z for $C_{78}H_{46}N_{16}Ru_2S$; calcd 721.0944. found 721.0971.

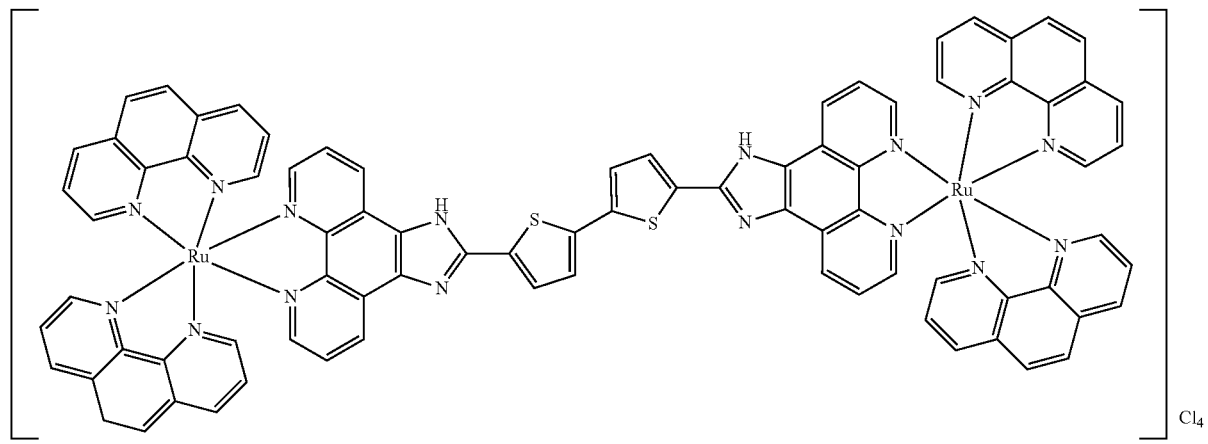

3b

Preparation of 3b: Compound 3b was prepared by the same procedure as 2a using Ru(phen)$_2$Cl$_2$. $^1$H NMR (300 MHz) [CD$_3$CN]: 8.94 (d; 4H; J=20.31 Hz), 8.63 (d; 8H; J=7.95 Hz), 8.28 (s; 8H), 8.11 (br; 4H), 8.04 (br; 4H), 7.99 (br; 4H), 7.93 (br; 2H), 7.63-7.70 (m; 12H), 7.56 (br; 2H). Anal. Calc. C$_{82}$H$_{50}$F$_{24}$N$_{16}$P$_4$Ru$_2$S$_2$.3(C$_6$H$_{14}$).8(CH$_3$OH): C, 49.50%; H, 4.77%; N, 8.55%. Found: C, 49.15%; H, 3.94%; N, 7.64%. MS (ESI+) m/z: 908.1 [M-2PF$_6$]$^{2+}$, 508.4 [M-4 PF$_6$-1H]$^{3+}$, 381.5 [M-4 PF$_6$]$^{4+}$. HRMS (ESI+) m/z for C$_{82}$H$_{50}$F$_{12}$N$_{16}$P$_2$Ru$_2$S$_2$; calcd 908.0603. found 908.0641. The PF$_6^-$ complex was dissolved in a 1:1 solution of MeCN/MeOH and converted to its corresponding Cl$^-$ salt on Amberlite IRA-410 ion exchange resin (30 cm×1.5 cm, 30 g of resin) eluting MeOH.

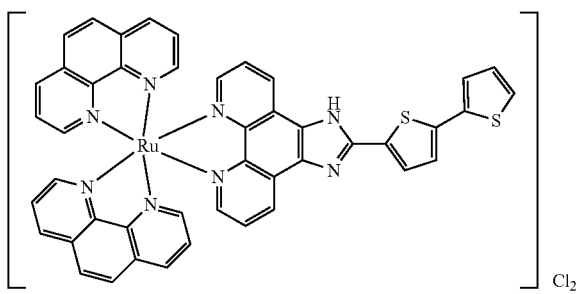

10b

Preparation of 10b: Compound 10b was prepared by the same procedure as 2a using Ru(phen)$_2$Cl$_2$. $^1$H NMR (DMSO-d$_6$) δ 7.17 (m, 1H), 7.50 (m, 2H), 7.63 (d, 1H), 7.77 (m, 6H), 7.90 (m, 1H), 7.99 (d, 2H), 8.07 (d, 2H), 8.12 (d, 2H), 8.40 (s, 4H), 8.78 (d, 4H), 8.99 (d, 2H). MS (ESI+) m/z: 845.0 [M-2PF$_6$]$^+$, 423.0 [M-2PF$_6$]$^{2+}$. HRMS (ESI+) m/z for C$_{45}$H$_{28}$N$_8$RuS$_2$; calcd 846.0922. found 846.0910. The PF$_6^-$ complex was dissolved in a 1:1 solution of MeCN/MeOH and converted to its corresponding Cl$^-$ salt on Amberlite IRA-410 ion exchange resin (30 cm×1.5 cm, 30 g of resin) eluting MeOH.

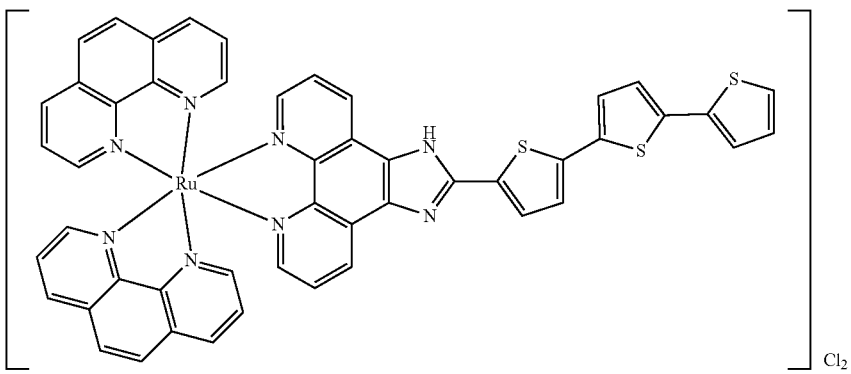

14b

Preparation of 14b: Compound 14b was prepared by the same procedure as 2a using Ru(phen)$_2$Cl$_2$. $^1$H NMR (300 MHz) [CD$_3$CN]: 8.56-8.63 (m; 6H; C, 7, 4), 8.31-8.26 (m; 8H; 6, 5, 9), 8.01 (d; 2H; J=5.10 Hz; 2), 7.88 (d; 2H; J=4.95 Hz; A), 7.72 (br; 2H; B), 7.60 (m; 3H; 8, 1H—R), 7.29-7.40 (m; 3H; 3, 1H—R), 7.02 (m; 2H; 2H—R), 6.87 (d; 1H; J=3.72 Hz; 1H—R), 6.68-7.73 (m; 2H; 2H—R). MS (ESI+) m/z: 464.0 [M-2PF$_6$]$^{2+}$. HRMS (ESI+) m/z for C$_{49}$H$_{30}$N$_8$RuS$_3$; calcd 464.0400. found 464.0381. The PF$_6^-$ complex was dissolved in a 1:1 solution of MeCN/MeOH and converted to its corresponding Cl$^-$ salt on Amberlite IRA-410 ion exchange resin (30 cm×1.5 cm, 30 g of resin) eluting MeOH. Anal. Calc. C$_{49}$H$_{30}$N$_8$Cl$_2$RuS$_3$.4(H$_2$O).6(CH$_3$OH): C, 52.29%; H, 4.95%; N, 8.87%. Found: C, 53.11%; H, 4.31%; N, 8.33%.

FORMULATIONS

The present invention also relates to compositions or formulations which comprise the photodynamic compounds according to the present invention. In general, the compositions of the present invention comprise an effective amount of one or more photodynamic compounds and salts thereof according to the present invention which are effective for providing photodynamic therapy; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known photodynamic compounds. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, pre-filled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In certain embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more photodynamic compounds according to the present invention and one or more excipients; from about 0.01 mg to about 100 mg of one or more photodynamic compounds according to the present invention and one or more excipients; and from about 0.1 mg to about 10 mg of one or more photodynamic compounds according to the present invention; and one or more excipients.

PROCEDURES

The following procedures can be utilized in evaluating and selecting compounds as photodynamic compounds.

Extraction of topoisomerase II activity from HL60 cells

Nuclear extracts were affinity precipitated as described in 'Small Scale Preparation of Topo I and II Extracts from Tissue Culture Cells (Optimized for HeLa Cells)' on the TopoGEN website (http:www.topogen.com/html/extracts.html). All steps were conducted on ice or at 4° C. Briefly, 10 mL of exponentially growing HL-60 cells ($1\times10^6$ cells/mL) were transferred to a sterile 15 mL conical centrifuge tube (Fisher Scientific, Canada) and pelleted in an eppendorf 5804R centrifuge (16.1 cm radius) at 2100 rpm for 3 min at 4° C. The cells were washed twice with 3 mL of ice cold phosphate buffered saline (PBS) containing 2.68 mM potassium chloride, 1.47 mM potassium phosphate monobasic, 0.137 M sodium chloride, and 8.10 mM sodium phosphate dibasic, pH 7.4, as follows: the cell pellet was resuspended with PBS buffer (mixed by pipetting up and down), centrifuged at 2100 rpm (3 min, 4° C.), and the supernatant gently poured off. After the second wash, the cells were resuspended in 3 mL of cold hypotonic buffer (10 mM Tris-HCl, pH 7.5, 1 mM EDTA, 4 mM $MgCl_2$, 0.5 mM phenylmethylsulfonyl fluoride (PMSF)), and clumps were dispersed by pipetting up and down. The cells were pelleted again (2100 rpm, 3 min, 4° C.), resuspended and dispersed in 3 mL of the same cold hypotonic buffer, and left on ice for 10 min to swell. Cell membranes were disrupted with a cold Dounce homogenizer (Pyrex, 15 mL), using 6-8 strokes. The lysate was transferred to a clean sterile 1.5 mL microcentrifuge tube (Fisher Scientific, Canada) and centrifuged (2900 rpm, 10 min, 4° C.). The pellet, containing nuclei, was washed twice with the same cold hypotonic buffer, as follows: cold buffer was added to the pellet and the nuclei was resuspended by pipetting up and down, then pelleted (2900 rpm, 10 min, 4° C.), the supernatant gently removed and discarded. After the second wash, the nuclei were resuspended in 4 pellet volumes (approximately 500 µL) of cold hypotonic buffer without $MgCl_2$. An equal volume of cold 1 M NaCl was added to the resuspended pellet and left on ice for 45 min, followed by pelleting in a microcentrifuge (14,000 rpm, 15 min, 4° C.). The supernatant (nuclear extract), suspended in 5 mM Tris-HCl (pH 7.5), 0.5 mM EDTA, 0.25 mM PMSF, and 0.5 M NaCl, was used for DNA relaxation assays.

Total protein concentration (BSA equivalent) of the extract was determined by using a Micro Lowry total protein kit (Total Protein Kit, Micro Lowry, Peterson's modification), following the manufacturer's instruction for 'Protein Determination without Protein Precipitation.' Briefly, five BSA protein standards were prepared from a 400 µg/mL stock solution in pure water to a volume of 200 µL in 1.5 mL sterile microcentrifuge tubes (final concentrations of BSA were 10, 20, 40, 60, 80 µg). A sixth tube containing pure water only was used as a blank. A seventh tube, containing 50 µL nuclear extract and 150 µL (dilution chosen randomly) was prepared in order to measure its protein content against the BSA standards. All tubes were mixed well with vortexing, then 200 µL Lowry reagent solution was added to all tubes followed by vortexing to mix. The solutions sat at room temperature for 20 min, then 100 µL Folin Ciocalteu phenol reagent (6× dilution of 2 N stock solution) was added to each tube, followed by vortexing to mix. The colour was allowed to develop for 30 min. The solutions were transferred one at a time to a quartz cuvette, with a pathlength of 1 cm, and the absorbance of the standards and sample tubes versus the blank were measured at a wavelength of 750 nm. A plot was constructed (Excel, 2007) of the absorbance values of the standards versus their corresponding protein concentrations and linear regression was used to calculate the protein concentration in the nuclear extract sample, taking into account the 10× dilution. The result was a protein concentration of 559 µg/mL or 279 µg (BSA equivalents) of the nuclear extract.

Topoisomerase Extract Activity in DNA Relaxation Assays:

Relaxation activity of the nuclear extract, containing topo I and II, was determined by detecting the conversion of supercoiled plasmid DNA to its relaxed form in the presence of ATP. Reaction tubes (20 µL volumes) were assembled on ice by the ordered addition of: (i) pure water (variable, made up to 20 µL volume); (ii) 4 µL relaxation buffer (250 mM Tris-HCl, pH 8, 0.75 M NaCl, 50 mM $MgCl_2$, 2.5 mM dithiothreitol, 150 µg BSA/mL, and 10 mM ATP); (iii) pUC19 supercoiled plasmid DNA (250 ng, or 38.6 µM bases); and (iv) topo extract (1, 2, 3, or 4 µL). The reaction was initiated by heating the tubes in a 37° C. incubator for 30 min. The reaction was stopped by adding 2 µL of 10% SDS (in sterile water), and the DNA-bound protein was then digested by adding 2 µL proteinase K (0.50 mg/mL stock in 10 mM Tris-HCl, 1 mM EDTA, pH 7.5) and incubating at 37° C. for 15 min. Then, 2 µL loading dye with ficoll (0.25% bromophenol blue, 15% ficoll, in 1×TBE buffer) was added and DNA samples were then analyzed by 1.5% agarose gel electrophoresis using 1×TBE buffer (50 V, 180 min). The gels were stained with ethidium bromide (1 µg/mL) for 30 min with subsequent destaining for 30 min in water, and visualized with UV-transillumination (UVP transilluminator) using the Gel-Doc-It Imaging system (UVP). One unit of DNA topoisomerase II activity was defined as the amount of enzyme capable of relaxing 250 ng of supercoiled DNA in 30 minutes at 37° C. (in this case, one unit=2 µL extract). The presence of topo I was assessed by testing for relaxation of pUC19 plasmid (250 ng) in the absence of ATP for 30 min at 37° C. Under these conditions, relaxation of pUC19 plasmid was not detected (indicating little to no topo I).

Topoisomerase II Assays:

Inhibition of topoisomerase II activity by compounds of the disclosure was measured by a supercoiled DNA relaxation assay using a topoisomerase II drug screening kit (Topo-GEN). Briefly, 0.23 µg supercoiled pUC19 plasmid DNA (3.5 µL of 64.5 ng/µL stock solution in 10 mM Tris-Cl, pH 8.5) was suspended in pH 8.0 reaction buffer (250 mM Tris-HCl, 0.75 M NaCl, 50 mM $MgCl_2$, 2.5 mM dithreitol, 150 µg BSA/mL, and 10 mM ATP). Pure water was added (variable, made up to 20 µL volume), then 2 µL aliquots of ruthenium compounds (1, 10, 50, 100, 500, 1000 µM serial dilutions) were added, making final sample concentrations of 0.1, 1, 5, 10, 50, and 100 µM. Control samples were prepared as follows: (i) plasmid only (no nuclear extract); (ii) plasmid with nuclear extract; (iii) plasmid with the highest ruthenium concentration (no nuclear extract); and (iv) plasmid with nuclear extract (no ATP in the buffer). The tubes were mixed well (gently shaken and spun down) prior to initiating the reaction by the addition of 2 µL (one unit) nuclear extract. After 30 min incubation at 37° C., the reaction was stopped by adding 2 µL of 10% SDS (in sterile water). The DNA-bound protein was digested by adding 2 µL of proteinase K (0.50 mg/mL stock in 10 mM Tris-HCl, 1 mM EDTA, pH 7.5) at 37° C. for 15 min, without the optional chloroform:isoamyl alcohol extraction (earlier extractions showed no cosmetic improvement in results). Lastly, 2 µL ficoll loading dye (0.25% bromophenol blue, 15% ficoll, in 1×TBE buffer) was added and DNA samples were analyzed by 1.5% agarose gel electrophoresis using 1×TBE buffer (50 V, 180 min). The gel was stained with ethidium bromide (1 µg/mL) for 30 min with subsequent destaining for 30 min in pure water, and visualized with UV-transillumination (UVP transilluminator) using the Gel-Doc-It Imaging system (UVP).

DNA Binding by UV-Vis:

Optical titrations were carried out on 0.5-2 mL solutions of the PDCs with increasing amounts of calf thymus or herring sperm DNA to give [DNA bases]/[PDC] between 0.1 and 10. DNA was added in 1-5 µL increments to solutions of compound (10 µM) in 10 mM MOPS, 10 mM MOPS with 50 mM NaCl, 5 mM Tris-HCl, or 5 mM Tris-HCl with 50 mM NaCl at pH 7.5. The dilution of compounds of the disclosure at the end of each titration, although negligible, was accounted for in the binding constant analyses. The DNA binding constant ($K_b$) was obtained from fits of the titration data to eq. 1 (FIG. 36), where $b=1+K_bC_t+K_b[DNA]_t/2_s$, $C_t$ and $[DNA]_t$ represent the total PDC and DNA concentrations, respectively, s is the binding site size, and $\epsilon_a$, $\epsilon_f$, and $\epsilon_b$ represent the molar extinction coefficients of the apparent, free, and bound PDCs, respectively. $\epsilon_f$ was calculated at 414 nm for 7 and 412 nm for 8 before the addition of DNA, and $\epsilon_a$ was determined at these wavelengths after each addition of DNA. The value of $\epsilon_b$, was determined from the plateau of the DNA titration, where addition of DNA did not result in any further decrease in the absorption signal. Detailed fits of the titration data were obtained using both Kaleidagraph and Gnuplot.

DNA melting curves were constructed by measuring the absorbance ($A_{260}$) of a 2 mL, 25 µM DNA solution (40 mM MOPS, pH 7.5) as a function of temperature (20-100° C.) in the absence and presence of a compound of the disclosure (5 µM). Solutions of DNA and a compound of the disclosure for melting experiments were allowed to equilibrate for 30 min at 25° C. prior to measurement. The ETC-505T temperature controller was cooled with ice water (4° C.) using a fishaquarium pump, and a stream of argon gas was supplied via the gas inlet valve to the sample compartment to prevent condensation on the cuvette windows during variable-temperature experiments.

Photocleavage Titrations:

DNA photocleavage experiments were performed according to a general plasmid DNA assay with 20 µL total sample volumes in 0.5 or 1.5 mL microfuge tubes containing transformed pUC19 plasmid (200 ng, >95% Form I) in 10 mM MOPS buffer and 100 mM NaCl, pH 7.4. DNA (1-5 µL) was delivered to the assay tubes as a solution in 10 mM Tris-Cl (pH 8.5) and diluted with MOPS (pH 7.5, final concentration 10 mM) and NaCl (final concentration 100 mM). Solutions of the compounds of the disclosure were added to give the from 0 to 500 µM, and the reaction mixtures were diluted to a final volume of 20 µL, when necessary, with ddH$_2$O. Complexes were dissolved initially in acetonitrile (2 µM stock solutions), and all subsequent dilutions were made with ddH$_2$O where final assay tubes contained <1% acetonitrile. For concentration-based assays, samples (no pre-incubation period) were irradiated in air for 30 min with 420 nm light inside a photoreactor (Luzchem LZC-4×). Where irradiation of deoxygenated samples was required, argon was bubbled through the solutions for 15 min prior to irradiation under a positive pressure of argon. All samples were quenched by the addition of gel loading buffer (4 µL), loaded onto 1% agarose gels containing ethidium bromide (0.75 µg mL$^{-1}$), and electrophoresed for 30 min at 8-12 V cm$^{-1}$ in 1×TAE (40 mM Trisacetate, 1 mM EDTA, pH 8.2). The bands were visualized with UV-transillumination (UVP transilluminator) and quantified using the Get Doc-It Imaging system (UVP) or GNU Image Manipulation Program (GIMP).

HL-60 Cell Culture:

HL-60 human promyelocytic leukemia cells (ATCC CCL-240) were cultured at 37° C. under 5% CO$_2$ in Hyclone's IMDM, supplemented with 20% FBS and were passaged 3-4 times per week according to standard aseptic procedures. Cultures were started at 200,000 cells mL$^{-1}$ in 25 cm$^2$ tissue culture flasks and were subcultured before growth reached 750,000 cells mL$^{-1}$ to avoid senescence associated with prolonged high cell density. Complete media was prepared in 200 mL portions as needed by combining IMDM (160 mL), FBS (40 mL, pre-aliquoted and heat inactivated), and gentamicin sulfate (100 µL of 50 mg mL$^{-1}$ stock solution) in a 250 mL Millipore vacuum stericup (0.22 µm) and filtering.

Cytotoxicity and Photocytotoxicity Assays

HL-60 cells growing in log phase (approximately 8×10$^5$) were transferred in 50 µL aliquots to two 96-well tissue-culture microplates (Corning Costar, Acton, Mass.) containing 100 µL warm culture medium and placed in a 37° C., 5% CO$_2$ water-jacketed incubator (Thermo Electron Corp., Form a Series II, Model 3110, HEPA Class 100) for one hour to equilibrate. All empty microplate wells contained 200 µL phosphate buffered saline (PBS) containing 2.68 mM potassium chloride, 1.47 mM potassium phosphate monobasic, 0.137 M sodium chloride, and 8.10 mM sodium phosphate dibasic, pH 7.4, to help minimize evaporation loss. Warm 50 µL aliquots of solution of compounds of the disclosure (4, 20, 40, 200 µM), freshly made in PBS, were added to the cells and incubated at 37° C. under 5% CO$_2$ for 4 hr (final concentrations were 1, 5, 10, 50 µM). One of the microplates was irradiated with visible light (400-700 nm) in a Luzchem photoreactor (cool white fluorescent tubes, 21 W/m$^2$) for 15 min; the other microplate was incubated under identical conditions in the dark. Both microplates were then incubated (37° C. under 5% CO$_2$) for 40 hr. A Cellometer Auto T4 (ESBE Scientific) was used to determine the cell number, viability, diameter, and % cell viability. Cell suspensions (20 µL) were diluted 1:1 with 0.2% trypan blue dye (Sigma Aldrich, Canada), loaded into a cell counting chamber-slide, and inserted into the imaging-based automatic cell counter. Cell concentration and cell viability were automatically determined (Cellometer Auto Counter Software) on the basis of the total cell count, the dilution factor, and the trypan blue dye exclusion. The optimal cell type parameters were established by importing the settings for HL-60 cells, and the data was subsequently imported into a Microsoft excel spreadsheet (Microsoft Office 2010) for data analysis.

Cytotoxicity and Photocytotoxicity Assays:

HL-60 cells growing in log phase were transferred (typically 25 µL aliquots) to 96-well tissue-culture plates (Corning Costar, Acton, Mass.) containing culture medium either with or without varying concentrations of the compounds of the disclosure to give final volumes in the culture wells of 100 µL and 10,000-20,000 cells. Solutions of compounds of the disclosure in complete media were prepared in 1 mL portions, where acetonitrile from the initial compounds of the disclosure stock solution was <0.5% v/v, and sterile-filtered in 3 mL syringes equipped with 0.22 µm Nalgene filters. Plates were incubated at 37° C. under 5% CO$_2$ for 30 min prior to exposure to 420 nm light in a Luzchem photoreactor for 30 min; dark controls were incubated under identical conditions in the dark. Dark controls, or cytotoxicity (CT) assays, refer to assays that include compounds of the disclosure but were not exposed to light, and light controls refer to light-exposed assays that did not contain compounds of the disclosure. Photocytotoxicity (PCT) assays contained PDC and were exposed to light. Cell counts and viability staining were carried out immediately and at ~24 h following light exposure. Manual counts were performed on 25 µL 1:1 mixtures of assay culture and trypan Hue solution in a Neubauer hemocytometer viewed under an inverted light microscope in phase-contrast mode (4× objective, 60× total magnification). Under these conditions, viable cells appeared bright white, and nonviable cells were blue. All experiments were carried out in triplicate, and the graphed data is the average of three trials.

Viability Staining:

Viability was established according to a published protocol whereby a 100× stock solution of ethidium bromide/acridine orange (EB/AO) was prepared by dissolving ethidium bromide (50 mg) and acridine orange (15 mg) in 95% ethanol (1 mL) and diluting $\frac{1}{50}$ with ddH$_2$O. The 100× solution was divided into 1 mL aliquots and stored at −20° C. A 1× working solution was made by thawing a 1 mL aliquot of the 100× stock solution and diluting $\frac{1}{100}$ with phosphate-buffered saline. The working solution was stored in an amber bottle at 4° C. for up to 1 month. For cellular viability staining, an aliquot of cell suspension was adjusted to 1-5×10$^6$ cells mL$^-$ in phosphate-buffered IMDM. A 25 aliquot of this cell suspension was mixed with 1×EB/AO staining solution (25 in a microfuge tube; a 25 µL aliquot of this cell-stain mixture was transferred to a hemocytometer and viewed under a Nikon Eclipse TE2000-U inverted light microscope operating in epi-fluorescence mode (10× or 40× objective, 150× or 600× total magnification). Under these conditions, viable cells took up AO and excluded EB, resulting in only green fluorescence with UV-excitation, Nonviable cells (apoptotic or necrotic) assimilated EB and fluoresced red with green excitation, overwhelming any green fluorescence from AO. Apoptotic cells were discerned from the formation of smaller, apoptotic bodies that fluoresced red.

Nuclear Staining for Laser Scanning Confocal Microscopy (LSCM)

HL-60 human promyelocytic leukemia cells (ATCC CCL-240) growing in log phase were transferred in aliquots of 100 µL (approximately 50,000 cells) to a 96-well tissue-culture microplate (Corning Costar, Acton, Mass.) containing 150 µL warm culture medium (Hyclone's IMDM supplemented with 20% FBS), and placed in a 37° C., 5% CO$_2$ water-jacketed incubator (Thermo Electron Corp., Form a Series II, Model 3110, HEPA Class 100) for one hour to equilibrate. Then, 50 µL of a 600 µM solution of a compounds of the disclosure (warmed to 37° C.), made in phosphate buffered saline (PBS) containing 2.68 mM potassium chloride, 1.47 mM potassium phosphate monobasic, 0.137 M sodium chloride, and 8.10 mM sodium phosphate dibasic, pH 7.4, was added. The microplate was returned to the incubator for 15 min. The 300 µL sample was then transferred to a collagen-coated glass-bottom tissue culture dish (FluoroDish FD35COL, World Precision Instruments Inc.) and returned to the incubator for 10-15 min to allow cells to adhere to the coated dish. The volume of the tissue culture dish was subsequently topped up to 2 mL with warm PBS for LSCM.

While the invention has been described in detail and with reference to specific examples thereof, it will be apparent to one skilled in the art that various changes and modifications can be made therein without departing from the spirit and scope thereof.

What is claimed is:

1. A compound having formula (I):

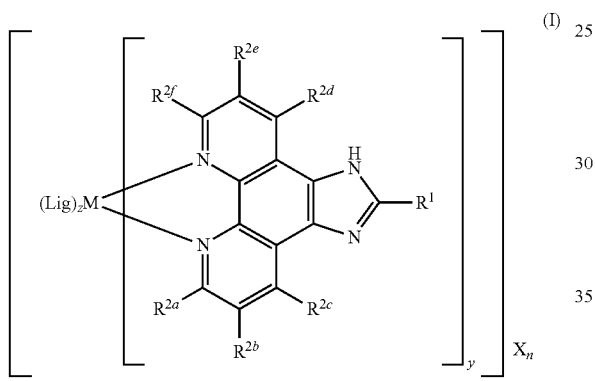

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=1, 2, 3, 4, or 5;

y=1, 2, or 3;

z=0, 1, or 2;

Lig at each occurrence is independently selected from the group consisting of

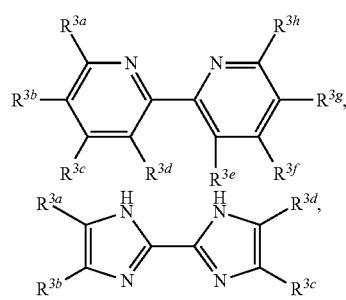

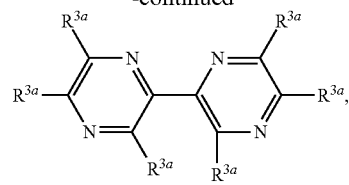

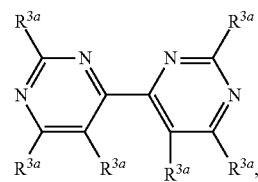

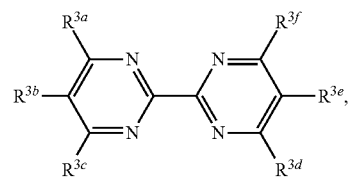

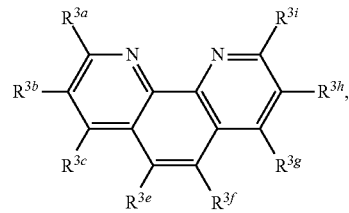

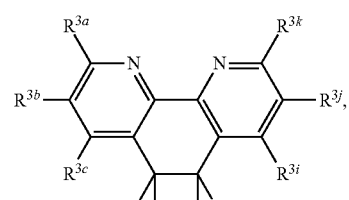

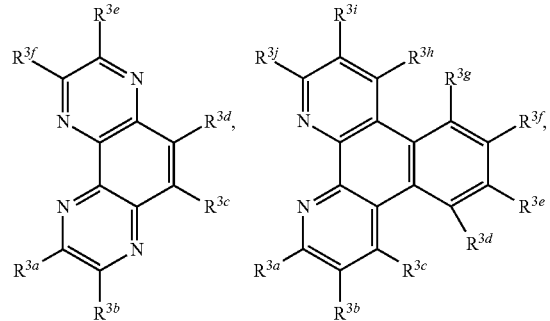

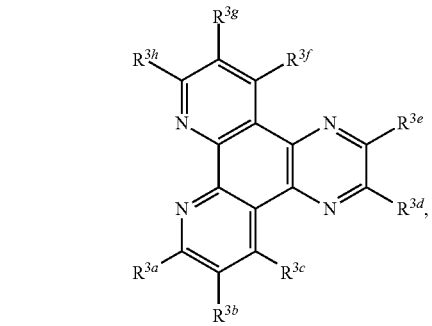

-continued

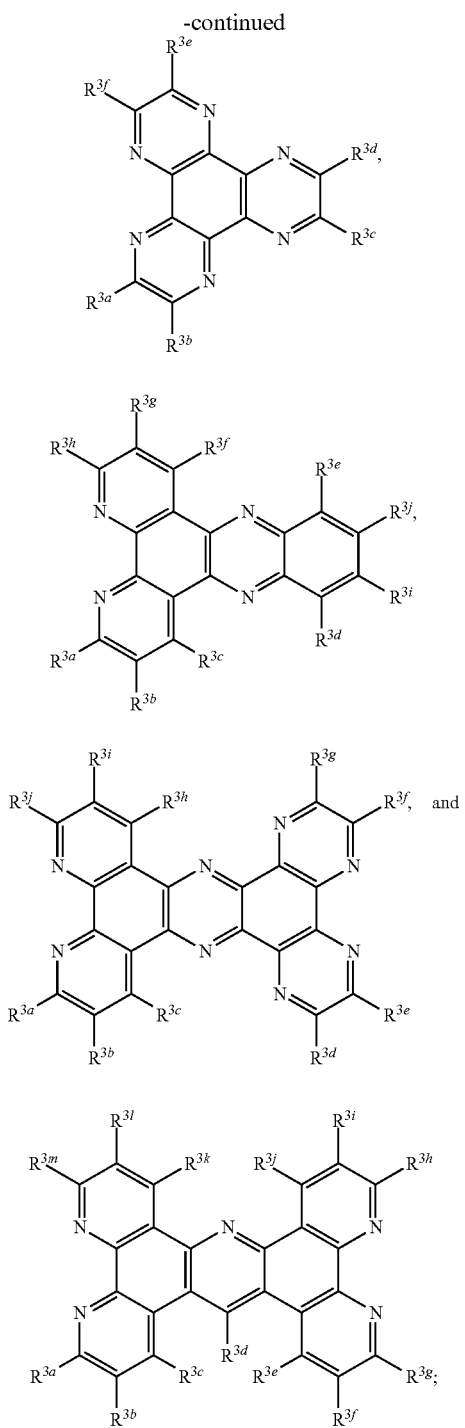

R[1] is selected from the group consisting of

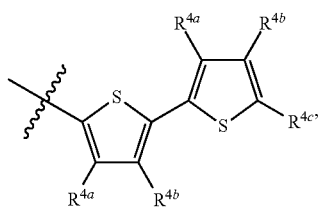

-continued

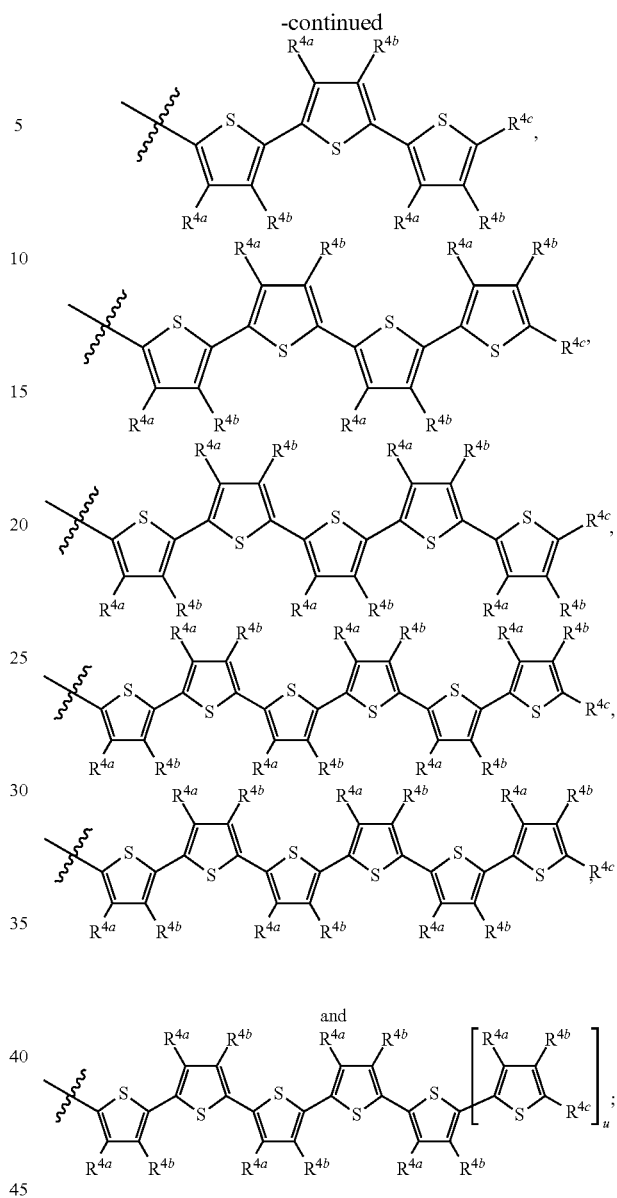

u is an integer;
$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;
$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;
$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl;

$R^8$ at each occurrence is independently selected from the group consisting of hydrogen and optionally substituted alkyl;

wherein compounds of the following structures are excluded:

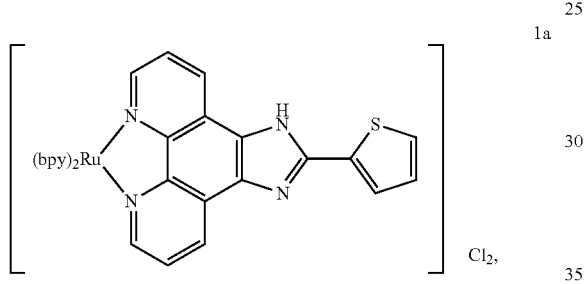

1a

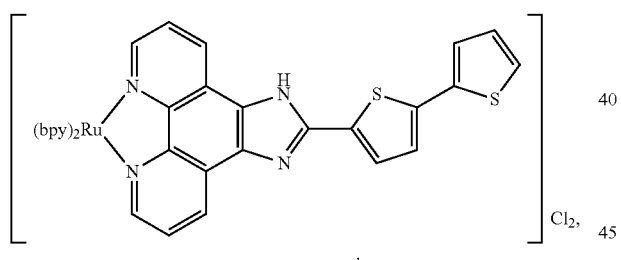

10a and

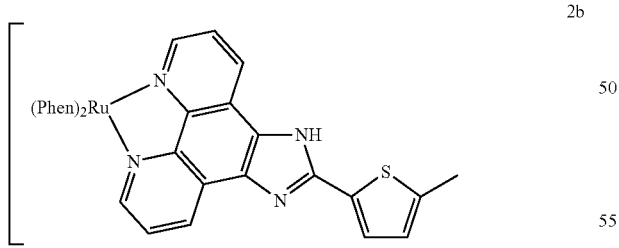

2b

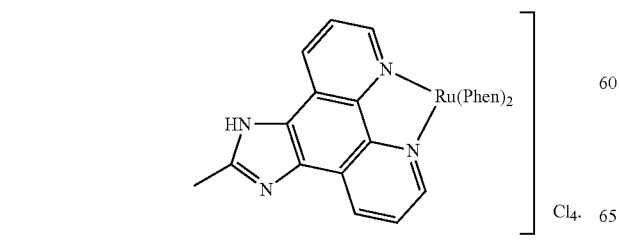

2. The compound of claim 1, having the formula (II):

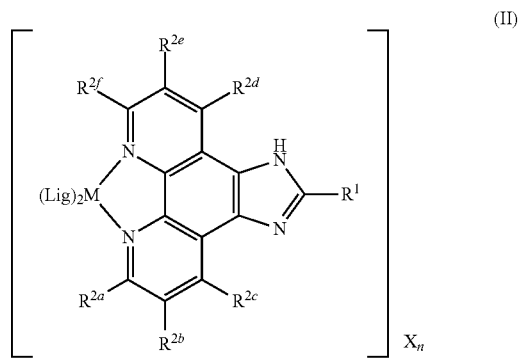

(II)

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{-2}$;

n=1, 2, or 3;

Lig at each occurrence is independently selected from the group consisting of

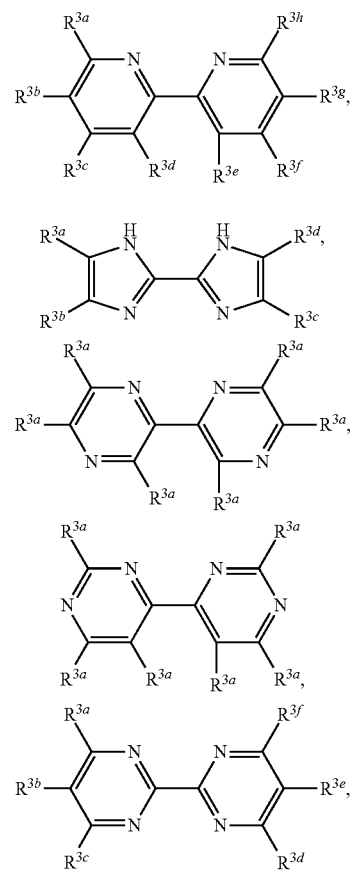

497
-continued
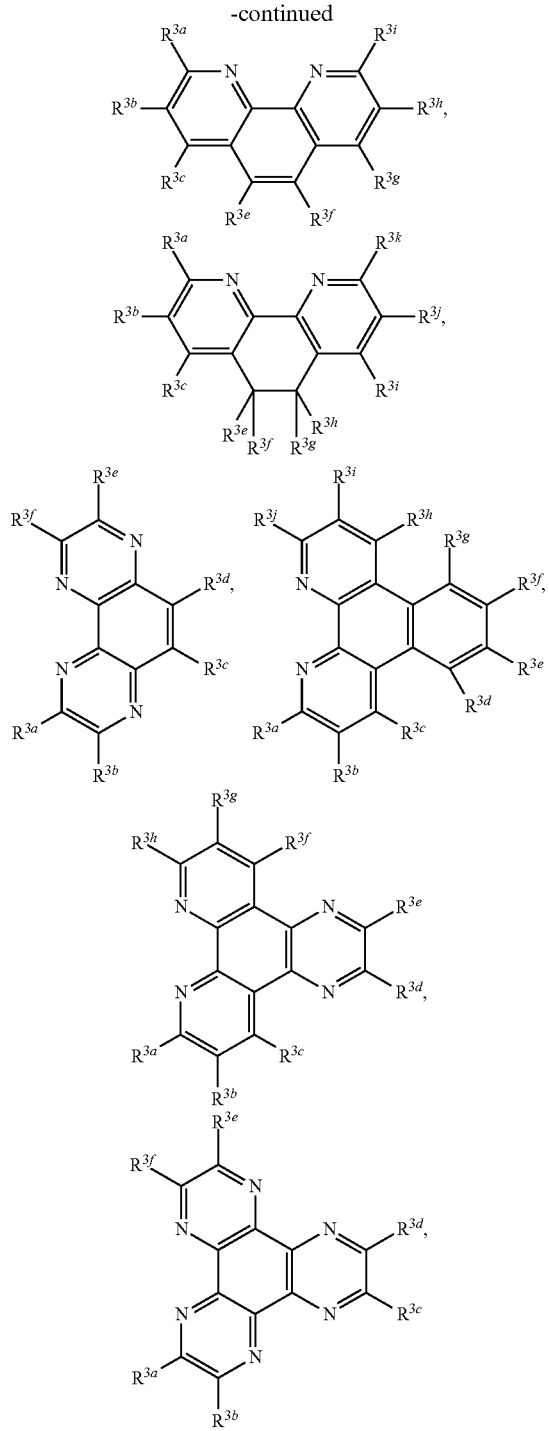
498
-continued
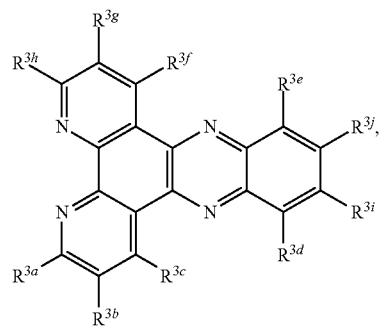
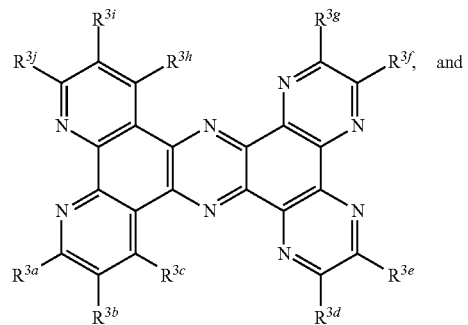
$R^1$ is selected from the group consisting of
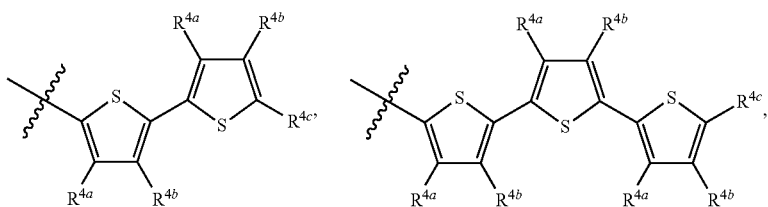

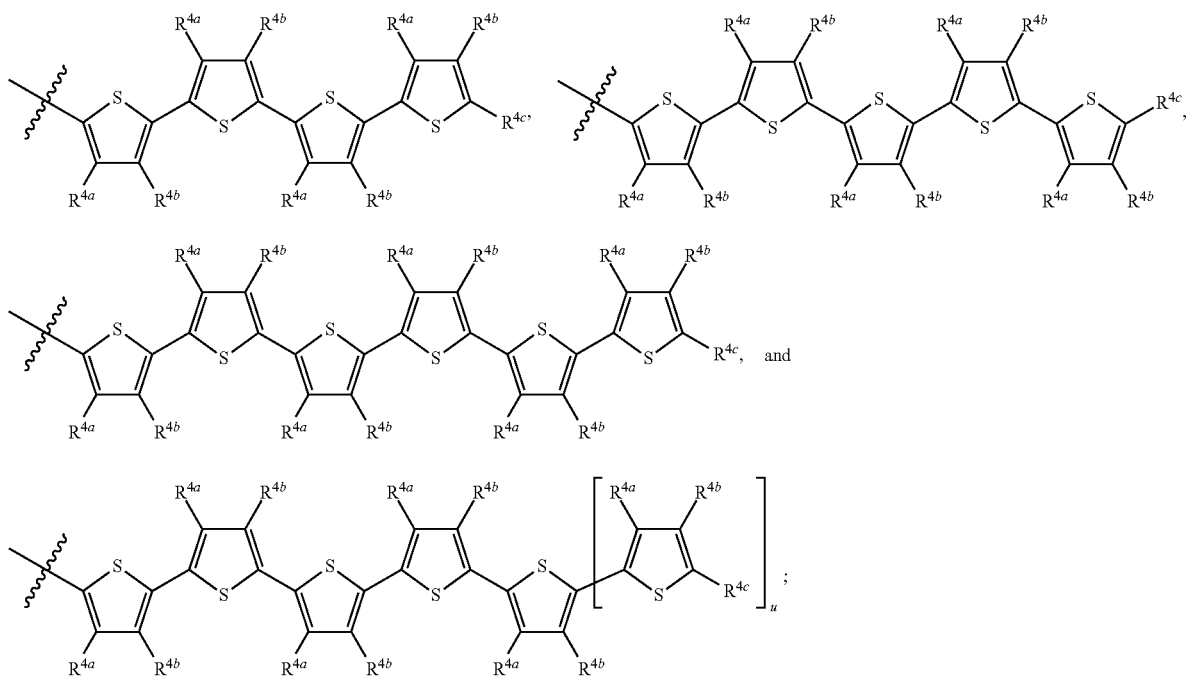

u is an integer;

$R^{2a}$, $R^{2b}$, $R^{2c}$, $R^{2d}$, and $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$ $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl;

$R^8$ at each occurrence is independently selected from the group consisting of hydrogen and optionally substituted alkyl;

wherein compounds of the following structures are excluded:

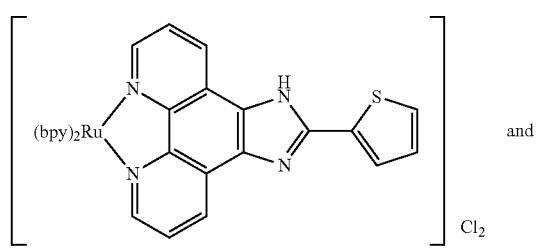

1a

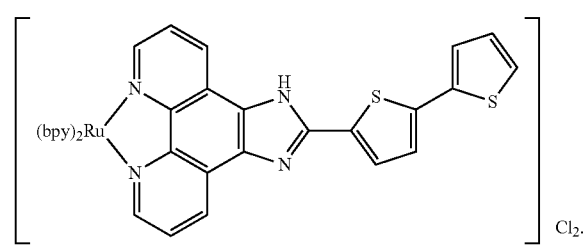

10a

3. The compound of claim 1, having the formula (III):

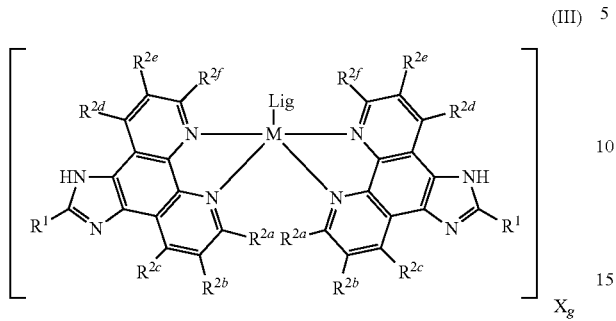

(III)

including hydrates, solvates, pharmaceutically acceptable salts, prodrugs and complexes thereof wherein:
g=0, 1, 2, 3, 4, or 5.

4. The compound of claim 1, having the formula (IV):

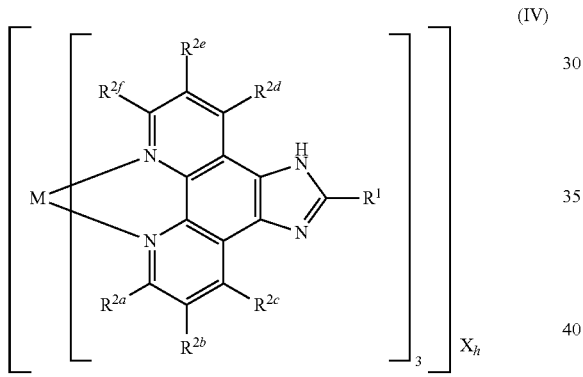

(IV)

including hydrates, solvates, pharmaceutically acceptable salts, prodrugs and complexes thereof wherein:
h=0, 1, 2, 3, 4, or 5.

5. A compound having formula (V):

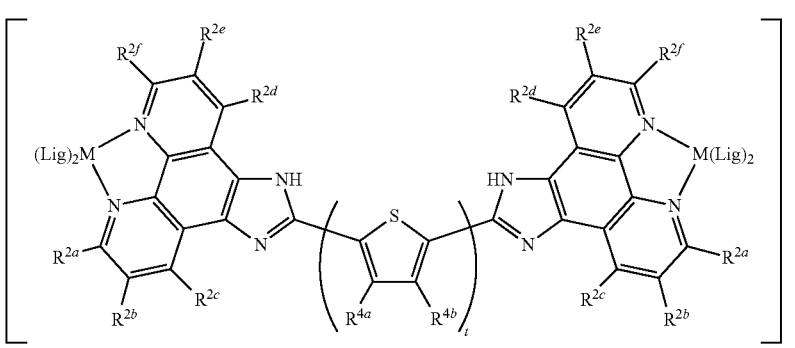

(V)

including hydrates, solvates, pharmaceutically acceptable salts, prodrugs and complexes thereof, wherein:

M is manganese, molybdenum, rhenium, iron, ruthenium, osmium, cobalt, rhodium, iridium, nickel, platinum or copper:

Lig at each occurrence is independently selected from the group consisting of

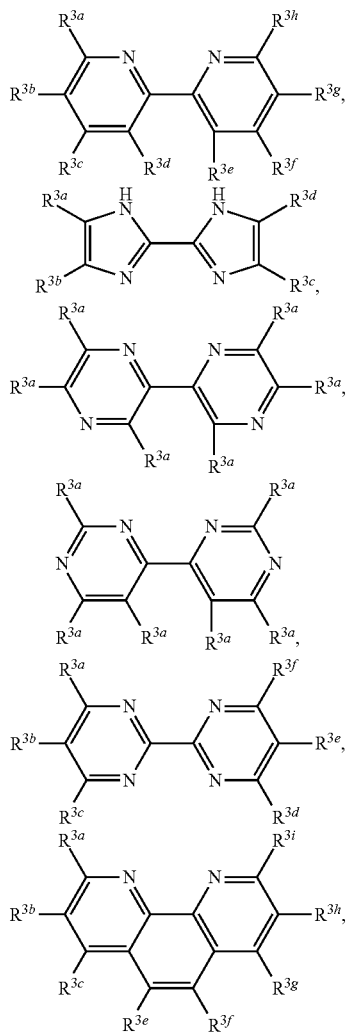

-continued

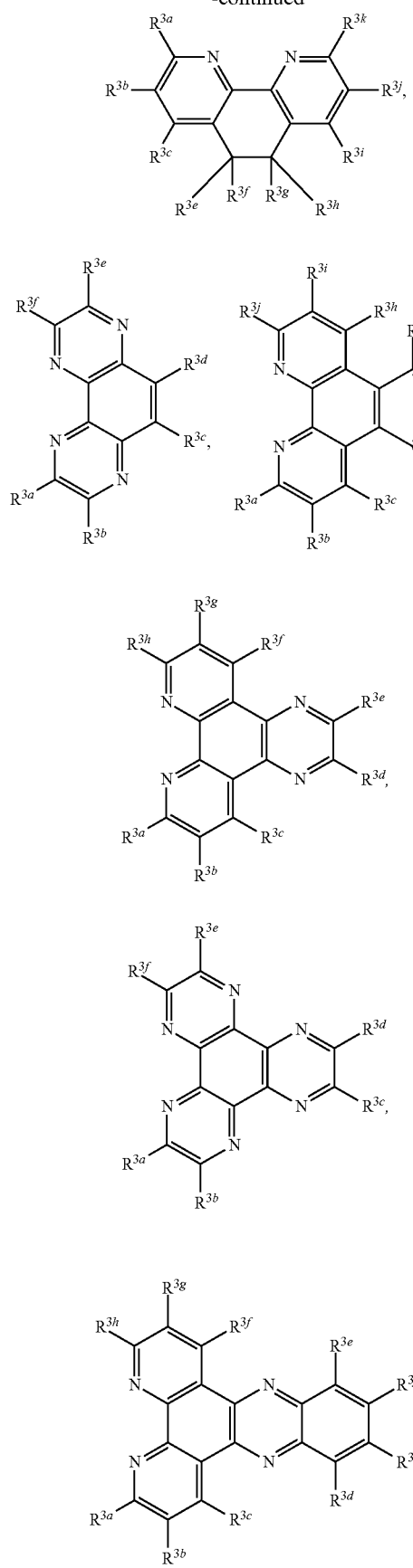

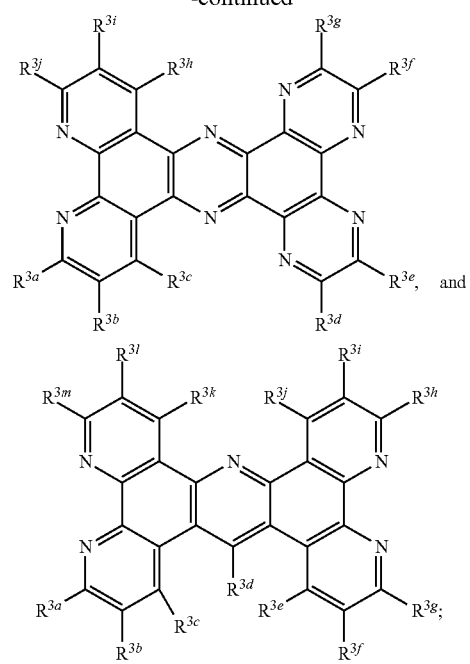

$R^{2a}, R^{2b}, R^{2c}, R^{2d}, R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{3a}, R^{3b}, R^{3c}, R^{3d}, R^{3e}, R^{3f}, R^{3g}, R^{3h}, R^{3i}, R^{3j}, R^{3k}, R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl;

$R^8$ at each occurrence is independently selected from the group consisting of hydrogen and optionally substituted alkyl;

t is an integer;

X is $Cl^-$, $PF_6{}^-$, $Br^-$, $BF_4{}^-$, $ClO_4{}^-$, $CF_3SO_3{}^-$, or $SO_4{}^{2-}$; and q=0, 1, 2, 3, 4 or 5;

wherein the following compound is excluded:

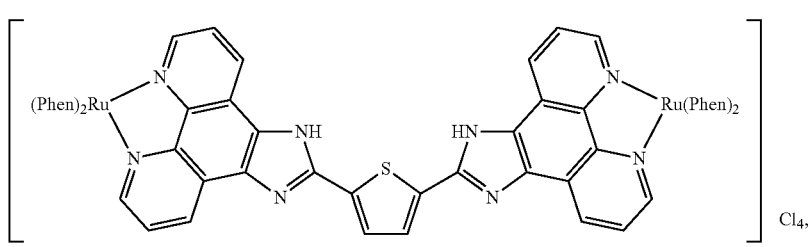

and
wherein when M is ruthenium, Lig is not

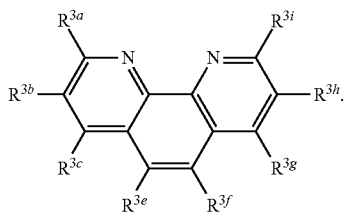

6. A method for treating a disease associated with hyperproliferating cells, said method comprising administering to a subject an effective amount of at least one compound according to claim 1.

7. The method of claim 6, wherein the at least one compound is administered in a composition further comprising at least one excipient.

8. A method for treating a disease associated with hyperproliferating cells, said method comprising administering to a subject an effective amount of at least one compound according to claim 2.

9. The method of claim 8, wherein the at least one compound is administered in a composition further comprising at least one excipient.

10. A method for treating a disease associated with hyperproliferating cells, said method comprising administering to a subject an effective amount of at least one compound according to claim 3.

11. The method of claim 10, wherein the at least one compound is administered in a composition further comprising at least one excipient.

12. A method for treating a disease associated with hyperproliferating cells, said method comprising administering to a subject an effective amount of at least one compound according to claim 4.

13. The method of claim 12, wherein the at least one compound is administered in a composition further comprising at least one excipient.

14. A method for treating a disease associated with hyperproliferating cells, said method comprising administering to a subject an effective amount of at least one compound according to claim 5.

15. The method of claim 14, wherein the at least one compound is administered in a composition further comprising at least one excipient.

16. A method for treating a disease associated with hyperproliferating cells, said method comprising administering to a subject an effective amount of at least
one compound of the structure

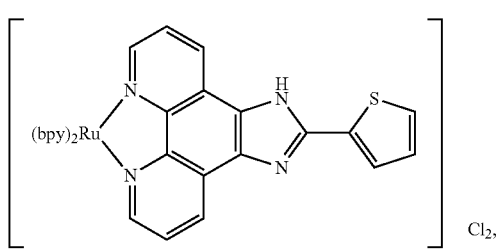

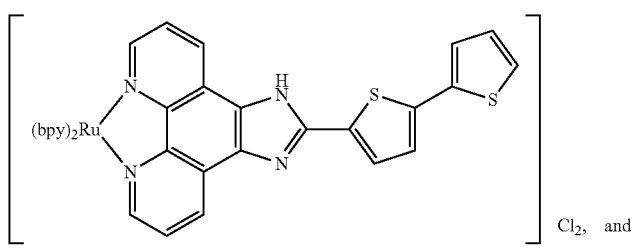

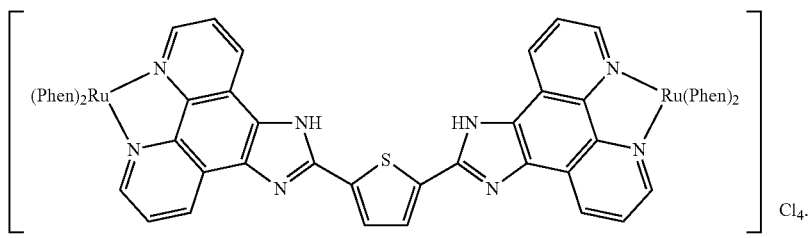

17. The method of claim 16, wherein the at least one compound is administered in a composition further comprising at least one excipient.

18. A method for treating a disease associated with hyperproliferating cells, said method comprising administering to a subject an effective amount of at least one compound having formula (I):

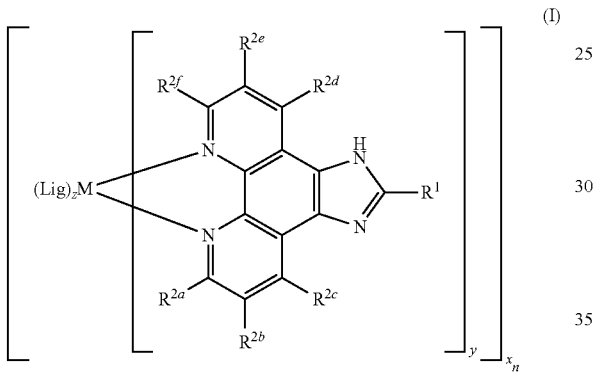

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{2-}$;

n=0, 1, 2, 3, 4, or 5;

y=1, 2, or 3;

z=0, 1, or 2;

Lig at each occurrence is independently selected from the group consisting of

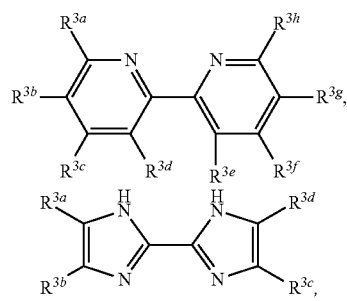

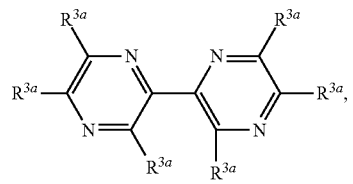

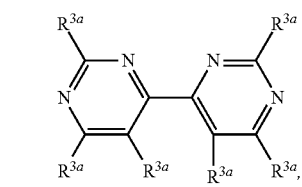

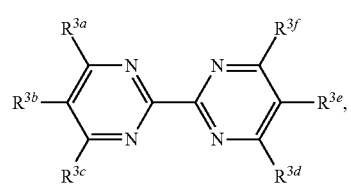

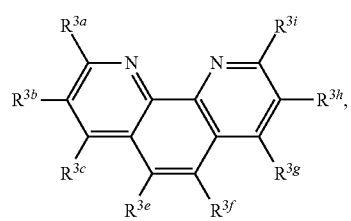

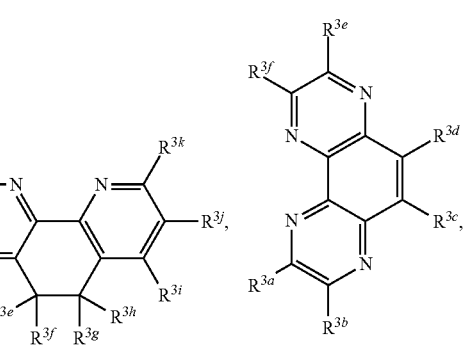

509
-continued
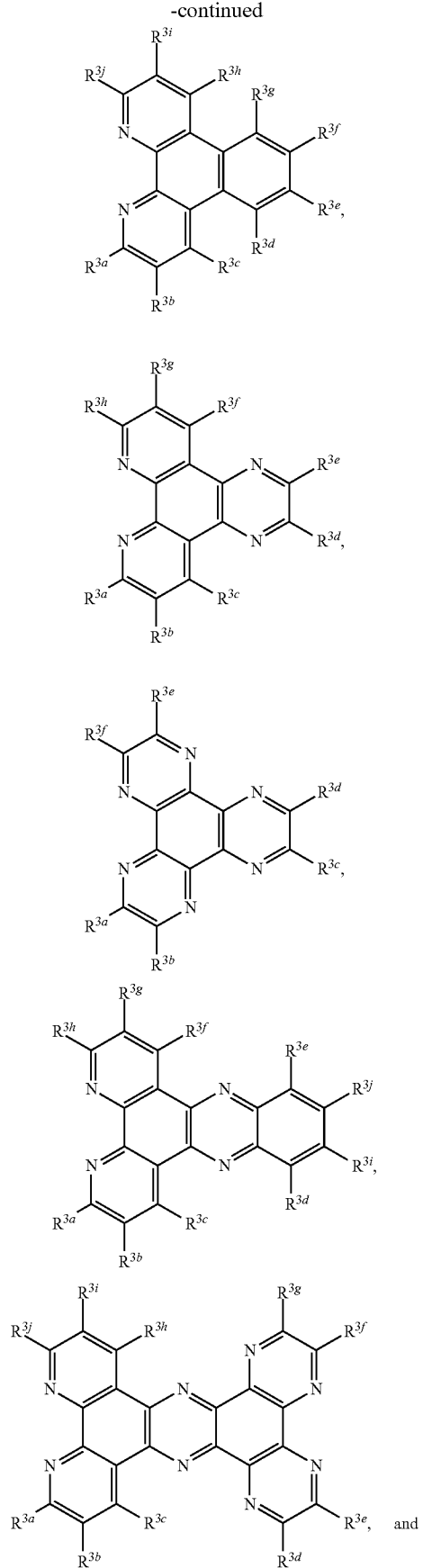
510
-continued
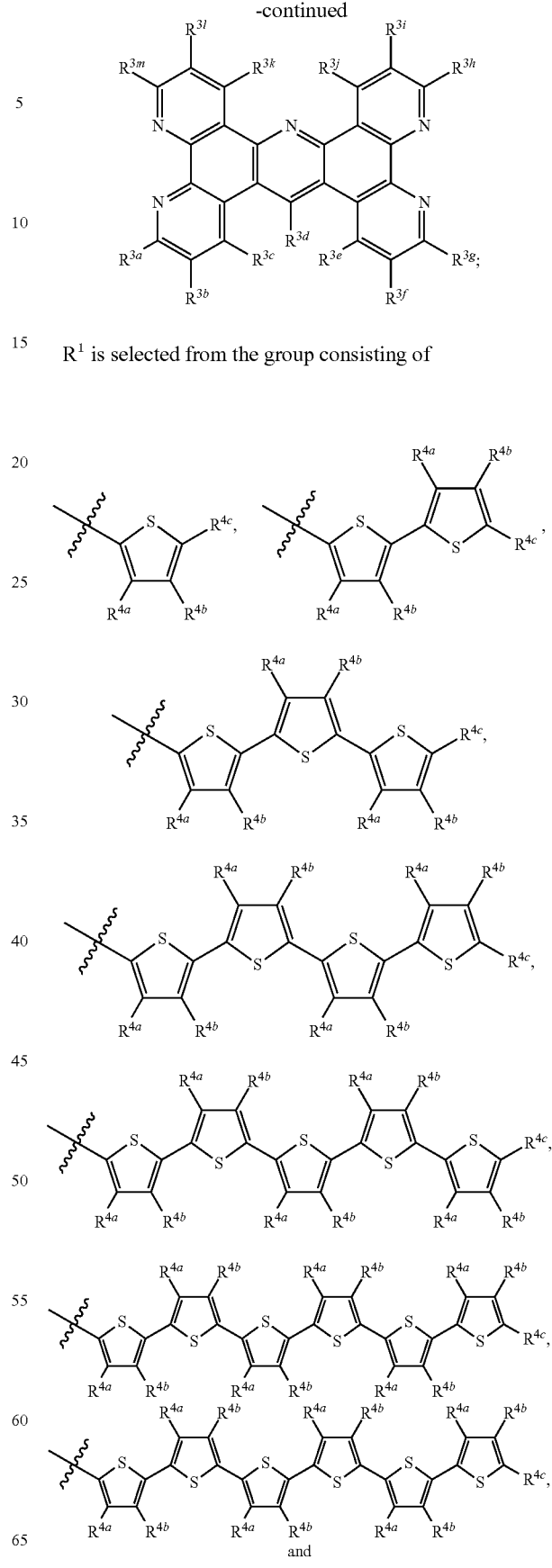
$R^1$ is selected from the group consisting of -continued

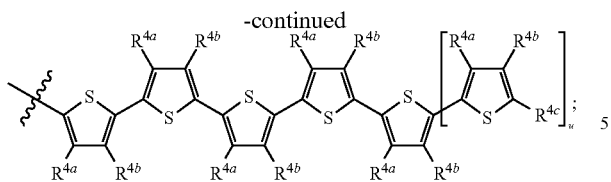

u is an integer;

$R^{2a}, R^{2b}, R^{2c}, R^{2d}, R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{3a}, R^{3b}, R^{3c}, R^{3d}, R^{3e}, R^{3f}, R^{3g}, R^{3h}, R^{3i}, R^{3j}, R^{3k}, R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}, R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl;

$R^8$ at each occurrence is independently selected from the group consisting of hydrogen and optionally substituted alkyl;

wherein compounds of the following structures are excluded:

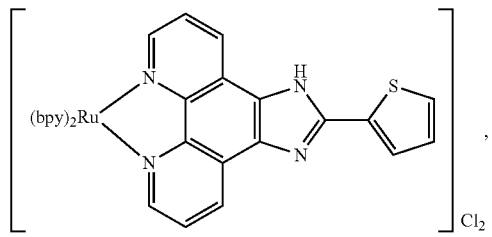

1a

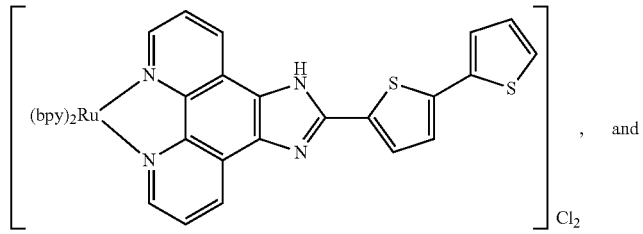

, and

10a

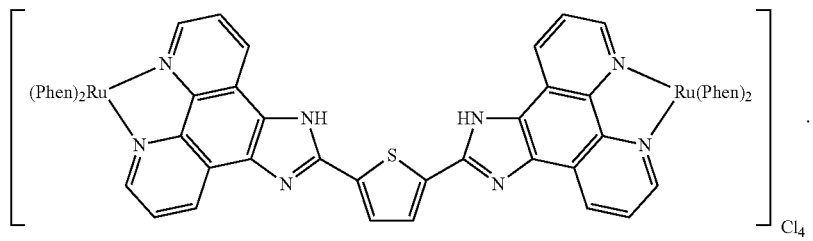

2b

19. A method for treating a disease associated with hyperproliferating cells, said method comprising administering to a subject an effective amount of at least one compound having formula (II):

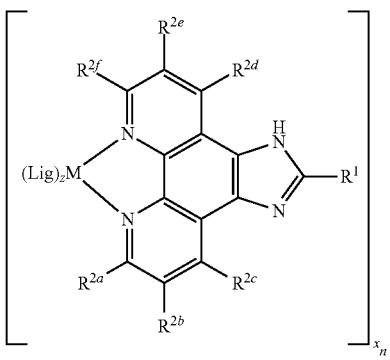

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of $Cl^-$, $PF_6^-$, $Br^-$, $BF_4^-$, $ClO_4^-$, $CF_3SO_3^-$, and $SO_4^{2-}$;

n=0, 1, 2, or 3;

Lig at each occurrence is independently selected from the group consisting of

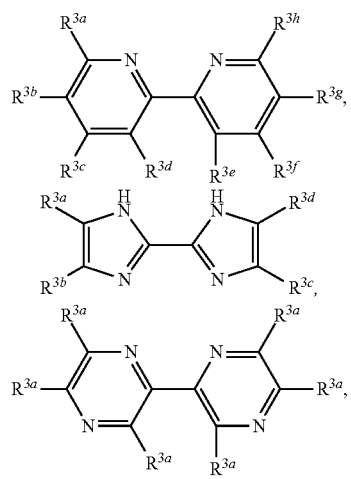

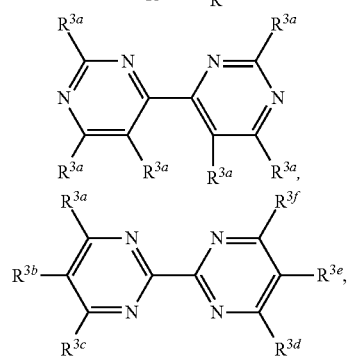

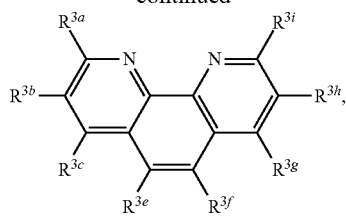

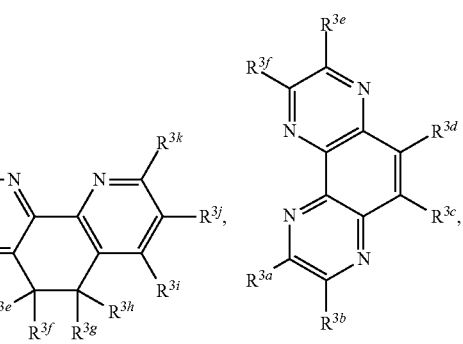

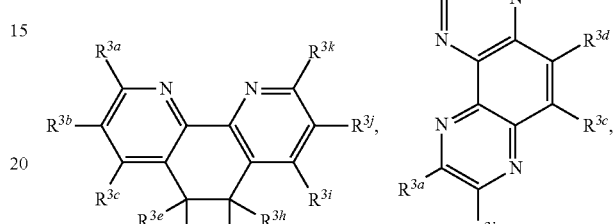

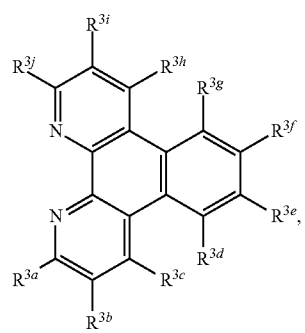

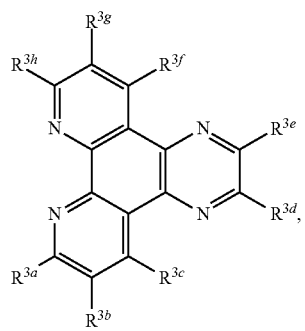

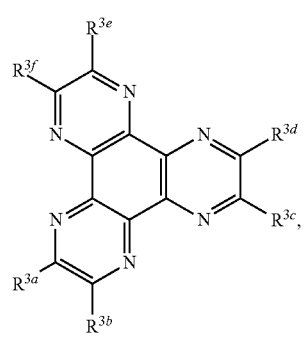

-continued

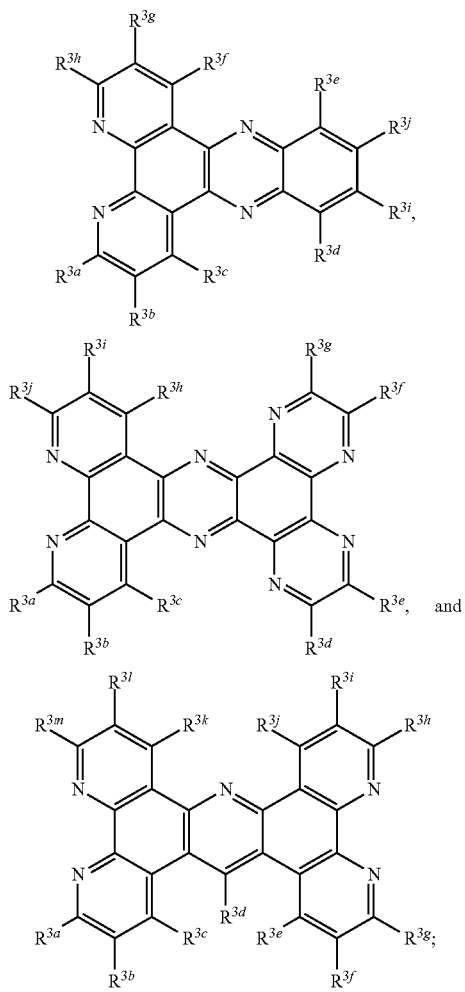

R¹ is selected from the group consisting of

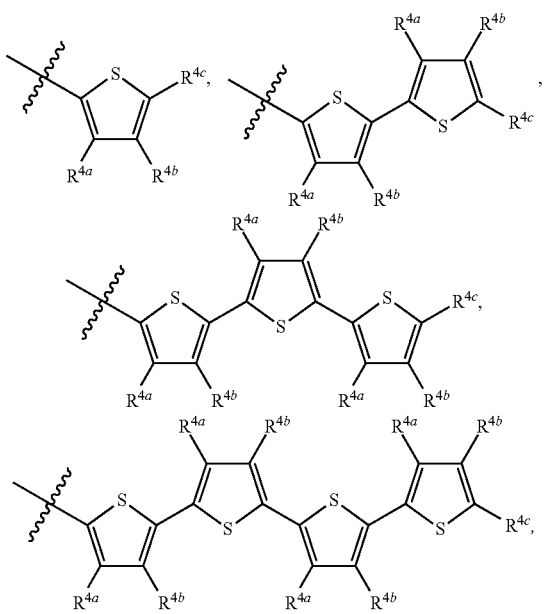

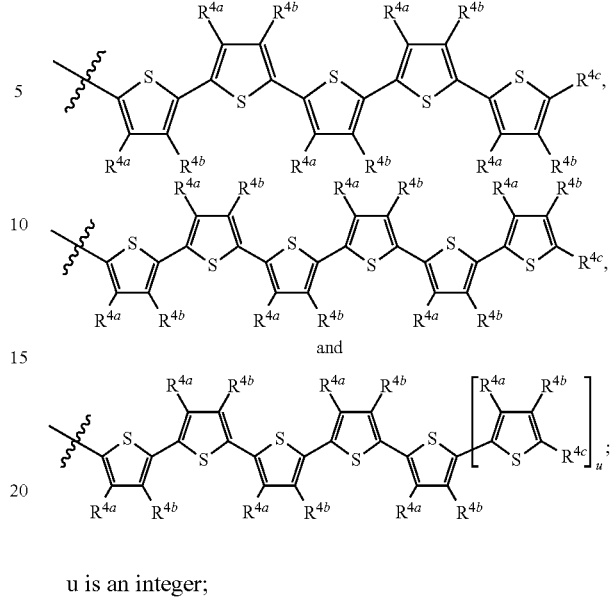

u is an integer;

$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$ $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl;

$R^8$ at each occurrence is independently selected from the group consisting of hydrogen and optionally substituted alkyl;

wherein compounds of the following structures are excluded:

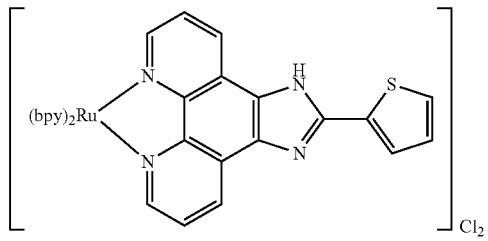

1a and

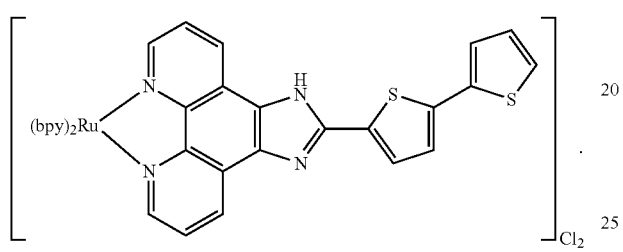

10a

20. A method for treating a disease associated with hyperproliferating cells, said method comprising administering to a subject an effective amount of at least one compound having formula (V):

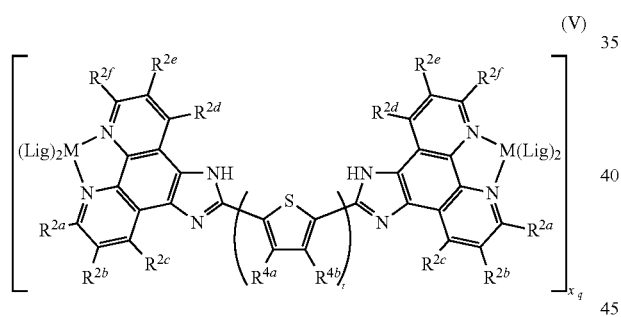

(V)

including hydrates, solvates, pharmaceutically acceptable salts, prodrugs and complexes thereof, wherein:
M is manganese, molybdenum, rhenium, iron, ruthenium, osmium, cobalt, rhodium, iridium, nickel, platinum or copper;
Lig at each occurrence is independently selected from the group consisting of

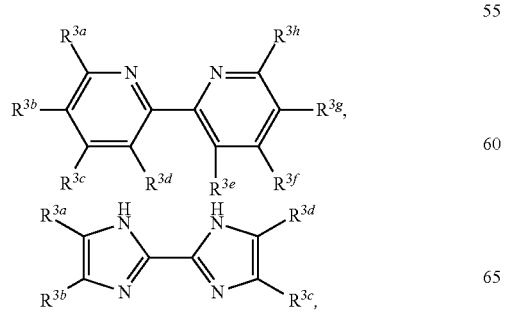

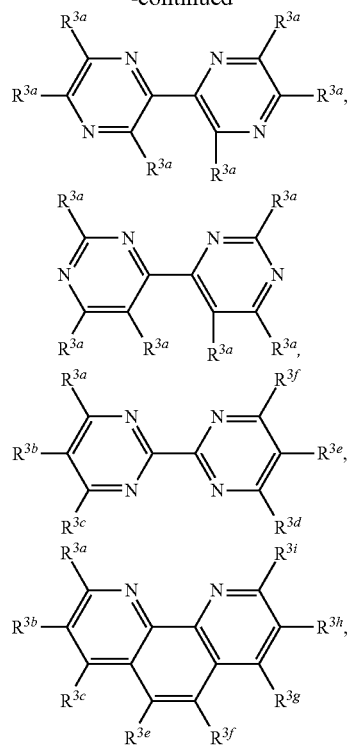

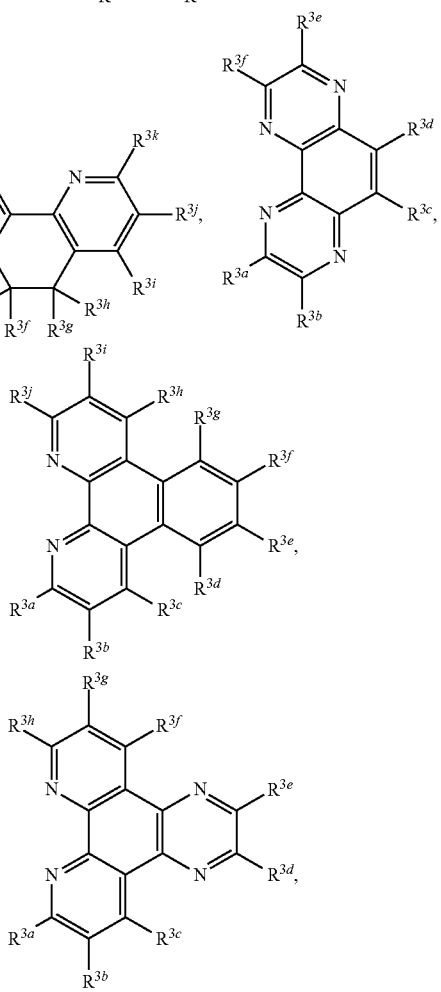

$R^{2a}, R^{2b}, R^{2c}, R^{2d}, R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{3a}, R^{3b}, R^{3c}, R^{3d}, R^{3e}, R^{3f}, R^{3g}, R^{3h}, R^{3i}, R^{3j}, R^{3k}, R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl;

$R^8$ at each occurrence is independently selected from the group consisting of hydrogen and optionally substituted alkyl;

t is an integer;

X is $Cl^-$, $PF_6^-$, $Br^-$, $BF_4^-$, $ClO_4^-$, $CF_3SO_3^-$, or $SO_4^{2-}$; and q=0, 1, 2, 3, 4 or 5;

wherein the following compound is excluded:

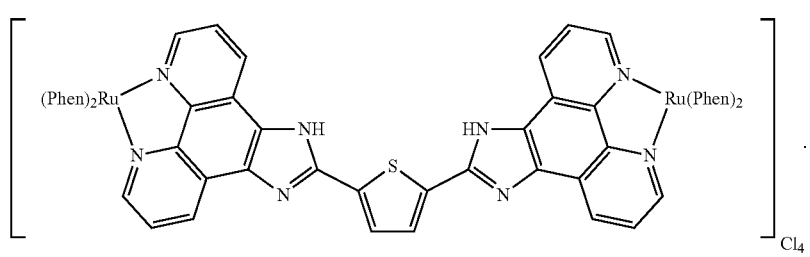

* * * * *